(12) United States Patent
Forrest

(10) Patent No.: US 12,410,143 B2
(45) Date of Patent: Sep. 9, 2025

(54) THERAPEUTIC INHIBITORS OF THE REVERSE MODE OF ATP SYNTHASE

(71) Applicant: Michael David Forrest, Poole (GB)

(72) Inventor: Michael David Forrest, Poole (GB)

( * ) Notice: Subject to any disclaimer, the term of this patent is extended or adjusted under 35 U.S.C. 154(b) by 0 days.

(21) Appl. No.: 16/478,497

(22) PCT Filed: Jan. 17, 2018

(86) PCT No.: PCT/EP2018/051127
§ 371 (c)(1),
(2) Date: Jul. 17, 2019

(87) PCT Pub. No.: WO2018/134265
PCT Pub. Date: Jul. 26, 2018

(65) Prior Publication Data
US 2020/0247758 A1    Aug. 6, 2020

(30) Foreign Application Priority Data

| Jan. 17, 2017 | (GB) | 1700772 |
| Apr. 14, 2017 | (GB) | 1706046 |
| May 17, 2017 | (GB) | 1707945 |
| Jun. 27, 2017 | (GB) | 1710198 |
| Jul. 13, 2017 | (GB) | 1711250 |
| Sep. 28, 2017 | (GB) | 1715756 |
| Sep. 28, 2017 | (GB) | 1715758 |
| Oct. 1, 2017 | (GB) | 1715938 |
| Oct. 9, 2017 | (GB) | 1716492 |
| Jan. 4, 2018 | (GB) | 1800092 |
| Jan. 8, 2018 | (GB) | 1800291 |
| Jan. 15, 2018 | (GB) | 1800581 |

(51) Int. Cl.
C07D 233/61    (2006.01)
A61K 45/06    (2006.01)

(52) U.S. Cl.
CPC ............ C07D 233/61 (2013.01); *A61K 45/06* (2013.01)

(58) Field of Classification Search
CPC .................................................. C07D 233/61
See application file for complete search history.

(56) References Cited

U.S. PATENT DOCUMENTS

| 3,647,794 A | 3/1972 | Regnier et al. |
| 4,364,946 A | 12/1982 | Labeyrie et al. |
| 4,492,696 A | 1/1985 | Reginier et al. |
| 4,514,398 A | 4/1985 | Regnier et al. |
| 4,514,399 A | 4/1985 | Regnier et al. |
| 4,593,026 A | 6/1986 | Regnier et al. |
| 5,225,405 A | 7/1993 | Paramelle et al. |
| 5,670,617 A | 9/1997 | Frankel et al. |
| 5,674,980 A | 10/1997 | Frankel et al. |
| 5,747,641 A | 5/1998 | Frankel et al. |
| 5,804,604 A | 9/1998 | Frankel et al. |
| 5,869,478 A | 2/1999 | Ding et al. |
| 5,907,030 A | 5/1999 | Shen et al. |
| 6,093,692 A | 7/2000 | Shen et al. |
| 6,225,445 B1 | 5/2001 | Shen et al. |
| 6,316,003 B1 | 11/2001 | Frankel et al. |
| 6,372,717 B1 | 4/2002 | Greff |
| 6,498,020 B1 | 12/2002 | Walker et al. |
| 6,620,419 B1 | 9/2003 | Lintner |
| 6,730,293 B1 | 5/2004 | Rothbard et al. |
| 6,846,836 B2 | 1/2005 | Hamann et al. |
| 6,916,813 B2 | 7/2005 | Atwal et al. |
| 6,974,799 B2 | 12/2005 | Lintner |
| 6,992,169 B2 | 1/2006 | Fischer et al. |
| 7,049,286 B2 | 5/2006 | Tchelingerian |
| 7,052,704 B2 | 5/2006 | Shen et al. |
| 7,182,963 B2 | 2/2007 | Lintner |
| 7,265,092 B2 | 9/2007 | Li |
| 7,393,835 B2 | 7/2008 | Mochly-Rosen |
| 7,507,711 B2 | 3/2009 | Mochly-Rosen |
| 7,538,085 B2 | 5/2009 | Pei |
| 7,659,252 B2 | 2/2010 | Wen et al. |
| 7,671,009 B2 | 3/2010 | Ludin et al. |
| 7,833,984 B2 | 11/2010 | Mochly-Rosen |

(Continued)

FOREIGN PATENT DOCUMENTS

| AU | 2019208238 A1 | 2/2021 |
| CA | 3050553 A1 | 1/2021 |

(Continued)

OTHER PUBLICATIONS

Bisaha et al., Bioorganic & Medicinal Chemistry Letters, 15 (2005), pp. 2749-2751.*

(Continued)

*Primary Examiner* — Alicia L Otton

(57) ABSTRACT

Compounds of the following formula, and pharmaceutically-acceptable salts, solvates, hydrates and prodrugs thereof, formula (A) are useful to preferentially inhibit the ATP-hydrolysing mode of ATP synthase, and are thereby useful for treating various diseases and orders including cancer, particularly cancers that utilise the Warburg effect.

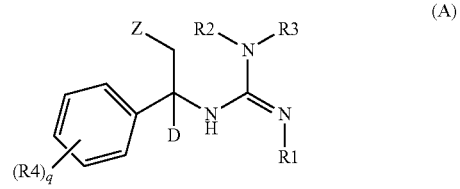

(A)

34 Claims, 20 Drawing Sheets

(56) References Cited

U.S. PATENT DOCUMENTS

| | | |
|---|---|---|
| 7,863,417 B2 | 1/2011 | Ziegler et al. |
| 7,985,401 B2 | 7/2011 | Jiang et al. |
| 7,998,493 B2 | 8/2011 | Lintner |
| 8,080,517 B2 | 12/2011 | Bonny |
| 8,183,339 B1 | 5/2012 | Bonny |
| 8,278,413 B2 | 10/2012 | Bonny |
| 8,404,648 B2 | 3/2013 | Lintner et al. |
| 8,410,045 B2 | 4/2013 | Michel et al. |
| 8,680,022 B2 | 3/2014 | Gregory et al. |
| 8,729,010 B2 | 5/2014 | Rothbard et al. |
| 8,791,062 B2 | 7/2014 | Hsu et al. |
| 8,865,881 B2 | 10/2014 | Balazs et al. |
| 8,946,166 B2 | 2/2015 | Garcia Sanz et al. |
| 8,974,774 B2 | 3/2015 | Dake et al. |
| 9,067,967 B2 | 6/2015 | García Antó et al. |
| 9,132,198 B2 | 9/2015 | Kelley et al. |
| 9,211,248 B2 | 12/2015 | Dake et al. |
| 9,255,124 B2 | 2/2016 | MacLean |
| 9,315,564 B2 | 4/2016 | Serraïma et al. |
| 9,351,972 B2 | 5/2016 | Dax et al. |
| 9,642,895 B2 | 5/2017 | Dai et al. |
| 9,657,288 B2 | 5/2017 | Winter et al. |
| 9,695,251 B2 | 7/2017 | Tsien et al. |
| 9,790,483 B2 | 10/2017 | Raines et al. |
| 10,053,677 B2 | 8/2018 | Greenfield |
| 10,258,695 B2 | 4/2019 | Raines et al. |
| 10,287,331 B2 | 5/2019 | Lorberboum-Galski et al. |
| 10,293,020 B2 | 5/2019 | Wilson |
| 10,385,380 B2 | 8/2019 | Whitney et al. |
| 10,428,323 B2 | 10/2019 | Raines et al. |
| 10,501,496 B2 | 12/2019 | Pei et al. |
| 10,577,303 B1 | 3/2020 | Raines et al. |
| 10,596,259 B2 | 3/2020 | Savariar et al. |
| 10,624,968 B2 | 4/2020 | Bennett et al. |
| 10,626,147 B2 | 4/2020 | Pei et al. |
| 10,660,839 B2 | 5/2020 | Peschard et al. |
| 10,668,000 B2 | 6/2020 | Peschard et al. |
| 10,729,749 B2 | 8/2020 | Greenfield et al. |
| 10,736,932 B2 | 8/2020 | Briesewitz et al. |
| 2003/0026781 A1 | 2/2003 | Anderson et al. |
| 2003/0032593 A1 | 2/2003 | Wender et al. |
| 2004/0009972 A1 | 1/2004 | Ding et al. |
| 2004/0072739 A1 | 4/2004 | Anderson et al. |
| 2004/0132667 A1 | 7/2004 | Lintner |
| 2005/0272723 A1 | 12/2005 | Glick |
| 2006/0041105 A1 | 2/2006 | Jiang et al. |
| 2007/0077259 A1 | 4/2007 | Dake et al. |
| 2008/0038203 A1 | 2/2008 | Dake et al. |
| 2008/0089950 A1 | 4/2008 | Chen et al. |
| 2008/0234183 A1 | 9/2008 | Hallbrink et al. |
| 2009/0202540 A1 | 8/2009 | Gant |
| 2009/0275099 A1 | 11/2009 | Glick |
| 2010/0093639 A1 | 4/2010 | Waugh et al. |
| 2010/0311671 A1 | 12/2010 | Johnson et al. |
| 2012/0134922 A1 | 5/2012 | Tsien et al. |
| 2013/0053433 A1 | 2/2013 | Cho et al. |
| 2013/0078295 A1 | 3/2013 | Cebrian Puche et al. |
| 2014/0140929 A1 | 5/2014 | Ahmed et al. |
| 2014/0161871 A1 | 6/2014 | Hsu et al. |
| 2014/0227174 A1 | 8/2014 | Muraski et al. |
| 2014/0234275 A1 | 8/2014 | Williams |
| 2014/0322307 A1 | 10/2014 | Ferrer Montiel et al. |
| 2015/0025221 A1 | 1/2015 | Hsu et al. |
| 2015/0359902 A1 | 12/2015 | Savariar et al. |
| 2017/0190743 A1 | 7/2017 | Pei et al. |
| 2017/0258930 A1 | 9/2017 | Muraski et al. |
| 2017/0355730 A1 | 12/2017 | Pei et al. |
| 2018/0000717 A1 | 1/2018 | Peschard et al. |
| 2018/0015137 A1 | 1/2018 | de Keizer |
| 2018/0280525 A1 | 10/2018 | Teufel et al. |
| 2019/0282654 A1 | 9/2019 | Pei et al. |
| 2019/0284239 A1 | 9/2019 | Pei |
| 2019/0284240 A1 | 9/2019 | Pei et al. |
| 2019/0358346 A1 | 11/2019 | Frost et al. |
| 2020/0032238 A1 | 1/2020 | Raines et al. |
| 2020/0138829 A1 | 5/2020 | Chen |
| 2020/0247758 A1 | 8/2020 | Forrest |
| 2020/0291070 A1 | 9/2020 | Pei |
| 2020/0306253 A1 | 10/2020 | Forrest |
| 2021/0038729 A1 | 2/2021 | Zonari et al. |

FOREIGN PATENT DOCUMENTS

| | | |
|---|---|---|
| CN | 105693806 A | 6/2016 |
| JP | 06-072878 A | 3/1994 |
| SU | 320118 A3 | 2/1973 |
| WO | 8808011 A1 | 10/1988 |
| WO | 1992000091 A1 | 1/1992 |
| WO | 1992009300 A1 | 6/1992 |
| WO | 9622773 A1 | 8/1996 |
| WO | 9703657 A1 | 2/1997 |
| WO | 9712912 A1 | 4/1997 |
| WO | 0062743 A2 | 10/2000 |
| WO | 0196369 A1 | 12/2001 |
| WO | 2003050261 A2 | 6/2003 |
| WO | WO 03/050261 * | 6/2003 |
| WO | 2005042034 A1 | 5/2005 |
| WO | 2006073448 A2 | 7/2006 |
| WO | 2007035474 A2 | 3/2007 |
| WO | 2007108749 A1 | 9/2007 |
| WO | 2008148063 A1 | 12/2008 |
| WO | 2009036092 A2 | 3/2009 |
| WO | 2009098450 A2 | 8/2009 |
| WO | 2011008996 A2 | 1/2011 |
| WO | 2012142529 A2 | 10/2012 |
| WO | 2013086020 A1 | 6/2013 |
| WO | 2013185046 A1 | 12/2013 |
| WO | 2014123543 A2 | 8/2014 |
| WO | 2014170347 A1 | 10/2014 |
| WO | 2015179691 A2 | 11/2015 |
| WO | 2016033314 A1 | 3/2016 |
| WO | 2016067035 A1 | 5/2016 |
| WO | 2017048812 A1 | 3/2017 |
| WO | 2017191460 A1 | 11/2017 |
| WO | 2018134265 A1 | 7/2018 |
| WO | 2018232491 A1 | 12/2018 |
| WO | 2019012149 A1 | 1/2019 |
| WO | 2019148194 A2 | 8/2019 |
| WO | 2019148195 A2 | 8/2019 |
| WO | 2019149450 A1 | 8/2019 |
| WO | 2020125073 A | 8/2020 |
| WO | 2021186325 A1 | 9/2021 |

OTHER PUBLICATIONS

"Deuterium" Encyclopedia Britannica. 2009. Encyclopedia Britannica Online. Feb. 18, 2009 <http://www.britannica.com/EBchecked/topic/159684/deuterium>.*

Bisaha SN, Malley MF, Pudzianowski A, Monshizadegan H, Wang P, Madsen CS, Gougoutas JZ, Stein PD (2005) A switch in enantiomer preference between mitochondrial F1F0-ATPase chemotypes. Bioorganic and medicinal chemistry letters. 15(11):2749-51.

Atwal KS, Ahmad S, Ding CZ, Stein PD, Lloyd J, Hamann LG, Green DW, Ferrara FN, Wang P, Rogers WL, Doweyko LM, Miller AV, Bisaha SN, Schmidt JB, Li L, Yost KJ, Lan HJ, Madsen CS (2004) N-[1-Aryl-2-(1-imidazolo)ethyl]-guanidine derivatives as potent inhibitors of the bovine mitochondrial F1F0 ATP hydrolase. Bioorganic and medicinal chemistry letters. 14(4):1027-1030.

Foster AB (1985) Deuterium isotope effects in the metabolism of drugs and xenobiotics: implications for drug design. Advances in Drug Research. 14:1-40.

Vander Heiden MG, Cantley LC, Thompson CB (2009) Understanding the Warburg effect: the metabolic requirements of cell proliferation. Science. 324(5930):1029-1033.

Patani GA, Lavoie EJ (1996) Bioisosterism: a rational approach in drug design. Chemical reviews. 96(8):3147-3176.

Hong S, Pedersen PL (2008) ATP synthase and the actions of inhibitors utilized to study its roles in human health, disease, and other scientific areas. Microbiology and Molecular Biology Reviews. 72(4):590-641.

(56) References Cited

OTHER PUBLICATIONS

Written Opinion of the International Searching Authority (ISA, which was the EPO) for WO2018/134265A1.
Written Opinion of the International Searching Authority (ISA, which was the EPO) for WO2019/012149A1.
Chinese patent Examiner's examination report for Chinese patent application CN105693806A. Machine translation thereof is also submitted.
Salomon AR, Voehringer DW, Herzenberg LA, Khosla C (2000) Understanding and exploiting the mechanistic basis for selectivity of polyketide inhibitors of F0F1-ATPase. Proceedings of the National Academy of Sciences. 97(26):14766-14771.
"Deuterium" Encyclopedia Britannica online. Accessed Dec. 22, 2021. https://www.britannica.com/science/deuterium.
Sgarbi G, Barbato S, Costanzini A, Solaini G, Baracca A (2018) The role of the ATPase inhibitor factor 1 (IF1) in cancer cells adaptation to hypoxia and anoxia. Biochimica et Biophysica Acta (BBA)—Bioenergetics. 1859(2):99-109.
Yin T, Lu L, Xiong Z, Wei S, Cui D (2015) ATPase inhibitory factor 1 is a prognostic marker and contributes to proliferation and invasion of human gastric cancer cells. Biomedicine & Pharmacotherapy. 70:90-6.
Johnson KM, Swenson L, Opipari JR AW, Reuter R, Zarrabi N, Fierke CA, . . . & Glick GD (2009) Mechanistic basis for differential inhibition of the F1F0-ATPase by aurovertin. Biopolymers: Original Research on Biomolecules. 91(10):830-840.
Shimada K, Fujisaki H, Oketani K, Murakami M, Shoji T, Wakabayashi T, . . . Tanaka S (1984) Synthesis and gastric antisecretory activity of N-cyano-N'-(phenyl-pyridinylmethyl) guanidine derivatives. Chemical and pharmaceutical bulletin. 32(12):4893-4906.
Forrest MD (2015) Why cancer cells have a more hyperpolarised mitochondrial membrane potential and emergent prospects for therapy. bioRxiv. 025197.
Unpublished U.S. Appl. No. 16/571,759, filed Sep. 16, 2019. Inventor/Applicant: Michael David Forrest.
Unpublished U.S. Appl. No. 16/514,246, filed Jul. 17, 2019. Inventor/Applicant: Michael David Forrest.
Unpublished U.S. Appl. No. 16/679,184, filed Nov. 9, 2019. Inventor/Applicant: Michael David Forrest.
Unpublished U.S. Appl. No. 16/907,195, filed Jun. 20, 2020. Inventor/Applicant: Michael David Forrest.
Unpublished U.S. Appl. No. 17/092,271, filed Nov. 8, 2020. Inventor/Applicant: Michael David Forrest.
Unpublished U.S. Appl. No. 17/166,011, filed Feb. 3, 2021. Inventor/Applicant: Michael David Forrest.
Unpublished U.S. Appl. No. 17/316,787, filed May 11, 2021. Inventor/Applicant: Michael David Forrest.
Unpublished U.S. Appl. No. 17/383,575, filed Jul. 23, 2021. Inventor/Applicant: Michael David Forrest.
Unpublished U.S. Appl. No. 17/493,887, filed Oct. 5, 2021. Inventor/Applicant: Michael David Forrest.
Unpublished U.S. Appl. No. 16/939,094, filed Jul. 27, 2020. Inventor/Applicant: Michael David Forrest.
Unpublished US (provisional) U.S. Appl. No. 62/878,418, filed Jul. 25, 2019. Inventor/Applicant: Michael David Forrest.
Title: "Patents, yes; ideas, maybe". The Economist, Hong Kong. Oct. 14, 2010. Online: https://www.economist.com/business/2010/10/14/patents-yes-ideas-maybe (accessed on Oct. 14, 2021).
Title: "CNIPA clamps down on 'abnormal' application practices in fresh drive for patent quality". Author: Xiaoling Duan (of Wanhuida Intellectual Property, China). Publisher: IAM Media. With offices in London, Hong Kong, and Washington DC. Online: https://www.iam-media.com/cnipa-clamps-down-abnormal-application-practices-in-fresh-drive-patent-quality (accessed on Oct. 14, 2021).
Notice of passing examination, and acceptance of patent application, in Australia. For AU application No. 2018209175. Includes a list of prior art documents considered during Examination. Also submitted, in a separate document, are the accepted claims for AU application No. 2018209175.
Unpublished U.S. Appl. No. 17/201,570, filed Mar. 15, 2021. Inventor/Applicant: Michael David Forrest.

Unpublished U.S. Appl. No. 17/576,963, filed Jan. 16, 2022. Inventor/Applicant: Michael David Forrest.
Unpublished US (provisional) U.S. Appl. No. 63/302,034, filed Jan. 22, 2022. Inventor/Applicant: Michael David Forrest.
Meanwell NA (2011) Synopsis of some recent tactical application of bioisosteres in drug design. Journal of medicinal chemistry. 54(8):2529-2591.
Unpublished U.S. Appl. No. 17/705,283, filed Mar. 26, 2022. Inventor/Applicant: Michael David Forrest.
Dhainaut A, Regnier G, Atassi G, Pierre A, Leonce S, Kraus-Berthier L, Prost JF (1992) New triazine derivatives as potent modulators of multidrug resistance. Journal of medicinal chemistry. 35(13):2481-96.
Unpublished U.S. Appl. No. 17/832,579, filed Jun. 4, 2022. Inventor/Applicant: Michael David Forrest.
Atwal KS, Wang P, Rogers WL, Sleph P, Monshizadegan H, Ferrara FN, Traeger S, Green DW, Grover GJ (2004) Small molecule mitochondrial F1F0 ATPase hydrolase inhibitors as cardioprotective agents. Identification of 4-(N-arylimidazole)-substituted benzopyran derivatives as selective hydrolase inhibitors. Journal of medicinal chemistry. 47(5):1081-1084.
Hamann LG, Ding CZ, Miller AV, Madsen CS, Wang P, Stein PD, Pudzianowski AT, Green DW, Monshizadegan H, Atwal KS (2004) Benzodiazepine-based selective inhibitors of mitochondrial F1F0 ATP hydrolase. Bioorganic & medicinal chemistry letters. 14(4):1031-1034.
Grover GJ, Marone PA, Koetzner L, Seto-Young D (2008) Energetic signalling in the control of mitochondrial F1F0 ATP synthase activity in health and disease. The international journal of biochemistry & cell biology. 40(12):2698-2701.
Grover GJ, Malm J (2008) Pharmacological Profile of the Selective Mitochondrial F1F0 ATP Hydrolase Inhibitor BMS-199264 in Myocardial Ischemia. Cardiovascular therapeutics. 26(4):287-296.
Grover GJ, Atwal KS, Sleph PG, Wang FL, Monshizadegan H, Monticello T, Green DW (2004) Excessive ATP hydrolysis in ischemic myocardium by mitochondrial F1F0-ATPase: effect of selective pharmacological inhibition of mitochondrial ATPase hydrolase activity. American Journal of Physiology—Heart and Circulatory Physiology. 287(4):H1747-H1755.
Ivanes F (2013) New mechanisms of protection of cardiomyocytes from ischemia/reperfusion injury. Doctoral dissertation. Université Claude Bernard-Lyon 1, Lyon, France.
Ivanes F, Faccenda D, Gatliff J, Ahmed AA, Cocco S, Cheng CHK, Allan E, Russell C, Duchen MR, Campanella M (2014) The compound BTB06584 is an IF1-dependent selective inhibitor of the mitochondrial F1Fo-ATPase. British journal of pharmacology. 171(18):4193-4206.
Kramar R, Hohenegger M, Srour AN, Khanakah G (1984) Oligomycin toxicity in intact rats. Inflammation Research. 15(5):660-3.
Gao C, Shen Y, Jin F, Miao Y, Qiu X (2016) Cancer stem cells in small cell lung cancer cell line H446: higher dependency on oxidative phosphorylation and mitochondrial substrate-level phosphorylation than non-stem cancer cells. PloS one. 11(5):e0154576.
Cuezva JM, Krajewska M, De Heredia ML, Krajewski S, Santamaría G, Kim H, Zapata JM, Marusawa H, Chamorro M, Reed JC (2002) The bioenergetic signature of cancer. Cancer research. 62(22):6674-81.
Aldea M, Clofent J, De Arenas CN, Chamorro M, Velasco M, Berrendero JR, Navarro C, Cuezva JM (2011) Reverse phase protein microarrays quantify and validate the bioenergetic signature as biomarker in colorectal cancer. Cancer letters. 311(2):210-8.
Hjerpe E, Brage SE, Carlson J, Stolt MF, Schedvins K, Johansson H, Shoshan M, Åvall-Lundqvist E (2013) Metabolic markers GAPDH, PKM2, ATP5B and BEC-index in advanced serous ovarian cancer. BMC clinical pathology. 13(1):30.
Johnson KM, Chen X, Boitano A, Swenson L, Opipari JR AW, Glick GD (2005) Identification and validation of the mitochondrial F1F0-ATPase as the molecular target of the immunomodulatory benzodiazepine Bz-423. Chemistry & biology. 12(4):485-96.
Hanahan D, Weinberg RA (2000) The hallmarks of cancer. Cell. 100(1):57-70.
Walenta S, Wetterling M, Lehrke M, Schwickert G, Sundfør K, Rofstad EK, Mueller-Klieser W (2000) High lactate levels predict

(56) References Cited

OTHER PUBLICATIONS likelihood of metastases, tumor recurrence, and restricted patient survival in human cervical cancers. Cancer research. 60(4):916-21.
Paull KD, Shoemaker RH, Hodes L, Monks A, Scudiero DA, Rubinstein L, Plowman J, Boyd MR (1989) Display and analysis of patterns of differential activity of drugs against human tumor cell lines: development of mean graph and COMPARE algorithm. JNCI: Journal of the National Cancer Institute. 81(14):1088-92.
Holbeck SL, Collins JM, Doroshow JH (2010) Analysis of Food and Drug Administration-approved anticancer agents in the NCI60 panel of human tumor cell lines. Molecular cancer therapeutics. 9(5):1451-60.
Reinhold WC, Sunshine M, Liu H, Varma S, Kohn KW, Morris J, Doroshow J, Pommier Y (2012) CellMiner: a web-based suite of genomic and pharmacologic tools to explore transcript and drug patterns in the NCI-60 cell line set. Cancer research. 72(14):3499-511.
Gholami AM, Hahne H, Wu Z, Auer FJ, Meng C, Wilhelm M, Kuster B (2013) Global proteome analysis of the NCI-60 cell line panel. Cell reports. 4(3):609-20.
Shoemaker RH (2006) The NCI60 human tumour cell line anticancer drug screen. Nature Reviews Cancer. 6:813-23.
Martineau LC (2012) Simple thermodynamic model of unassisted proton shuttle uncoupling and prediction of activity from calculated speciation, lipophilicity, and molecular geometry. Journal of theoretical biology. 303:33-61.
Jacques V, Czarnik AW, Judge TM, Van Der Ploeg LH, Dewitt SH (2015) Differentiation of antiinflammatory and antitumorigenic properties of stabilized enantiomers of thalidomide analogs. Proceedings of the National Academy of Sciences. 112(12):E1471-9.
Houston MA, Augenlicht LH, Heerdt BG (2011) Stable differences in intrinsic mitochondrial membrane potential of tumor cell subpopulations reflect phenotypic heterogeneity. International journal of cell biology.
Heerdt BG, Houston MA, Augenlicht LH (2005) The intrinsic mitochondrial membrane potential of colonic carcinoma cells is linked to the probability of tumor progression. Cancer Research. 65:9861-9867.
Heerdt BG, Houston MA, Augenlicht LH (2006) Growth properties of colonic tumor cells are a function of the intrinsic mitochondrial membrane potential. Cancer Research. 66(3):1591-6.
Bonnet S, Archer SL, Allalunis-Turner J, Haromy A, Beaulieu C, Thompson R, Lee CT, Lopaschuk GD, Puttagunta L, Bonnet S, Harry G (2007) A mitochondria-K+ channel axis is suppressed in cancer and its normalization promotes apoptosis and inhibits cancer growth. Cancer cell. 11(1):37-51.
Ye XQ, Wang GH, Huang GJ, Bian XW, Qian GS, Yu SC (2011) Heterogeneity of mitochondrial membrane potential: a novel tool to isolate and identify cancer stem cells from a tumor mass? Stem Cell Reviews and Reports. 7(1):153-60.
Lee DG, Choi BK, Kim YH, Oh HS, Park SH, Bae YS, Kwon BS (2016) The repopulating cancer cells in melanoma are characterized by increased mitochondrial membrane potential. Cancer Letters. 382(2):186-94.
Boonstra J, Post JA (2004) Molecular events associated with reactive oxygen species and cell cycle progression in mammalian cells. Gene. 337:1-3.
Fantin VR, St-Pierre J, Leder P (2006) Attenuation of LDH-A expression uncovers a link between glycolysis, mitochondrial physiology, and tumor maintenance. Cancer cell. 9(6):425-434.
Christofk HR, Vander Heiden MG, Harris MH, Ramanathan A, Gerszten RE, Wei R, Fleming MD, Schreiber SL, Cantley LC (2008) The M2 splice isoform of pyruvate kinase is important for cancer metabolism and tumour growth. Nature. 452(7184):230-233.
Bonnet S, Archer SL, Allalunis-Turner J, Haromy A, Beaulieu C, Thompson R, Lee CT, Lopaschuk GD, Puttagunta L, Bonnet S, Harry G, Hashimoto K, Porter CJ, Andrade MA, Thebaud B, Michelakis EE (2007) A mitochondria-K+ channel axis is suppressed in cancer and its normalization promotes apoptosis and inhibits cancer growth. Cancer cell. 11(1):37-51.

Wadhwa R, Sugihara T, Yoshida A, Nomura H, Reddel RR, Simpson R, Maruta H, Kaul SC (2000) Selective toxicity of MKT-077 to cancer cells is mediated by its binding to the hsp70 family protein mot-2 and reactivation of p53 function. Cancer Research. 60:6818-6821.
Schulz TJ, Thierbach R, Voigt A, Drewes G, Mietzner B, Steinberg P, Pfeiffer AFH, Ristow M (2006) Induction of oxidative metabolism by mitochondrial frataxin inhibits cancer growth: Otto Warburg revisited. Journal of Biological Chemistry. 281:977-81.
Devi GS, Prasad MH, Saraswathi I, Raghu D, Rao DN, Reddy PP (2000) Free radicals antioxidant enzymes and lipid peroxidation in different types of leukemias. Clinica Chimica Acta. 293:53-62.
Szatrowski TP, Nathan CF (1991) Production of large amounts of hydrogen peroxide by human tumor cells. Cancer research. 51(3):794-798.
Lu W, Hu Y, Chen G, Chen Z, Zhang H, Wang F, Feng L, Pelicano H, Wang H, Keating MJ, Liu J (2012) Novel role of NOX in supporting aerobic glycolysis in cancer cells with mitochondrial dysfunction and as a potential target for cancer therapy. PLOS biology. 10(5):e1001326.
Block K, Gorin Y (2012) Aiding and abetting roles of NOX oxidases in cellular transformation. Nature Reviews Cancer. 12(9):627-37.
Ben-Porath I, Thomson MW, Carey VJ, Ge R, Bell GW, Regev A, Weinberg RA (2008) An embryonic stem cell-like gene expression signature in poorly differentiated aggressive human tumors. Nature genetics. 40(5):499.
Chung S, Dzeja PP, Faustino RS, Perez-Terzic C, Behfar A, Terzic A (2007) Mitochondrial oxidative metabolism is required for the cardiac differentiation of stem cells. Nature Clinical Practice Cardiovascular Medicine. 4:S60-S67.
Teslaa T, Teitell MA (2014) Pluripotent stem cell energy metabolism: an update. The EMBO journal. e201490446.
Hong Y, Stambrook PJ (2004) Restoration of an absent G1 arrest and protection from apoptosis in embryonic stem cells after ionizing radiation. Proceedings of the National Academy of Sciences (PNAS). 101(40):14443-14448.
Gordon CJ (1991) Toxic-induced hypothermia and hypometabolism: Do they increase uncertainty in the extrapolation of toxicological data from experimental animals to humans? Neuroscience & Biobehavioral Reviews. 15(1):95-8.
Zamzami N, Kroemer G (2001) The mitochondrion in apoptosis: how Pandora's box opens. Nature Reviews Molecular Cell Biology. 2:67-71.
Donadelli M, Dando I, Dalla Pozza E, Palmieri M (2015) Mitochondrial uncoupling protein 2 and pancreatic cancer: A new potential target therapy. World journal of gastroenterology. 21(11):3232.
Ayyasamy V, Owens KM, Desouki MM, Liang P, Bakin A, Thangaraj K, Buchsbaum DJ, Lobuglio AF, Singh KK (2011) Cellular Model of Warburg Effect Identifies Tumor Promoting Function of UCP2 in Breast Cancer and Its Suppression by Genipin. PLoS ONE. 6(9):e24792. doi:10.1371/journal.pone.0024792.
Gordon CJ (2012) Thermal physiology of laboratory mice: Defining thermoneutrality. Journal of Thermal Biology. 37(8):654-85.
Bindu B, Bindra A, Rath G (2017) Temperature management under general anesthesia: Compulsion or option. Journal of anaesthesiology, clinical pharmacology. 33(3):306.
Bell EF (1983) Infant incubators and radiant warmers. Early human development. 8(3-4):351-75.
Nair AB, Jacob S (2016) A simple practice guide for dose conversion between animals and human. Journal of basic and clinical pharmacy. 7(2):27.
Ward TH, Cummings J, Dean E, Greystoke A, Hou JM, Backen A, Ranson M, Dive C (2008) Biomarkers of apoptosis. British journal of cancer. 99(6):841.
Zheng J, Ramirez VD (2000) Inhibition of mitochondrial proton F0F1-ATPase/ATP synthase by polyphenolic phytochemicals. British journal of pharmacology. 130(5):1115-23.
Zhu A, Lee D, Shim H (2011) Metabolic positron emission tomography imaging in cancer detection and therapy response. In Seminars in oncology (vol. 38, No. 1, pp. 55-69). WB Saunders.
Zhang L, Martins AF, Mai Y, Zhao P, Funk AM, Clavijo Jordan MV, Zhang S, Chen W, Wu Y, Sherry AD (2017) Imaging Extracellular

(56) References Cited

OTHER PUBLICATIONS

Lactate In Vitro and In Vivo Using CEST MRI and a Paramagnetic Shift Reagent. Chemistry—A European Journal. 23(8):1752-6.
Chen LQ, Pagel MD (2015) Evaluating pH in the Extracellular Tumor Microenvironment Using CEST MRI and Other Imaging Methods. Advances in radiology.
Anderson M, Moshnikova A, Engelman DM, Reshetnyak YK, Andreev OA (2016) Probe for the measurement of cell surface pH in vivo and ex vivo. Proceedings of the National Academy of Sciences (PNAS). 113(29):8177-8181.
Manzoor AA, Schroeder T, Dewhirst MW (2008) One-stop-shop tumor imaging: buy hypoxia, get lactate free. The Journal of clinical investigation. 118(5):1616.
Ng J, Shuryak I (2015) Minimizing second cancer risk following radiotherapy: current perspectives. Cancer management and research. 7:1.
Armstrong GT, Kawashima T, Leisenring W, Stratton K, Stovall M, Hudson MM, Sklar CA, Robison LL, Oeffinger KC (2014) Aging and risk of severe, disabling, life-threatening, and fatal events in the childhood cancer survivor study. Journal of clinical oncology. 32(12):1218.
Castro RF, Azzalis LA, Feder D, Perazzo FF, Pereira EC, Junqueira VB, Rocha KC, Machado CD, Paschoal FC, Gnann LA, Fonseca FL (2012) Safety and efficacy analysis of liposomal insulin-like growth factor-1 in a fluid gel formulation for hair-loss treatment in a hamster model. Clinical and Experimental Dermatology: Experimental dermatology. 37(8):909-12.
Patel A, Cholkar K, Agrahari V, Mitra AK (2013) Ocular drug delivery systems: an overview. World journal of pharmacology. 2(2):47.
Gaudana R, Ananthula HK, Parenky A, Mitra AK (2010) Ocular drug delivery. The AAPS journal. 12(3):348-60.
Wong WL, Su X, Li X, Cheung CM, Klein R, Cheng CY, Wong TY (2014) Global prevalence of age-related macular degeneration and disease burden projection for 2020 and 2040: a systematic review and meta-analysis. The Lancet Global Health. 2(2):e106-16.
Hao J, Li SK (2019) Inner ear drug delivery: Recent advances, challenges, and perspective. European Journal of Pharmaceutical Sciences. 126:82-92.
Liu H, Hao J, Li KS (2013) Current strategies for drug delivery to the inner ear. Acta Pharmaceutica Sinica B. 3(2):86-96.
Lin MT, Beal MF (2006) Mitochondrial dysfunction and oxidative stress in neurodegenerative diseases. Nature. 443(7113):787-95.
Kang YS, Jung HJ, Oh JS, Song DY (2016) Use of PEGylated Immunoliposomes to Deliver Dopamine Across the Blood-Brain Barrier in a Rat Model of Parkinson's Disease. CNS Neuroscience & Therapeutics. 22(10):817-23.
Di Gioia S, Trapani A, Mandracchia D, De Giglio E, Cometa S, Mangini V, Arnesano F, Belgiovine G, Castellani S, Pace L, Lavecchia MA (2015) Intranasal delivery of dopamine to the striatum using glycol chitosan/sulfobutylether-β-cyclodextrin based nanoparticles. European Journal of Pharmaceutics and Biopharmaceutics. 94:180-93.
Oorschot DE (1996) Total No. of neurons in the neostriatal, pallidal, subthalamic, and substantia nigral nuclei of the rat basal ganglia: a stereological study using the cavalieri and optical disector methods. Journal of Comparative Neurology. 366:580-599.
Naoi M, Maruyama W (1999) Cell death of dopamine neurons in aging and Parkinson's disease. Mechanisms of ageing and development. 111(2):175-88.
Strong R, Miller RA, Astle CM, Baur JA, De Cabo R, Fernandez E, Guo W, Javors M, Kirkland JL, Nelson JF, Sinclair DA (2012) Evaluation of resveratrol, green tea extract, curcumin, oxaloacetic acid, and medium-chain triglyceride oil on life span of genetically heterogeneous mice. Journals of Gerontology Series A: Biomedical Sciences and Medical Sciences. 68(1):6-16.
Harrison DE, Strong R, Sharp ZD, Nelson JF, Astle CM, Flurkey K, Nadon NL, Wilkinson JE, Frenkel K, Carter CS, Pahor M (2009) Rapamycin fed late in life extends lifespan in genetically heterogeneous mice. Nature. 460(7253):392.
Colman RJ, Anderson RM, Johnson SC, Kastman EK, Kosmatka KJ, Beasley TM, Allison DB, Cruzen C, Simmons HA, Kemnitz JW, Weindruch R (2009) Caloric restriction delays disease onset and mortality in rhesus monkeys. Science. 325(5937):201-4.
Ackert-Bicknell CL, Anderson LC, Sheehan S, Hill WG, Chang B, Churchill GA, Chesler EJ, Korstanje R, Peters LL (2017) Aging research using mouse models. Current protocols in mouse biology. 5(2):95-133.
Sukoff Rizzo SJ, Anderson LC, Green TL, McGarr T, Wells G, Winter SS (2018) Assessing Healthspan and Lifespan Measures in Aging Mice: Optimization of Testing Protocols, Replicability, and Rater Reliability. Current Protocols in Mouse Biology. 8(2):e45.
Richardson A, Fischer KE, Speakman JR, De Cabo R, Mitchell SJ, Peterson CA, Rabinovitch P, Chiao YA, Taffet G, Miller RA, Rentería RC (2015) Measures of healthspan as indices of aging in mice-a recommendation. Journals of Gerontology Series A: Biomedical Sciences and Medical Sciences. 71(4):427-30.
Vermeij WP, Hoeijmakers JH, Pothof J (2016) Genome integrity in aging: human syndromes, mouse models, and therapeutic options. Annual review of pharmacology and toxicology. 56:427-45.
Harkema L, Youssef SA, De Bruin A (2016) Pathology of mouse models of accelerated aging. Veterinary pathology. 53(2):366-89.
Hasty P, Campisi J, Hoeijmakers J, Van Steeg H, Vijg J (2003) Aging and genome maintenance: lessons from the mouse? Science. 299(5611):1355-9.
De Boer J, Hoeijmakers JH (1999) Cancer from the outside, aging from the inside: mouse models to study the consequences of defective nucleotide excision repair. Biochimie. 81(1-2):127-37.
Baker DJ, Jeganathan KB, Cameron JD, Thompson M, Juneja S, Kopecka A, Kumar R, Jenkins RB, De Groen PC, Roche P, Van Deursen JM (2004) BubR1 insufficiency causes early onset of aging-associated phenotypes and infertility in mice. Nature genetics. 36(7):744.
De Boer J, De Wit J, Van Steeg H, Berg RJ, Morreau H, Visser P, Lehmann AR, Duran M, Hoeijmakers JH, Weeda G (1998) A mouse model for the basal transcription/DNA repair syndrome trichothiodystrophy. Molecular cell. 1(7):981-90.
De Boer J, Andressoo JO, De Wit J, Huijmans J, Beems RB, Van Steeg H, Weeda G, Van Der Horst GT, Van Leeuwen W, Themmen AP, Meradji M (2002) Premature aging in mice deficient in DNA repair and transcription. Science. 296(5571):1276-9.
Andressoo JO, Mitchell JR, De Wit J, Hoogstraten D, Volker M, Toussaint W, Speksnijder E, Beems RB, Van Steeg H, Jans J, De Zeeuw CI (2006) An Xpd mouse model for the combined xeroderma pigmentosum/Cockayne syndrome exhibiting both cancer predisposition and segmental progeria. Cancer cell. 10(2):121-32.
Cheo DL, Ruven HJ, Meira LB, Hammer RE, Burns DK, Tappe NJ, Van Zeeland AA, Mullenders LH, Friedberg EC (1997) Characterization of defective nucleotide excision repair in XPC mutant mice. Mutation Research/Fundamental and Molecular Mechanisms of Mutagenesis. 374(1):1-9.
Melis JP, Wijnhoven SW, Beems RB, Roodbergen M, Van Den Berg J, Moon H, Friedberg E, Van Der Horst GT, Hoeijmakers JH, Vijg J, Van Steeg H (2008) Mouse models for xeroderma pigmentosum group A and group C show divergent cancer phenotypes. Cancer research. 68(5):1347-53.
Niedernhofer LJ, Garinis GA, Raams A, Lalai AS, Robinson AR, Appeldoorn E, Odijk H, Oostendorp R, Ahmad A, Van Leeuwen W, Theil AF (2006) A new progeroid syndrome reveals that genotoxic stress suppresses the somatotroph axis. Nature. 444(7122):1038.
Weeda G, Donker I, De Wit J, Morreau H, Janssens R, Vissers CJ, Nigg A, Van Steeg H, Bootsma D, Hoeijmakers JH (1997) Disruption of mouse ERCC1 results in a novel repair syndrome with growth failure, nuclear abnormalities and senescence. Current Biology. 7(6):427-39.
Spoor M, Nagtegaal AP, Ridwan Y, Borgesius NZ, Van Alphen B, Van Der Pluijm I, Hoeijmakers JH, Frens MA, Borst JG (2012) Accelerated loss of hearing and vision in the DNA-repair deficient Ercc1δ/- mouse. Mechanisms of ageing and development. 133(2-3):59-67.
Vogel H, Lim DS, Karsenty G, Finegold M, Hasty P (1999) Deletion of Ku86 causes early onset of senescence in mice. Proceedings of the National Academy of Sciences (PNAS). 96(19):10770-5.

(56) References Cited

OTHER PUBLICATIONS

Reiling E, Dollé ME, Youssef SA, Lee M, Nagarajah B, Roodbergen M, De Bruin A, Hoeijmakers JH, Vijg J, Van Steeg H, Hasty P (2014) The progeroid phenotype of Ku80 deficiency is dominant over DNA-PKCS deficiency. PloS one. 9(4):e93568.
Zhang Y, Padalecki SS, Chaudhuri AR, De Waal E, Goins BA, Grubbs B, Ikeno Y, Richardson A, Mundy GR, Herman B (2007) Caspase-2 deficiency enhances aging-related traits in mice. Mechanisms of ageing and development. 128(2):213-21.
Bergeron L, Perez GI, MacDonald G, Shi L, Sun Y, Jurisicova A, Varmuza S, Latham KE, Flaws JA, Salter JC, Hara H (1998) Defects in regulation of apoptosis in caspase-2-deficient mice. Genes & development. 12(9):1304-14.
Nadon NL, Strong R, Miller RA, Nelson J, Javors M, Sharp ZD, Peralba JM, Harrison De (2008) Design of aging intervention studies: the NIA interventions testing program. Age. 30(4):187-99.
Miller RA, Harrison DE, Astle CM, Floyd RA, Flurkey K, Hensley KL, Javors MA, Leeuwenburgh C, Nelson JF, Ongini E, Nadon NL (2007) An aging interventions testing program: study design and interim report. Aging cell. 6(4):565-75.
Martin-Montalvo A, Mercken EM, Mitchell SJ, Palacios HH, Mote PL, Scheibye-Knudsen M, Gomes AP, Ward TM, Minor RK, Blouin MJ, Schwab M (2013) Metformin improves healthspan and lifespan in mice. Nature communications. 4:2192.
Miller RA, Harrison DE, Astle CM, Baur JA, Boyd AR, De Cabo R, Fernandez E, Flurkey K, Javors MA, Nelson JF, Orihuela CK (2011) Rapamycin, but not resveratrol or simvastatin, extends life span of genetically heterogeneous mice. The Journals of Gerontology: Series A. 66(2):191-201.
Strong R, Miller RA, Astle CM, Floyd RA, Flurkey K, Hensley KL, Javors MA, Leeuwenburgh C, Nelson JF, Ongini E, Nadon NL (2008) Nordihydroguaiaretic acid and aspirin increase lifespan of genetically heterogeneous male mice. Aging cell. 7(5):641-50.
Baur JA, Pearson KJ, Price NL, Jamieson HA, Lerin C, Kalra A, Prabhu VV, Allard JS, Lopez-Lluch G, Lewis K, Pistell PJ (2006) Resveratrol improves health and survival of mice on a high-calorie diet. Nature. 444(7117):337.
Spilman P, Podlutskaya N, Hart MJ, Debnath J, Gorostiza O, Bredesen D, Richardson A, Strong R, Galvan V (2010) Inhibition of mTOR by rapamycin abolishes cognitive deficits and reduces amyloid-β levels in a mouse model of Alzheimer's disease. PloS one. 5(4):e9979.
Morley JE, Armbrecht HK, Farr SA, Kumar VB (2012) The senescence accelerated mouse (SAMP8) as a model for oxidative stress and Alzheimer's disease. Biochimica et Biophysica Acta (BBA)-Molecular Basis of Disease. 1822(5):650-6.
Zahr NM, Mayer D, Pfefferbaum A, Sullivan EV (2008) Low striatal glutamate levels underlie cognitive decline in the elderly: evidence from in vivo molecular spectroscopy. Cerebral Cortex. 18(10):2241-50.
Rupsingh R, Borrie M, Smith M, Wells JL, Bartha R (2011) Reduced hippocampal glutamate in Alzheimer disease. Neurobiology of aging. 32(5):802-10.
Fayed N, Modrego PJ, Rojas-Salinas G, Aguilar K (2011) Brain glutamate levels are decreased in Alzheimer's disease: a magnetic resonance spectroscopy study. American Journal of Alzheimer's Disease & Other Dementias. (6):450-6.
Yurko-Mauro K (2010) Cognitive and cardiovascular benefits of docosahexaenoic acid in aging and cognitive decline. Current Alzheimer Research. 7(3):190-6.
Matjusaitis M, Chin G, Sarnoski EA, Stolzing A (2016) Biomarkers to identify and isolate senescent cells. Ageing research reviews. 29:1-2.
Gorisse L, Pietrement C, Vuiblet V, Schmelzer CE, Köhler M, Duca L, Debelle L, Fornès P, Jaisson S, Gillery P (2016) Protein carbamylation is a hallmark of aging. Proceedings of the National Academy of Sciences (PNAS). 113(5):1191-6.
Syslová K, Böhmová A, Mikoška M, Kuzma M, Pelclová D, Kačer P (2014) Multimarker screening of oxidative stress in aging. Oxidative medicine and cellular longevity. 2014.
Stadtman ER, Berlett BS (1998) Reactive oxygen-mediated protein oxidation in aging and disease. Drug metabolism reviews. 30(2):225-43.
Nomura Y, Wang BX, Qi SB, Namba T, Kaneko S (1989) Biochemical changes related to aging in the senescence-accelerated mouse. Experimental gerontology. 24(1):49-55.
Kitamura Y, Zhao XH, Ohnuki T, Takei M, Nomura Y (1992) Age-related changes in transmitter glutamate and NMDA receptor/channels in the brain of senescence-accelerated mouse. Neuroscience letters. 137(2):169-72.
Nomura Y, Kitamura Y, Ohnuki T, Arima T, Yamanaka Y, Sasaki K, Oomura Y (1997) Alterations in acetylcholine, NMDA, benzodiazepine receptors and protein kinase C in the brain of the senescence-accelerated mouse: an animal model useful for studies on cognitive enhancers. Behavioural brain research. 83(1-2):51-5.
Nomura Y, Okuma Y (1999) Age-related defects in lifespan and learning ability in SAMP8 mice. Neurobiology of aging. 20(2):111-5.
Tomobe K, Nomura Y (2009) Neurochemistry, neuropathology, and heredity in SAMP8: a mouse model of senescence. Neurochemical research. 34(4):660-9.
Zhao XH, Kitamura Y, Nomura Y (1992) Age-related changes in NMDA-induced [3H] acetylcholine release from brain slices of senescene-accelerated mouse. International journal of developmental neuroscience. 10(2):121-9.
Mills KF, Yoshida S, Stein LR, Grozio A, Kubota S, Sasaki Y, Redpath P, Migaud ME, Apte RS, Uchida K, Yoshino J (2016) Long-term administration of nicotinamide mononucleotide mitigates age-associated physiological decline in mice. Cell metabolism. 24(6):795-806.
Peto MV, De La Guardia C, Winslow K, Ho A, Fortney K, Morgen E (2017) MortalityPredictors.org: a manually-curated database of published biomarkers of human all-cause mortality. Aging (Albany NY). 9(8):1916.
Cheng D, Logge W, Low JK, Garner B, Karl T (2013) Novel behavioural characteristics of the APP Swe/PS1ΔE9 transgenic mouse model of Alzheimer's disease. Behavioural brain research. 245:120-7.
Borgesius NZ, De Waard MC, Van Der Pluijm I, Omrani A, Zondag GC, Van Der Horst GT, Melton DW, Hoeijmakers JH, Jaarsma D, Elgersma Y (2011) Accelerated age-related cognitive decline and neurodegeneration, caused by deficient DNA repair. Journal of Neuroscience. 31(35):12543-53.
Rangaraju S, Solis GM, Thompson RC, Gomez-Amaro RL, Kurian L, Encalada SE, Niculescu III AB, Salomon DR, Petrascheck M (2015) Suppression of transcriptional drift extends C. elegans lifespan by postponing the onset of mortality. Elife. 4:e08833.
Barger JL, Anderson RM, Newton MA, Da Silva C, Vann JA, Pugh TD, Someya S, Prolla TA, Weindruch R (2015) A conserved transcriptional signature of delayed aging and reduced disease vulnerability is partially mediated by SIRT3. PLoS One. 10(4):e0120738.
Yaku K, Okabe K, Nakagawa T (2018) NAD metabolism: Implications in aging and longevity. Ageing research reviews. 47:1-17.
Ivanisevic J, Stauch KlLPetrascheck M, Benton HP, Epstein AA, Fang M, Gorantla S, Tran M, Hoang L, Kurczy ME, Boska MD (2016) Metabolic drift in the aging brain. Aging (Albany NY). 8(5):1000.
Huxley AF (1959) Ion movements during nerve activity. Annals of the New York Academy of Sciences. 81(2):221-46.
Chapman RA (1967) Dependence on temperature of the conduction velocity of the action potential of the squid giant axon. Nature. 213(5081):1143.
Maldonado CC, Wooley BD, Pancrazio JJ (2015) The excitatory effect of temperature on the Hodgkin-Huxley model. The Premier Undergraduate Neuroscience Journal.[interaktyvus].
Fitzhugh R (1966) Theoretical effect of temperature on threshold in the Hodgkin-Huxley nerve model. The Journal of general physiology. 49(5):989-1005.
Kuang S, Wang J, Zeng T, Cao A (2008) Thermal impact on spiking properties in Hodgkin-Huxley neuron with synaptic stimulus. Pramana. 70(1):183-90.

(56) References Cited

OTHER PUBLICATIONS

Goldin MA, Mindlin GB (2017) Temperature manipulation of neuronal dynamics in a forebrain motor control nucleus. PLoS computational biology. 13(8):e1005699.
Garedew A, Henderson SO, Moncada S (2010) Activated macrophages utilize glycolytic ATP to maintain mitochondrial membrane potential and prevent apoptotic cell death. Cell Death & Differentiation. 17(10):1540-50.
Mantovani A, Marchesi F, Malesci A, Laghi L, Allavena P (2017) Tumour-associated macrophages as treatment targets in oncology. Nature reviews Clinical oncology. 14(7):399-416.
Colotta F, Allavena P, Sica A, Garlanda C, Mantovani A (2009) Cancer-related inflammation, the seventh hallmark of cancer: links to genetic instability. Carcinogenesis. 30(7):1073-81.
Honeycutt JB, Wahl A, Baker C, Spagnuolo RA, Foster J, Zakharova O, Wietgrefe S, Caro-Vegas C, Madden V, Sharpe G, Haase AT (2016) Macrophages sustain HIV replication in vivo independently of T cells. The Journal of clinical investigation. 126(4):1353.
Arainga M, Edagwa B, Mosley RL, Poluektova LY, Gorantla S, Gendelman HE (2017) A mature macrophage is a principal HIV-1 cellular reservoir in humanized mice after treatment with long acting antiretroviral therapy. Retrovirology. 14(1):17.
Appelberg KS, Wallet MA, Taylor JP, Cash MN, Sleasman JW, Goodenow Mm (2017) HIV-1 Infection Primes Macrophages through STAT Signaling to Promote Enhanced Inflammation and Viral Replication. AIDS Research and Human Retroviruses. 33(7):690-702.
Burdo TH, Lentz MR, Autissier P, Krishnan A, Halpern E, Letendre S, Rosenberg ES, Ellis RJ, Williams KC (2011) Soluble CD163 made by monocyte/macrophages is a novel marker of HIV activity in early and chronic infection prior to and after anti-retroviral therapy. Journal of Infectious Diseases. 204(1):154-63.
Blond D, Raoul H, Le Grand R, Dormont D (2000) Nitric oxide synthesis enhances human immunodeficiency virus replication in primary human macrophages. Journal of virology. 74(19):8904-12.
Blond D, Cheret A, Raoul H, Le Grand R, Caufour P, Theodoro F, Dormont D (1998) Nitric oxide synthesis during acute SIVmac251 infection of macaques. Research in virology. 149(2):75-86.
Rostasy K, Monti L, Yiannoutsos C, Kneissl M, Bell J, Kemper TL, Hedreen JC, Navia BA (1999) Human immunodeficiency virus infection, inducible nitric oxide synthase expression, and microglial activation: pathogenetic relationship to the acquired immunodeficiency syndrome dementia complex. Annals of neurology. 46(2):207-16.
Torre D, Ferrario G (1996) Immunological aspects of nitric oxide in HIV-1 infection. Medical hypotheses. 47(5):405-7.
Lamers SL, Salemi M, Galligan DC, De Oliveira T, Fogel GB, Granier SC, Zhao L, Brown JN, Morris A, Masliah E, McGrath MS (2009) Extensive HIV-1 intra-host recombination is common in tissues with abnormal histopathology. PloS one. 4(3):e5065.
Rock RB, Gekker G, Hu S, Sheng Ws, Cheeran M, Lokensgard JR, Peterson PK (2004) Role of microglia in central nervous system infections. Clinical microbiology reviews. 17(4):942-64.
Carballo M, Conde M, Tejedo J, Gualberto A, Jimenez J, Monteseirín J, Santa María C, Bedoya FJ, Hunt III SW, Pintado E, Baldwin AS (2002) Macrophage inducible nitric oxide synthase gene expression is blocked by a benzothiophene derivative with anti-HIV properties. Molecular genetics and metabolism. 75(4):360-8.
Zhang X, Goncalves R, Mosser DM (2008) The isolation and characterization of murine macrophages. Current protocols in immunology. 83(1):14-1.
Samaniego R, Palacios BS, Domiguez-Soto Á, Vidal C, Salas A, Matsuyama T, Sánchez-Torres C, Torre I, Miranda-CarúS ME, Sánchez-Mateos P, Puig-Kröger A (2014) Macrophage uptake and accumulation of folates are polarization-dependent in vitro and in vivo and are regulated by activin A. Journal of leukocyte biology. 95(5):797-808.
Bukrinsky MI, Nottet HS, Schmidtmayerova H, Dubrovsky L, Flanagan CR, Mullins Me, Lipton S, Gendelman HE (1995) Regulation of nitric oxide synthase activity in human immunodeficiency virus type 1 (HIV-1)-infected monocytes: implications for HIV associated neurological disease. Journal of Experimental Medicine. 181(2):735-45.
Jin X, McGrath MS, Xu H (2015) Inhibition of HIV expression and integration in macrophages by methylglyoxal-bis-guanylhydrazone. Journal of virology. 89(22):11176-11189.
Yamasaki K, Chuang VT, Maruyama T, Otagiri M (2013) Albumin-drug interaction and its clinical implication. Biochimica et Biophysica Acta (BBA)—General Subjects. 1830(12):5435-43.
Karimi M, Sahandi Zangabad P, Ghasemi A, Amiri M, Bahrami M, Malekzad H, Ghahramanzadeh Asl H, Mahdieh Z, Bozorgomid M, Ghasemi A, Rahmani Taji Boyuk MR (2016) Temperature-responsive smart nanocarriers for delivery of therapeutic agents: applications and recent advances. ACS applied materials & interfaces. 8(33):21107-33.
Ta T, Porter TM (2013) Thermosensitive liposomes for localized delivery and triggered release of chemotherapy. Journal of controlled release. 169(1-2):112-25.
Zangabad PS, Mirkiani S, Shahsavari S, Masoudi B, Masroor M, Hamed H, Jafari Z, Taghipour YD, Hashemi H, Karimi M, Hamblin MR (2017) Stimulus-responsive liposomes as smart nanoplatforms for drug delivery applications. Nanotechnology reviews. 7(1):95-122.
Kneidl B, Peller M, Winter G, Lindner LH, Hossann M (2014) Thermosensitive liposomal drug delivery systems: state of the art review. International journal of nanomedicine. 9:4387.
Sun T, Zhang YS, Pang B, Hyun DC, Yang M, Xia Y (2014) Engineered nanoparticles for drug delivery in cancer therapy. Angewandte Chemie International Edition. 53(46):12320-64.
Zhang L, Wei MJ, Zhao CY, Qi HM (2008) Determination of the inhibitory potential of 6 fluoroquinolones on CYP1A2 and CYP2C9 in human liver microsomes. Acta Pharmacologica Sinica. 29(12):1507-14.
O'Ferrall RM (2010) A pictorial representation of zero-point energy and tunnelling contributions to primary hydrogen isotope effects. Journal of Physical Organic Chemistry. 23(7):572-579.
Slaughter LM, Wolczanski PT, Klinckman TR, Cundari TR (2000) Inter- and intramolecular experimental and calculated equilibrium isotope effects for (silox)2(tBu3SIND) TIR + RH (silox = tBu3SiO): Inferred kinetic isotope effects for RH/D addition to transient (silox)2TiNSitBu3. Journal of the American Chemical Society. 122(33):7953-7975.
Elison C, Rapoport H, Laursen R, Elliott HW (1961) Effect of deuteration of N—CH3 group on potency and enzymatic N-demethylation of morphine. Science. 134(3485):1078-9.
Slebocka-Tilk H, Motallebi S, Nagorski RW, Turner P, Brown RS, McDonald R (1995) Electrophilic Bromination of 7-Norbornylidene-7'- orbornane. The Observation of an Unusually Large Inverse Deuterium Kinetic Isotope Effect. Journal of the American Chemical Society. 117(34):8769-8776.
Parker VD, Reitstoen B (1997) Radical cation-nucleophile combination reactions. The effect of structure of nitrogen-centered nucleophiles on reaction rates. Acta Chemica Scandinavica. 51(10):1035-1040.
Hayflick L (1965) The limited in vitro lifetime of human diploid cell strains. Experimental cell research. 37(3):614-36.
Owen SC, Doak AK, Wassam P, Shoichet MS, Shoichet BK (2012) Colloidal aggregation affects the efficacy of anticancer drugs in cell culture. ACS chemical biology. 7(8):1429-35.
Owen SC, Doak AK, Ganesh AN, Nedyalkova L, McLaughlin CK, Shoichet BkK Shoichet MS (2014) Colloidal drug formulations can explain "bell-shaped" concentration-response curves. ACS chemical biology. 9(3):777-84.
Dolfi SC, Chan LL, Qiu J, Tedeschi PM, Bertino JR, Hirshfield KM, Oltvai ZN, Vazquez A (2013) The metabolic demands of cancer cells are coupled to their size and protein synthesis rates. Cancer & metabolism. 1(1):20.
Cabanac A, Briese E (1992) Handling elevates the colonic temperature of mice. Physiology & behavior. 51(1):95-8.
Michel C, Cabanac M (1999) Opposite effects of gentle handling on body temperature and body weight in rats. Physiology & behavior. 67(4):617-22.
McCullough L, Arora S (2004) Diagnosis and treatment of hypothermia. American family physician. 70(12):2325-32.

(56) References Cited

OTHER PUBLICATIONS

Freund G (1973) Hypothermia after acute ethanol and benzyl alcohol administration. Life sciences. 13(4):345-9.
Myers RD (1981) Alcohol's effect on body temperature: hypothermia, hyperthermia or poikilothermia? Brain research bulletin. 7(2):209-20.
Kalant H, Le AD (1983) Effects of ethanol on thermoregulation. Pharmacology & therapeutics. 23(3):313-64.
Malcolm RD, Alkana RL (1983) Temperature dependence of ethanol lethality in mice. Journal of Pharmacy and Pharmacology. 35(5):306-11.
Briese E, Hernandez L (1996) Ethanol anapyrexia in rats. Pharmacology Biochemistry and Behavior. 54(2):399-402.
Lomax P, Bajorek JG, Bajorek TA, Chaffee RR (1981) Thermoregulatory mechanisms and ethanol hypothermia. European journal of pharmacology. 71(4):483-7.
Gad SC, Spainhour CB, Shoemake C, Pallman DR, Stricker-Krongrad A, Downing PA, Seals RE, Eagle LA, Polhamus K, Daly J (2016) Tolerable levels of nonclinical vehicles and formulations used in studies by multiple routes in multiple species with notes on methods to improve utility. International journal of toxicology 2:95-178.
Gad SC, Cassidy CD, Aubert N, Spainhour B, Robbe H (2006) Nonclinical vehicle use in studies by multiple routes in multiple species. International journal of toxicology. 25(6):499-521.
Gordon CJ, Puckett ET, Repasky ES, Johnstone AF (2017) A Device that Allows Rodents to Behaviorally Thermoregulate when Housed in Vivariums. Journal of the American Association for Laboratory Animal Science. 56(2):173-6.
Boily P (2009) Role of voluntary motor activity on menthol-induced hyperthermia in mice. Journal of Thermal Biology. 34(8):420-5.
Gaskill BN, Rohr SA, Pajor EA, Lucas JR, Garner JP (2009) Some like it hot: mouse temperature preferences in laboratory housing. Applied Animal Behaviour Science. 116(2):279-85.
Marschner JA, Schäfer h H, Holderied A, Anders HJ (2016) Optimizing mouse surgery with online rectal temperature monitoring and preoperative heat supply. Effects on post-ischemic acute kidney injury. PLoS One. 11(2):e0149489.
Lindstedt SL, Calder III WA (1981) Body size, physiological time, and longevity of homeothermic animals. The Quarterly Review of Biology. 56(1):1-6.
Rouslin WI (1987) The mitochondrial adenosine 5'-triphosphatase in slow and fast heart rate hearts. American Journal of Physiology—Heart and Circulatory Physiology. 252(3):H622-7.
Tacutu R, Thornton D, Johnson E, Budovsky A, Barardo D, Craig T, Diana E, Lehmann G, Toren D, Wang J, Fraifeld VE, De Magalhaes JP (2018) Human Ageing Genomic Resources: new and updated databases. Nucleic Acids Research 46(D1):D1083-D1090.
Wilson DJ (2019) The harmonic mean p-value for combining dependent tests. Proceedings of the National Academy of Sciences. 116(4):1195-1200.
Rouslin W, Broge CW (1994) Analysis of factors affecting functional assays for estimating IF1, the mitochondrial ATPase Inhibitor. Analytical biochemistry. 222(1):68-75.
Rouslin W (1988) Factors affecting the loss of mitochondrial function during zero-flow ischemia (autolysis) in slow and fast heart-rate hearts. Journal of molecular and cellular cardiology. 20(11):999-1007.
Rouslin W, Broge CW (1989) Regulation of mitochondrial matrix pH and adenosine 5'-triphosphatase activity during ischemia in slow heart-rate hearts. Role of Pi/H+ symport. Journal of Biological Chemistry. 264(26):15224-9.
Rouslin W, Broge CW (1990) Regulation of the mitochondrial adenosine 5'-triphosphatase in situ during ischemia and in vitro in intact and sonicated mitochondria from slow and fast heart-rate hearts. Archives of biochemistry and biophysics. 280(1):103-11.
Rouslin WI, Broge CW, Grupp IL (1990) ATP depletion and mitochondrial functional loss during ischemia in slow and fast heart-rate hearts. American Journal of Physiology-Heart and Circulatory Physiology. 259(6):H1759-66.
Rouslin W, Broge CW (1992) Why the Mitochondrial ATPase Inhibitor IF1 Fails to Inhibit the Mitochondrial ATPase in Situ in Fast Heart-Rate Mammalian and Avian Hearts. Annals of the New York Academy of Sciences. 671(1):505-6.
Rouslin W, Broge CW (1993) Factors affecting the species-homologous and species-heterologous binding of mitochondrial ATPase inhibitor, IF1, to the mitochondrial ATPase of slow and fast heart-rate hearts. Archives of biochemistry and biophysics. 303(2):443-50.
Rouslin W, Broge CW (1993) Mechanisms of ATP conservation during ischemia in slow and fast heart rate hearts. American Journal of Physiology—Cell Physiology. 264(1):C209-16.
Rouslin W, Frank GD, Broge CW (1995) Content and binding characteristics of the mitochondrial ATPase inhibitor, IF1 in the tissues of several slow and fast heart-rate homeothermic species and in two poikilotherms. Journal of bioenergetics and biomembranes. 27(1):117-25.
Rouslin W, Broge CW, Guerrieri F, Capozza G (1995) ATPase activity, IF1 content, and proton conductivity of ESMP from control and ischemic slow and fast heart-rate hearts. Journal of bioenergetics and biomembranes. 27(4):459-66.
Rouslin W, Broge CW (1996) IF1 function in situ in uncoupler-challenged ischemic rabbit, rat, and pigeon hearts. Journal of Biological Chemistry. 271(39):23638-41.
Ballard A, Ahmad HO, Narduolo S, Rosa L, Chand N, Cosgrove DA, Varkonyi P, Asaad N, Tomasi S, Buurma NJ, Leach AG (2018) Quantitative Prediction of Rate Constants for Aqueous Racemization To Avoid Pointless Stereoselective Syntheses. Angewandte Chemie. 130(4):994-7.
Takahashi M, Oshima K, Matsubara S (2005) Ruthenium catalyzed deuterium labelling of a-carbon in primary alcohol and primary/secondary amine in D2O. Chemistry letters. 34(2):192-3.
Chatterjee B, Krishnakumar V, Gunanathan C (2016) Selective a—Deuteration of Amines and Amino Acids Using D20. Organic letters. 18(22):5892-5.
Michelotti A, Rodrigues F, Roche M (2017) Development and Scale-Up of Stereoretentive a-Deuteration of Amines. Organic Process Research & Development. 21(11):1741-4.
Neubert L, Michalik D, Bahn S, Imm S, Neumann H, Atzrodt J, Derdau V, Holla W, Beller M (2012) Ruthenium-catalyzed selective a,β-deuteration of bioactive amines. Journal of the American Chemical Society. 134(29):12239-44.
Taglang C, Martínez-Prieto LM, Del Rosal I, Maron L, Poteau R, Philippot K, Chaudret B, Perato S, Sam Lone A, Puente C, Dugave C (2015) Enantiospecific C—H Activation Using Ruthenium Nanocatalysts. Angewandte Chemie International Edition. 54(36):10474-7.
Pieters G, Taglang C, Bonnefille E, Gutmann T, Puente C, Berthet JC, Dugave C, Chaudret B, Rousseau B (2014) Regioselective and stereospecific deuteration of bioactive aza compounds by the use of ruthenium nanoparticles. Angewandte Chemie International Edition. 53(1):230-4.
Bhatia S, Spahlinger G, Boukhumseen N, Boll Q, Li Z, Jackson JE (2016) Stereoretentive H/D Exchange via an Electroactivated Heterogeneous Catalyst at sp3 C—H Sites Bearing Amines or Alcohols. European Journal of Organic Chemistry. 24:4230-5.
Chatterjee B, Gunanathan C (2015) Ruthenium Catalyzed Selective a- and a, β-Deuteration of Alcohols Using D20. Organic letters. 17(19):4794-7.
Khaskin E, Milstein D (2013) Simple and Efficient Catalytic Reaction for the Selective Deuteration of Alcohols. ACS Catalysis. 3(3):448-52.
Bai W, Lee KH, Tse SK, Chan KW, Lin Z, Jia G (2015) Ruthenium-catalyzed deuteration of alcohols with deuterium oxide. Organometallics. 34(15):3686-98.
Breno KL, Tyler DR (2001) C—H Bond Activation in Aqueous Solution: A Linear Free Energy Relationship Investigation of the Rate-Limiting Step in the H/D Exchange of Alcohols Catalyzed by a Molybdocene. Organometallics. 20(18):3864-8.
Balzarek C, Weakley TJ, Tyler DR (2000) C—H Bond Activation in Aqueous Solution: Kinetics and Mechanism of H/D Exchange in Alcohols Catalyzed by Molybdocenes. Journal of the American Chemical Society. 122(39):9427-34.

(56) References Cited

OTHER PUBLICATIONS

Balzarek C, Tyler DR (1999) Intra-and Intermolecular H/D Exchange in Aqueous Solution Catalyzed by Molybdocenes. Angewandte Chemie International Edition. 38(16):2406-8.
Maegawa T, Fujiwara Y, Inagaki Y, Monguchi Y, Sajiki H (2008) A convenient and effective method for the regioselective deuteration of alcohols. Advanced Synthesis & Catalysis. 350(14-15):2215-8.
Bossi G, Putignano E, Rigo P, Baratta W (2011) Pincer Ru and Os complexes as efficient catalysts for racemization and deuteration of alcohols. Dalton Transactions. 40(35):8986-95.
Zhang L, Nguyen DH, Raffa G, Desset S, Paul S, Dumeignil F, Gauvin RM (2016) Efficient deuterium labelling of alcohols in deuterated water catalyzed by ruthenium pincer complexes. Catalysis Communications. 84:67-70.
Palmer WN, Chirik PJ (2017) Cobalt-Catalyzed Stereoretentive Hydrogen Isotope Exchange of C (sp3)—H Bonds. ACS Catalysis. 7(9):5674-8.
Sajiki H, Aoki F, Esaki H, Maegawa T, Hirota K (2004) Efficient C—H/C—D Exchange Reaction on the Alkyl Side Chain of Aromatic Compounds Using Heterogeneous Pd/C in D2O. Organic letters. 6(9):1485-7.
Esaki H, Aoki F, Umemura M, Kato M, Maegawa T, Monguchi Y, Sajiki H (2007) Efficient H/D Exchange Reactions of Alkyl-Substituted Benzene Derivatives by Means of the Pd/C—H2—D2O System. Chemistry—A European Journal. 13(14):4052-63.
Hale LV, Szymczak NK (2016) Stereoretentive deuteration of a-chiral amines with D2O. Journal of the American Chemical Society. 138(41):13489-92.
Derdau V, Atzrodt J (2006) CH/CD exchange reactions of aromatic compounds in D2O with NaBD4-activated catalysts. Synlett. (12):1918-22.
Derdau V, Atzrodt J, Zimmermann J, Kroll C, Brückner F (2009) Hydrogen-Deuterium Exchange Reactions of Aromatic Compounds and Heterocycles by NaBD4-Activated Rhodium, Platinum and Palladium Catalysts. Chemistry—A European Journal. 15(40): 10397-404.
Ito N, Watahiki T, Maesawa T, Maegawa T, Sajiki H (2008) HD exchange reaction taking advantage of the synergistic effect of heterogeneous palladium and platinum mixed catalyst. Synthesis. 09:1467-78.
Kar S, Goeppert A, Sen R, Kothandaraman J, Prakash GS (2018) Regioselective deuteration of alcohols in D2O catalysed by homogeneous manganese and iron pincer complexes. Green Chemistry. 20(12):2706-2710.
Segler MH, Preuss M, Waller MP (2018) Planning chemical syntheses with deep neural networks and symbolic AI. Nature. 555(7698):604.
Klucznik T, Mikulak-Klucznik B, McCormack MP, Lima H, Szymkuć S, Bhowmick M, Molga K, Zhou Y, Rickershauser L, Gajewska EP, Toutchkine A, Dittwald P, Startek MP, Kirkovits GJ, Roszak R, Adamski A, Sieredzińska B, Mrksich M, Trice SLI, Grzybowski BA (2018) Efficient syntheses of diverse, medicinally relevant targets planned by computer and executed in the laboratory. Chem. 4(3):522-32.
Segler MH, Preuss M, Waller MP (2017) Learning to Plan Chemical Syntheses. arXiv preprint. arXiv:1708.04202.
Loh YY, Nagao K, Hoover AJ, Hesk D, Rivera NR, Colletti SL, Davies IW, MacMillan DW (2017) Photoredox-catalyzed deuteration and tritiation of pharmaceutical compounds. Science. 358(6367):1182-1187.
Yu RP, Hesk D, Rivera N, Pelczer I, Chirik PJ (2016) Iron-catalysed tritiation of pharmaceuticals. Nature. 529(7585): 195.
Zhan M, Zhang T, Huang H, Xie Y, Chen Y (2014) A simple method for α- position deuterated carbonyl compounds with pyrrolidine as catalyst. Journal of Labelled Compounds and Radiopharmaceuticals. 57(8):533-9.
Fodor-Csorba K, Galli G, Holly S, Gács-Baitz E (2002) Microwave-assisted deuterium exchange reactions for the preparation of reactive intermediates. Tetrahedron letters. 43(21):3789-92.
Bloom S, Pitts CR, Woltornist R, Griswold A, Holl MG, Lectka T (2013) Iron (II)-catalyzed benzylic fluorination. Organic letters. 15(7):1722-4.
Bloom S, Sharber SA, Holl MG, Knippel JL, Lectka T (2013) Metal-Catalyzed Benzylic Fluorination as a Synthetic Equivalent to 1, 4-Conjugate Addition of Fluoride. The Journal of organic chemistry. 78(21):11082-6.
Xia JB, Zhu C, Chen C (2013) Visible light-promoted metal-free C—H activation: diarylketone-catalyzed selective benzylic mono- and difluorination. Journal of the American Chemical Society. 135(46):17494-500.
Cantillo D, De Frutos O, Rincon JA, Mateos C, Kappe CO (2014) A continuous-flow protocol for light-induced benzylic fluorinations. The Journal of organic chemistry. 79(17):8486-90.
Liu W, Groves JT (2013) Manganese-Catalyzed Oxidative Benzylic C—H Fluorination by Fluoride Ions. Angewandte Chemie. 125(23):6140-3.
Nodwell MB, Bagai A, Halperin SD, Martin RE, Knust H, Britton R (2015) Direct photocatalytic fluorination of benzylic C—H bonds with N-fluorobenzenesulfonimide. Chemical Communications. 51(59):11783-6.
Ma JJ, Yi WB, Lu GP, Cai C (2015) Transition-metal-free C—H oxidative activation: persulfate-promoted selective benzylic mono- and difluorination. Organic & biomolecular chemistry. 13(10):2890-4.
Champagne PA, Desroches J, Hamel JD, Vandamme M, Paquin JF (2015) Monofluorination of organic compounds: 10 years of innovation. Chemical reviews. 115(17):9073-174.
Sasmal S, Rana S, Lahiri GK, Maiti D (2018) Manganese-salen catalyzed oxidative benzylic chlorination. Journal of Chemical Sciences. 130(7):88.
Combe SH, Hosseini A, Parra A, Schreiner PR (2017) Mild Aliphatic and Benzylic Hydrocarbon C—H Bond Chlorination Using Trichloroisocyanuric Acid. The Journal of organic chemistry. 82(5):2407-13.
Ayonon A, Nalbandian C, Guillemard L, Gustafson J (2017) Benzylic bromination catalyzed by triphenylphosphine selenide via Lewis basic activation. Tetrahedron Letters. 58(30):2940-3.
Shibatomi K, Zhang Y, Yamamoto H (2008) Lewis acid catalyzed benzylic bromination. Chemistry—An Asian Journal. 3(8-9):1581-4.
Cantillo D, De Frutos O, Rincon JA, Mateos C, Kappe CO (2013) A scalable procedure for light-induced benzylic brominations in continuous flow. The Journal of organic chemistry. 79(1):223-9.
Combe SH, Hosseini A, Song L, Hausmann H, Schreiner PR (2017) Catalytic Halogen Bond Activation in the Benzylic C—H Bond Iodination with Iodohydantoins. Organic letters. 19(22):6156-9.
Laduron F, Tamborowski V, Moens L, Horváth A, De Smaele D, Leurs S (2005) Efficient and scalable method for the selective alkylation and acylation of secondary amines in the presence of primary amines. Organic process research & development. 9(1):102-4.
Takeda R, Abe H, Shibata N, Moriwaki H, Izawa K, Soloshonok VA (2017) Asymmetric synthesis of α-deuterated α-amino acids. Organic & biomolecular chemistry. 15(33):6978-83.
O'Reilly E, Balducci D, Paradisi F (2010) A stereoselective synthesis of α-deuterium-labelled (S)-α-amino acids. Amino acids. 39(3):849-58.
Johns RB, Whelan DJ (1966) Synthesis of α-deuterated amino acids. Australian Journal of Chemistry. 19(11):2143-7.
Mosin O, Ignatov I, Skladnev D, Shvets V (2015) The Biosynthesis of Deuterium Labeled Amino Acids Using a Strain of Facultative Methylotrophic Bacterium Brevibacterium Methylicum 5662 With RuMP Cycle of Carbon Assimilation. European Journal of Molecular Biotechnology. (1):37-52.
Blomquist AT, Cedergren RJ, Hiscock BF, Tripp SL, Harpp DN (1966) Synthesis of highly deuterated amino acids. Proceedings of the National Academy of Sciences (PNAS). 55(3):453-6.
Thanassi JW (1971) General procedure for the preparation of deuterated and tritiated amino acids by incorporation of solvent isotope during synthesis. The Journal of organic chemistry. 36(20):3019-21.

(56) References Cited

OTHER PUBLICATIONS

Rigoulet M, Ouhabi R, Leverve X, Putod-Paramelle F, Guérin B (1989) Almitrine, a new kind of energy-transduction inhibitor acting on mitochondrial ATP synthase. Biochimica et Biophysica Acta (BBA)—Bioenergetics. 975(3):325-9.
Rigoulet M, Fraisse L, Ouhabi R, Guérin B, Fontaine E, Leverve X (1990) Flux-dependent increase in the stoichiometry of charge translocation by mitochondrial ATPase/ATP synthase induced by almitrine. Biochimica et Biophysica Acta (BBA)—Bioenergetics. 1018(1):91-7.
Leverve XM, Fontaine E, Putod-Paramelle F, Rigoulet M (1994) Decrease in cytosolic ATP/ADP ratio and activation of pyruvate kinase after in vitro addition of almitrine in hepatocytes isolated from fasted rats. The FEBS Journal. 224(3):967-74.
Rigoulet M (1990) Control processes in oxidative phosphorylation: kinetic constraints and stoichiometry. Biochimica et Biophysica Acta (BBA)—Bioenergetics. 1018(2-3):185-9.
European Medicines Agency (May 23, 2013) Assessment report for almitrine-containing medicinal products for oral use. http://www.ema.europa.eu/docs/en_GB/document_library/Referrals_document/Almitrine/Recommendation_provided_by_Pharmacovigilance_Risk_Assessment_Committee/WC500144134.pdf (accessed on Dec. 7, 2017).
Stavchansky S, Doluisio JT, MacLeod CM, Szalkowski MB, Bachand RT, Heilman R, Sebree TB, Geary RS (1989) Single oral dose proportionality pharmacokinetics of almitrine bismesylate in humans. Biopharmaceutics & drug disposition. 10(3):229-37.
Stavchansky S, Doluisio JT, MacLeod CM, Sebree TB, Heilman R, Bachand JR RT, Szalkowski MB, Geary RS (1989) Relative bioavailability of almitrine bismesylate in humans. Biopharmaceutics & drug disposition. 10(3):239-46.
Stavchansky S, Doluisio JT, MacLeod CM, Szalkowski MB, Bachand JR RT, Heilman R, Sebree TB, Geary RS (1989) One year administration of almitrine bismesylate (Vectarion) to chronic obstructive pulmonary disease patients: pharmacokinetic analysis. Biopharmaceutics & drug disposition. 10(3):247-55.
Bury T, Jeannot JP, Ansquer JC, Radermecker M (1989) Dose-response and pharmacokinetic study with almitrine bismesylate after single oral administrations in COPD patients. European Respiratory Journal. 2(1):49-55.
European Medicines Agency (May 29, 2013) Oral almitrine to be withdrawn by EU Member States. http://www.ema.europa.eu/docs/en_GB/document_library/Referrals_document/Almitrine/Position_provided_by_CMDh/WC500143802.pdf (accessed on Jun. 20, 2018).
Gordon BH (1995) The pharmacokinetics and metabolism of almitrine bismesylate. Doctoral dissertation, College of Medicine, Biological Sciences and Psychology, University of Leicester, United Kingdom.
Yang X, Yu Y, Xu J, Shu H, Liu H, Wu Y, . . . & Shang Y (2020) Clinical course and outcomes of critically ill patients with SARS-CoV-2 pneumonia in Wuhan, China: a single-centered, retrospective, observational study. The Lancet Respiratory Medicine. 8(5):475-481.
Esnault P, Hraiech S, Bordes J, Forel JM, Adda M, Rambaud R, . . . & Guervilly C (2019) Evaluation of Almitrine Infusion During Veno-Venous Extracorporeal Membrane Oxygenation for Severe Acute Respiratory Distress Syndrome in Adults. Anesthesia & Analgesia. 129(2):e48-e51.
Cotton JF (2014) The latest pharmacologic ventilator. Anesthesiology: The Journal of the American Society of Anesthesiologists. 121(3):442-4.
Golder FJ, Hewitt MM, McLeod JF (2013) Respiratory stimulant drugs in the post-operative setting. Respiratory physiology & neurobiology. 189(2):395-402.
Howard P (1989) Hypoxia, almitrine, and peripheral neuropathy. Thorax. 44(4):247.
Winkelmann BR, Kullmer TH, Kneissl DG, Trenk D, Kronenberger H (1994) Low-dose almitrine bismesylate in the treatment of hypoxemia due to chronic obstructive pulmonary disease. Chest. 105(5):1383-91.

Weitzenblum E, Schrijen F, Apprill M, Prefaut C, Yernault JC (1991) One year treatment with almitrine improves hypoxaemia but does not increase pulmonary artery pressure in COPD patients. European Respiratory Journal. 4(10):1215-22.
Górecka D, Sliwinski P, Palasiewicz G, Pachocki R, Zielinski J (2003) Effects of almitrine bismesylate on arterial blood gases in patients with chronic obstructive pulmonary disease and moderate hypoxaemia: a multicentre, randomised, double-blind, placebo-controlled study. Respiration. 70(3):275-83.
Kayacan O, Beder S, Deda G, Karnak D (2001) Neurophysiological changes in COPD patients with chronic respiratory insufficiency. Acta neurologica belgica. 101(3):160-5.
Allen MB, Prowse KE (1989) Peripheral nerve function in patients with chronic bronchitis receiving almitrine or placebo. Thorax. 44(4):292-7.
Jarratt JA, Morgan CN, Twomey JA, Abraham R, Sheaff PC, Pilling JB, Payan J, Mitchell JD, Tang O, Arnaud F (1992) Neuropathy in chronic obstructive pulmonary disease: a multicentre electrophysiological and clinical study. European Respiratory Journal. 5(5):517-24.
Appenzeller O, Parks RD, MacGee J (1968) Peripheral neuropathy in chronic disease of the respiratory tract. The American journal of medicine. 44(6):873-80.
Faden A, Mendoza E, Flynn F (1981) Subclinical neuropathy associated with chronic obstructive pulmonary disease: possible pathophysiologic role of smoking. Archives of neurology. 38(10):639-42.
Moore N, Lerebours G, Senant J, Ozenne G, David PH, Nouvet G (1985) Peripheral neuropathy in chronic obstructive lung disease. The Lancet. 326(8467):1311.
Nowak D, Brüch M, Arnaud F, Fabel H, Kiessling D, Nolte D, Overlack A, Rolke M, Ulmer WT, Worth H, Wywiol A (1990) Peripheral neuropathies in patients with chronic obstructive pulmonary disease: a multicenter prevalence study. Lung. 168(1):43-51.
Malik RA, Masson EA, Sharma AK, Lye RH, Ah-See AK, Compton AM, Tomlinson DR, Hanley SP, Boulton AJ (1990) Hypoxic neuropathy: relevance to human diabetic neuropathy. Diabetologia. 33(5):311-8.
Hendriksen PH, Oey PL, Wieneke GG, Van Huffelen AC, Gispen WH (1992) Hypoxic neuropathy versus diabetic neuropathy An electrophysiological study in rats. Journal of the neurological sciences. 110(1):99-106.
Bulut Çelik S, Can H, Sözmen MK, Şengezer T, Kaplan YC, Utlu G, Şener A, Aybek Yilmaz A, Aygün O (2017) Evaluation of the neuropathic pain in the smokers. Ağrı—The Journal of The Turkish Society of Algology. 29(3):122-6.
Pohjanpää AK, Rimpelä AH, Rimpelä M, Karvonen JS (1997) Is the strong positive correlation between smoking and use of alcohol consistent over time? A study of Finnish adolescents from 1977 to 1993. Health Education Research. 12(1):25-36.
Rogliani P, Lucà G, Lauro D (2015) Chronic obstructive pulmonary disease and diabetes. COPD research and practice. 1(1):3.
Das M (2017) Treating chemotherapy-induced peripheral neuropathy. The Lancet Oncology. 18(4):e202.
Shah A, Hoffman EM, Mauermann ML, Loprinzi CL, Windebank AJ, Klein CJ, Staff NP (2018) Incidence and disease burden of chemotherapy-induced peripheral neuropathy in a population-based cohort. Journal of Neurology, Neurosurgery & Psychiatry. 89(6):636-641.
Miaskowski C, Mastick J, Paul SM, Abrams G, Cheung S, Sabes JH, Kober KM, Schumacher M, Conley YP, Topp K, Smoot B (2018) Impact of chemotherapy-induced neurotoxicities on adult cancer survivors' symptom burden and quality of life. Journal of Cancer Survivorship. 12(2):234-45.
Seretny M, Currie GL, Sena ES, Ramnarine S, Grant R, MacLeod MR, . . . & Fallon M (2014) Incidence, prevalence, and predictors of chemotherapy-induced peripheral neuropathy: a systematic review and meta-analysis. Pain. 155(12):2461-2470.
Savage L (2007) Chemotherapy-Induced Pain Puzzles Scientists. Journal of the National Cancer Institute. 99(14):1070-1071.
Wallington M, Saxon EB, Bomb M, Smittenaar R, Wickenden M, McPhail S, Rashbass J, Chao D, Dewar J, Talbot D, Peake M (2016) 30-day mortality after systemic anticancer treatment for breast and

(56) References Cited

OTHER PUBLICATIONS lung cancer in England: a population-based, observational study. The Lancet Oncology. 17(9):1203-16.
Smith EM, Pang H, Cirrincione C, Fleishman S, Paskett EE, Ahles T, Bressler LR, Fadul CE, Knox C, Le-Lindqwister N, Gilman PB (2013) Effect of duloxetine on pain, function, and quality of life among patients with chemotherapy-induced painful peripheral neuropathy: a randomized clinical trial. Jama. 309(13):1359-67.
B'Chir A, Mebazaa A, Losser MR, Romieu M, Payen D (1998) Intravenous almitrine bismesylate reversibly induces lactic acidosis and hepatic dysfunction in patients with acute lung injury. Anesthesiology: The Journal of the American Society of Anesthesiologists. 89(4):823-30.
Chan SC, Liu CL, Lo CM, Lam BK, Lee EW, Wong Y, Fan ST (2006) Estimating liver weight of adults by body weight and gender. World journal of gastroenterology. 12(14):2217.
Michard F, Wolff MA, Herman B, Wysocki M (2001) Right ventricular response to high-dose almitrine infusion in patients with severe hypoxemia related to acute respiratory distress syndrome. Critical care medicine. 29(1):32-36.
Yamanaka Y, Shimada T, Mochizuki R, Suzuki Y, Takenouchi K, Takeda T, Uno H, Izawa Y, Fujiwara K (1997) Neuronal and muscular inclusions in rats with hindlimb dysfunction after treating with difluorobenzhydrylpiperadine. Toxicologic pathology. 25(2):150-7.
Yamanaka Y, Sakamoto E, Sakuma Y, Uno H, Koyama T, Izawa Y, Fujiwara K (1995) Lipidosis of the dorsal root ganglia in rats treated with an almitrine metabolite. Archives of toxicology. 69(6):391.
Polavarapu S, Mani AM, Gundala NK, Hari AD, Bathina S, Das UN (2014) Effect of polyunsaturated fatty acids and their metabolites on bleomycin-induced cytotoxic action on human neuroblastoma cells in vitro. PloS one. 9(12):e114766.
Dilly SJ, Clark AJ, Marsh A, Mitchell DA, Cain R, Fishwick CW, Taylor PC (2017) A chemical genomics approach to drug reprofiling in oncology: Antipsychotic drug risperidone as a potential adenocarcinoma treatment. Cancer letters. 393:16-21.
Barker HE, Paget JT, Khan AA, Harrington KJ (2015) The tumour microenvironment after radiotherapy: mechanisms of resistance and recurrence. Nature reviews Cancer. 15(7):409.
Zhou Y, Hileman EO, Plunkett W, Keating MJ, Huang P (2003) Free radical stress in chronic lymphocytic leukemia cells and its role in cellular sensitivity to ROS-generating anticancer agents. Blood. 101(10):4098-104.
Wondrak GT (2009) Redox-directed cancer therapeutics: molecular mechanisms and opportunities. Antioxidants & redox signaling. 11(12):3013-69.
Berndtsson M, Hägg M, Panaretakis T, Havelka AM, Shoshan MC, Linder S (2007) Acute apoptosis by cisplatin requires induction of reactive oxygen species but is not associated with damage to nuclear DNA. International journal of cancer. 120(1):175-80.
Sullivan R, Pare GC, Frederiksen LJ, Semenza GL, Graham CH (2008) Hypoxia-induced resistance to anticancer drugs is associated with decreased senescence and requires hypoxia-inducible factor-1 activity. Molecular cancer therapeutics. 7(7):1961-73.
Doktorova H, Hrabeta J, Khalil MA, Eckschlager T (2015) Hypoxia-induced chemoresistance in cancer cells: The role of not only HIF-1. Biomedical Papers of the Medical Faculty of Palacky University in Olomouc. 159(2).
Payen D, Muret J, Beloucif S, Gatecel C, Kermarrec N, Guinard N, Mateo J (1998) Inhaled nitric oxide, almitrine infusion, or their coadministration as a treatment of severe hypoxemic focal lung lesions. Anesthesiology: The Journal of the American Society of Anesthesiologists. 89(5):1157-65.
Saadjian AY, Philip-Joel FF, Barret A, Levy S, Arnaud AG (1994) Effect of almitrine bismesylate on pulmonary vasoreactivity to hypoxia in chronic obstructive pulmonary disease. European Respiratory Journal. 7(5):862-8.
Prost JF, Desche P, Jardin F, Margairaz A (1991) Comparison of the effects of intravenous almitrine and positive end-expiratory pressure on pulmonary gas exchange in adult respiratory distress syndrome. European Respiratory Journal. 4(6):683-7.
Gallart L, Lu Qi, Puybasset L, Umamaheswara Rao GS, Coriat P, Rouby JJ, No Almitrine Study Group (1998) Intravenous almitrine combined with inhaled nitric oxide for acute respiratory distress syndrome. American journal of respiratory and critical care medicine. 158(6):1770-7.
Silva-Costa-Gomes T, Gallart L, Valles J, Trillo L, Minguella J, Puig MM (2005) Low-vs high-dose almitrine combined with nitric oxide to prevent hypoxia during open-chest one-lung ventilation. British journal of anaesthesia. 95(3):410-6.
Amundson SA, Do KT, Vinikoor LC, Lee RA, Koch-Paiz CA, Ahn J, Reimers M, Chen Y, Scudiero DA, Weinstein JN, Trent JM (2008) Integrating global gene expression and radiation survival parameters across the 60 cell lines of the National Cancer Institute Anticancer Drug Screen. Cancer research. 68(2):415-24.
Mix KA, Lomax JE, Raines RT (2017) Cytosolic delivery of proteins by bioreversible esterification. Journal of the American Chemical Society. 139(41):14396-14398.
Ressler VT, Mix KA, Raines RT (2019) Esterification delivers a functional enzyme into a human cell. ACS chemical biology. 14(4):599-602.
Zorzi A, Middendorp SJ, Wilbs J, Deyle K, Heinis C (2017) Acylated heptapeptide binds albumin with high affinity and application as tag furnishes long-acting peptides. Nature communications. 8(1):1-9.
Ekrami HM, Kennedy AR, Shen WC (1995) Water-soluble fatty acid derivatives as acylating agents for reversible lipidization of polypeptides. FEBS letters. 371(3):283-286.
Gordon-Smith DJ, Carbajo RJ, Yang JC, Videler H, Runswick MJ, Walker JE, Neuhaus D (2001) Solution structure of a C-terminal coiled-coil domain from bovine IF1: The inhibitor protein of F1 ATPase. Journal of molecular biology. 308(2):325-339.
Cabezon E, Butler PJG, Runswick MJ, Walker JE (2000) Modulation of the oligomerization state of the bovine F1-ATPase inhibitor protein, IF1, by pH. Journal of Biological Chemistry. 275(33):25460-25464.
Lebowitz MS, Pedersen PL (1996) Protein inhibitor of mitochondrial ATP synthase: relationship of inhibitor structure to pH-dependent regulation. Archives of Biochemistry and Biophysics. 330(2):342-354.
Bason JV, Runswick MJ, Fearnley IM, Walker JE (2011) Binding of the inhibitor protein IF1 to bovine F1-ATPase. Journal of molecular biology. 406(3):443-453.
Yampolsky LY, Stoltzfus A (2005) The exchangeability of amino acids in proteins. Genetics. 170(4):1459-1472.
Wender PA, Mitchell DJ, Pattabiraman K, Pelkey ET, Steinman L, Rothbard JB (2000) The design, synthesis, and evaluation of molecules that enable or enhance cellular uptake: peptoid molecular transporters. Proceedings of the National Academy of Sciences. 97(24):13003-13008.
Vázquez J, Sun C, Du J, Fuentes L, Sumners C, Raizada MK (2003) Transduction of a functional domain of the AT1 receptor in neurons by HIV-Tat PTD. Hypertension. 41(3):751-756.
Tünnemann G, Martin RM, Haupt S, Patsch C, Edenhofer F, Cardoso MC (2006) Cargo-dependent mode of uptake and bioavailability of TAT-containing proteins and peptides in living cells. The FASEB journal. 20(11):1775-1784.
Rothbard JB, Garlington S, Lin Q, Kirschberg T, Kreider E, Mcgrane PL, . . . & Khavari PA (2000) Conjugation of arginine oligomers to cyclosporin A facilitates topical delivery and inhibition of inflammation. Nature medicine. 6(11):1253-1257.
Vivès E, Schmidt J, Pèlegrin A (2008) Cell-penetrating and cell-targeting peptides in drug delivery. Biochimica et Biophysica Acta (BBA)—Reviews on Cancer. 1786(2):126-138.
Begley R, Liron T, Baryza J, Mochly-Rosen D (2004) Biodistribution of intracellularly acting peptides conjugated reversibly to Tat. Biochemical and biophysical research communications. 318(4):949-954.
Miyaji Y, Walter S, Chen L, Kurihara A, Ishizuka T, Saito M, . . . Okazaki O (2011) Distribution of KAI-9803, a novel δ-protein kinase C inhibitor, after intravenous administration to rats. Drug metabolism and disposition. 39(10):1946-1953.

(56) References Cited

OTHER PUBLICATIONS

Borsello T, Clarke PG, Hirt L, Vercelli A, Repici M, Schorderet DF, . . . Bonny C (2003) A peptide inhibitor of c-Jun N-terminal kinase protects against excitotoxicity and cerebral ischemia. Nature medicine. 9(9):1180-1186.

Flynn CR, Cheung-Flynn J, Smoke CC, Lowry D, Roberson R, Sheller MR, Brophy CM (2010) Internalization and intracellular trafficking of a PTD-conjugated anti-fibrotic peptide, AZX100, in human dermal keloid fibroblasts. Journal of pharmaceutical sciences. 99(7):3100-3121.

Brewer SJ, Sassenfeld HM (1985) The purification of recombinant proteins using C-terminal polyarginine fusions. Trends in Biotechnology. 3(5):119-122.

Holm T, Räägel H, Andaloussi SE, Hein M, Mäe M, Pooga M, Langel Ü (2011) Retro-inversion of certain cell-penetrating peptides causes severe cellular toxicity. Biochimica et Biophysica Acta (BBA)—Biomembranes. 1808(6):1544-1551.

Brugidou J, Legrand C, Mery J, Rabie A (1995) The retro-inverso form of a homeobox-derived short peptide is rapidly internalized by cultured neurons: a new basis for an efficient intracellular delivery system. Biochemical and biophysical research communications. 214(2):685-693.

Chen L, Wright LR, Chen CH, Oliver SF, Wender PA, Mochly-Rosen D (2001) Molecular transporters for peptides: delivery of a cardioprotective EPKC agonist peptide into cells and intact ischemic heart using a transport system, R7. Chemistry & biology. 8(12):1123-1129.

Mitchell DJ, Steinman L, Kim DT, Fathman CG, Rothbard JB (2000) Polyarginine enters cells more efficiently than other polycationic homopolymers. The Journal of Peptide Research. 56(5):318-325.

Nasrollahi SA, Taghibiglou C, Azizi E, Farboud ES (2012) Cell-penetrating peptides as a novel transdermal drug delivery system. Chemical biology & drug design. 80(5):639-646.

Jiang T, Olson ES, Nguyen QT, Roy M, Jennings PA, Tsien RY (2004) Tumor imaging by means of proteolytic activation of cell-penetrating peptides. Proceedings of the National Academy of Sciences. 101(51):17867-17872.

Savariar EN, Felsen CN, Nashi N, Jiang T, Ellies LG, Steinbach P, . . . Nguyen QT (2013) Real-time in vivo molecular detection of primary tumors and metastases with ratiometric activatable cell-penetrating peptides. Cancer research. 73(2):855-864.

Unkart JT, Chen SL, Wapnir IL, González JE, Harootunian A, Wallace AM (2017) Intraoperative tumor detection using a ratiometric activatable fluorescent peptide: a first-in-human phase 1 study. Annals of surgical oncology. 24(11):3167-3173.

Futaki S, Ohashi W, Suzuki T, Niwa M, Tanaka S, Ueda K, . . . & Sugiura Y (2001) Stearylated arginine-rich peptides: a new class of transfection systems. Bioconjugate chemistry. 12(6):1005-1011.

Katayama S, Hirose H, Takayama K, Nakase I, Futaki S (2011) Acylation of octaarginine: Implication to the use of intracellular delivery vectors. Journal of controlled release. 149(1):29-35.

Taylor BN, Mehta RR, Yamada T, Lekmine F, Christov K, Chakrabarty AM, . . . Gupta TK D (2009) Noncationic peptides obtained from azurin preferentially enter cancer cells. Cancer research. 69(2):537-546.

Kang Yc, Son M, Kang S, Im S, Piao Y, Lim KS, . . . Pak YK (2018) Cell-penetrating artificial mitochondria-targeting peptide-conjugated metallothionein 1A alleviates mitochondrial damage in Parkinson's disease models. Experimental & molecular medicine. 50(8):1-13.

Appiah Kubi G, Qian Z, Amiar S, Sahni A, Stahelin RV, Pei D (2018) Non-Peptidic Cell-Penetrating Motifs for Mitochondrion-Specific Cargo Delivery. Angewandte Chemie. 130(52):17429-17434.

Rath S, Sharma R, Gupta R, Ast T, Chan C, Durham TJ, . . . & Mootha VK (2021) MitoCarta3. 0: an updated mitochondrial proteome now with sub-organelle localization and pathway annotations. Nucleic acids research. 49(D1):D1541-D1547.

Armenteros JJA, Salvatore M, Emanuelsson O, Winther O, Von Heijne G, Elofsson A, Nielsen H (2019) Detecting sequence signals in targeting peptides using deep learning. Life science alliance:2(5).

Fukasawa Y, Tsuji J, Fu SC, Tomii K, Horton P, Imai K (2015) MitoFates: Improved Prediction of Mitochondrial Targeting Sequences and Their Cleavage Sites. Molecular & Cellular Proteomics. 14(4):1113-1126.

Formentini L, Pereira MP, Sánchez-Cenizo L, Santacatterina F, Lucas JJ, Navarro C, Martínez-Serrano A, Cuezva JM (2014) In vivo inhibition of the mitochondrial H+-ATP synthase in neurons promotes metabolic preconditioning. The EMBO journal. 33(7):762-78.

Mayford M, Bach ME, Huang YY, Wang L, Hawkins RD, Kandel ER (1996) Control of memory formation through regulated expression of a CaMKII transgene. Science. 274(5293):1678-83.

Wang P, Powell SR (2010) Decreased sensitivity associated with an altered formulation of a commercially available kit for detection of protein carbonyls. Free Radical Biology and Medicine. 49(2):119-21.

Sohal RS, Orr WC (2012) The redox stress hypothesis of aging. Free Radical Biology and Medicine. 52(3):539-55.

Santacatterina F, Sánchez-Cenizo L, Formentini L, Mobasher MA, Casas E, Rueda CB, Martínez-Reyes I, De Arenas CN, García-Bermúdez J, Zapata JM, Sánchez-Aragó M (2016) Down-regulation of oxidative phosphorylation in the liver by expression of the ATPase inhibitory factor 1 induces a tumor-promoter metabolic state. Oncotarget. 7(1):490.

Formentini L, Santacatterina F, De Arenas CN, Stamatakis K, López-Martínez D, Logan A, Fresno M, Smits R, Murphy MP, Cuezva JM (2017) Mitochondrial ROS production protects the intestine from inflammation through functional M2 macrophage polarization. Cell reports. 19(6):1202-13.

García-Bermúdez J, Sánchez-Aragó M, Soldevilla B, Del Arco A, Nuevo-Tapioles C, Cuezva JM (2015) PKA phosphorylates the ATPase inhibitory factor 1 and inactivates its capacity to bind and inhibit the mitochondrial H+-ATP synthase. Cell reports. 12(12):2143-55.

Green DW, Grover GJ (2000) The IF1 inhibitor protein of the mitochondrial F1F0-ATPase. Biochimica et Biophysica Acta (BBA)-Bioenergetics. 1458(2-3):343-55.

Van Raaij MJ, Orriss GL, Montgomery MG, Runswick MJ, Fearnley IM, Skehel JM, Walker JE (1996) The ATPase inhibitor protein from bovine heart mitochondria: the minimal inhibitory sequence. Biochemistry. 35(49):15618-25.

Schnizer R, Van Heeke G, Amaturo D, Schuster SM (1996) Histidine-49 is necessary for the pH-dependent transition between active and inactive states of the bovine F1-ATPase inhibitor protein. Biochimica et Biophysica Acta (BBA)—Protein Structure and Molecular Enzymology. 1292(2):241-8.

Satre M, De Jerphanion MB, Huet J, Vignais PV (1975) ATPase inhibitor from yeast mitochondria. Purification and properties. Biochimica et Biophysica Acta (BBA)—Bioenergetics. 387(2):241-55.

Ando C, Ichikawa N (2008) Glutamic acid in the inhibitory site of mitochondrial ATPase inhibitor, IF1, participates in pH sensing in both mammals and yeast. Journal of biochemistry. 144(4):547-53.

Ichikawa N, Ushida S, Kawabata M, Masazumi Y (1999) Nucleotide sequence of cDNA coding the mitochondrial precursor protein of the ATPase inhibitor from humans. Bioscience, biotechnology, and biochemistry. 63(12):2225-7.

Gledhill JR, Montgomery MG, Leslie AG, Walker JE (2007) How the regulatory protein, IF1, inhibits F1-ATPase from bovine mitochondria. Proceedings of the National Academy of Sciences. 104(40):15671-6.

Stout JS, Partridge BE, Dibbern DA, Schuster SM (1993) Peptide analogs of the beef heart mitochondrial F1-ATPase inhibitor protein. Biochemistry. 32(29):7496-502.

Papa S, Zanotti F, Cocco T, Perrucci C, Candita C, Minuto M (1996) Identification of functional domains and critical residues in the adenosinetriphosphatase inhibitor protein of mitochondrial F0F1 ATP synthase. European journal of biochemistry. 240(2):461-7.

(56) References Cited

OTHER PUBLICATIONS

Zanotti F, Raho G, Vuolo R, Gaballo A, Papa F, Papa S (2000) Functional domains of the ATPase inhibitor protein from bovine heart mitochondria. FEBS letters. 482(1-2):163-6.

Zanotti F, Raho G, Gaballo A, Papa S (2004) Inhibitory and anchoring domains in the ATPase inhibitor protein IF1 of bovine heart mitochondrial ATP synthase. Journal of bioenergetics and biomembranes. 36(5):447-57.

De Chiara C, Nicastro G, Spisni A, Zanotti F, Cocco T, Papa S (2002) Activity and NMR structure of synthetic peptides of the bovine ATPase inhibitor protein, IF1. Peptides. 23(12):2127-41.

Yu C, Li Y, Holmes A, Szafranski K, Faulkes CG, Coen CW, Buffenstein R, Platzer M, De Magalhães JP, Church GM (2011) RNA sequencing reveals differential expression of mitochondrial and oxidation reduction genes in the long-lived naked mole-rat when compared to mice. PloS one. 6(11):e26729.

Gautam A, Singh H, Tyagi A, Chaudhary K, Kumar R, Kapoor P, Raghava GP (2012) CPPsite: a curated database of cell penetrating peptides. Database.

Horton KL, Stewart KM, Fonseca SB, Guo Q, Kelley SO (2008) Mitochondria-penetrating peptides. Chemistry & biology. 15(4):375-82.

Jean SR, Ahmed M, Lei EK, Wisnovsky SP, Kelley SO (2016) Peptide-mediated delivery of chemical probes and therapeutics to mitochondria. Accounts of chemical research. 49(9):1893-902.

Appiah Kubi G, Qian Z, Amiar S, Sahni A, Stahelin RV, Pei D (2018) Non-Peptidic Cell-Penetrating Motifs for Mitochondrion-Specific Cargo Delivery. Angewandte Chemie. 130(52):17429-34.

Zielonka J, Joseph J, Sikora A, Hardy M, Ouari O, Vasquez-Vivar J, Cheng G, Lopez M, Kalyanaraman B (2017) Mitochondria-targeted triphenylphosphonium-based compounds: syntheses, mechanisms of action, and therapeutic and diagnostic applications. Chemical reviews. 117(15):10043-120.

Pathak RK, Marrache S, Harn DA, Dhar S (2014) Mito-DCA: a mitochondria targeted molecular scaffold for efficacious delivery of metabolic modulator dichloroacetate. ACS chemical biology. 9(5):1178-87.

Naso MF, Tomkowicz B, Perry WL, Strohl WR (2017) Adeno-associated virus (AAV) as a vector for gene therapy. BioDrugs. 31(4):317-34.

Whittemore K, Derevyanko A, Martinez P, Serrano R, Pumarola M, Bosch F, Blasco MA (2019) Telomerase gene therapy ameliorates the effects of neurodegeneration associated to short telomeres in mice. Aging (Albany NY). 11(10):3280.

Qian Z, Liu T, Liu YY, Briesewitz R, Barrios AM, Jhiang SM, Pei D (2012) Efficient delivery of cyclic peptides into mammalian cells with short sequence motifs. ACS chemical biology. 8(2):423-31.

Qian Z, Martyna A, Hard RL, Wang J, Appiah-Kubi G, Coss C, Phelps MA, Rossman JS, Pei D (2016) Discovery and mechanism of highly efficient cyclic cell-penetrating peptides. Biochemistry. 55(18):2601-12.

Lian W, Jiang B, Qian Z, Pei D (2014) Cell-permeable bicyclic peptide inhibitors against intracellular proteins. Journal of the American Chemical Society. 136(28):9830-3.

Qian Z, Rhodes CA, McCroskey LC, Wen J, Appiah-Kubi G, Wang DJ, Guttridge DC, Peid (2017) Enhancing the cell permeability and metabolic stability of peptidyl drugs by reversible bicyclization. Angewandte Chemie International Edition. 56(6):1525-9.

Heinis C, Rutherford T, Freund S, Winter G (2009) Phage-encoded combinatorial chemical libraries based on bicyclic peptides. Nature chemical biology. 5(7):502.

Baeriswyl V, Rapley H, Pollaro L, Stace C, Teufel D, Walker E, Chen S, Winter G, Tite J, Heinis C (2012) Bicyclic peptides with optimized ring size inhibit human plasma kallikrein and its orthologues while sparing paralogous proteases. ChemMedChem. 7(7):1173-6.

Angelini A, Cendron L, Chen S, Touati J, Winter G, Zanotti G, Heinis C (2012) Bicyclic peptide inhibitor reveals large contact interface with a protease target. ACS chemical biology. 7(5):817-21.

Teufel DP, Bennett G, Harrison H, Van Rietschoten K, Pavan S, Stace C, Le Floch F, Van Bergen T, Vermassen E, Barbeaux P, Hu TT (2018) Stable and long-lasting, novel bicyclic peptide plasma kallikrein inhibitors for the treatment of diabetic macular edema. Journal of medicinal chemistry. 61(7):2823-36.

Eder M, Pavan S, Bauder-Wüst U, Van Rietschoten K, Baranski AC, Harrison H, Campbell S, Stace CL, Walker EH, Chen L, Bennett G (2019) Bicyclic peptides as a new modality for imaging and targeting of proteins overexpressed by tumors. Cancer research. 79(4):841-52.

Rhodes CA, Pei D (2017) Bicyclic Peptides as Next-Generation Therapeutics. Chemistry—A European Journal. 23(52):12690-703.

Lee YW, Luther DC, Kretzmann JA, Burden A, Jeon T, Zhai S, Rotello VM (2019) Protein delivery into the cell cytosol using non-viral nanocarriers. Theranostics. 9(11):3280-3292.

Chatin B, Mével M, Devallière J, Dallet L, Haudebourg T, Peuziat P, Colombani T, Berchel M, Lambert O, Edelman A, Pitard B (2015) Liposome-based formulation for intracellular delivery of functional proteins. Molecular Therapy-Nucleic Acids. 4:e244.

Shi B, Keough E, Matter A, Leander K, Young S, Carlini E, Sachs AB, Tao W, Abrams M, Howell B, Sepp-Lorenzino L (2011) Biodistribution of small interfering RNA at the organ and cellular levels after lipid nanoparticle-mediated delivery. Journal of Histochemistry & Cytochemistry. 59(8):727-740.

Reist M, Carrupt PA, Francotte E, Testa B (1998) Chiral inversion and hydrolysis of thalidomide: mechanisms and catalysis by bases and serum albumin, and chiral stability of teratogenic metabolites. Chemical research in toxicology. 11(12):1521-1528.

Cundy KC, Crooks PA (1983) Unexpected pehnomenon in the high-performance liquid chromatographic anlaysis of racemic 14C-labelled nicotine: Separation of enantiomers in a totally achiral system. Journal of Chromatography A. 281:17-33.

Pepper C, Smith HJ, Barrell KJ, Nicholls PJ, Hewlins MJ (1994) Racemisation of drug enantiomers by benzylic proton abstraction at physiological pH. Chirality. 6(5):400-404.

Fulmer GR, Miller AJ, Sherden NH, Gottlieb HE, Nudelman A, Stoltz BM, Bercaw JE, Goldberg KI (2010) NMR chemical shifts of trace impurities: common laboratory solvents, organics, and gases in deuterated solvents relevant to the organometallic chemist. Organometallics. 29(9):2176-9.

Tillack K, Aboutalebi H, Kramer ER (2015) An efficient and versatile system for visualization and genetic modification of dopaminergic neurons in transgenic mice. PloS one. 10(8):e0136203.

Pickrell AM, Pinto M, Hida A, Moraes CT (2011) Striatal dysfunctions associated with mitochondrial DNA damage in dopaminergic neurons in a mouse model of Parkinson's disease. Journal of Neuroscience. 31(48):17649-58.

Chen L, Xie Z, Turkson S, Zhuang X (2015) A53T human α-synuclein overexpression in transgenic mice induces pervasive mitochondria macroautophagy defects preceding dopamine neuron degeneration. Journal of Neuroscience. 35(3):890-905.

Schönig K, Freundlieb S, Gossen M (2013) Tet-Transgenic Rodents: a comprehensive, up-to date database. Transgenic research. 22(2):251-4.

Premsrirut PK, Dow LE, Kim SY, Camiolo M, Malone CD, Miething C, Scuoppo C, Zuber J, Dickins RA, Kogan SC, Shroyer KR (2011) A rapid and scalable system for studying gene function in mice using conditional RNA interference. Cell. 145(1):145-58.

Zinn E, Pacouret S, Khaychuk V, Turunen HT, Carvalho LS, Andres-Mateos E, Shah S, Shelke R, Maurer AC, Plovie E, Xiao R (2015) In silico reconstruction of the viral evolutionary lineage yields a potent gene therapy vector. Cell reports. 12(6):1056-68.

Ginn SL, Amaya AK, Alexander IE, Edelstein M, Abedi MR (2018) Gene therapy clinical trials worldwide to 2017: An update. The journal of gene medicine. 20(5):e3015.

Coune PG, Schneider BL, Aebischer P (2012) Parkinson's disease: gene therapies. Cold Spring Harbor perspectives in medicine. 2(4):a009431.

Feng LR, Maguire-Zeiss KA (2010) Gene Therapy in Parkinson's Disease. CNS drugs. 24(3):177-92.

Axelsen TM, Woldbye DP (2018) Gene therapy for Parkinson's disease, an update. Journal of Parkinson's disease. 8(2):195-215.

Palfi S, Gurruchaga JM, Ralph GS, Lepetit H, Lavisse S, Buttery PC, Watts C, Miskin J, Kelleher M, Deeley S, Iwamuro H (2014) Long-term safety and tolerability of ProSavin, a lentiviral vector-

(56) References Cited

OTHER PUBLICATIONS based gene therapy for Parkinson's disease: a dose escalation, open-label, phase 1/2 trial. The Lancet. 383(9923):1138-46.

Lewitt PA, Rezai AR, Leehey MA, Ojemann SG, Flaherty AW, Eskandar EN, Kostyk SK, Thomas K, Sarkar A, Siddiqui MS, Tatter SB (2011) AAV2-GAD gene therapy for advanced Parkinson's disease: a double-blind, sham-surgery controlled, randomised trial. The Lancet Neurology. 10(4):309-19.

Schriner SE, Linford NJ, Martin GM, Treuting P, Ogburn CE, Emond M, Coskun PE, Ladiges W, Wolf N, Van Remmen H, Wallace DC (2005) Extension of murine life span by overexpression of catalase targeted to mitochondria. Science. 308(5730):1909-11.

Mitsui A, Hamuro J, Nakamura H, Kondo N, Hirabayashi Y, Ishizaki-Koizumi S, Hirakawa T, Inoue T, Yodoi J (2002) Overexpression of human thioredoxin in transgenic mice controls oxidative stress and life span. Antioxidants and Redox Signaling. 4(4):693-696.

\* cited by examiner

FIGURE 8 cont.

Uncoupling = increased O₂ consumption

| | VG025 | VG007 | VG013 | VG019 | BENCHMARK DRUGS |
|---|---|---|---|---|---|
| ΔO₂ consumption (without respiratory chain inhibitor) | -1.19% (10 µM)<br>+75% (100 µM) | +25% (100 µM) | +3.32% (10 µM)<br>+20% (100 µM) | -0.34% (100 µM) | Oligomycin (3 µM) -40%<br>FCCP (500 nM) +50% |
| ΔΨ$_{IM}$ (without respiratory chain inhibitor) | -7.3% (10 µM)<br>-47.5% (100 µM) | 0% | 0% | 0% | Oligomycin (3 µM) none µ<br>FCCP (500 nM) -50% |
| ΔΨ$_{IM}$ (with respiratory chain inhibitor) | -46% (10 µM)<br>-64% (100 µM) | -42.61% (100 µM) | -30.15% (10 µM)<br>-40.79% (100 µM) | -29.74% (100 µM) | Oligomycin (3 µM) -49.1%<br>FCCP (500 nM) -52.5% |

µ, should hyperpolarize the membrane slightly; presumably the assay used isn't sensitive enough to detect small hyperpolarizations

THERAPEUTIC INHIBITORS OF THE REVERSE MODE OF ATP SYNTHASE

RELATED APPLICATIONS

This application claims the priority benefit of GB application numbers GB1700772.5 (filed 17 Jan. 2017), GB1706046.8 (filed 14 Apr. 2017), GB1707945.0 (filed 17 May 2017), GB1710198.1 (filed 27 Jun. 2017), GB1711250.9 (filed 13 Jul. 2017), GB1715756.1 (filed 28 Sep. 2017), GB1715758.7 (filed 28 Sep. 2017), GB1715938.5 (filed 1 Oct. 2017), GB1716492.2 (filed 9 Oct. 2017), GB1800092.7 (filed 4 Jan. 2018), GB1800291.5 (filed 8 Jan. 2018) and GB1800581.9 (filed 15 Jan. 2018). The entire teachings of these applications are incorporated herein by reference.

FIELD OF THE INVENTION

This invention discloses compounds that preferentially inhibit the ATP-hydrolysing mode of ATP synthase, pharmaceutical compositions of these compounds, and methods of use for treating subjects known to have various diseases or disorders including cancer (e.g. diagnosed with), subjects suspected of having various diseases or disorders including cancer or subjects at risk of developing various diseases or disorders including cancer. In a particular embodiment, the subject is a human.

BACKGROUND OF THE INVENTION

ATP Synthase

ATP synthase (also known as $F_1F_0$ ATP synthase, $F_0F_1$ ATP synthase, $F_1F_0$-ATPase, $F_0F_1$-ATPase) is located at the inner mitochondrial membrane (IM). It can use the proton motive force (pmf) to generate ATP from ADP and Pi [1-3]. ATP synthase is reversible and—depending on its substrate/product concentrations, the pmf and the voltage across inner mitochondrial membrane $\{\psi_{IM}\}$—it can work "forwards" (passaging protons, making ATP) or "backwards" (pumping protons, consuming ATP): its "forward" and "reverse" modes respectively, which may also be termed $F_1F_0$ ATP synthesis and $F_1F_0$ ATP hydrolysis respectively.

Inhibitors of ATP Synthase

There are drug inhibitors of ATP synthase, reviewed in [4] (herein incorporated in its entirety). Some inhibitors disproportionally/selectively inhibit the reverse mode, as compared to the forward mode, of ATP synthase [4-13]. Macrolides are a class of polyketide. So macrolide $F_1F_0$ ATP synthase inhibitors are polyketide $F_1F_0$ ATP synthase inhibitors, and these terms are used interchangeably herein. Polyketide $F_1F_0$ ATP synthase inhibitors (e.g. oligomycin) inhibit the forward mode, more than the reverse mode, of ATP synthase [11]. Oligomycin is well known in the art as an inhibitor of $F_1F_0$ ATP synthase, and thence oxidative phosphorylation and aerobic respiration [3]. Human life relies upon aerobic respiration. Indeed, the importance of breathing ($O_2$ in, $CO_2$ out) is widely appreciated. Thence the danger of oligomycin is easily apparent.

$IF_1$ is an endogenous protein, encoded by the ATPIF1 gene, which can selectively block the reverse mode of ATP synthase [4]. Its activity is pH sensitive and low, but non-zero, at normal matrix pH, and significant upon matrix acidification, caused by collapse of the proton motive force across the mitochondrial inner membrane.

Prior Art Teaches That Molecules of This Disclosure are Not Anti-Cancer Therapeutics Polyketide $F_1F_0$ ATP synthase inhibitors (e.g. oligomycin) are poisonous to cancer [14] and normal [15] cells. Indeed, just 1 mg/kg oligomycin kills healthy rats (n=10) within 48 hours; $LD_{33}$=0.5 mg/kg [15]. Normal cells typically need to use $F_1F_0$ ATP synthase in its forward mode and so blocking this mode is typically lethal. Thus, polyketide $F_1F_0$ ATP synthase inhibitors are not suitable as anti-cancer therapeutics: indeed, cytovaricin, ossamycin and peliomycin don't work in xenograft mouse models of cancer (data in [16], oligomycin untested) because a therapeutic window is absent because, to repeat, polyketide $F_1F_0$ ATP synthase inhibitors are highly poisonous to normal cells, whilst not even being poisonous to all cancer cells: e.g. ineffective against glycolytic cancers exhibiting the Warburg effect [14]. [17] used oligomycin in a xenograft cancer mouse model but only by applying oligomycin to the cancer cells before they were inoculated into mice, and washing the excess oligomycin off before inoculation into the mice (by culture for 2 days in drug free medium). They did the study like this (atypical, as clear to someone of the art) because oligomycin toxicity is not discriminate for cancer in a mammal. Obviously this experiment has no clinical parallel or utility. The synthesis/structure of some molecules of this disclosure has been disclosed in prior disclosures [P1, P2, P3], wherein these structures are speculated to be anti-cancer medicines merely by analogy to the anti-cancer activity of polyketide $F_1F_0$ ATP synthase inhibitors in [14]. Indeed, to mirror and use the restriction of [14], these disclosures restrict their suggestion to "cancers having tumor cells that do not exhibit the Warburg effect" [P3] i.e. they restrict to cancers using oxidative phosphorylation (OXPHOS) and ATP synthase, in its forward mode, to generate ATP. But what undermines this (postulated) approach is that this aerobic profile is what normal cells typically use also, especially on aggregate across an organism: well known to those of the art (evidence: importance of breathing to mammalian life). By this analogy to polyketide $F_1F_0$ ATP synthase inhibitors, these disclosures speculate these molecules are safe anti-cancer therapeutics. When in fact, by this analogy, they actually teach the opposite. This is clear when [14] isn't considered in isolation, as it shouldn't be, but alongside the rest of the literature e.g. [15], [16] and the knowledge of someone of the art (well known that normal cells need to use $F_1F_0$ ATP synthase in its forward mode, to generate ATP, and that oligomycin blocks this, and is potently dangerous). So, these prior disclosures [P1, P2, P3] teach someone of the art, that these structures are, by their chosen analogy to polyketide $F_1F_0$ ATP synthase inhibitors, not suitable for anti-cancer therapy. It isn't sufficient to kill cancer to be an anti-cancer therapeutic. This killing must be selective, leaving normal cells alive. Metabolic poisons such as cyanide or oligomycin do not fit this criterion. By distinction, the present invention discloses selective killing of cancer cells, at compound concentrations harmless to normal cells. This couldn't have been anticipated from the prior art. Furthermore, this selective anti-cancer activity is pronounced for cancers that do exhibit the Warburg effect.

Distinctly, the present disclosure discloses experimental data. Its inventive step is to show that its compounds are safe anti-cancer therapeutics, exactly because of their distinction from polyketide $F_1F_0$ ATP synthase inhibitors. There is a broad therapeutic margin for the compounds of this disclosure as a virtue of the distinctive (from oligomycin) way they work, leveraging differences between normal and cancer cells, discovered and disclosed as part of this invention.

Indeed, the compounds of this disclosure can kill highly glycolytic cancers exhibiting the Warburg effect. These cancers tend to be the most dangerous, with the worst prognosis (numerous studies find this: representatives: [18-20]).

Molecules of this disclosure don't just exert anti-cancer activity. They can also affect normal cells, making their metabolism more efficient, which can cause weight gain/reduce weight loss/maintain body weight, all of which combats cachexia. For example, cancer driven cachexia, which is the leading cause of death in cancer patients. By contrast, polyketide $F_1F_0$ ATP synthase inhibitors are toxic to normal cells, denying them energy, rather than enabling them more energy, by efficiency gain, as molecules of this disclosure can do.

In this disclosure, molecules are shown to exert anti-cancer activity by inhibiting $F_1F_0$ ATP hydrolysis. This directly opposes the prior art, wherein experimental "results indicate that [even] under severe hypoxic conditions, ATP synthase does not hydrolyze ATP in cancer cells" and that "in cancer cells $IF_1$ overexpression fully prevents ATP synthase hydrolytic activity" [21]. Indeed, the prior art finds that inhibiting $F_1F_0$ ATP hydrolysis conveys advantage to cancer [21]. Thence the prior art teaches that the compounds of this disclosure, which inhibit $F_1F_0$ ATP hydrolysis, will assist rather than compromise cancer, and thence this invention, which discloses discovery of the opposite, is novel over the prior art.

All publications, patents and patent applications mentioned or cited in this disclosure are herein incorporated, in entirety, by reference. This disclosure uses $IC_{50}$ and $EC_{50}$ interchangeably, for a process being inhibited or reduced. Chemical structures were drawn using the chemical drawing feature in [31], and if a drawing feature is unknown to the reader they are referred to its documentation, or to explore the software themselves: all clear to those of the art. Hydrogen on structures is typically not shown, present implicitly, but it is shown for some presented structures "On Hetero and Terminal" [31] groups.

SUMMARY OF THE INVENTION

Disclosed is the discovery of a cancer-specific drug target: the reverse mode of ATP synthase. Indeed, new experimental data, disclosed herein, demonstrates that molecules which specifically inhibit $F_1F_0$ ATP hydrolysis can exert specific anti-cancer activity, at concentrations that do not harm normal cells. Any anti-cancer drug that targets/inhibits $F_1F_0$ ATP hydrolysis is componentry to this invention. This disclosure discloses numerous anti-cancer drug working examples, some of which are also new compositions of matter, and discloses rationale and methods to find further working examples, which are, in turn, componentry to this invention and encompassed by this disclosure. The best mode for prevention or treatment of cancer in a subject, particularly with cancer exhibiting the Warburg effect, is to use a pharmaceutical composition with an effective amount of one or compounds of the following formula,

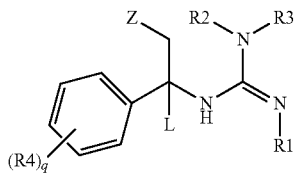

or a pharmaceutically-acceptable salt, solvate, hydrate or prodrug thereof, wherein:

L is alkyl, substituted alkyl or any atom or isotope permitted by valence;

$R_1$ is cyano, —$SO_2R_8$, —$C(=O)R_9$, or heteroaryl;

$R_2$ is (i) independently hydrogen, alkyl, or substituted alkyl, or (ii) taken together with $R_3$ forms a heterocyclo;

$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) taken together with $R_2$ forms a heterocyclo;

Z is heteroaryl provided that when $R_1$ is cyano, Z is not 2-pyridinyl;

$B_B$ is a bond, $C_{1-4}$alkylene, $C_{2-4}$alkenylene, substituted $C_{1-4}$alkylene, substituted $C_{2-4}$alkenylene, —$C(=O)NR_{19}$—, —$C_{1-4}$alkylene-$C(=O)NR_{19}$—, or substituted $C_{1-4}$alkylene-$C(=O)NR_{19}$—;

$R_4$ at each occurrence is selected independently of each other $R_4$ from the group consisting of halogen, alkyl, haloalkyl, nitro, cyano, haloalkoxy, $OR_{25}$, $SR_{25}$, $NR_{25}R_{26}$, $NR_{25}SO_2R_{27}$, $SO_2R_{27}$, $SO_2NR_{25}R_{26}$, $CO_2R_{26}$, $C(=O)R_{26}$, $C(=)NR_{25}R_{26}$, $OC(=O)R_{25}$, —$OC(=O)NR_{25}R_{26}$, $NR_{25}C(=O)R_{26}$, $NR_{25}CO_2R_{26}$, aryl, heteroaryl, heterocyclo and cycloalkyl;

$R_8$ is alkyl, substituted alkyl, aryl, or heteroaryl;

$R_9$ is —$NR_{10}R_{11}$, alkyl, substituted alkyl, alkoxy, alkylthio, cycloalkyl, aryl, heteroaryl, heterocycle, or —$CO_2R_{12}$;

$R_{10}$ and $R_{11}$, are (i) independently selected from hydrogen, alkyl, substituted alkyl, alkoxy, heterocyclo, cycloalkyl, aryl, and heteroaryl; or (ii) taken together form a hetero cyclo or heteroaryl;

$R_{12}$ and $R_{19}$ are hydrogen or alkyl;

$R_{25}$ and $R_{26}$ are independently selected from hydrogen, alkyl, or substituted alkyl, or taken together form a heterocyclo or heteroaryl ring;

$R_{27}$ is alkyl or substituted alkyl, and q is 0, 1, 2, or 3.

In some embodiments, the S-enantiomer of the compound is in enantiomeric excess. In some embodiments, the enantiomeric excess of S-enantiomer exceeds 70%.

In some embodiments, L is hydrogen or deuterium.

In some embodiments, the compound is a compound according to the formula

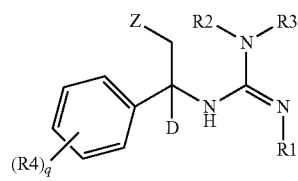

or pharmaceutically-acceptable salts, solvates, hydrates and prodrugs thereof, wherein D is deuterium (enrichment, for example, exceeding 40% deuterium incorporation at shown position, and optionally at other positions also).

In some embodiments, the compound is a compound according to the formula

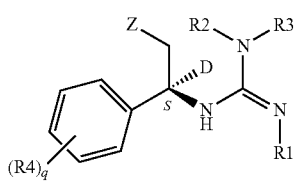

or pharmaceutically-acceptable salts, solvates, hydrates and prodrugs thereof, wherein D is deuterium (enrichment, for example, exceeding 40% deuterium incorporation at shown position, and optionally at other positions also);

S symbolises the S stereoisomer, for example, in enantiomeric excess (ee) exceeding 70%.

Herein, the terms "S-stereoisomer" and "S-enantiomer" refer to the arrangement of groups around the chiral centre shown in the structure above, regardless of the specific identities of the variables such as Z, L and $R_4$ within the structure.

DETAILED DESCRIPTION OF THE INVENTION

As used herein with reference to the utilities described, the terms "treating" or "treatment" encompass both responsive and prophylaxis measures designed to inhibit or delay the onset of the disease or disorder, or to alleviate, ameliorate, lessen, reduce, modulate or cure the disease or disorder and/or one or more of its symptoms. The terms "subject" and "patient" refer to organisms to be treated by the compounds/methods of the present invention and can refer to a human or animal.

The invention of this disclosure hinges on its discovery, disclosed herein, that some cancers rely on $F_1F_0$ ATP hydrolysis, even under normoxia (indeed under hyperoxia: ~21% $O_2$), during some or all of their cell cycle. Evidence herein: compounds of this disclosure, which specifically inhibit $F_1F_0$ ATP hydrolysis, slow cancer proliferation at concentrations that they do not harm normal cells.

In some of the most dangerous cancers, refractory to present [chemo/radio] therapies, during some or all of their cell cycle, reactive oxygen species (ROS) decrease [NADPH], because it is consumed in ROS mitigation processes, and this then pulls through increased pentose phosphate pathway (PPP) and glycolytic flux. But such a pivotal increase in glycolytic/PPP flux can only occur because of $F_1F_0$ ATP hydrolysis, a distinctive feature to these cancers, which stops ATP produced by glycolysis from accumulating and slowing glycolysis by negative feedback inhibition of key glycolytic enzymes. This increased PPP flux maintains [NADPH] and ROS mitigation. In this way, these cancers can maintain a very high ROS mitigation capability, maintain very low intracellular [ROS], and tend to be the most resistant to conventional [chemo/radio] therapies, which work, or often don't work (!), by increasing [ROS]. Compounds of this disclosure undermine this process/resistance. By inhibiting $F_1F_0$ ATP hydrolysis, they increase the anti-cancer efficacy of any chemical or treatment that increases reactive oxygen species (ROS) in cancer cells. An embodiment of this disclosure is any such co-treatment(s). Indeed, a compound(s) of this disclosure increases the success rate of standard of care [chemo/radio] therapies and permits their use at lower dosing, which reduces their horrendous side-effects. This disclosure encompasses a compound(s) of this invention in co-therapy with chemotherapy, or radiotherapy or any US Food and Drug Administration (FDA) approved drug(s) or treatment, for example, a drug approved for cancer treatment. Chemotherapies are well known to those of the art, including, but not limited to, cisplatin, carboplatin, taxol, oxaliplatin etc.

In other embodiments, a compound(s) of this disclosure is used as cancer therapy alone. Indeed, this is a much more cancer-targeted therapeutic approach. The most dangerous cancers use this distinctive metabolism, with ATP synthase distinctively in reverse, consuming glycolytic ATP, to yield high glycolytic rate, thence abundant glycolytic intermediates for biosynthesis and, crucially, to keep [ROS] low (as prior disclosed), which is necessary to cancer immortality (limitless replicative potential) and thence danger. This distinction is targeted, by compound(s) of this disclosure, without significant damage to normal cells. Normal adult cells normally use a different metabolism, with ATP synthase more in forward mode, and a higher ATP yield from glucose, but at the cost of higher [ROS] and mortality.

This reliance of normal cells upon the forward mode of ATP synthase makes them exquisitely susceptible to oligomycin. The compounds of this disclosure are useful for anti-cancer treatment, unlike oligomycin, because of their distinction from oligomycin, which couldn't have been foreseen without the inventive steps of this disclosure. In normal cells that are actively respiring (known as state 3 respiration [3]), inhibitors of the forward mode of ATP synthase (e.g. oligomycin) cause a state 3 to state 4 transition, hyperpolarize $\psi_{IM}$, decrease $O_2$ consumption and reduce [ATP] (so called "modulators" of the forward mode of ATP synthase, e.g. Bz-423, can also cause one or more of these effects) whilst a specific inhibitor of the reverse mode of ATP synthase does not exert these effects at a working concentration ([12-13], herein incorporated in their entirety). However, at this working concentration, after inhibition of the respiratory chain (e.g. blocked by rotenone, or some other respiratory chain inhibitor, or by a reduced $O_2$ concentration), a specific inhibitor of the reverse mode of ATP synthase will depolarise $\psi_{IM}$. This feature distinguishes a molecule that inhibits the reverse mode of ATP synthase significantly more than it inhibits/modifies the forward mode of ATP synthase, and/or inhibits/modifies ATP synthesis. Such a molecule, put into use as an anti-cancer therapeutic, is an embodiment of this invention. A further embodiment is the process/method of seeking new anti-cancer molecules by assaying whether a candidate molecule can depolarise $\psi_{IM}$, when $\psi_{IM}$ is maintained by $F_1F_0$ ATP hydrolysis (e.g. when OXPHOS is blocked by a respiratory chain inhibitor or insufficient $O_2$), but that can't hyperpolarize $\psi_{IM}$ and/or decrease $O_2$ consumption, when $\psi_{IM}$ is maintained by proton pumping by complexes of the respiratory chain. If a candidate molecule meets these requirements, it is an anti-cancer therapeutic, as determined by the invention of this disclosure.

Some cancers intrinsically rely upon ATP synthase in reverse, as revealed by experimental data of this disclosure, and further cancers can have this reliance imposed upon them, to maintain $\psi_{IM}$ in the hypoxia of a solid tumour, which also makes them susceptible to drugs of this disclosure. Significant lactate release is correlated with the most dangerous cancers and poor patient outcomes (numerous studies find this: example: [22]). High lactate release indicates high glycolytic rate, which $F_1F_0$ ATP hydrolysis enables, and which drugs of this disclosure attack. This invention confronts the most deadly cancers by discovering/disclosing a cancer-specific weakness, and the means to selectively attack it.

All the following molecules are—in use as anti-cancer therapeutics—embodiments of this invention: (1) Molecules that inhibit the reverse, and not the forward, mode of ATP synthase, (2) Molecules that inhibit the reverse more than than forward mode of ATP synthase, (3) Molecules that inhibit the reverse mode of ATP synthase, and not its forward mode, but that shuttle protons across the mitochondrial inner membrane, dissipating the pmf as heat (uncoupling [3]), which reduces $F_1F_0$ ATP synthesis, and in a further embodiment: uncoupling molecules that reduce $F_1F_0$ ATP hydrolysis more than $F_1F_0$ ATP synthesis, (4) Molecules that inhibit ATP hydrolysis more than ATP synthesis at the mitochondrial inner membrane, (5) Molecules that have a lower $IC_{50}$ or $EC_{50}$ for $F_1F_0$ ATP hydrolysis than $F_1F_0$ ATP synthesis. This invention discloses the process/method of using one or more molecular species, each with one or more of the characteristics in the aforementioned numbered points, as an anti-cancer medicine or treatment. Some examples are presented in this disclosure. Any cancer therapy or treatment or drug that leverages, relies upon, utilises or targets that cancers employ ATP synthase in its reverse mode is an embodiment of this disclosure.

Mechanistic Distinction From Polyketide $F_1F_0$ ATP Synthase Inhibitors

The compounds of this invention act by a distinctly different mechanism, upon cancer cells, than oligomycin. Drugs that act against the same molecular target have a similar pattern of activity against the different cancer cell lines of the NCI-60 assay i.e. the smaller, and the larger, of their GI50 values are against the same cell lines (GI50 is compound concentration that causes 50% growth inhibition of a cell line relative to no-drug control). The degree of (dis)similarity can be measured using the COMPARE algorithm [23-24], which employs a Pearson correlation coefficient. For example, [25] found that the COMPARE algorithm can successfully group different FDA-approved anti-cancer drugs by their method of action using their NCI-60 GI50 data. Oligomycin A (NSC: 717694 [16]) inhibits $F_1F_0$ ATP synthase [4, 14] and so do other polyketides: cytovaricin (NSC: 349622 [16]), ossamycin (NSC: 76627 [16]) and peliomycin (NSC: 76455 [16]); indeed, their NCI-60 pattern responses (GI50 values) correlate with that of oligomycin A: 0.896, 0.809 and 0.865 respectively (COMPARE algorithm output, all significant at p<0.05). However, the NCI-60 pattern response (GI50 values) of BMS-199264 is uncorrelated to that of oligomycin A (0.009). This mechanistic distinction is vital because polyketide $F_1F_0$ ATP synthase inhibitors are poisonous to normal cells [15], which means they fail in cancer xenograft mouse experiments [16] and are without clinical utility.

Higher HIF-1α (and lower pyruvate kinase {liver isoenzyme}, lower aspartate aminotransferase 2 {mitochondrial} and lower ATP synthase) gene expressions are reported to be a marker of the Warburg effect [14] and correlate (at p<0.05) with insensitivity to the polyketide $F_1F_0$ ATP synthase inhibitor, cytovaricin (Table 1 of [14]). By contrast, using the same cell lines and gene expression data set used to make Table 1 of [14], BMS-199264 sensitivity (GI50) does not correlate (at p<0.05) with any of these gene expressions. And actually higher HIF-1α expression, a marker of the Warburg effect, correlates (0.714, but statistically insignificant at p<0.05) with higher sensitivity to BMS-199264. FIG. 5 of [14] presents apoptolidin resistant NCI-60 cell lines, resistant because they utilise the Warburg effect [14], but the majority of these cell lines are more sensitive to BMS-19264 than the average, with a lower GI50 value than the average GI50 value (3.9 µM) for BMS-199264.

The lower the bioenergetic cellular index (BEC) of a cancer cell [18], the more it demonstrates the Warburg effect and the more it relies on glycolytic rather than oxidative metabolism. BEC is, by one measure [19], the ratio amount of the β subunit of F1 ATPase (β-F1-ATPase; gene: ATP5B) to that of Glyceraldehyde 3-phosphate dehydrogenase (GAPDH). I calculated BEC for the same cell lines analysed for Table 1 of [14], using the mRNA transcript amounts of ATP5B and GAPDH in each cell line, data sourced from [26-27], and then calculating the ([ATP5B]/[GAPDH] transcript ratio) for each of these cancer cell lines. Using transcript data rather than protein data is a limitation, but [28] report that a protein's cellular amount is generally well correlated (0.76) to its mRNA transcript amount, at least for cells in the NCI-60 assay, for the protein subset they studied. And furthermore, [14] relied on transcript data, so best comparison with [14] is made using such data. Polyketide $F_1F_0$ ATP synthase inhibitors don't work well against cancer cells exhibiting the Warburg effect [14] and, indeed, for the cell lines analysed (same ones used as for Table 1 in [14]) there is a significant (at p<0.05) negative Pearson correlation between $\log_{10}$(GI50) and BEC for oligomycin A (−0.9411). So, this correlation shows that the more a cancer uses Warburg metabolism, the less its danger is mitigated by oligomycin A. This significantly reduces the utility of oligomycin A as a cancer medicine because a low BEC score (indicating Warburg metabolism) is characteristic to some of the most dangerous cancers, with the worst patient outcomes [18-20]. By contrast, there is no significant (at p<0.05) Pearson correlation (+0.3639) for BMS-199264 and BEC. This means that, distinctly from the polyketide $F_1F_0$ ATP synthase inhibitors, its anti-cancer action is not restricted to those, often less dangerous, cancers that don't utilise Warburg metabolism.

Molecules of this disclosure undermine cancer by inhibiting the reverse mode of ATP synthase. It is true that polyketide $F_1F_0$ ATP synthase inhibitors also inhibit this mode, but distinctly, in addition, they also inhibit the forward mode of ATP synthase, indeed more potently [11], and whilst they can exert anti-cancer activity, because this forward mode is vital to many cancers, it is also vital to many normal cells. This makes polyketide $F_1F_0$ ATP synthase inhibitors unsuitable as clinical molecules. Molecules of this disclosure are therapeutic because of their distinction from, not their similarity to, polyketide $F_1F_0$ ATP synthase inhibitors.

[14] sum up with "Many cancer cells maintain a high level of anaerobic carbon metabolism even in the presence of oxygen, a phenomenon that is historically known as the Warburg effect. From our results, we conclude that macrolide inhibitors of the mitochondrial $F_0F_1$-ATP synthase selectively kill metabolically active tumor cells that do not exhibit the Warburg effect". So, [14] find that these macrolides only kill cancers reliant upon OXPHOS, so using $F_1F_0$-ATP synthase in its forward mode to generate ATP (which unfortunately is also the metabolic profile of many key types of normal cell) and thus macrolide inhibition of the forward mode of $F_1F_0$-ATP synthase is key to this (unspecific) anti-cancer activity. By contrast, the molecules of this disclosure exert anti-cancer activity by inhibition of the reverse mode of ATP synthase. BMS-199264 [4, 7, 9, 10, 11], BTB06584 [13] and 19a [5] have been described previously, as molecules that can inhibit this mode, and this invention discloses their utility as anti-cancer therapeutics, with supporting experimental data, thence identifying new cancer drugs and, more importantly, a new cancer specific drug target: $F_1F_0$-ATP hydrolysis, which is the most fundamental invention of this disclosure. BTB06584 (100 μM) exerts anti-cancer activity (FIG. 2), despite not inhibiting $F_1F_0$-ATP synthesis, as a function of inhibiting $F_1F_0$-ATP hydrolysis (at ≥100 μM), and critically it isn't harmful to normal cells (mouse cortical neurons) at this concentration [13]. Its anti-cancer potency (none at 10 μM, observed at 100 μM) matches its inhibitory potency for $F_1F_0$-ATP hydrolysis (none at 10 μM, requires ≥100 μM [13]). BMS-199264 (10 μM) exerts anti-cancer activity (FIG. 3). It doesn't harm normal cells (ex vivo rat heart) at this concentration [11]. In NCI five-dose testing [29-30], the mean GI50 for BMS-199264 is 3.9 μM (FIG. 7), which is lower/better than 62% of the 102 FDA approved cancer drugs in [24], their mean GI50 values sourced from Table 1 of [24]: all are directly comparable because they too are sourced from the NCI-60 five-dose assay. At 10 μM, 19a exerts more anti-cancer activity than BMS-199264 (FIG. 6), despite it having less effect on $F_1F_0$-ATP synthesis, because it inhibits the reverse mode of ATP synthase more potently than BMS-199264. Again, a vindication that the molecules of this disclosure exert anti-cancer activity by inhibiting the reverse mode of ATP synthase, which distinguishes them from the macrolides and, distinctly, makes them usable therapeutically. Indeed, molecules of this disclosure don't appreciably inhibit the forward mode of ATP synthase, in sharp distinction to the macrolides. The compounds that contain a protonable nitrogen atom in their imidazole reduce $F_1F_0$-ATP synthesis in SMPs because they shuttle protons across the mitochondrial inner membrane, dissipating the proton motive force (uncoupling). FIG. 8 presents structure-activity data for such uncoupling in whole cells, using compounds that are also componentry to this invention as anti-cancer drugs. BMS-199264 (logP=3.79, calculated [31]) uncouples more than 19a (logP=5.97, calculated [31]) because its logP is closer to the logP=3.2 (calculated) optimum for uncoupling [32].

19a is a racemate, wherein the S stereoisomer, and not the R stereoisomer, inhibits $F_1F_0$-ATP hydrolysis [5-6]. I tried to test the anti-cancer activity of the separated stereoisomers. They were successfully separated by superfluid chromatography (SFC). But subsequently underwent racemization during the NCI-60 tests. One stereoisomer sample conveyed slightly better anti-cancer activity than the other, revealing a slight enduing enantiomeric excess (ee) of S stereoisomer. Both samples ultimately contained a significant proportion of S stereoisomer and both had strong anti-cancer activity (FIG. 5). The Pearson correlation coefficient (R=0.8) for their patterns of anti-cancer activity is significant (at p<0.05). Racemization of the S stereoisomer is slowed by replacing the hydrogen atom on its chiral carbon with a deuterium atom and this is a new composition of matter, which is componentry to this invention, as is the method/process of using it for anti-cancer therapy. With this modification, the enantiomeric excess (ee) of the eutomer endures for longer and so per-unit anti-cancer activity is better, for longer. Analogy by the macrolide inhibitors of [14] would suggest that the S and R stereoisomers have equal anti-cancer activity, and that this would be weak, because they are both comparably weak reducers of $F_1F_0$-ATP synthesis ($EC_{50}$>100 μM in SMP assays). By contrast, by the invention of this disclosure, the S stereoisomer specifically is revealed to be a potent anti-cancer therapeutic.

Stereoisomerism

For some molecules of this disclosure, one of its stereoisomers has much lower $IC_{50}$ than the other for inhibiting $F_1F_0$ATP hydrolysis, and so, by the invention of this disclosure, this is the preferred stereoisomer for anti-cancer use. Indeed, a form with high enantiomeric excess (ee) for this preferred stereoisomer is the preferred embodiment for anti-cancer therapy, e.g. ee=>70%, ee=>95%, >99% more preferred, =100% most preferred. However, ee can be eroded by racemization. This invention discloses an improvement. Embodied by this disclosure are permutations of each of its chiral molecules, wherein the hydrogen attached to each chiral carbon is replaced with a deuterium, wherein the natural abundance of deuterium (0.015%) at this position is enhanced (non-limiting example: >3000 times greater than the natural abundance of deuterium, i.e. a >40% incorporation of deuterium). The deuterium Kinetic Isotope Effect (KIE) [33] slows racemization.

Best Mode

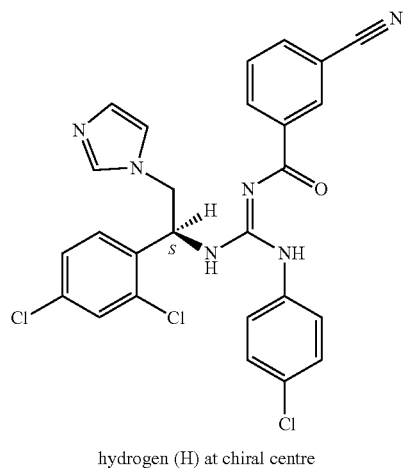

hydrogen (H) at chiral centre

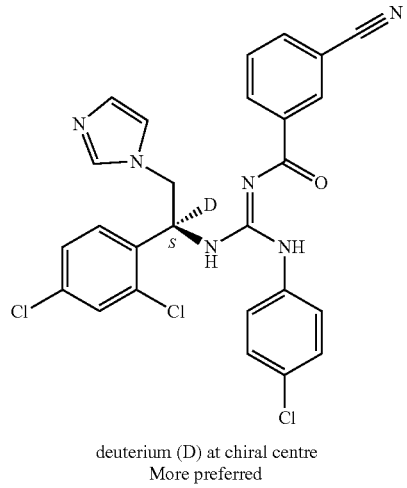

deuterium (D) at chiral centre
More preferred

The structure on the left has a low $EC_{50}$ against $F_1F_0$ATP hydrolysis (0.018 μM), its [$EC_{50}$ $F_1F_0$ ATP synthesis/$EC_{50}$ $F_1F_0$ ATP hydrolysis] ratio>5,556. In rats, this drug (administered in polyethyleneglycol:water:ethanol, 1:1:1) is orally bioavailable (47%) with good pharmacokinetics (intravenously applied drug half-life in blood=2.1 hours, $C_{max}$=21 μM, volume of distribution=2.37 L/kg). The deuterated analogue on the right, wherein the hydrogen atom on the chiral carbon is replaced with deuterium, conferring greater stereoisomeric stability because of the kinetic isotope effect (KIE, [33]), is more preferred and is the best mode anti-cancer therapy. The greater the % deuterium enrichment at the chiral carbon (carbon atom number 21) and the greater the enantiomeric excess, the more preferred the embodiment.

The most valuable innovation of this invention is not a presented structure but a discovered, disclosed principle: the best anti-cancer compound of this invention is a molecule that inhibits $F_1F_O$ ATP hydrolysis as potently and specifically as possible, whilst it inhibits, by direct binding, the forward mode of the ATP synthase molecule as little as possible: most preferably not at all.

Cachexia

Inhibiting $F_1F_O$-ATP hydrolysis, as compounds of this invention do, treats/ameliorates/prevents/combats the cachexia driven by some highly glycolytic (Warburg) cancers. These cancers rely upon $F_1F_O$ ATP hydrolysis to burn glycolytic ATP, to release glycolysis from ATP feedback inhibition and permit a high glycolytic rate, with high lactate efflux, which the liver converts back to glucose at an energetic cost (Cori cycle, 6 ATP per lactate to glucose conversion [1]), which the cancer then recycles to lactate de novo: iteratively this contributes to cachexia. Compounds of this invention treat/ameliorate/prevent/combat this cachexia drive. In the next section, a $2^{nd}$ mechanism that treats/ameliorates/prevents/combats cachexia is disclosed, whereby compounds of this invention inhibit $F_1F_O$-ATP hydrolysis in normal, rather than cancer, cells.

Temperature

An effective amount of a compound of this invention, when applied to a subject, inhibits $F_1F_O$-ATP hydrolysis, which conserves ATP, so less ATP needs to be synthesized, therefore respiration rate slows, thence metabolic heat production falls and body temperature can fall towards ambient temperature (if ambient<body temperature). So, when the ambient temperature isn't arduous (not requiring significant energy consuming physiological/behavioural adaptations to maintain body temperature) and dietary intake stays constant, weight gain/maintenance can occur, which can assist cachexia, for example cancer driven cachexia. This is clinically valuable because cachexia is the leading cause of death in cancer patients. If the ambient temperature is sufficiently close to the required body temperature, then the aforementioned decrease in heat generation is safe, because the body temperature can't fall below the ambient temperature. So, for example, if the ambient temperature is 37° C., inhibiting $F_1F_O$-ATP hydrolysis could make body temperature fall to this ambient temperature, but not below it, and this is safe because ~37° C. body temperature is safe Inhibiting $F_1F_O$-ATP hydrolysis will reduce, but not abolish, metabolic heat production. So, body metabolism will still contribute to heating the body, just less so, which will shift the thermoneutral and thermal comfort zones (terms well known to those of the art [34], temperatures vary by species, as is well known to those of the art) to higher temperature(s). If the subject is located at a higher temperature to account for this shift, for example at their updated, higher thermoneutral temperature, or make behavioural adaptations (e.g. wearing more clothes), then this shift is harmless. An embodiment of this invention is setting the dosage of a compound(s) that inhibits $F_1F_O$ ATP hydrolysis with consideration of the ambient temperature, wherein higher dosages are permissible at higher ambient temperatures. The preferred ambient temperature for a dosage permits the subject to be thermoneutral, and/or thermal comfortable, without the metabolic heat (respiration) fraction driven by the $F_1F_O$ ATP hydrolysis that is lost because of this dosage. This temperature management issue is more important for smaller than larger animals, because surface area scales to volume by a fractional power (e.g. refer Kleiber's law) and so larger animals retain their generated heat better, and so a given percentage drop in (per unit mass) metabolism will cause a smaller drop in body temperature in a bigger animal. The aforementioned weight gain can be of great clinical/health/nutritional value, or aesthetic value (by non-limiting example: bodybuilders), or commercial value when applied to livestock/farm animals or any animal with a commercial value e.g. racing animals, such as horses. This invention encompasses the method/process of using molecules of this disclosure for these applications, or any others wherein weight, nutritional or energetic gain is wanted in an animal or human. An embodiment of this invention is a method in which a subject takes or is administered an effective amount of a compound(s) of this invention, for example a compound of Formula (I), (II), (III), (IV) or (V) or another compound that selectively inhibits $F_1F_O$ ATP hydrolysis, or a pharmaceutically-acceptable salt, solvate, hydrate or prodrug thereof, to treat/ameliorate/prevent/combat cachexia, cancer-associated/driven cachexia, weight loss or a disease or disorder that causes a higher than normal body temperature which can include, but isn't limited to, fever, pyrexia, hyperpyrexia, hyperthermia, malignant hyperthermia, neuroleptic malignant syndrome, serotonin syndrome, thyroid storm, or to cause greater metabolic/bioenergetic efficiency in the subject, enhancing their physical or mental performance or causing body weight gain.

This temperature aspect to the molecules of this disclosure isn't relevant to the NCI-60 studies. Because in these studies, the ambient temperature is controlled at 37° C. [30], which is optimal for cells, and so if these drugs make cellular temperature fall to ambient temperature, this is not detrimental. It can be an issue for laboratory animal studies though. Laboratory mice, for example, are typically kept at room temperature (e.g. 20 to 23° C.) which renders them very reliant upon additional metabolic/physiological/behavioural heat production because their thermoneutral zone is much higher, at 30 to 32° C. (can vary depending on strain, size, age, gender etc. [34]). An administered compound(s) of this disclosure, which inhibits $F_1F_O$ ATP hydrolysis, can add to the cold stress that laboratory mice endure when kept at room temperature. An embodiment of this invention is the process/method of keeping laboratory animals at, or close to, their thermoneutral zone when performing animal studies with a compound(s) of this disclosure. For example, keeping mice at 30 to 32° C. And in a further embodiment, at even higher temperature to compensate for the amount that an administered compound(s) of this disclosure, by inhibiting $F_1F_O$ ATP hydrolysis, shifts the animal's thermoneutral zone to a zone of higher temperature. The amount shifted will depend on the administered dosage, so in a further embodiment, the ambient temperature is set according to the dosage used. Wherein, for a compound of this disclosure, a higher ambient temperature, within safe limits, can make a greater compound dosage safer.

An embodiment of this invention is a method in which a subject takes or is administered an effective amount of a compound(s) of this invention, for example a compound of Formula (I), (II), (III), (IV) or (V) or another compound that selectively inhibits $F_1F_O$ ATP hydrolysis, or a pharmaceutically-acceptable salt, solvate, hydrate or prodrug thereof, to treat/ameliorate/prevent/combat a medical disease/disorder, wherein the subject is monitored, for example by a healthcare/research professional/worker (doctor, nurse, vet, pharmacist, laboratory technician, scientist) or machine/artificial intelligence substitute, for any adverse signs/symptoms/non-normality after compound administration (in an embodiment for 5 minutes, in a further embodiment for 10 minutes, and in a further embodiment for longer) and in a particular embodiment for signs of reduction in body temperature (methods well known to those of the art, in a particular embodiment the subject's body temperature is monitored) and/or the dosage administered is set, and/or modified (e.g. increased in graduations), by information from this subject wellness/normality/temperature monitoring and/or the subject is located at an ambient temperature (e.g. in a temperature controlled room/enclosure/confine or climate) that maintains their body temperature within safe limits whilst they have an effective amount of compound in their system. An embodiment of this invention is the process/method of considering the ambient temperature in the decision of whether to take or administer a compound(s) of this disclosure, and at what dosage. In an embodiment, a period of medical observation, by a clinical or healthcare professional (e.g. pharmacist), occurs after the subject takes or is administered a compound(s) of this disclosure for the first time, and in a further embodiment when the compound dosage is increased or decreased. In a further embodiment, during this period of medical observation, the subject stays in a location that has medical facilities and/or expertise to treat/combat hypothermia (well known to those of the art), in non-limiting example embodiments this is a hospital or clinic or pharmacy or workplace of healthcare professionals. In an embodiment, during this period of medical observation, the patient stays in a temperature controlled room or area, or at a location where one is available nearby, and if the patient displays signs or symptoms of hypothermia, feels uncomfortable, or their body temperature falls, they can be located in a higher ambient temperature. In an embodiment, while the subject takes or is administered a compound(s) of this invention, or in a monitoring period after it, they stay in a room at a safe ambient temperature for having a compound(s) of this disclosure (non-limiting examples: wherein the ambient temperature is close to the desired body temperature, ~37° C., or exceeding it within safe limits) and are monitored by observation, and in a further embodiment their body temperature is monitored (methods well known to those of the art), as the controlled room temperature is reduced to a different temperature, in a further embodiment to, at or near, the ambient climatic temperature of that geography at that time, or colder. In a further embodiment, this process/method is iterated until the greatest dosage is found at which the subject has a safe body temperature at, or near, the ambient climatic temperature of that geography at that time or at the ambient temperature(s) at which the subject will spend their time at over their course of compound administration, or that their ambient temperature might fall to at some time over their course of compound administration, wherein the course of compound administration is the period during which the subject has an effective amount of compound in their body.

Uncoupling is Virtuous

The imidazole containing compounds of this disclosure inhibit $F_1F_0$ ATP hydrolysis and uncouple (shuttle protons across the mitochondrial inner membrane (IM), eroding the proton motive force, pmf). The former can exert a specific anti-cancer activity, because it undermines the means some cancers maintain $\psi_{IM}$ in normoxia (experimentally shown by data of this disclosure) or in hypoxic tumours, and the compound's uncoupling can also exert specific anti-cancer activity, explained now. The imidazole containing compounds of this disclosure bind ATP synthase at the $IF_1$ binding site. In normal cells they bind ATP synthase at this site and are sequestered from uncoupling, and the ATP they "save" by binding and inhibiting $F_1F_0$ ATP hydrolysis can (over)compensate for the ATP "lost" to their uncoupling. But some cancers have very high $IF_1$ expression (numerous studies show this, e.g. refer [21]). And for some cancers, this is to inhibit $F_1F_0$ ATP hydrolysis, to make their OXPHOS more efficient, which allows them to maintain [ATP] at low [$O_2$], and thence survive using OXPHOS in hypoxia (their heat generation is less but their temperature is maintained by heat conduction from surrounding tissues). This high $IF_1$ expression blocks the binding of these compounds to their binding site on ATP synthase, so the compounds aren't sequestered from uncoupling, and this uncoupling increases the $O_2$ requirement of this cancer which can't be met in the hypoxic microenvironment of its tumour, thence the cancer's intracellular [ATP] can't be maintained and its proliferation is slowed and/or it dies. So, herein, this invention discloses that the uncoupling aspect to the imidazole containing compounds of this disclosure can deliver additional, specific, anti-cancer activity, for example, against those cancers that don't rely upon $F_1F_0$ ATP hydrolysis. This invention discloses the process/method of using a compound(s) that can inhibit $F_1F_0$ ATP hydrolysis, and that can shuttle protons across the IM to dissipate the pmf (uncouple), as an anti-cancer therapeutic. Wherein the compound inhibits $F_1F_0$ ATP hydrolysis by direct interaction with ATP synthase, and reduces $F_1F_0$ ATP synthesis (primarily) by uncoupling. So, a compound needn't necessarily have a much lower $EC_{50}$ for $F_1F_0$ ATP hydrolysis than $F_1F_0$ ATP synthesis, in an SMP assay, to be componentry to this invention as an anti-cancer therapeutic. Indeed, even compounds with a lower $EC_{50}$ for $F_1F_0$ ATP synthesis than $F_1F_0$ ATP hydrolysis in an SMP assay can be componentry to this invention, as anti-cancer therapeutics, provided they do inhibit $F_1F_0$ ATP hydrolysis and provided their inhibition of $F_1F_0$ ATP synthesis is (primarily) because of uncoupling rather than inhibiting the forward mode of ATP synthase. Oligomycin, for example, does not fit these requisites. So, this invention discloses the method of using compounds that inhibit $F_1F_0$ ATP hydrolase, that don't inhibit $F_1F_0$ ATP synthase, and that uncouple the proton motive force, as anti-cancer therapeutics.

Deuterated Compounds of the Invention

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D ($^2H$ or deuterium), and T ($^3H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, distinct from their non-enriched counterparts. All percentages given for the amount of deuterium present are mole percentages. It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the compound with deuterium enriched starting materials, which are commercially available.

Deuterium enriched refers to the feature that the compound has a quantity of deuterium that is greater than in naturally occurring compounds or synthetic compounds prepared from substrates having the naturally occurring distribution of isotopes. Embodiments of this invention include compounds of Formula (I), (II), (III), (IV) and (V)

with one or more of their hydrogen atoms replaced by deuterium, at a greater frequency than the natural abundance of deuterium (0.015%) e.g. a non-limiting example: >3000 times greater than the natural abundance of deuterium (i.e. a >40% incorporation of deuterium at a hydrogen replacement position). Additional examples of the abundance of deuterium at a position in, or positions of, a compound embodiment of this invention include 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%. In certain embodiments, the abundance of deuterium at a position in, or positions of, a compound embodiment of this invention is at least 40%. In certain other embodiments, the abundance of deuterium at a position in, or positions of, a compound embodiment of this invention is at least 60%. In further embodiments, the abundance of deuterium is at least 75%. In yet other embodiments, the abundance of deuterium is at least 90%. It is to be understood that the deuterium-enriched compounds described herein can be combined with a pharmaceutically acceptable carrier to form a pharmaceutical composition.

In the Description and Claims of this invention, when a position on a compound structure is designated deuterium (D), or said to have deuterium, or said to be enriched for deuterium, or even only said to be enriched, it is because the abundance of deuterium at that position is not at the natural value (0.015%) but instead, typically, in excess of 40%. The phrase 'enrichment at the chiral centre' herein, for example for a compound of Formula (I), means that the molar amount of deuterium at the chiral centre as a percentage of the total amount of all hydrogen isotopes at the chiral centre is greater than or equal to 40%, preferably greater than 40%, more preferably greater than 45%, and in ascending order of preference, ≥52.5% deuterium enrichment at the chiral centre, ≥60% deuterium enrichment at the chiral centre, ≥67.5% deuterium enrichment at the chiral centre, ≥75% deuterium enrichment at the chiral centre, ≥82.5% deuterium enrichment at the chiral centre, ≥90% deuterium enrichment at the chiral centre, ≥95% deuterium enrichment at the chiral centre, ≥97% deuterium enrichment at the chiral centre, ≥99% deuterium enrichment at the chiral centre, ≥99.5% deuterium enrichment at the chiral centre, 100% deuterium enrichment at the chiral centre. Greater % deuterium enrichment is preferred. Additional examples of the % deuterium enrichment at the chiral centre of a compound of this invention, for example a compound of Formula (I), are 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

Further possible isotopic variants of these structures are further embodiments of this disclosure. An embodiment of this disclosure is a molecule that inhibits the reverse mode, more than the forward mode, of ATP synthase, which has a deuterium in place of hydrogen (at a greater frequency than 0.015% e.g. >40%) at one or more places upon its structure, and/or any other isotopic substitution (at a greater than natural frequency).

General Compound Synthesis

A general synthetic route applicable to some compounds of the invention is set out in Scheme 1 below.

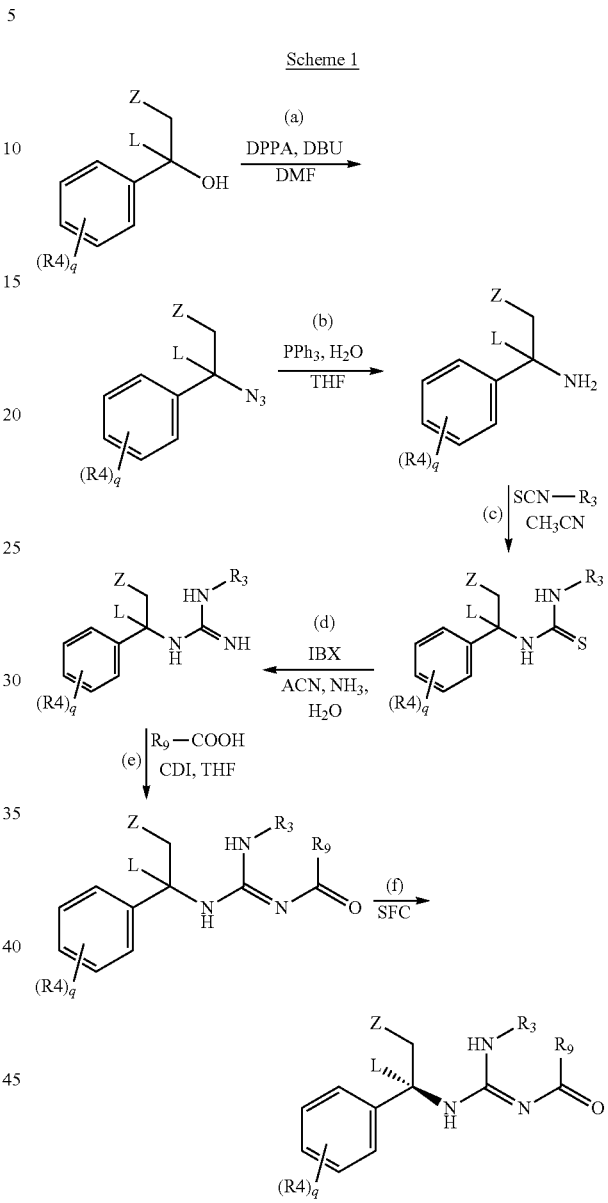

The person skilled in the art is able to make modifications to this general synthetic route, based on the common general knowledge and/or the content of prior art disclosures cited herein, in order to synthesise compounds of the invention where necessary.

Specific Compound Synthesis

To perform the anti-cancer testing of this disclosure. BMS-199264 hydrochloride (pure BMS-199264 described in [4, 7, 9, 10, 11]) was purchased from Sigma-Aldrich. BTB06584 [13] was purchased from AdooQ Bioscience. Racemate 19a [5] was synthesised by the following synthesis route and separated into component stereoisomers using superfluid chromatography (SFC). Starting reagents were sourced commercially.

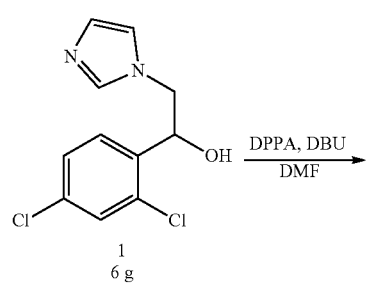
1
6 g
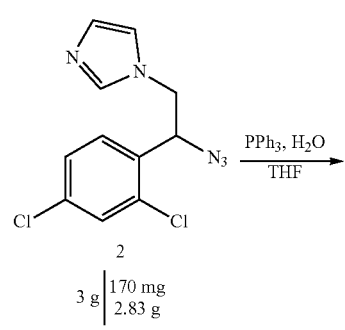
2
3 g | 170 mg
    | 2.83 g
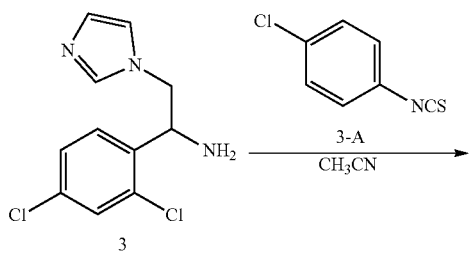
3
Use for next step directly
1.97 g
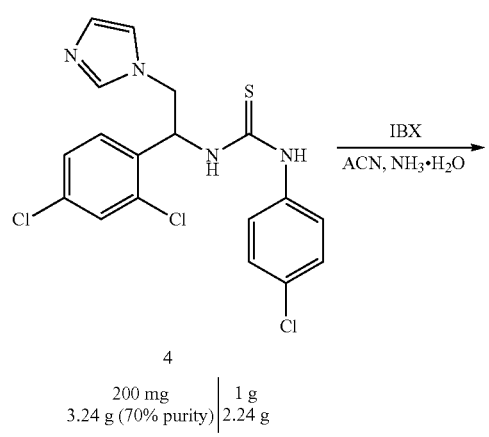
4
200 mg | 1 g
3.24 g (70% purity) | 2.24 g
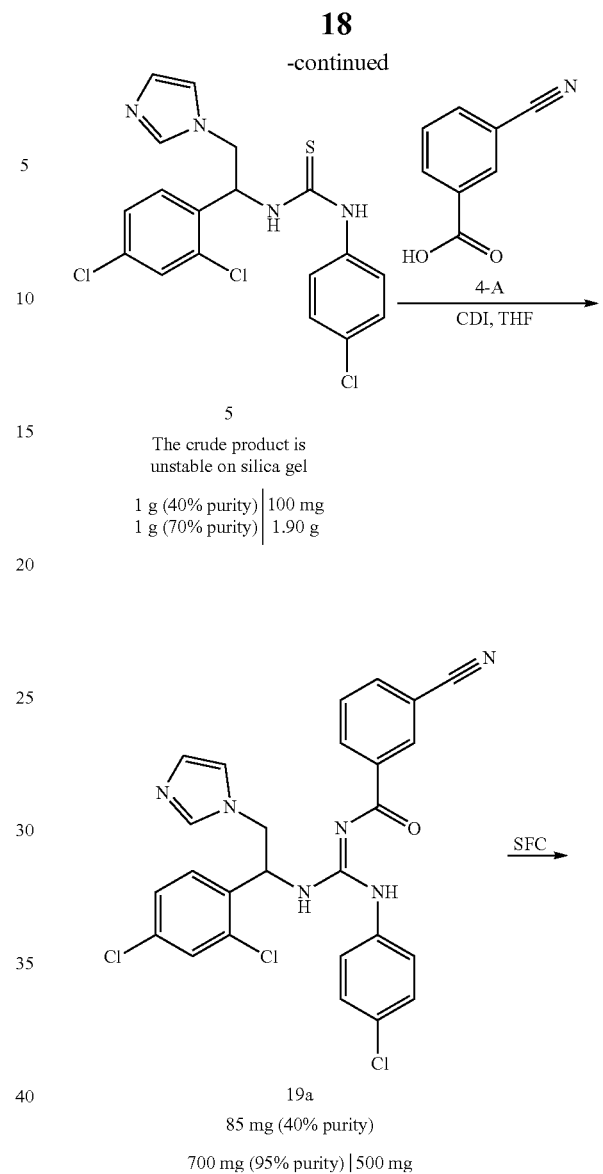
5
The crude product is unstable on silica gel
1 g (40% purity) | 100 mg
1 g (70% purity) | 1.90 g
19a
85 mg (40% purity)
700 mg (95% purity) | 500 mg
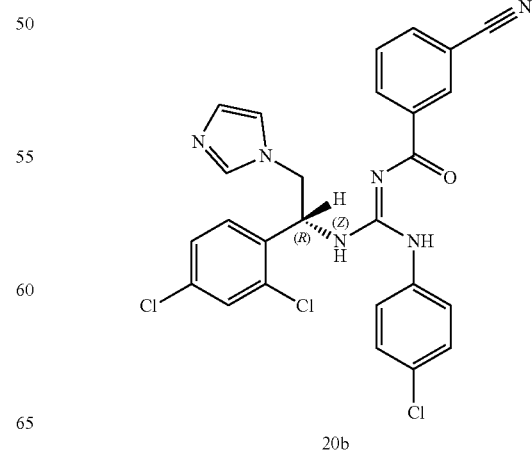
20b

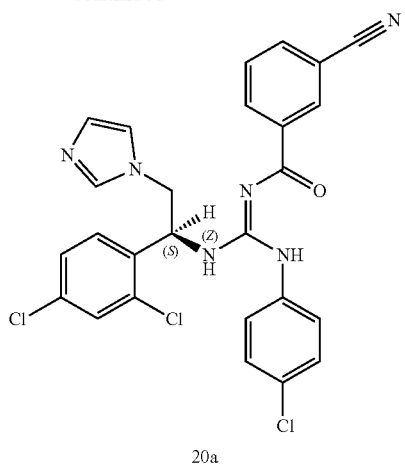

A synthesis route for structure 31 [8] as a formate.

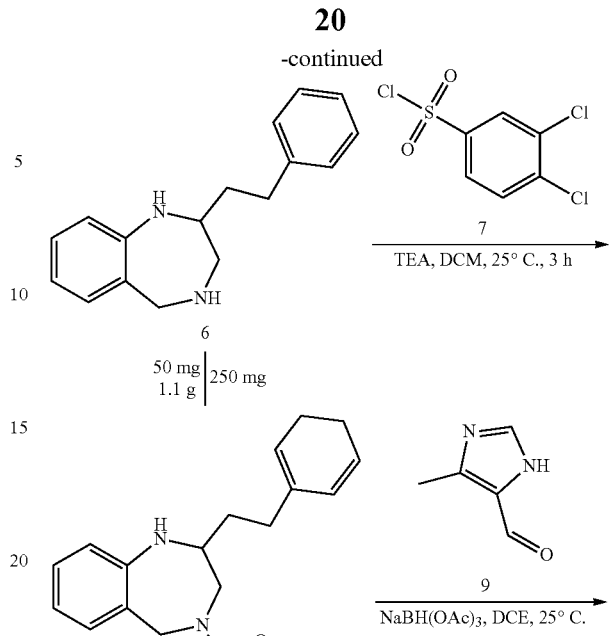

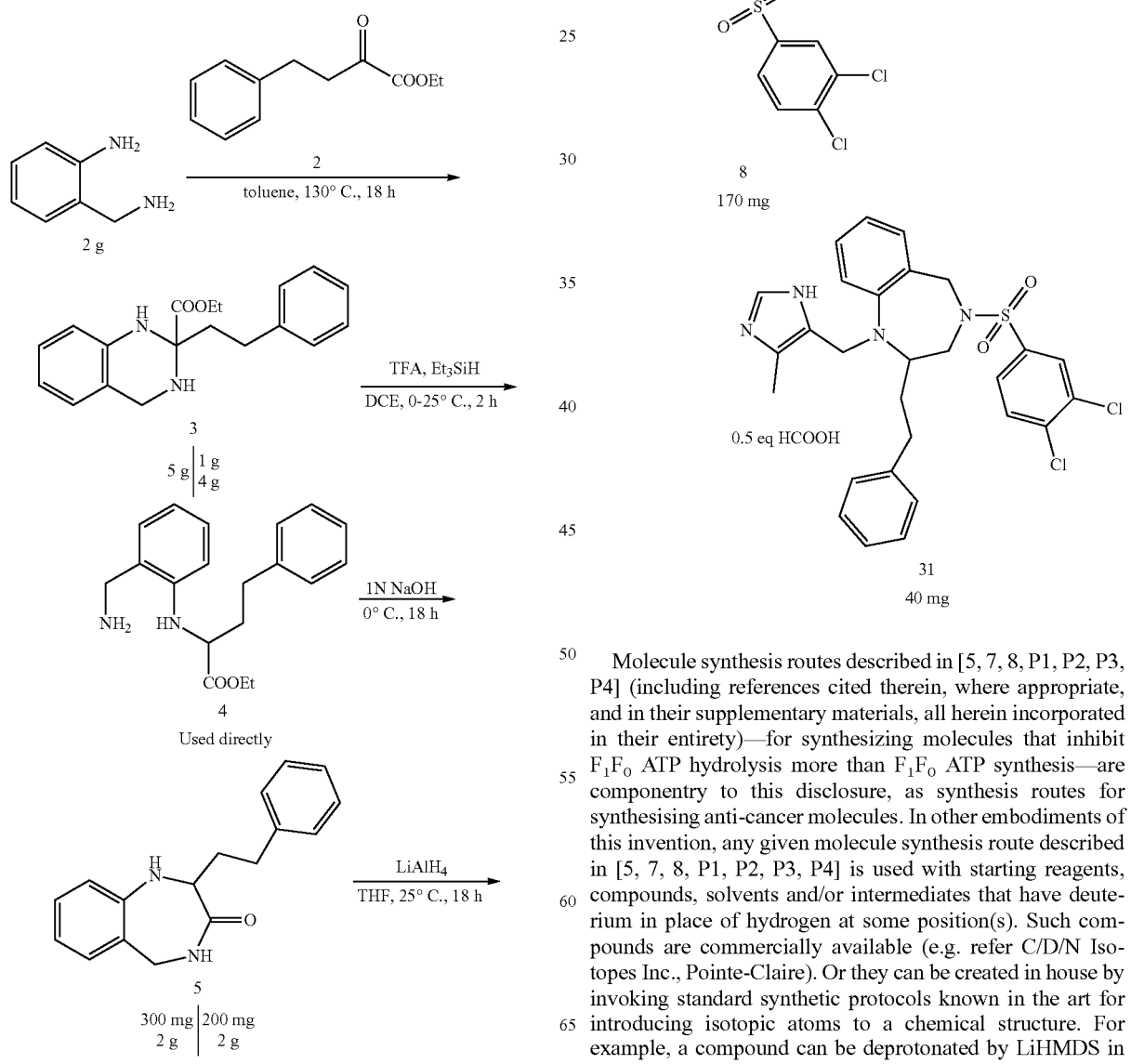

Molecule synthesis routes described in [5, 7, 8, P1, P2, P3, P4] (including references cited therein, where appropriate, and in their supplementary materials, all herein incorporated in their entirety)—for synthesizing molecules that inhibit $F_1F_0$ ATP hydrolysis more than $F_1F_0$ ATP synthesis—are componentry to this disclosure, as synthesis routes for synthesising anti-cancer molecules. In other embodiments of this invention, any given molecule synthesis route described in [5, 7, 8, P1, P2, P3, P4] is used with starting reagents, compounds, solvents and/or intermediates that have deuterium in place of hydrogen at some position(s). Such compounds are commercially available (e.g. refer C/D/N Isotopes Inc., Pointe-Claire). Or they can be created in house by invoking standard synthetic protocols known in the art for introducing isotopic atoms to a chemical structure. For example, a compound can be deprotonated by LiHMDS in tetrahydrofuran (THF) at −78 to −40° C. for 20 min, followed by quenching with deuterium oxide (D₂O, "heavy water"), to obtain a deuterated compound [33]. During these steps, a group upon which hydrogen is still desired over deuterium can be Boc protected and this Boc group removed subsequently using trifluoroacetic acid (TFA) treatment at room temperature. At the end, the level of deuterium can be checked by Proton NMR. The initial deprotonation step isn't absolutely necessary as H/D exchange will occur when a molecule is quenched with D₂O, and this reaction can be catalysed, by acid, base or metal catalysts such as platinum. If, after D₂O quenching, the level of compound deuteration is insufficient (observed using Proton NMR) then the compound is quenched with D₂O, or some other deuterium containing solvent, for a longer period of time. Compounds of this disclosure can be synthesised in D₂O, during one or more chemical steps, or a starting compound, intermediate or final molecule of this disclosure can be incubated in D₂O to produce a deuterated version(s). So, deuterium-enriched compounds of this invention can be prepared by substituting a deuterium-enriched reagent or solvent for a non-isotopically labeled reagent or solvent in the synthetic schemes reported in [5, 7, 8, P1, P2, P3, P4]. An example is presented below, which shows a modified synthesis route from that presented previously, in order to produce a deuterated analogue, with deuterium in place of hydrogen on the chiral carbon. The scheme is provided for the purpose of illustrating the invention, and should not be regarded in any manner as limiting the scope or the spirit of the invention.

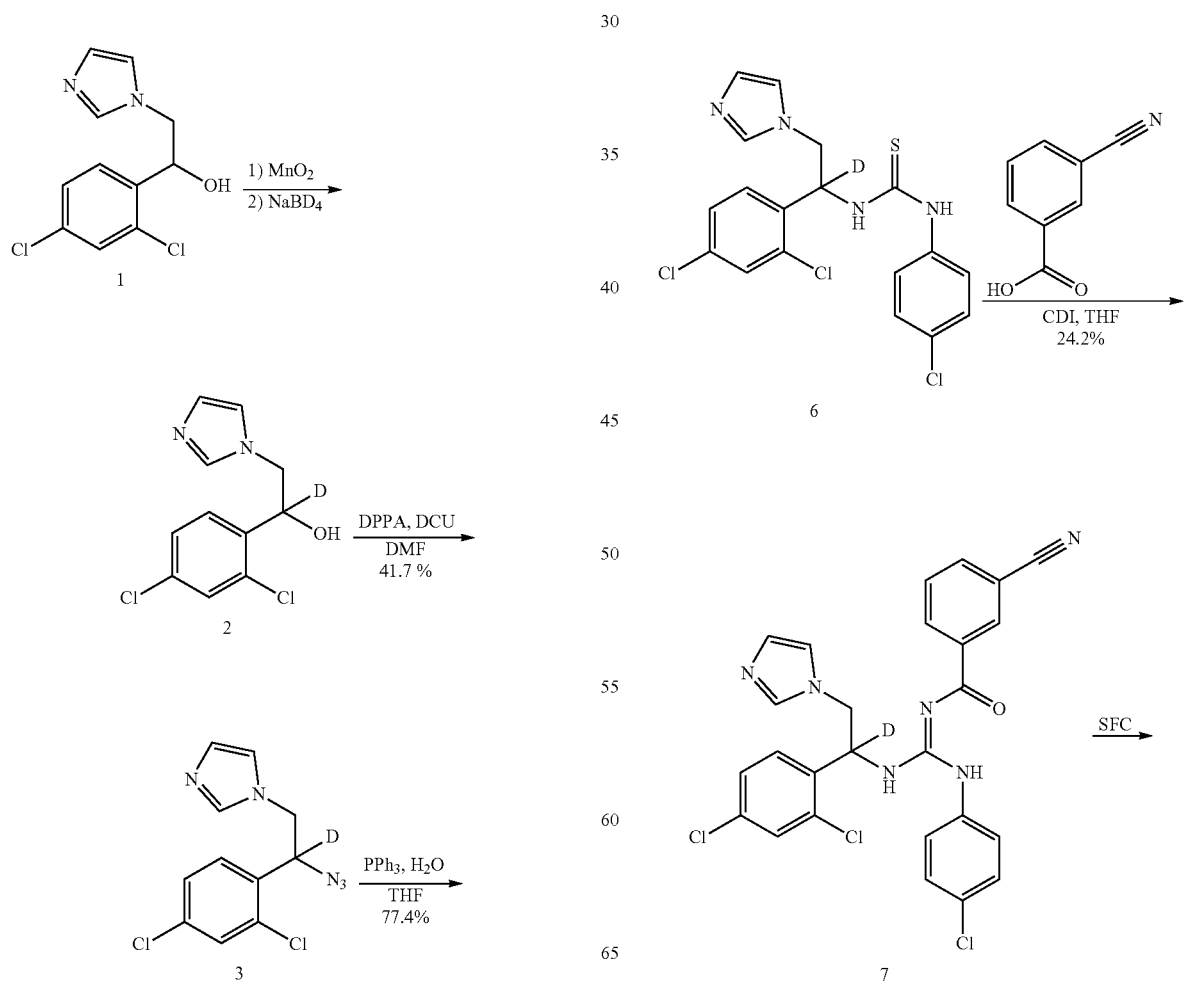

-continued

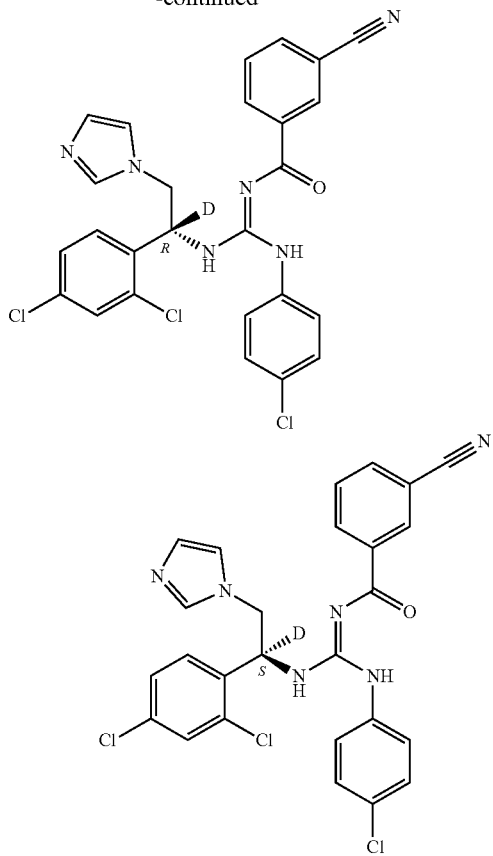

Methods to Find Further Compounds Component to This Invention

A method to find compounds that slow the proliferation of and/or kill cancer cells is by screening/seeking compounds that preferentially inhibit the reverse mode of ATP synthase. For example, by separately assaying (in space and/or time) the compounds's effect upon ATP synthesis and ATP hydrolysis by ATP synthase (in its entirety or, less preferably, a component part of it). Then comparing these assay results. The greater the inhibition of reverse vs. forward mode, the more preferred this compound is for anti-cancer use. A further method is by screening/seeking compounds that inhibit ATP hydrolysis more than synthesis in submitochondrial particles (SMPs). ATP hydrolysis can be assayed by (non-limiting example) a spectroscopic assay for NADH fluorescence that incubates the SMPs with pyruvate kinase and lactate dehydrogenase enzymes (assay well-known to those of the art). ATP synthesis can be assayed by (non-limiting example) a spectroscopic assay for NADPH fluorescence that incubates the SMPs with hexokinase and glucose-6-phosphate dehydrogenase enzymes (assay well-known to those of the art). These assays are reported in in any one of [5, 7, 8, 11, 12, 13, 36], and/or as referenced therein, all of which are herein incorporated in their entirety. In these SMP assays, the criteria for a candidate anti-cancer compound is a low $EC_{50}$ against ATP hydrolysis (thence anti-cancer activity) and a higher $EC_{50}$ against ATP synthesis (thence safe for normal cells).

Cancer Types Particularly Targeted by This Invention

Particularly vulnerable to compounds of this invention: cancers that exhibit the Warburg effect (i.e. that produce ATP primarily by glycolysis, rather than oxidative phosphorylation, even in abundant $O_2$), highly glycolytic cancers (which metabolize glucose and/or glutamine to lactate rather than metabolizing one or both fully with the use of oxidative phosphorylation) and cancers that reside in hypoxia, which forces them to produce ATP primarily by glycolysis. As explained in a preceding section, the imidazole containing molecules of this disclosure, with their uncoupling capability, can also attack cancers that reside in hypoxia, which use high $IF_1$ expression to enable oxidative phosphorylation at low $[O_2]$. Many cancers reside in hypoxia as tumours are often hypoxic.

So, if a cancer is highly glycolytic, either because of the Warburg effect (inherent glycolytic metabolism, regardless of $[O_2]$) or because of residing in hypoxia (imposed glycolytic metabolism, because of low $[O_2]$), or uses oxidative metabolism but resides in hypoxia (survival enabled by high $IF_1$ expression), it will be treated/ameliorated/prevented/combated by a compound of this invention. How to identify such cancers?

Cancers exhibiting the Warburg effect, or that have an imposed (by low $[O_2]$) glycolytic metabolism, are those that show up in positron emission tomography (PET) imaging using fluorine-18 ($^{18}F$) fluorodeoxyglucose (FDG), $^{18}F$-FDG PET, optionally integrated with computed tomography (CT) [40]. FDG is a glucose analogue and glycolytic cancers take up more FDG than their surrounding tissue because glycolysis is an inefficient metabolism of glucose (yielding only ~2 ATP per glucose compared to ~31 ATP per glucose yielded by aerobic respiration [1-2]) and so they must uptake more glucose to obtain even the equivalent energy yield to nearby normal cells, which are using oxidative metabolism, as most normal cells do. So, if a cancer presents in this FDG-PET diagnostic (higher glucose uptake than surround), it is susceptible to a compound of this invention. Highly glycolytic cancers also release much lactate. So, if a patient has a high blood lactate level, noticeably above the normal non-pathological range, as clear to someone of the art, then their cancer is susceptible to a compound of this invention. Higher lactate levels in and around the cancer or tumour (than surrounding tissue) can also be detected using imaging technologies, for example $^1H$ Magnetic Resonance Spectroscopy ($^1H$-MRS) or chemical exchange saturation transfer magnetic resonance imaging (CEST MRI) [41], or other imaging modalities and methods of the art. So, if a cancer presents (higher [lactate] than surround) in a lactate imaging diagnostic it is susceptible to a compound of this invention. Cancer release of lactic acid acidifies its extracellular space and this acidification can be detected by imaging modalities, well known to those of the art e.g. [42-43], and if a cancer can be discriminated from its surrounding tissue by this method then it is susceptible to a compound of this invention. An oxygen-sensitive chemical probe can be used to obtain 3D maps of tissue pO2 [44], and if a cancer is shown to reside in notable hypoxia then it is susceptible to a compound of this disclosure, because it is either glycolytic or using high $IF_1$ expression to enable oxidative metabolism, both of which make it susceptible to a compound of this invention. Imaging technologies can be integrated to improve signal to noise e.g. [44] integrate pO2 and lactate imaging. Such integration can give added information: for example, a cancer producing much lactate in a high pO2 environment is exhibiting the Warburg effect because it is heavily utilising glycolytic metabolism in abundant $O_2$. Cancer gene expression markers and indicators of the Warburg effect, well known to those of the art e.g. [18-20], specify that a cancer is susceptible to a compound of this invention, wherein the cancer's genetic material can be retrieved by biopsy, surgery, cancer cells or parts circulating in the bloodstream or some other method of the art.

If a cancer uses oxidative phosphorylation (OXPHOS) rather than glycolytic metabolism, and it does not already improve its OXPHOS efficiency by high $IF_1$ gene expression (which many cancers do e.g. refer [21]) then a compound of this invention, by preferentially inhibiting $F_1F_0$ ATP hydrolysis, will confer this efficiency gain and actually assist, rather than harm, this cancer. How to identify these cancers? A cancer's $IF_1$ gene expression, and particularly its gene expression ratio of $IF_1$ to a core ATP synthase sub-unit (e.g. ATP6), is informative. More so if compared to the corresponding gene expressions in a normal cell of its host tissue, so detecting difference from normal. If a cancer uses oxidative, rather than glycolytic, metabolism and does not have an appreciably higher $IF_1$ (or $IF_1$/ATP6 ratio) gene expression than its corresponding normal tissue then it isn't prudent to use a compound of this invention for cancer therapy. More simply, it is best to use a compound(s) of this invention against highly glycolytic cancers and some (non-limiting) imaging methods have been described herein to identify these.

This invention discloses a method of using a compound(s) that preferentially inhibits the ATP-hydrolysing mode of ATP synthase, for example a compound(s) of Formula (I), (II), (III), (IV) or (V), or a pharmaceutically-acceptable salt, solvate, hydrate or prodrug thereof, to treat/ameliorate/prevent/combat a cancer that preferentially uses glycolytic rather than oxidative metabolism, for example a cancer exhibiting the Warburg effect, and discloses methods to identify these cancers. Identification methods specified are to illustrate the invention and not to limit its scope: this invention encompasses all methods to identify highly glycolytic cancers, in order to identify cancers most amenable to treatment by a compound(s) of this invention.

So, innovatively and usefully, compounds of this disclosure are selected for anti-cancer therapy by metabolic feature of the cancer, which belie how the cancer survives and proliferates, and its weaknesses, weaknesses that compounds of this disclosure attack, rather than the typical, often too arbitrary, often unhelpful, allocation by tissue type, which is the present standard in the art. A diversity of cancers, from different tissues, will be susceptible to compounds of this invention, especially the most dangerous: glycolytic cancers, with high lactate efflux, often have the worst prognosis [18-20, 22]. Experimental data of this disclosure shows that compounds of this invention are effective against breast, prostate, renal, ovarian, skin, central nervous system, colon or lung cancer and leukaemia. Especially leukaemia.

Compounds of the present invention treat tumour growth, treat metastasis, treat metastatic cancer, treat non-metastatic cancer, treat tumour implantation, are useful as an adjunct to chemo-/radio-therapy, treat cancers including, but not limited to, Chondrosarcoma, Ewing's sarcoma, Malignant fibrous histiocytoma of bone/osteosarcoma, Osteosarcoma, Rhabdomyosarcoma, Heart cancer, brain cancer, Astrocytoma, Brainstem glioma, Pilocytic astrocytoma, ependymoma, primitive neuroectodermal tumor, Cerebellar astrocytoma, Cerebral astrocytoma, malignant glioma, Medulloblastoma, Neuroblastoma, Oligodendroglioma, Pineal astrocytoma, Pituitary adenoma, Visual pathway and hypothalamic glioma, Breast cancer, Invasive lobular carcinoma, Tubular carcinoma, Invasive cribriform carcinoma, Medullary carcinoma, Male breast cancer, Phyllodes tumor, Inflammatory Breast Cancer, Adrenocortical carcinoma, Islet cell carcinoma, Multiple endocrine neoplasia syndrome, Parathyroid cancer, Pheochromocytoma, Thyroid cancer, Merkel cell carcinoma, intraocular melanoma, retinoblastoma, Anal cancer, Appendix cancer, cholangiocarcinoma, Carcinoid tumor, Colon cancer, Extrahepatic bile duct cancer, Gallbladder cancer, Gastric (stomach) cancer, Gastrointestinal carcinoid tumor, Gastrointestinal stromal tumor (GIST), Hepatocellular cancer, Pancreatic cancer, Rectal cancer, Bladder cancer, Cervical cancer, Endometrial cancer, Extragonadal germ cell tumor, Ovarian cancer, Ovarian epithelial cancer (surface epithelial-stromal tumor), Ovarian germ cell tumor, Penile cancer, Renal cell carcinoma, Renal pelvis and ureter, transitional cell cancer, Prostate cancer, Testicular cancer, Gestational trophoblastic tumor, Ureter and renal pelvis, transitional cell cancer, Urethral cancer, Uterine sarcoma, Vaginal cancer, Vulvar cancer, Wilms tumor, Esophageal cancer, Head and neck cancer, Nasopharyngeal carcinoma, Oral cancer, Oropharyngeal cancer, Paranasal sinus and nasal cavity cancer, Pharyngeal cancer, Salivary gland cancer, Hypopharyngeal cancer, Acute biphenotypic leukemia, Acute eosinophilic leukemia, Acute lymphoblastic leukemia, Acute myeloid leukemia, Acute myeloid dendritic cell leukemia, AIDS-related lymphoma, Anaplastic large cell lymphoma, Angio-immunoblastic T-cell lymphoma, B-cell prolymphocytic leukemia, Burkitt's lymphoma, Chronic lymphocytic leukemia, Chronic myelogenous leukemia, Cutaneous T-cell lymphoma, Diffuse large B-cell lymphoma, Follicular lymphoma, Hairy cell leukemia, Hepatosplenic T-cell lymphoma, Hodgkin's lymphoma, Hairy cell leukemia, Intravascular large B-cell lymphoma, Large granular lymphocytic leukemia, Lymphoplasmacytic lymphoma, Lymphomatoid granulomatosis, Mantle cell lymphoma, Marginal zone B-cell lymphoma, Mast cell leukemia, Mediastinal large B cell lymphoma, Multiple myeloma/plasma cell neoplasm, Myelodysplastic syndromes, Mucosa-associated lymphoid tissue lymphoma, Mycosis fungoides, Nodal marginal zone B cell lymphoma, Non-Hodgkin lymphoma, Precursor B lymphoblastic leukemia, Primary central nervous system lymphoma, Primary cutaneous follicular lymphoma, Primary cutaneous immunocytoma, Primary effusion lymphoma, Plasmablastic lymphoma, Sézary syndrome, Splenic marginal zone lymphoma, T-cell prolymphocytic leukemia, Basal-cell carcinoma, Melanoma, Skin cancer (non-melanoma), Bronchial adenomas/carcinoids, Small cell lung cancer, Mesothelioma, Non-small cell lung cancer, Pleuropulmonary blastoma, Laryngeal cancer, Thymoma and thymic carcinoma, AIDS-related cancers, Kaposi sarcoma, Epithelioid hemangioendothelioma (EHE), Desmoplastic small round cell tumor, Liposarcoma. The compounds of the present invention treat cancers including, but not limited to, those that originate in the Testis, Cerebral cortex, Skin, Fallopian tube, Parathyroid gland, Small intestine, large intestine, Kidney, Skeletal muscle, Duodenun, Spleen, Epididymis, Bone marrow, Lymph node, Adrenal gland, Esophagus, Thyroid gland, Heart muscle, Tonsil, Lung, Prostate, Rectum, Anus, Adipose tissue, Colon, Stomach, Cervix, Gallbladder, Seminal vesicle, Breast, Ovary, Endometrium, Smooth muscle, Salivary gland, Pancreas, Urinary bladder, blood, brain, gum, head, liver, nasopharynx, neck, tongue, uterus.

Compounds of this Invention are Anti-Inflammatories

An embodiment of this invention is a method of using an effective amount of at least one compound of this disclosure, which inhibits $F_1F_0$ ATP hydrolysis, as an immunosuppressant and/or anti-inflammatory therapeutic. Because activated macrophages, unlike resting macrophages, use and rely upon ATP synthase in its reverse mode, hydrolysing ATP [45]. Activated macrophages produce nitric oxide (NO), which switches down/off OXPHOS (NO increases the Km of Complex IV for $O_2$) and makes them reliant upon $F_1F_0$ ATP hydrolysis to maintain $\psi_{IM}$. If $\psi_{IM}$ collapses, apoptosis ensues. Compounds of the present invention inhibit $F_1F_0$ ATP hydrolysis, thus attenuating the activated macrophage component to inflammation, and its pathologies, and treats/ameliorates/prevents/combats any disease or disorder associated with the undesirable activation or activity of macrophages, and/or any other NO producing cells of the innate immune system (e.g. monocyte-derived inflammatory dendritic cells), and/or immune or inflammation diseases/disorders/pathologies including, but not limited to, acute inflammation, chronic inflammation, systemic inflammation, inflammation because of infection or foreign bodies or injury or chemical or toxin or drug or stress or frostbite or burn or ionising radiation, inflammatory diseases/disorders/syndromes, Macrophage Activation Syndrome (MAS), autoinflammatory diseases/disorders/syndromes, age-related chronic inflammatory diseases ("inflammaging"), autoimmune diseases/disorders/syndromes, diseases/disorders of the innate immune system, sore throat, sore throat associated with cold or flu or fever, high-intensity exercise associated inflammation, ulcerative colitis, inflammatory bowel disease (IBD), irritable bowel syndrome (IBS), rheumatoid arthritis, osteoarthritis, psoriatic arthritis, atopic dermatitis, allergic airway inflammation, asthma, inflammation associated depression, exercise-induced acute inflammation, atherosclerosis, allergy, hay fever, anaphylaxis, inflammatory myopathies, drug-induced inflammation, systemic inflammatory response syndrome, sepsis-related multiple organ dysfunction/multiple organ failure, microbial infection, acute brain/lung/hepatic/renal injuries, acne vulgaris, celiac disease, celiac sprue, chronic prostatitis, colitis, diverticulitis, glomerulonephritis, hidradenitis suppurativa, hypersensitivities, interstitial cystitis, Mast Cell Activation Syndrome, mastocytosis, otitis, pelvic inflammatory disease (PID), reperfusion injury, rheumatic fever, rhinitis, sarcoidosis, transplant rejection, parasitosis, eosinophilia, type III hypersensitivity, ischaemia, chronic peptic ulcer, tuberculosis, Crohn's disease, hepatitis, chronic active hepatitis, immune hepatitis, ankylosing spondylitis, diverticulitis, fibromyalgia, systemic lupus erythematous (SLE), Alzheimer's disease, Parkinson's disease, neurodegenerative disease, cardiovascular disease, chronic obstructive pulmonary disease, bronchitis, acute bronchitis, appendicitis, acute appendicitis, bursitis, colitis, cystitis, dermatitis, encephalitis, gingivitis, meningitis, infective meningitis, myelitis, nephritis, neuritis, periodontitis, chronic periodontitis, phlebitis, prostatitis, RSD/CRPS, rhinitis, sinusitis, chronic sinusitis, tendonitis, testiculitis, tonsillitis, urethritis, vasculitis, respiratory bronchiolitis-associated interstitial lung disease and desquamative interstitial pneumonia, interstitial lung disease, Löfgren syndrome, Heerfordt syndrome, monocytosis, liver fibrosis, steatohepatitis, nonalcoholic steatohepatitis, silicosis, histiocytoses, Langerhans' cell histiocytosis, haemophagocytic lymphohistiocytosis, pulmonary langerhans cell histiocytosis, obesity, type II diabetes, gout, pseudogout, organ transplant rejection, epidermal hyperplasia, chronic fatigue syndrome, graft versus host disease (GVHD), lymphadenopathy.

In clinical utility, the anti-inflammatory activity of compounds of this invention juxtaposes well with their aforementioned ability to reduce body temperature.

The anti-inflammatory action by compounds of this invention has an anti-cancer action. Because it reduces the number of Tumour Associated Macrophages (TAMs) [46]. These can constitute a large component of tumour mass and their presence is often associated with poor patient prognosis because they can drive cancer pathology. Indeed, inflammation is now considered one of the hallmarks of cancer [47]. The anti-inflammatory action, and thence anti-cancer action, of these compounds synergises with their direct anti-cancer activities disclosed herein.

Macrophages can be subverted by pathogens, which hide inside them in safety from the immune system. Non-limiting examples of such pathogens are HIV (causes HIV/AIDS; HIV virus can lay latent in macrophages during antiretroviral therapy, wherein HIV virus becomes undetectable in blood, and then repopulate the virus in blood when antiretroviral therapy is interrupted or discontinued; HIV can replicate in macrophages [48]), *Mycobacterium tuberculosis* (causes tuberculosis), *Leishmania* parasite (causes Leishmaniasis), Chikungunya virus (causes Chikungunya), *Legionella pneumophila* (causes Legionnaires' disease), adenovirus (causes pink eye), *T. whipplei* (causes Whipple's Disease) and *Brucella* spp. (causes brucellosis). So, by exerting anti-macrophage activity, compounds of this disclosure can treat/ameliorate/prevent/combat such disorders and diseases. Because the compounds of this invention are selective for activated macrophages, an option is to activate macrophages before the compound administration, by administering to the patient an effective amount of a compound, protein, antibody or some other entity, e.g. pathogen, attenuated pathogen or pathogen component that activates macrophages. Some examples (non-limiting) of factors that can activate macrophages are cytokines such as interferon-gamma (IFN-gamma) and/or tumour necrosis factor (TNF), and/or IL-4, and/or IL-13, and/or IL-10, and/or IL-2, and/or IL-12, and/or IL-6, and/or IL-18 and/or chemokines (CCL3, CCL4, CCL5) and/or a bacterial endotoxin such as lipopolysaccharide (LPS), or a commercially available agent for macrophage activation in biological research (e.g. CAS 61512-20-7) or an antibody targeting a receptor on the macrophage cell surface or on the surface of a different cell type, which then activates a macrophage by mechanism. Macrophage activating antibodies are well known to those of the art.

An embodiment of this invention is the use of an effective amount of at least one compound of this invention, which inhibits $F_1F_0$ ATP hydrolysis, to treat/ameliorate/prevent/combat HIV infection, optionally with an effective amount of a compound, protein, antibody, pathogen or pathogen component that activates macrophages (isn't absolutely necessary because HIV activates macrophages [50-51], which drives the chronic inflammation pathology component to HIV infection) optionally in co-therapy with, or after, anti-retroviral therapy (ART) or combination anti-retroviral therapy (cART). Even after prolonged cART, which drives plasma HIV down to undetectable levels, HIV-1 DNA and RNA is detectable in macrophages: they are an HIV reservoir that remains extant, even during cART, and that the virus can spread from during any interruption or termination of cART [49]: thence the vital importance of the methods and compounds herein. Furthermore, these compounds treat/ameliorate/prevent/combat HIV-associated chronic inflammation.

Macrophages mediate HIV virus neuroinvasion (and neuroinvasion by other viruses also e.g. SARS coronavirus) and compounds of this invention oppose this and treat/ameliorate/prevent/combat HIV-associated neurocognitive disorders (HAND) (and neurocognitive and neurodegenerative diseases/disorders caused by other viruses also e.g. SARS coronavirus). The anti-HIV and anti-cancer activity of the compounds of this invention synergise to treat/ameliorate/prevent/combat HIV associated cancers: AIDS-defining cancers (Kaposi sarcoma, aggressive B-cell non-Hodgkin lymphoma, cervical cancer.) and non-AIDS defining cancers. This disclosure encompasses a compound(s) of this invention in co-therapy with any Food and Drug Administration (FDA) approved drug(s) or treatment for HIV or AIDS. Examples include, but aren't limited to, abacavir, didanosine, emtricitabine, lamivudine, stavudine, tenofovir, disoproxil fumarate (tenofovir DF, TDF), zidovudine (azidothymidine, AZT, ZDV), atazanavir, darunavir, fosamprenavir, indinavir, nelfinavir, ritonavir, saquinavir, tipranavir, enfuvirtide, maraviroc, dolutegravir, elvitegravir, raltegravir, cobicistat.

Non-limiting examples of autoinflammatory diseases/disorders/syndromes that the compounds of this invention treat/ameliorate/prevent/combat include, but aren't limited to, recurrent fever syndromes, which can be hereditary or acquired, characterized by recurrent fever associated with rash, serositis, lymphadenopathy and musculoskeletal involvement. Examples include familial mediterranean fever (FMF), TNF receptor —associated periodic syndrome (TRAPS), Hyperimmunoglobulinemia D with recurrent fever syndrome (HIDS), cryopyrin associated periodic syndrome (CAPS), Blau syndrome, Majeed syndrome, deficiency of interleukin-1 receptor antagonist (DIRA), mevalonate kinase deficiency, pyogenic-arthritis-pyoderma gangrenosum and acne syndrome (PAPA), periodic fever aphthous stomatitis pharyngitis adenitis (PFAPA) syndrome, Behcet's disease, Still's disease, Crohn's disease, Schnitzler's syndrome, Sweet's syndrome, NLRP12-associated autoinflammatory disorders, deficiency of interleukin-1 receptor antagonist (DIRA), pyoderma gangrenosum, cystic acne, aseptic arthritis, periodic Fever Associated with mevalonate kinase deficiency (hyperimmunoglobulin D Syndrome), Pyogenic Arthritis Pyoderma Gangrenosum Acne (PAPA) syndrome, Periodic Fever Aphthous Stomatitis, Pharyngitis and Adenopathy (PFAPA) syndrome, Adult-Onset Still's Disease (AOSD), Systemic Juvenile Idiopathic Arthritis (sJIA), Chronic Recurrent Multifocal Osteomyelitis (CRMO), Synovitis Acne Pustulosis Hyperostosis Osteitis (SAPHO) syndrome, Cryopyrin associated Periodic Syndrome (CAPS), Familial cold auto inflammatory syndrome (FCAS), Muckle-Wells syndrome (MWS), Familial cold urticarial, Neonatal onset multisystemic inflammatory disorder (NOMID), hereditary Periodic Fever Syndromes, Periodic Fever Syndromes, systemic autoinflammatory diseases.

Non-limiting examples of autoimmune diseases/disorders/syndromes that the compounds of this invention treat/ameliorate/prevent/combat include, but aren't limited to, Addison's disease, Agammaglobulinemia, Alopecia areata, Amyloidosis, Ankylosing spondylitis, Anti-GBM/Anti-TBM nephritis, Antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune pancreatitis, autoimmune retinopathy, autoimmune urticaria, axonal & neuronal neuropathy (AMAN), Baló disease, Behcet's disease, benign mucosal pemphigoid, Bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss, Cicatricial pemphigoid, Cogan's syndrome, cold agglutinin disease, congenital heart block, coxsackie myocarditis, CREST syndrome, Berger's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, immune hemolytic anemia, Henoch-Schonlein purpura (HSP), Herpes gestationis or pemphigoid gestationis (PG), hypogammalglobulinemia, IgA Nephropathy, IgG4-related sclerosing disease, Immune thrombocytopenic purpura (ITP), Inclusion body myositis (IBM), Interstitial cystitis (IC), juvenile arthritis, juvenile diabetes (Type 1 diabetes), juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism (PR) PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, peripheral neuropathy, perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Wegener's granulomatosis (or Granulomatosis with Polyangiitis (GPA)), idiopathic thrombocytopenia purpura, splenomegaly.

DESCRIPTION OF THE DRAWINGS

For purposes of clarity, not every component is labelled in every figure, nor is every component of each embodiment of the invention shown where illustration is not necessary to allow those of ordinary skill in the art to understand the invention.

FIGS. 1, 2, 3, 4, 5, 6 show results from the NCI-60 one-dose in vitro assay [29-30] at the Developmental Therapeutics Program (DTP), at the National Cancer Institute (NCI, Bethesda, MD, USA). Its protocol is well known to those of the art, and it tests the effect, if any, of a test compound on the growth/survivability of a cancer cell line as compared to the no compound control. When this protocol was first developed, a compound was tested against 60 cancer cell lines, hence the name NCI-60, but more recently this has been reduced to 59 cell lines, and there is some variation over time in the cancer cell lines making up this 59. However, a constant is that this 59 always has representative cell lines from leukemia, melanoma and cancers of the lung, colon, brain, ovary, breast, prostate and kidney. In a one-dose NCI compound test report, NCI report a number for each cell line, which they call "Growth Percent", which is its growth relative to the no-compound control, and relative to the time zero number of cells. This reported parameter allows detection of both growth inhibition (values between 0 and 100) and lethality (values less than 0). For example, an NCI "Growth Percent" value of 100 means no growth inhibition. Value of 40 means 60% growth inhibition. Value of 0 means no net growth over the course of the experiment. Value of −40 means 60% lethality. Value of −100 means all cells are dead. I don't present NCI one-dose data in this original format. Instead, if the NCI "Growth Percent" value for a cell is positive, it is manipulated: [100 minus this original NCI-60 "Growth Percent" data point], to yield the percentage "Growth Inhibition". If the original NCI "Growth Percent" value for a cell is negative, it is made positive to be the percentage of original cancer cells (at time zero) killed: "Percentage Killed" {and in these cases, of course, all growth has been inhibited, so percentage "Growth Inhibition" is then specified to be 100% for this cancer cell line}. In my one-dose figures, "Growth Inhibition" (0-100%) is presented on the x-axis and, if applicable, "Percentage Killed" (0-100%) further along on the x-axis. The latter is applicable when there is not just cancer growth inhibition but a reduction in the number of cancer cells from the start time i.e. when the compound is not merely slowing cancer growth, but is actively reducing the number of cancer cells from the starting number. In cases where there is only growth inhibition, only "Growth inhibition" is presented on the x-axis. In all cases, the greater the percentage number on the x-axis, for a given cancer cell line named on the y-axis, the greater the anti-cancer activity of this compound against this cancer cell line.

FIG. 1: No anti-cancer activity of BTB06584 at 10 μM (NCI one-dose assay).

FIG. 2: Anti-cancer activity of BTB06584 at 100 μM (NCI one-dose assay).

FIG. 3: Anti-cancer activity of BMS-199264 hydrochloride at 10 μM (NCI one-dose assay).

FIG. 4: Anti-cancer activity of BMS-199264 hydrochloride at 100 μM (NCI one-dose assay).

FIG. 5: 19a is a racemate. Superfluid chromatography (SFC) was used to separate 19a into its component R (6a) and S (6b) stereoisomers, which don't and do inhibit $F_1F_0$ ATP hydrolysis respectively, and two samples of opposite >97% enantiomeric excess (ee) were achieved. But during NCI one-dose (10 μM) testing, these samples underwent racemization and their ee was eroded. Such that both samples contained S stereoisomer and both exerted anti-cancer activity. Racemization was advanced (Pearson correlation between results, R=0.8) but yet incomplete and the S sample still had more S stereoisomer, and greater anti-cancer activity, than the other sample. $EC_{50}$ values are from SMP studies in [5-6].

FIG. 6: Anti-cancer potency of these molecules scales with their inhibition of ($EC_{50}$) $F_1F_0$ ATP hydrolysis. The experimental panels of this figure correspond to figures presented elsewhere in this disclosure and so, although cell lines aren't named on the y-axes (space didn't permit), any given horizontal bar in a panel can be linked to its cancer name by cross-correlating the panel to its corresponding figure herein, wherein cell line names are given. $EC_{50}$ values for BMS-199264 and 19a are from SMP studies in [5-7], BTB06584 potency information (isn't an $EC_{50}$) is from a whole cell study [13].

FIG. 7: Anti-cancer activity of BMS-199264 hydrochloride. Results from the NCI-60 five-dose in vitro assay [29-30] at the Developmental Therapeutics Program (DTP), at the National Cancer Institute (NCI, Bethesda, MD, USA). In this assay, which is well known to those of the art, a compound is tested, in vitro, against 59 different cancer cell lines, sourced from 9 different tissue types, across 5 different concentrations. On the y-axis is the aforementioned "Growth Percentage" parameter used by NCI, which is growth relative to the no-compound control, and relative to the time zero number of cells. This parameter allows detection of both growth inhibition (values between 0 and 100) and lethality (values less than 0). GI50 is the compound concentration that causes 50% growth inhibition of a cell line relative to the no-drug control. Each cancer cell line has a GI50 value and the "mean GI50" of all 59 cell lines can be calculated. The mean GI50 for BMS-199264 hydrochloride is 3.9 μM.

Figure 1:
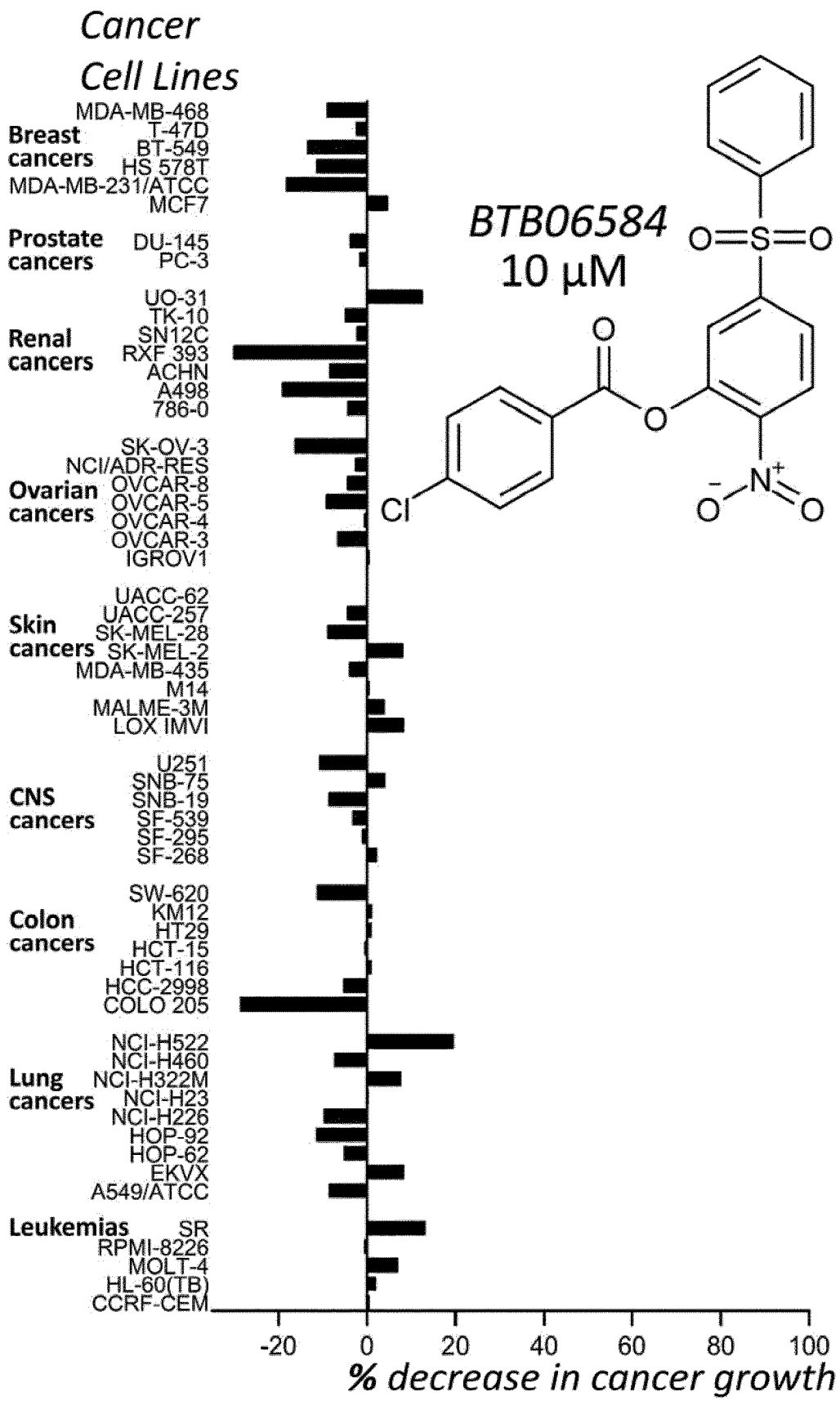
FIGS. 1, 2, 3, 4, 5, 6, 7: Experimental evidence: molecules that specifically inhibit the reverse mode of ATP synthase: specifically exert anti-cancer activity: representative, non-limiting examples.
Figure 2:
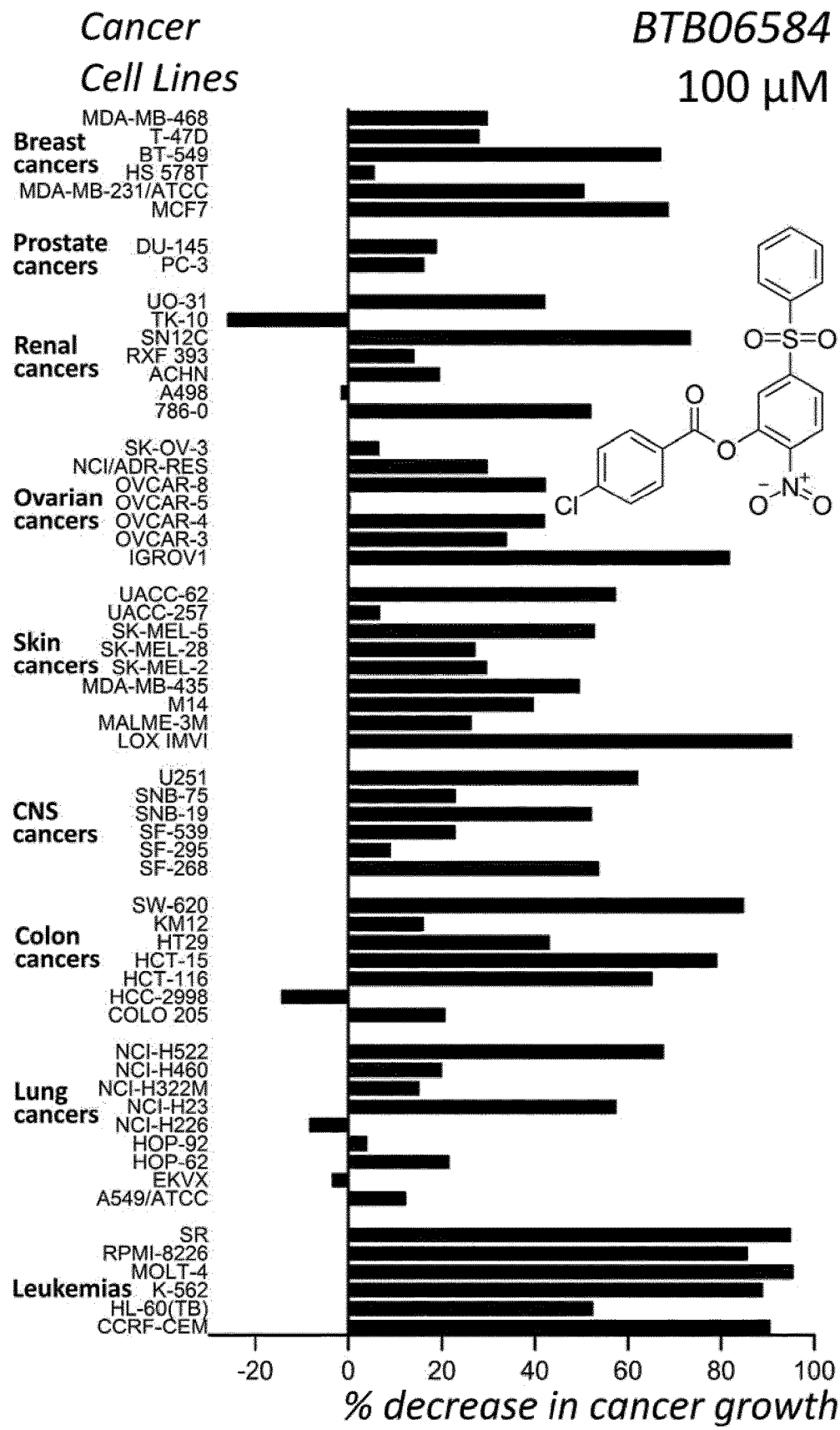
Figure 3:
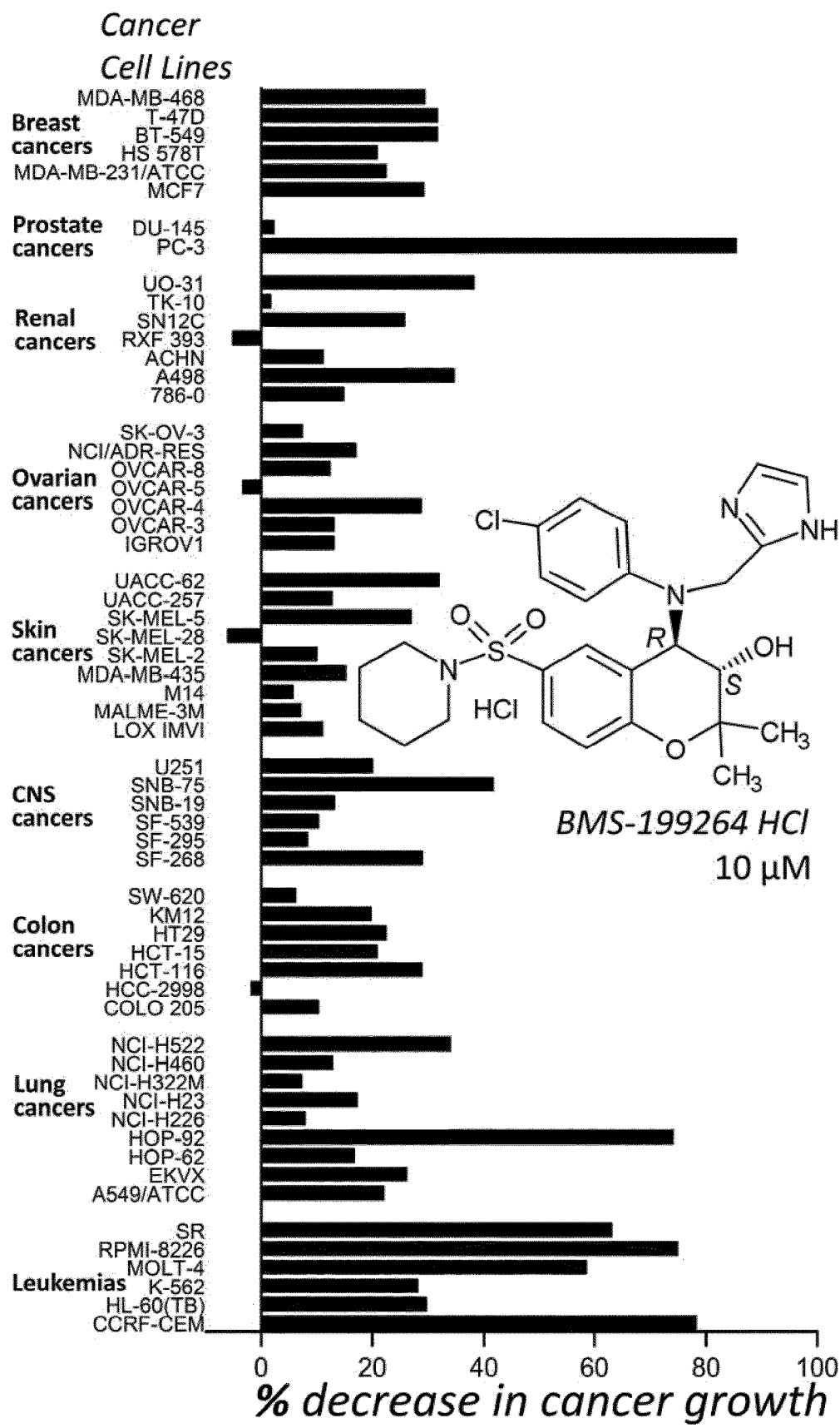
Figure 4:
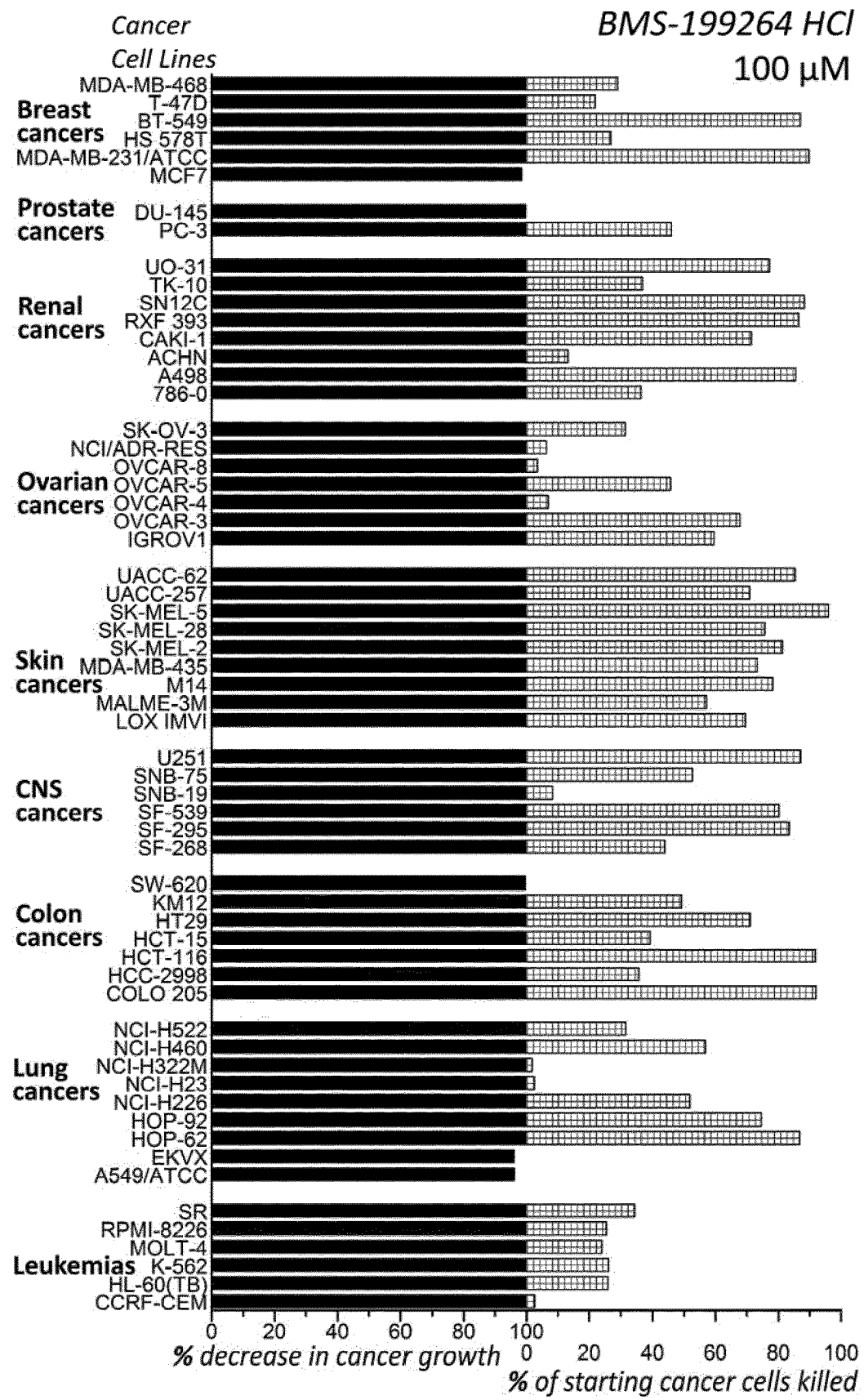
Figure 5:
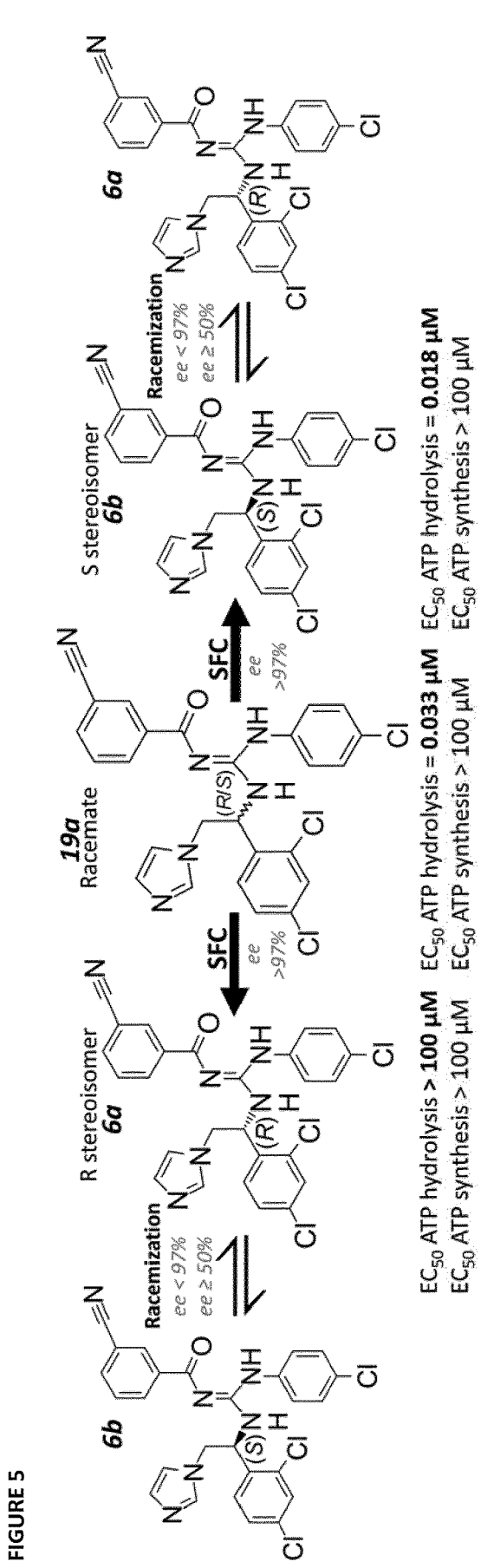
Figure 5:
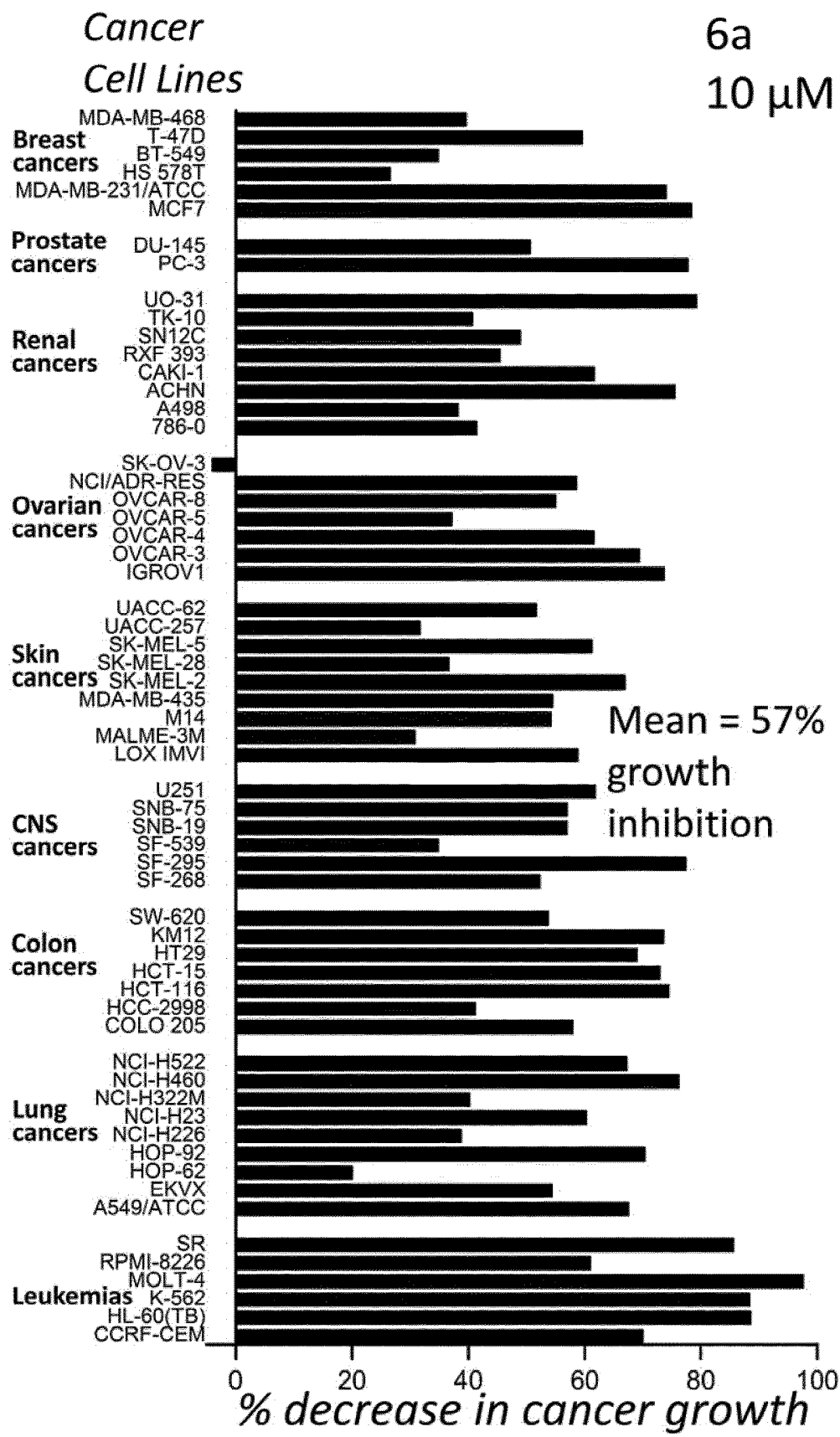
Figure 5:
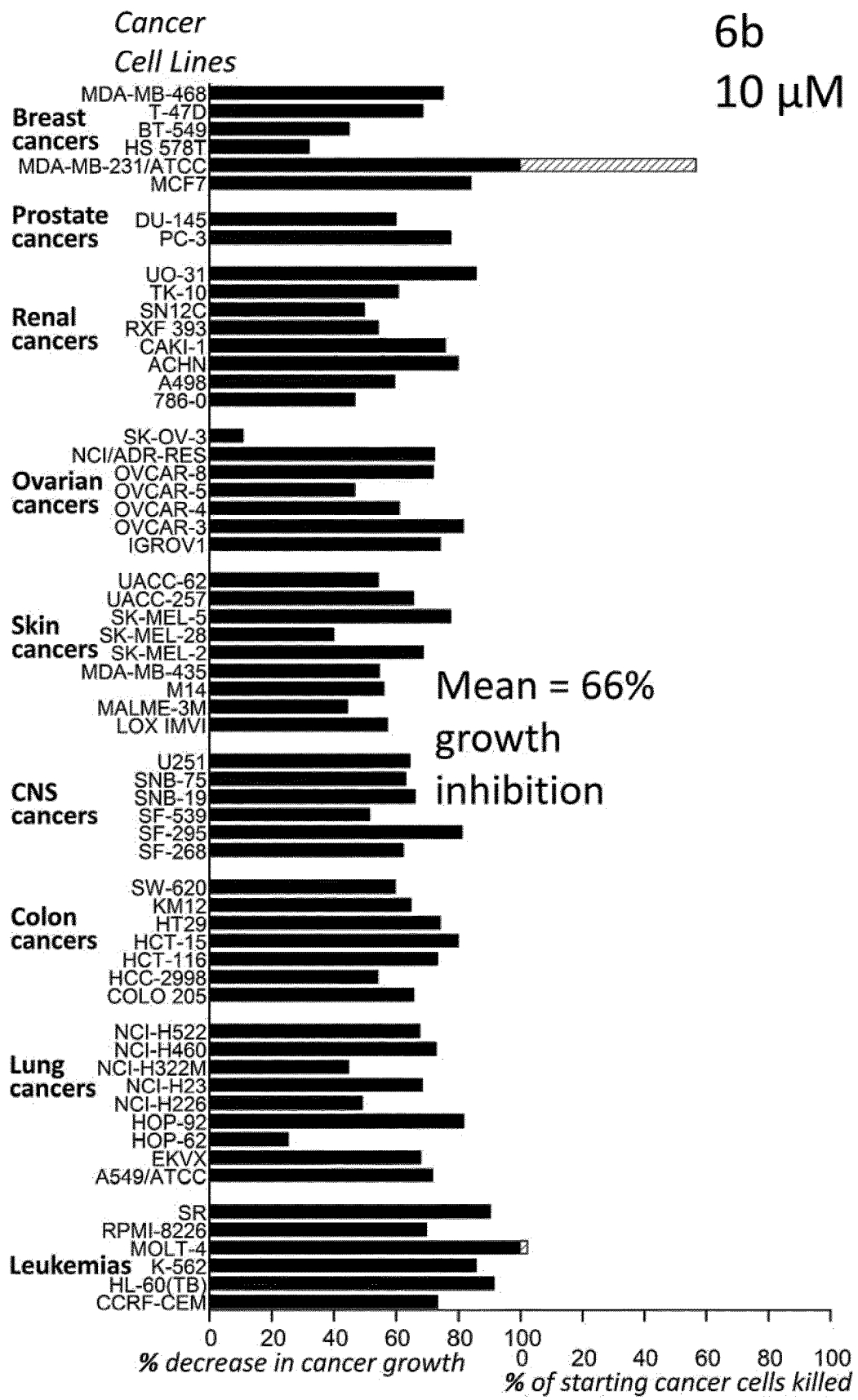
Figure 6:
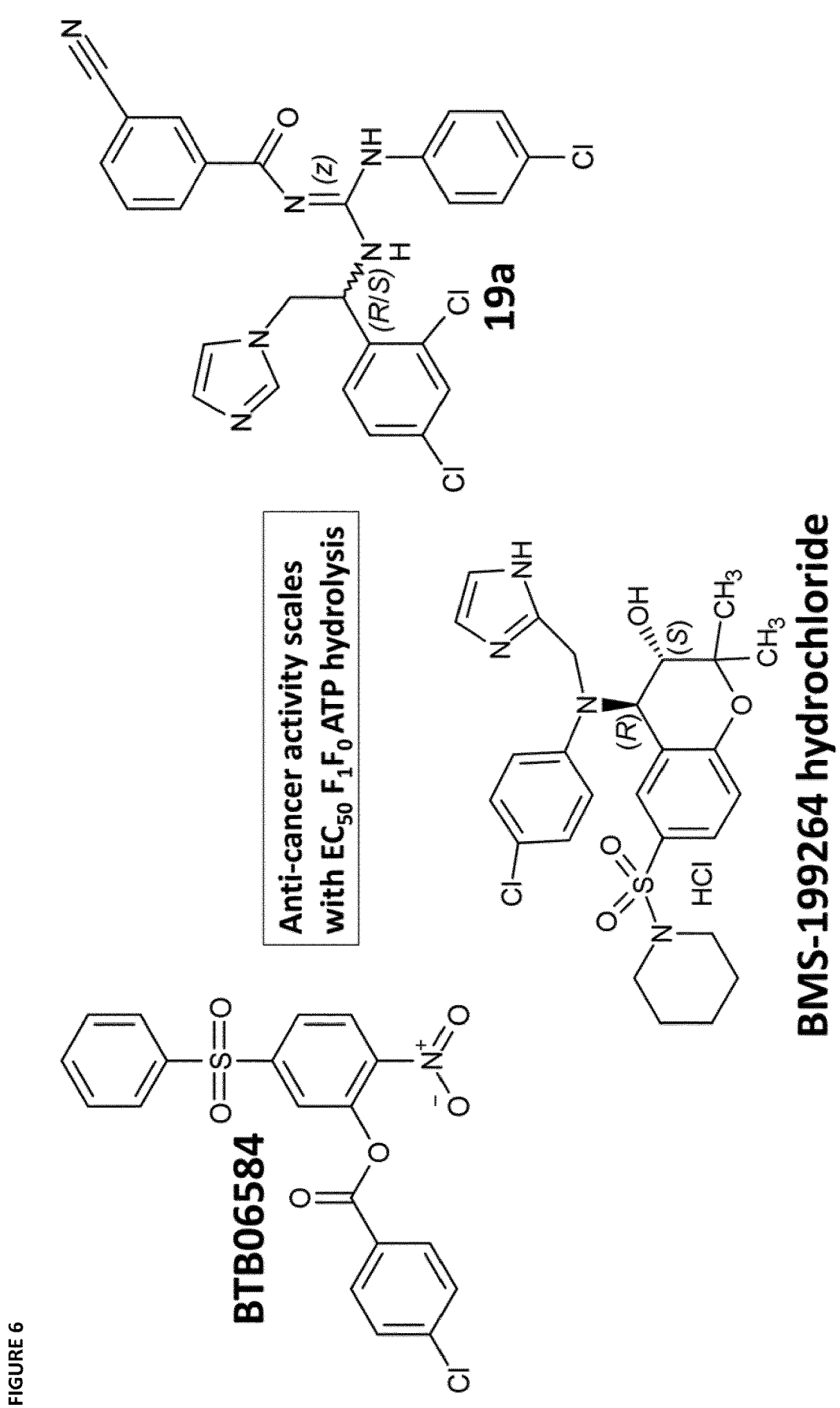
Figure 6:
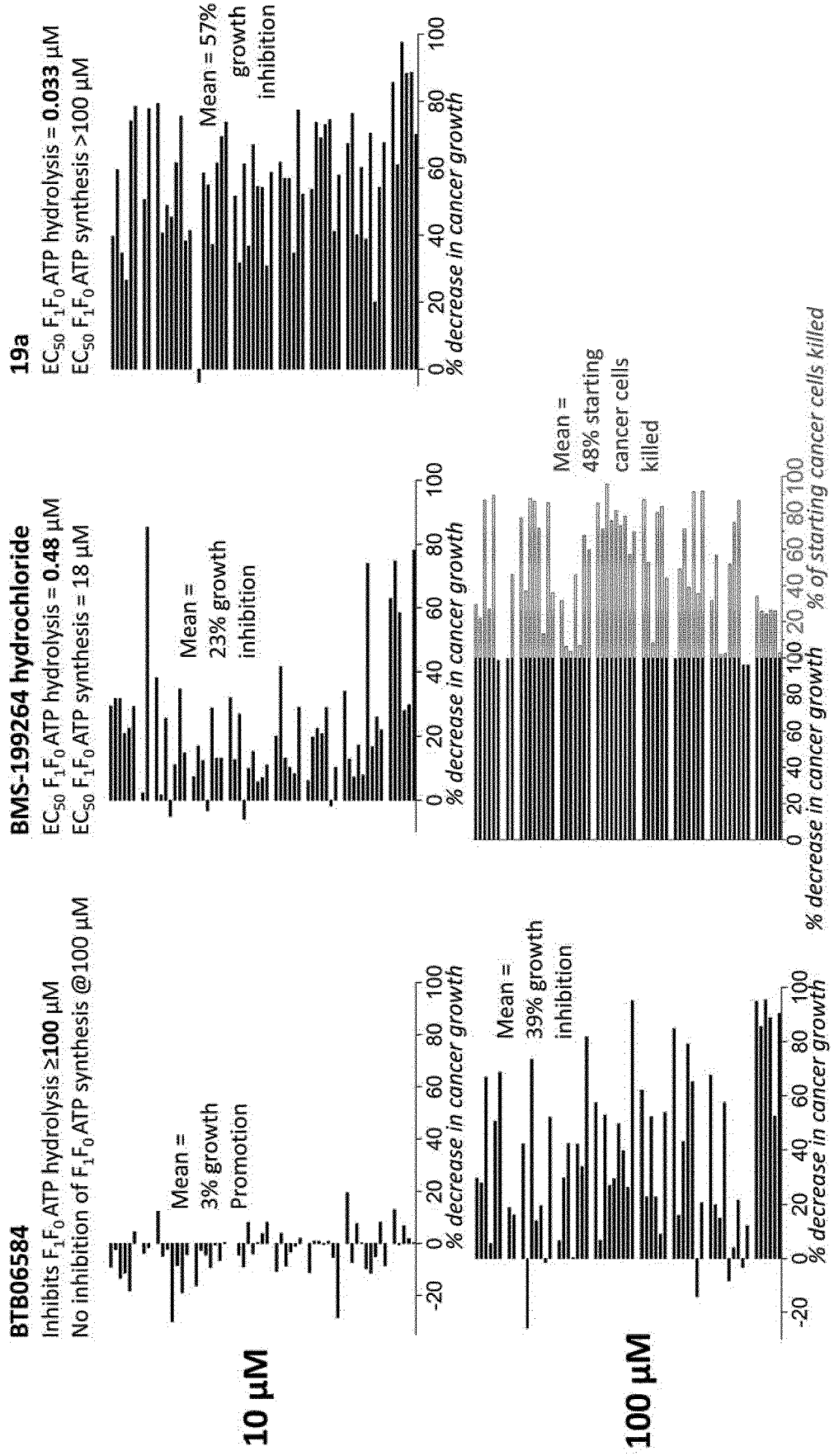
Figure 7A:
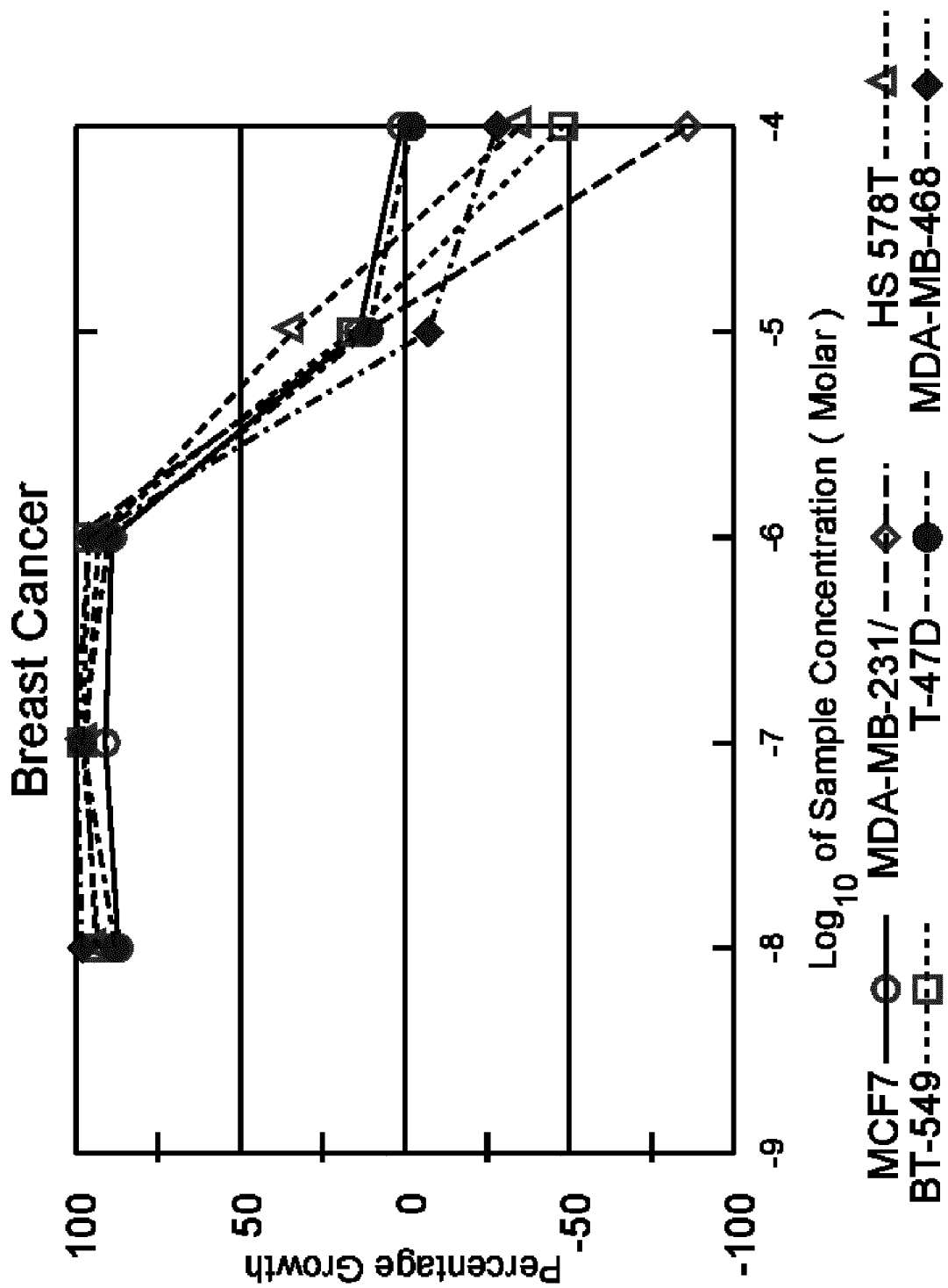
Figure 7B:
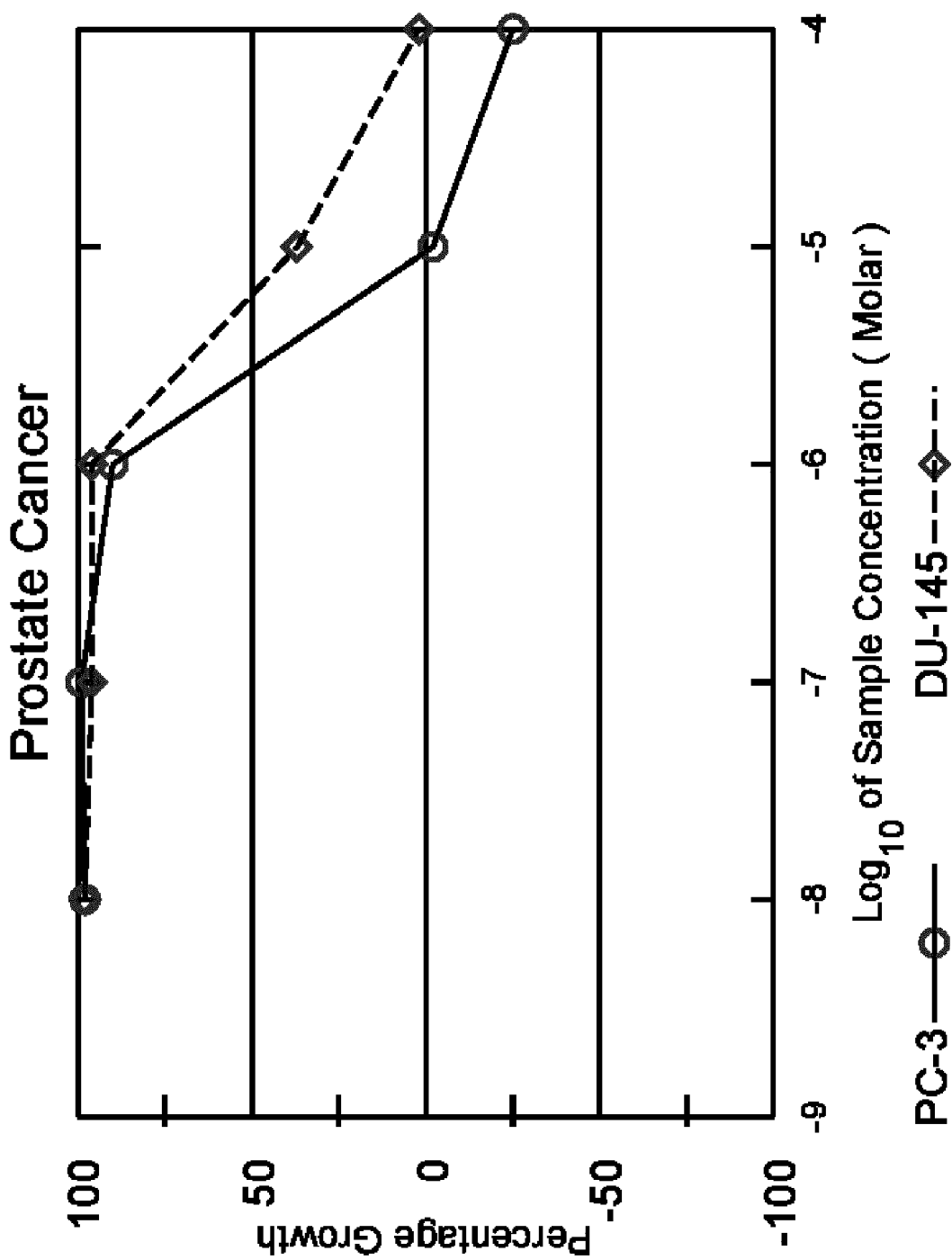
Figure 7C:
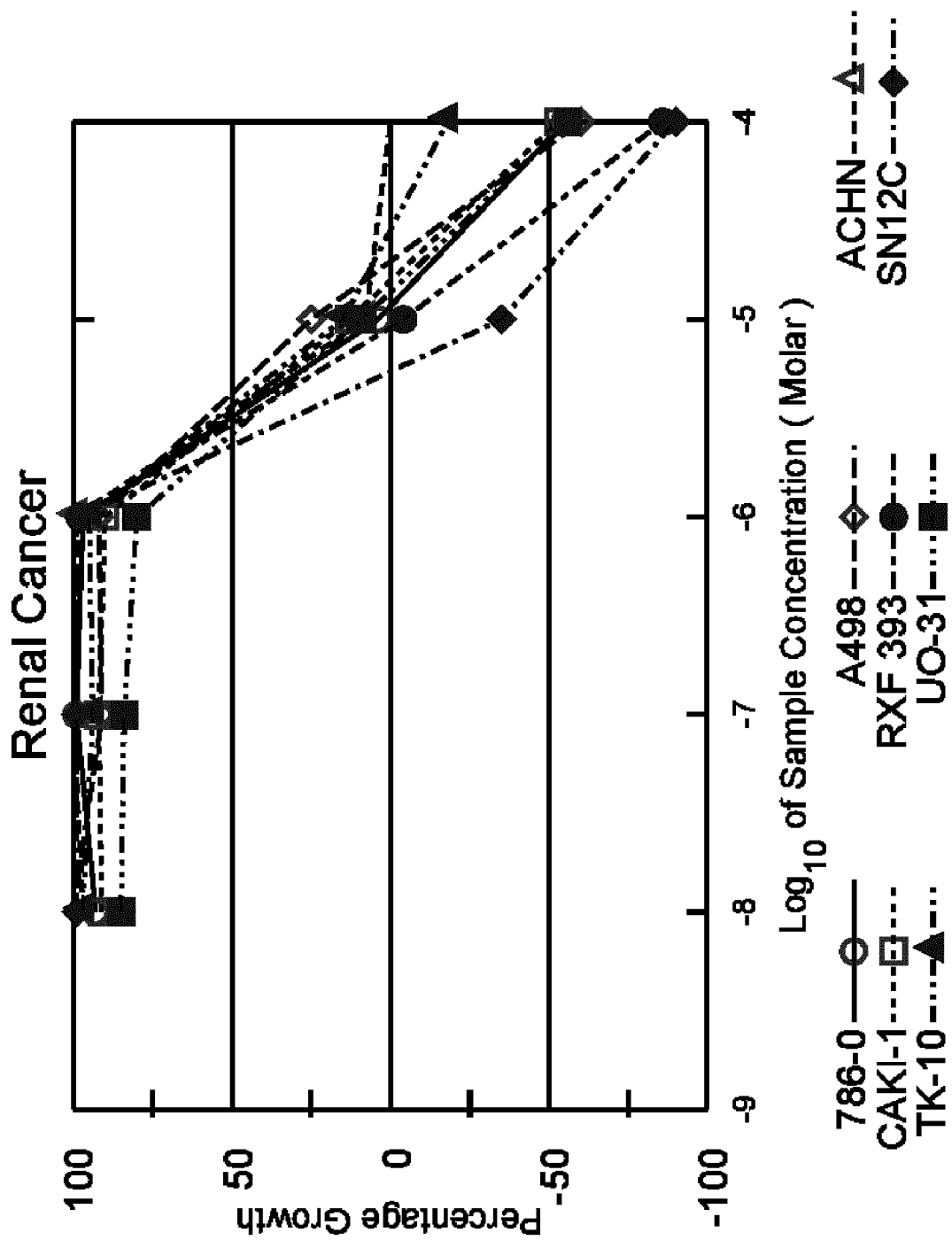
Figure 7D:
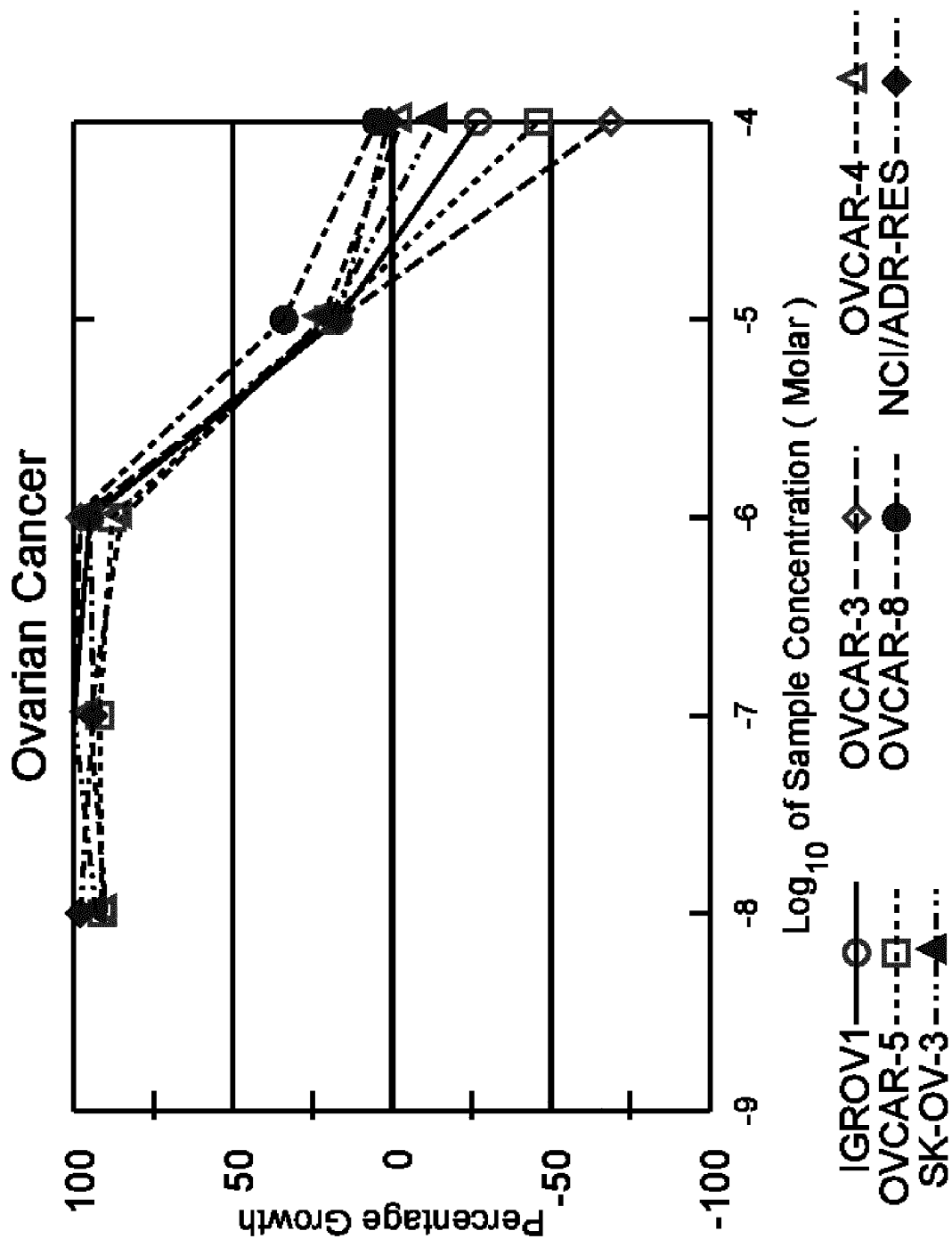
Figure 7E:
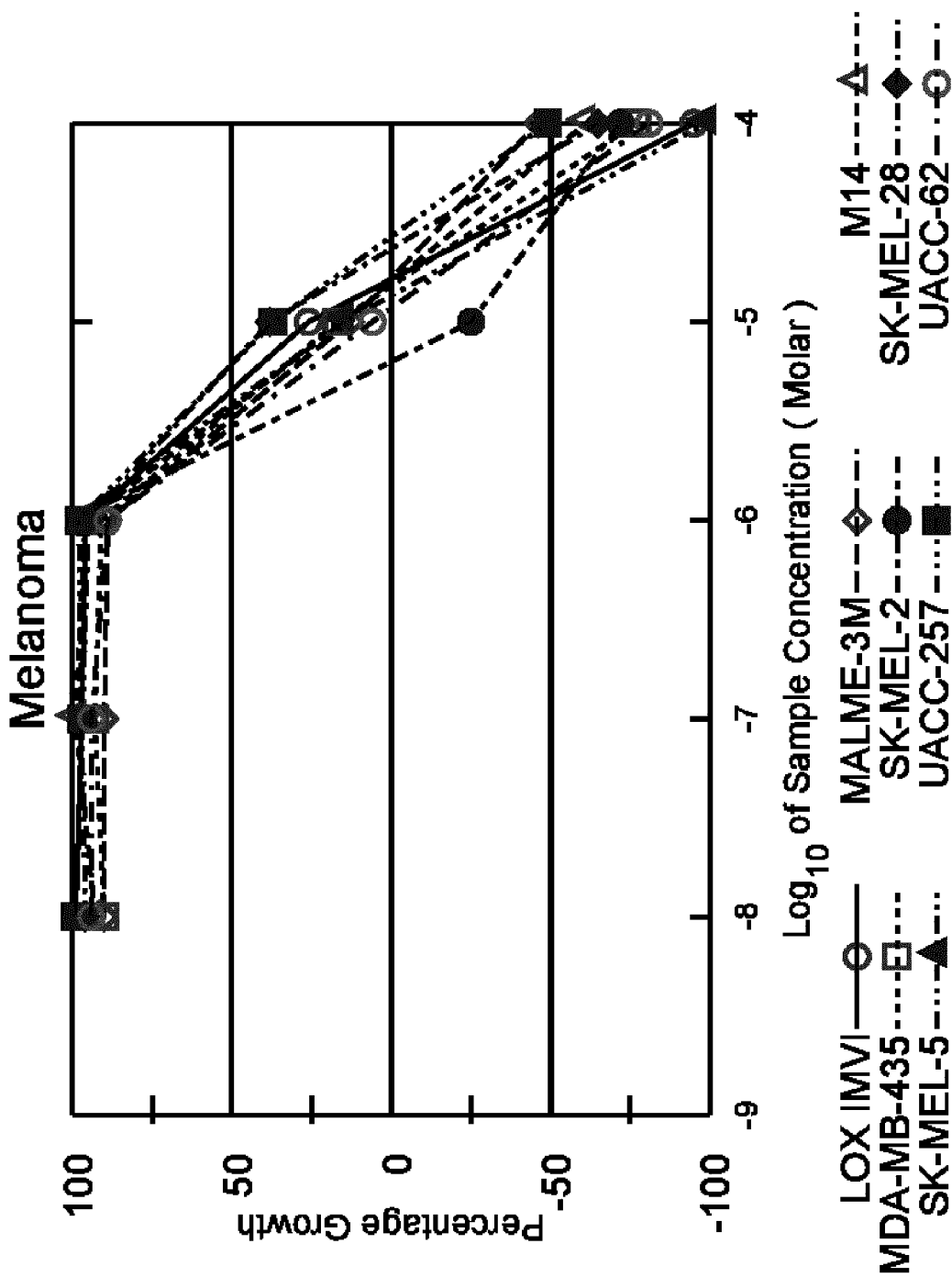
Figure 7F:
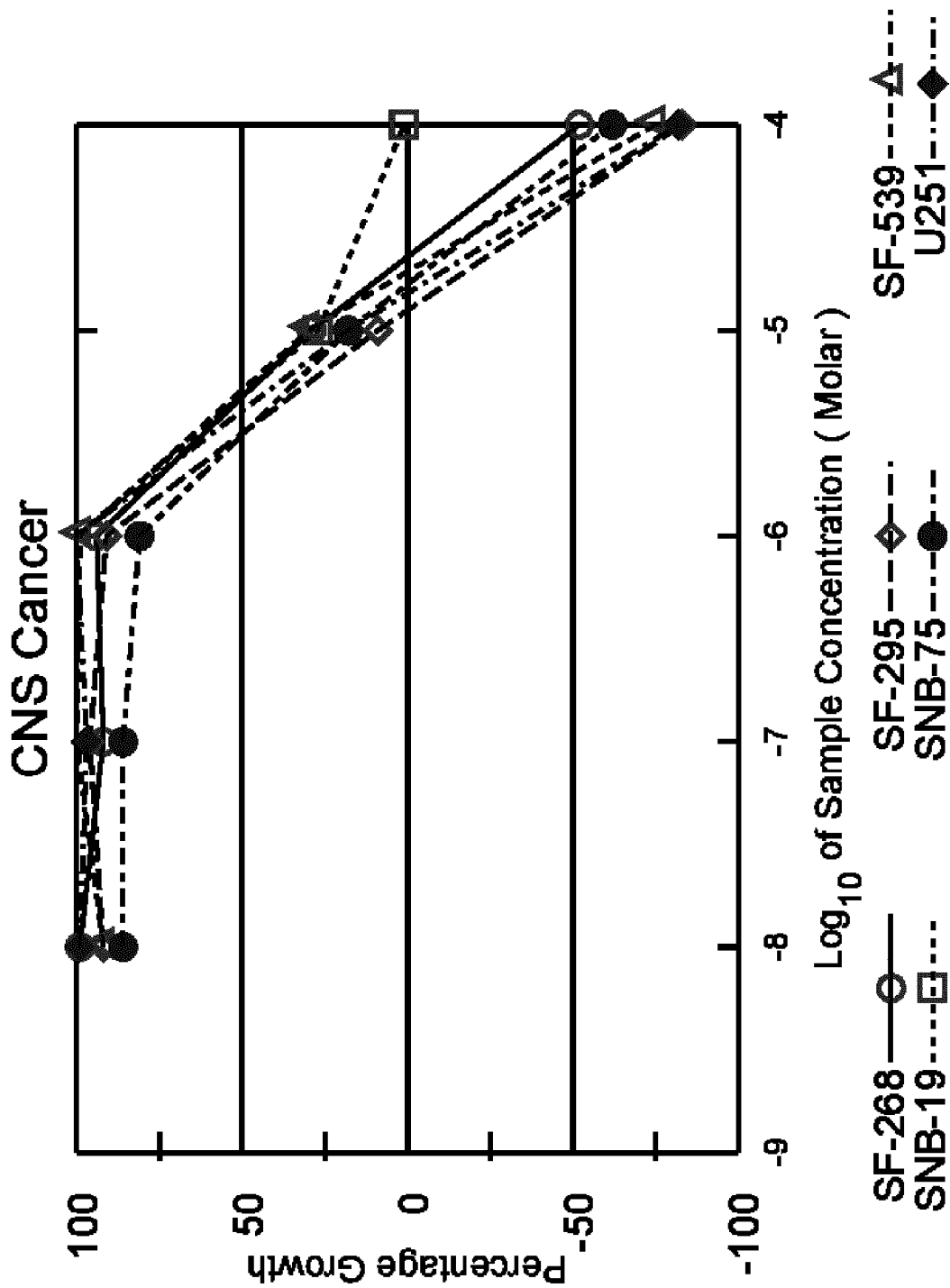
Figure 7G:
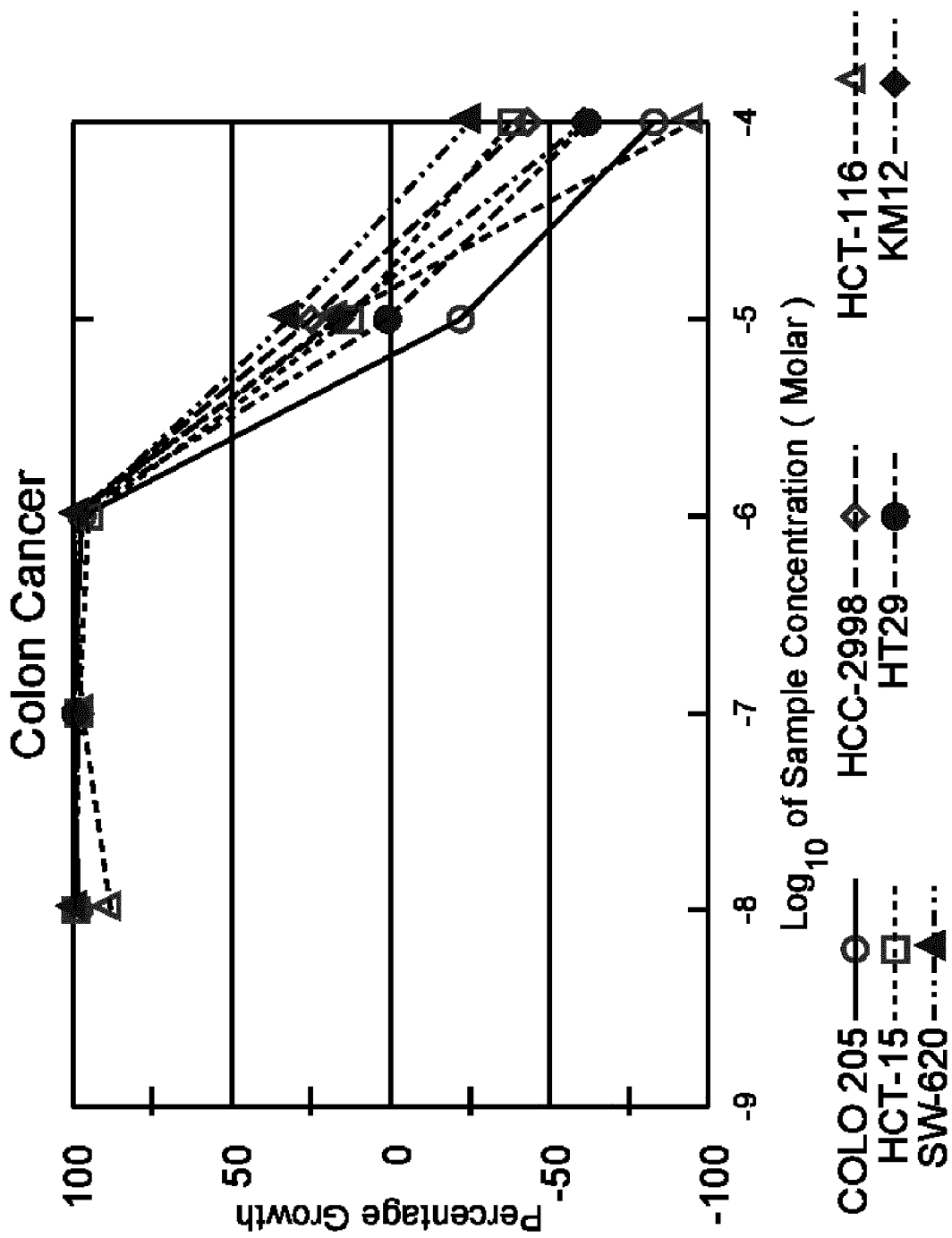
Figure 7H:
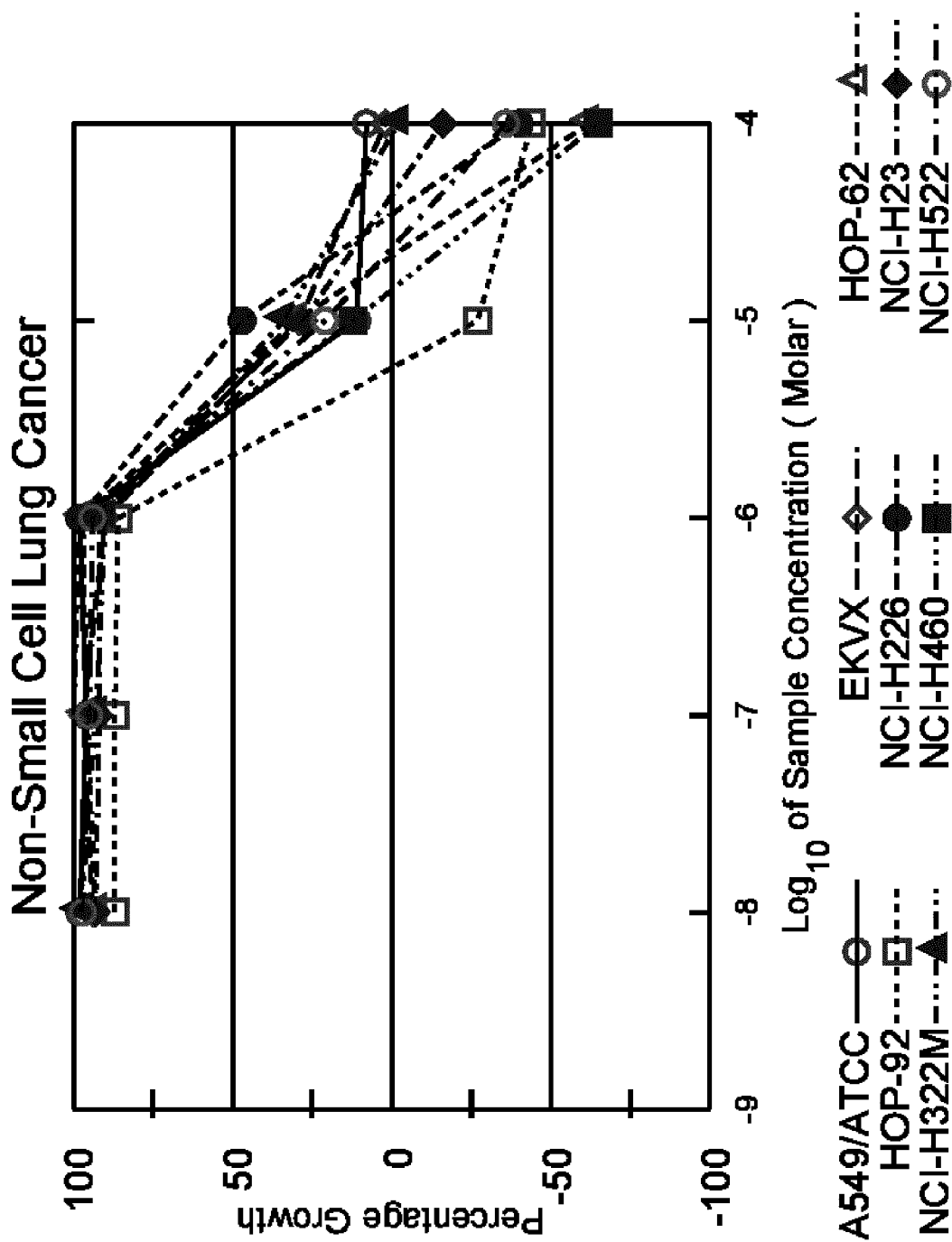
Figure 7I:
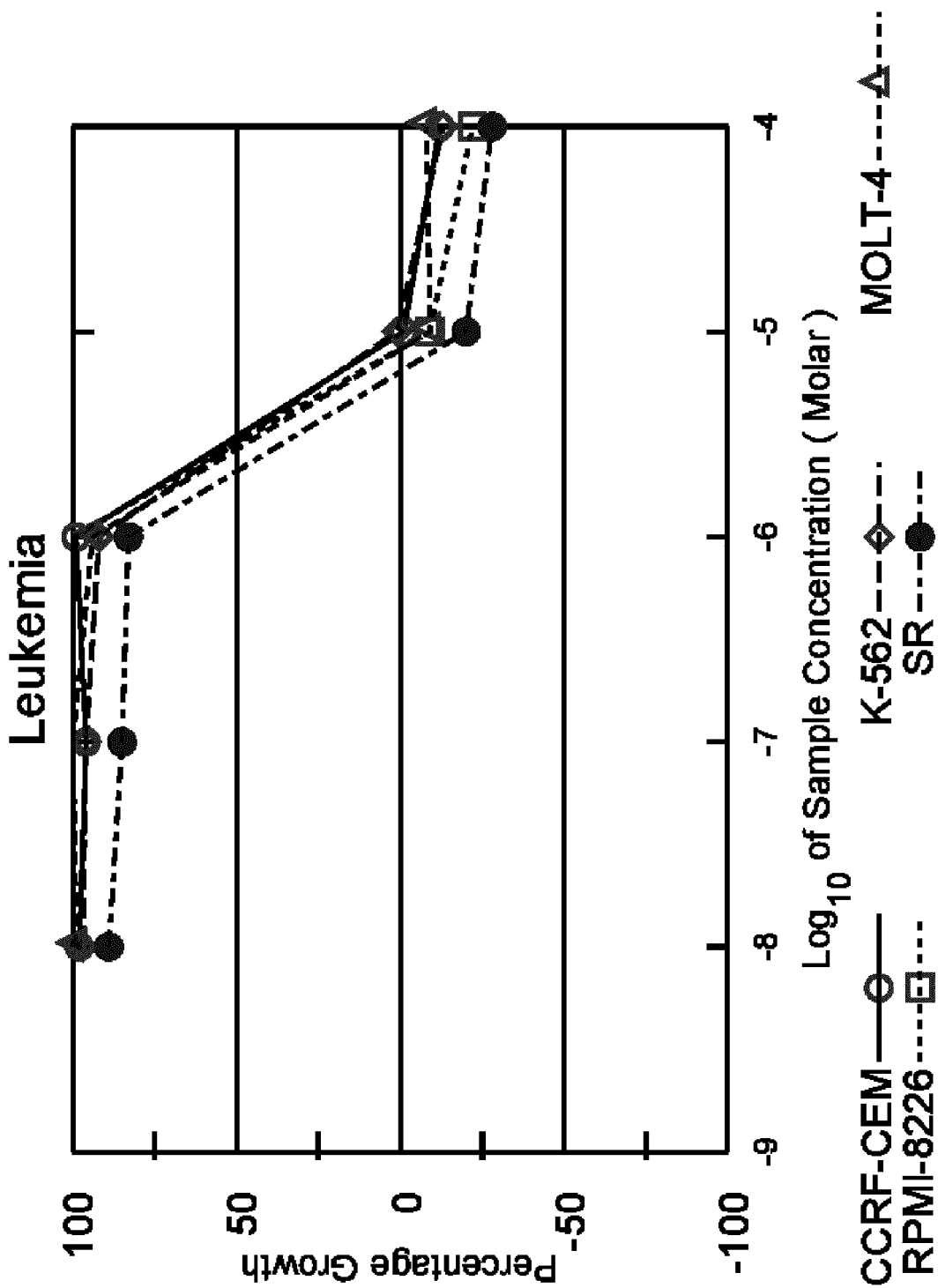
Figure 8:
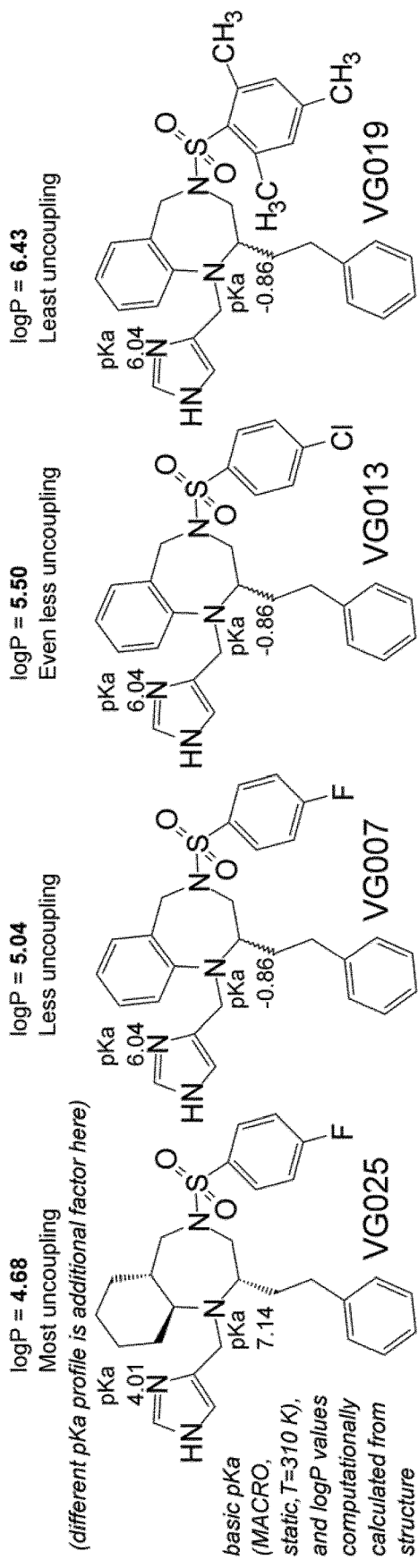
FIG. 8: Mechanistic distinction from oligomycin enables therapeutic utility. Drawn molecules of this figure have an imidazole group, with a protonable nitrogen atom that can shuttle protons across the mitochondrial inner membrane (IM), dissipating the proton motive force (pmf, uncoupling). This figure presents experimental data using the HL-1 cardiac muscle cell line (cancer derived, but now very cardiac differentiated e.g. spontaneously contracts and beats like heart cells). Refer to the "Benchmark Drugs" first, which produce cellular effects well known to those of the art [3]. Oligomycin here refers to Oligomycin B. Oligomycin binds ATP synthase and blocks its forward, proton passing, ATP synthesizing, mode. This means less protons pass through ATP synthase, less pmf is consumed per unit time, pmf increases, $\psi_{IM}$ hyperpolarizes, electron flow along the respiratory chain slows, and $O_2$ consumption is decreased. Carbonilcyanide p-triflouromethoxyphenylhydrazone (FCCP) is an uncoupler that shuttles protons across the IM, dissipates pmf (as heat), pmf decreases, $\psi_{IM}$ depolarizes, electron flow along the respiratory chain speeds, and $O_2$ consumption is increased. Distinct from oligomycin, 3 molecules of this figure increase, rather than decrease, $O_2$ consumption, which signifies their mechanistic distinction from oligomycin: they reduce ATP synthesis more by uncoupling than any inhibition of forward mode ATP synthase. They all contain a protonable nitrogen atom, with a basic pKa value conducive to uncoupling i.e. a pKa value reasonably close to {pH of mitochondrial intermembrane space+ pH of mitochondrial matrix)/2}. Although for VG025, its most conducive pKa is on its main ring rather than its imidazole. In a NADPH-linked sub-mitochondrial (SMP) assay of ATP synthesis, these molecules would decrease ATP production because they dissipate pmf as heat, and so there is less pmf available for ATP production. In interpretation, this uncoupling could be incorrectly attributed to inhibition of the forward mode of ATP synthase and so the full mechanistic distinction of these molecules from oligomycin could be missed. This has been the case with other imidazole containing compounds of this disclosure, also with a protonable nitrogen in their imidazole, also with a pKa conducive to uncoupling, and wherein their inhibition of $F_1F_0$ ATP synthesis in the NADPH-linked SMP assay has been attributed to inhibiting the forward mode of ATP synthase [5-8], but wherein their uncoupling is likely to be the more predominant factor (extrapolated from data of this figure) and wherein they do not inhibit the forward mode of ATP synthase much, if at all, in stark distinction to oligomycin. Uncoupling capability, which decreases with increased logP (refer next paragraph), explains why different molecules of the present figure exert different effects on $O_2$ consumption. The high logP value of VG019 means its uncoupling is minimal and its effect on $O_2$ consumption is zero (rounded) at a concentration (100 µM) it inhibits the reverse mode of ATP synthase, in stark distinction to oligomycin (3 µM), which dramatically decreases $O_2$ consumption (~40%), because, distinctly, it potently inhibits the forward mode of ATP synthase.

LogP=~3.2 is the optimal compromise for best passing a membrane: its hydrophobic core (selecting for high logP) and hydrophilic boundary layer (selecting for low logP) ([32], herein incorporated in its entirety). The imidazole containing molecules presented in this figure, and in this disclosure's drawings more generally, have logP>3.2 and present increased logP=decreased uncoupling. The uncoupling capability/liability of a molecule actually hinges on its intersection of pKa(s) and logP [32] but for the molecules in this disclosure's drawings, wherein the imidazole pKa values are, generally, all within a fairly narrow range, the more primary determinant to each molecule's uncoupling rate, relative to the others, is the molecule's logP value relative to the others.

The drawn molecules of this figure do inhibit the reverse mode of ATP synthase. When a respiratory chain inhibitor blocks electron flow, $\psi_{IM}$ is maintained, not by proton pumping by the respiratory complexes, but by proton pumping by ATP synthase i.e. the reverse mode of ATP synthase. In the presented data, when the respiratory chain is blocked, the presented molecules depolarise $\psi_{IM}$ because they block the reverse mode of ATP synthase. They don't affect $\psi_{IM}$ by these means when the respiratory chain is operational, because $\psi_{IM}$ isn't set/maintained by the reverse mode of ATP synthase in this case, but the molecules with stronger uncoupling capability, they can shuttle more protons across the IM (dissipate more pmf) than the respiratory chain can increase its rate to replace, and they do depolarise $\psi_{IM}$. When the respiratory chain is blocked, a stronger uncoupler in this figure depolarises $\psi_{IM}$ more. Because not only does it inhibit the generator of $\psi_{IM}$ (reverse mode ATP synthase), it simultaneously erodes $\psi_{IM}$ (uncoupling).

Oligomycin does inhibit the reverse mode of ATP synthase. But distinctly it inhibits its forward mode more [11]. So, using oligomycin, there is no margin to inhibit the reverse mode (anti-cancer), without adversely affecting cells using OXPHOS i.e. most normal cells. Contrast this with molecule VG019 of this figure, for example, which can inhibit the reverse mode of ATP synthase, and yet—in observed distinction to oligomycin—does not affect cells using OXPHOS: it does not change their $O_2$ consumption or $\psi_{IM}$ (at 100 µM). This grants it, in distinction to oligomycin, anti-cancer selectivity. Other molecules of this disclosure have even greater cancer selectivity. For example, the best mode (refer disclosure section of that name) inhibits $F_1F_0$ ATP hydrolysis>5,556 times more than $F_1F_0$ ATP synthesis, in NADH-linked and NADPH-linked SMP assays [5-6], whilst oligomycin—inversely—inhibits $F_1F_0$ ATP hydrolysis less than $F_1F_0$ ATP synthesis in such assays [11].

Computational calculations of logP and pKa were made using [31]. The data presented in this Figure is from [12] (herein incorporated in entirety), but the analysis/(re)interpretation is novel. As is the process/method of using these molecules as anti-cancer therapeutics, which is componentry to this invention. The imidazole of the drawn molecules is 4-yl. Permutations, with 5-yl instead, are also disclosed by this invention as anti-cancer therapeutics.

EXAMPLE EMBODIMENTS OF THE INVENTION

The Drawings present embodiments of the invention. Further examples are enumerations of Markush Formulas (I), (II), (III), (IV) and (V), presented henceforth. Note: none of these share Markush symbols, which are symbols of the type: $R_x$, wherein x is an integer, well known to those of the art. They each have their own, as specified for each, in their own sections of this disclosure.

In this disclosure, the term "Formula [X]" is used when a statement is true for Formula (I), (II), (III), (IV) and (V), and all are being referred to independently. A compound of Formula [X] is a compound of Formula (I), or Formula (II), or Formula (III), or Formula (IV), or Formula (V), or any compound presented in this disclosure's Drawings.

This invention is described using these example embodiments but it isn't limited to these. These merely illustrate the invention. Compounds of other structures, which are identified as therapeutic inhibitors by the rationale and methods of the present invention, are also encompassed by the present invention.

Encompassed by this invention are methods of treating a subject suffering from a medical disease or disorder by administering an effective amount of at least one compound of Formula (I), (II), (III), (IV) or (V) or a pharmaceutically-acceptable salt, solvate, hydrate or prodrug thereof, or a pharmaceutical composition(s) comprising one or compounds of Formula (I), (II), (III), (IV) or (V). A very large number of diseases/disorders can be treated using compounds described herein. For example, but not limited to, the compounds described herein can be used to treat/ameliorate/prevent/combat a disease or disorder selected from cancer, cachexia, cancer driven cachexia, weight loss or a disease or disorder that causes a higher than normal body temperature which can include, but isn't limited to, fever, pyrexia, hyperpyrexia, hyperthermia, malignant hyperthermia, neuroleptic malignant syndrome, serotonin syndrome, thyroid storm, or to treat/ameliorate/prevent/combat Tumour Associated Macrophages (TAMs) or treat/ameliorate/prevent/combat any macrophage associated disease or disorder including, but not limited to, Macrophage Activation Syndrome (MAS), HIV, AIDS, HIV-associated neurocognitive disorders (HAND), HIV associated cancers, AIDS-defining cancers, non-AIDS defining cancers or treat/ameliorate/prevent/combat virus neuroinvasion via macrophages, as used for example by HIV and SARS coronavirus, or treat/ameliorate/prevent/combat neurocognitive and neurodegenerative diseases/disorders, for example those caused by, but not limited to, a virus or treat/ameliorate/prevent/combat acute/chronic/systemic inflammation or any inflammatory disease/disorder/syndrome or any autoinflammatory disease/disorder/syndrome or any autoimmune disease/disorder/syndrome or to treat/ameliorate/prevent/combat cardiovascular diseases and conditions associated with ischemia and associated conditions including, without limitation, ischemia-reperfusion injury, myocardial ischemia, ischemic heart disease, chronic stable angina pectoris, myocardial infarction, congestive heart failure, an acute coronary syndrome, muscle cell damage, necrosis, cardiac arrhythmias, non-Q wave MI, unstable angina, high blood pressure, coronary artery disease, ischemic hypoxia, cyanosis, gangrene, acute limb ischemia, stroke, ischemic stroke, brain ischemia, vascular dementia, transient ischemic attack (TIA), ischemic colitis, mesenteric ischemia, angina pectoris, ischemic heart disease, ischemic neuropathy, hypoxic-ischemic encephalopathy, cerebral hypoxia, brain hypoxia, ischemia resulting from vascular occlusion, cerebral infarction, stroke and related cerebral vascular diseases (including cerebrovascular accident and transient ischemic attack), muscle cell damage and necrosis or to cause greater metabolic/bioenergetic efficiency in a subject, enhancing their physical or mental performance or causing body weight gain.

Example (I)

Summary of Formula (I)

This invention embodiment relates to compounds having the following formula:

Formula (I)

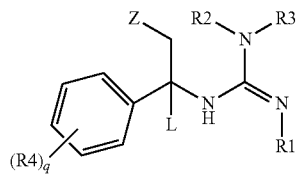

or a pharmaceutically-acceptable salt, solvate, hydrate or prodrug thereof, wherein:

L is alkyl, or substituted alkyl, or any atom or isotope permitted by valence;

$R_1$ is cyano, —$SO_2R_8$, —$C(=O)R_9$, or heteroaryl;

$R_2$ is (i) independently hydrogen, alkyl, or substituted alkyl, or (ii) taken together with $R_3$ forms a heterocyclo;

$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) taken together with $R_2$ forms a heterocyclo;

Z is heteroaryl provided that when $R_1$ is cyano, Z is not 2-pyridinyl;

$B_B$ is a bond, $C_{1-4}$alkylene, $C_{2-4}$alkenylene, substituted $C_{1-4}$alkylene, substituted $C_{2-4}$alkenylene, —C(=O)$NR_{19}$—, —$C_{1-4}$-alkylene-C(=O)$NR_{19}$—, or substituted $C_{1-4}$alkylene-C(=O)$NR_{19}$—;

$R_4$ at each occurrence is selected independently of each other $R_4$ from the group consisting of halogen, alkyl, haloalkyl, nitro, cyano, haloalkoxy, $OR_{25}$, $SR_{25}$, $NR_{25}R_{26}$, $NR_{25}SO_2R_{27}$, $SO_2R_{27}$, $SO_2NR_{25}R_{26}$, $CO_2R_{26}$, $C(=O)R_{26}$, $C(=)NR_{25}R_{26}$, $OC(=O)R_{25}$, —$OC(=O)NR_{25}R_{26}$, $NR_{25}C(=O)R_{26}$, $NR_{25}CO_2R_{26}$, aryl, heteroaryl, heterocyclo and cycloalkyl;

$R_8$ is alkyl, substituted alkyl, aryl, or heteroaryl;

$R_9$ is —$NR_{10}R_{11}$, alkyl, substituted alkyl, alkoxy, alkylthio, cycloalkyl, aryl, heteroaryl, heterocycle, or —$CO_2R_{12}$;

$R_{10}$ and $R_{11}$, are (i) independently selected from hydrogen, alkyl, substituted alkyl, alkoxy, heterocyclo, cycloalkyl, aryl, and heteroaryl; or (ii) taken together form a hetero cyclo or heteroaryl;

$R_{12}$ and $R_{19}$ are hydrogen or alkyl;

$R_{25}$ and $R_{26}$ are independently selected from hydrogen, alkyl, or substituted alkyl, or taken together form a heterocyclo or heteroaryl ring;

$R_{27}$ is alkyl or substituted alkyl, and q is 0, 1, 2, or 3.

Preferred Compounds of Formula (I)

Preferred methods are to use, and preferred compounds are, compounds with the following formula, or pharmaceutically-acceptable salts, solvates, hydrates or prodrugs thereof,

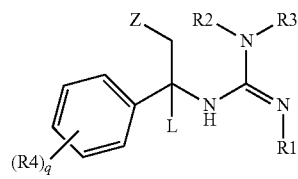

and even more preferred methods are to use, and preferred compounds are, compounds with the following formula, or pharmaceutically-acceptable salts, solvates, hydrates or prodrugs thereof,

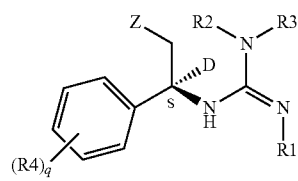

in which, in the preceding two structures shown:

L is hydrogen or deuterium;

D is deuterium (enrichment, for example, exceeding 40% deuterium incorporation at shown position, and optionally at other positions also);

S symbolises the S stereoisomer, for example, in enantiomeric excess (ee) exceeding 70%;

Z is triazolyl optionally substituted with one to two $R_7$ or imidazolyl optionally substituted with one to two $R_7$ and/or having fused thereto a benzene ring in turn optionally substituted with one to two $R_7$;

$R_1$ is cyano or —C(=O)$R_9$;

$R_2$ is hydrogen, alkyl, or benzyl;

$R_3$ is aryl or arylalkyl optionally substituted with alkyl, halogen, trifluoromethyl, $OCF_3$, cyano, nitro, amino, hydroxy, or methoxy;

$R_4$ is halogen, alkyl, trifluoromethyl, or $OCF_3$;

$R_7$ is alkyl, carbamyl or carbamyl$C_{1-4}$alkyl;

$R_9$ is —$NR_{10}R_{11}$, alkyl, substituted alkyl, alkoxy, alkylthio, cycloalkyl, aryl, heteroaryl, heterocycle, or —$CO_2R_{12}$;

$R_{10}$ and $R_{11}$ are (i) independently selected from hydrogen, alkyl, substituted alkyl, alkoxy, heterocyclo, cycloalkyl, aryl, and heteroaryl; or (ii) taken together form a heterocyclo or heteroaryl;

$R_{12}$ is hydrogen or alkyl; and q is 0, 1, 2, or 3.

Further preferred are compounds having the following formula, or pharmaceutically-acceptable salts, solvates, hydrates or prodrugs thereof,

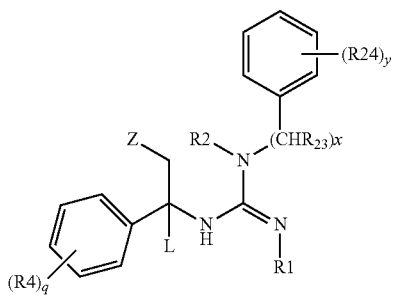

and even more preferred are compounds having the following formula, or pharmaceutically-acceptable salts, solvates, hydrates or prodrugs thereof,

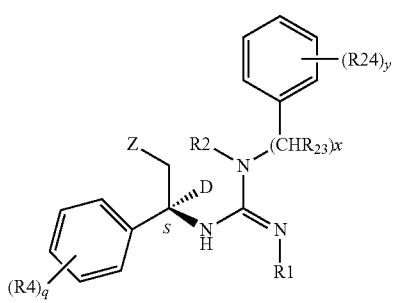

in which, for the preceding two structures shown:
z is

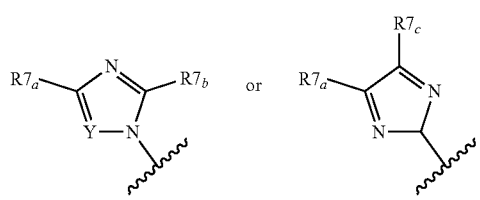

L is hydrogen or deuterium;
D is deuterium (enrichment, for example, exceeding 40% deuterium incorporation at shown position, and optionally at other positions also);
S symbolises the S stereoisomer, for example, in enantiomeric excess (ee) exceeding 70%;
Y is N, CH or $CR_{7c}$;
$R_1$ is cyano or —C(=O)$R_9$;
$R_2$ is hydrogen or $C_{1-4}$alkyl;
$R_4$ is halogen, $C_{1-4}$alkyl, trifluoromethyl; or $OCF_3$;
$R_{7a}$, $R_{7b}$, and $R_{7c}$ are hydrogen, alkyl, carbamyl or carbamyl$C_{1-4}$alkyl, or $R_{7a}$ and $R_{7c}$ join to form an optionally substituted fused phenyl ring;
$R_9$ is —$NR_{10}R_{11}$, alkyl, substituted alkyl, alkoxy, alkylthio, cycloalkyl, aryl, heteroaryl, heterocycle, or —$CO_2R_{12}$;
$R_{10}$ and $R_{11}$ are (i) independently selected from hydrogen, alkyl, substituted alkyl, alkoxy, heterocyclo, cycloalkyl, aryl, and heteroaryl; or (ii) taken together form a heterocyclo or heteroaryl;
$R_{12}$ is hydrogen or alkyl;
$R_{23}$ is hydrogen, alkyl, hydroxyalkyl, or phenyl;
$R_{24}$ is alkyl, halogen, trifluoromethyl, cyano, halogen, hydroxy, $OCF_3$, methoxy, phenyloxy, benzyloxy, cyano, or acyl, or two $R_{24}$ groups join to form a fused cycloalkyl or benzene ring;

q is 1 or 2;
x is 0, 1, or 2; and
y is 0, 1, 2, or 3.

More preferred are compounds having the following formula, or pharmaceutically-acceptable salts, solvates, hydrates or prodrugs thereof,

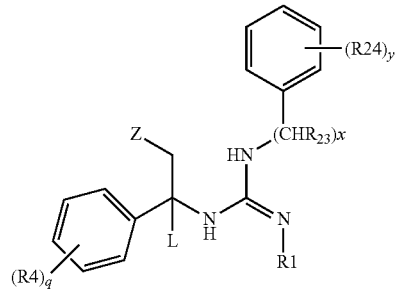

and even more preferred are compounds having the following formula, or pharmaceutically-acceptable salts, solvates, hydrates or prodrugs thereof,

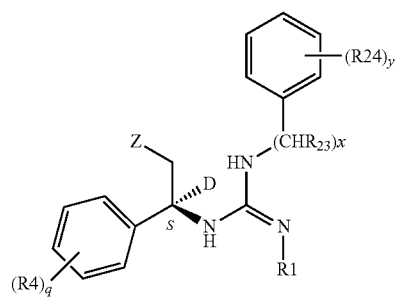

in which, for the preceding two structures shown:
z is

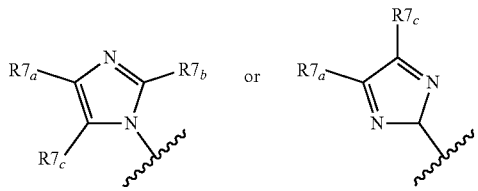

L is hydrogen or deuterium;
D is deuterium (enrichment, for example, exceeding 40% deuterium incorporation at shown position, and optionally at other positions also);
S symbolises the S stereoisomer, for example, in enantiomeric excess (ee) exceeding 70%;
$R_1$ is cyano or —C(=O)$R_9$;
$R_4$ is halogen, $C_{1-4}$alkyl, trifluoromethyl, or $OCF_3$;
$R_{7c}$ is hydrogen or $R_7$ and $R_{7c}$ join to form a fused benzene ring optionally substituted with $C_{1-4}$alkyl or —$(CH_2)_{1-2}$—NHC(=O)$C_{1-4}$alkyl,
$R_{7b}$ is hydrogen, $C_{1-4}$alkyl, or —$(CH_2)_{1-2}$—NHC(=O)$C_{1-4}$alkyl;
$R_9$ is a) —$NR_{10}R_{11}$ b) $C_{1-8}$alkyl optionally substituted with one to two of:
  i) $SR_{13}$, $OR_{13}$, $NR_{13a}R_{13b}$, halogen, trifluoromethyl, $CO_2R_{13a}$, and $C(=O)NR_{13a}R_{13b}$;
  ii) cycloalkyl optionally substituted with one to two of $C(=O)H$, $C_{1-4}$acyl, alkenyl, carbamyl, and/or phenyl in turn optionally substituted with halogen;
  iii) phenyl or napthyl optionally substituted with one to two of halogen, nitro, amino, alkyl, hydroxy, $C_{1-4}$alkoxy, or having fused thereto a five or six membered heterocyclo;
  iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;
c) $C_{1-4}$alkoxy;
d) $C_{1-4}$alkylthio;
e) $CO_2$alkyl;
f) 3 to 6 membered cycloalkyl optionally having up to four substituents selected from alkyl, halogen, cyano, alkenyl, acyl, alkylthio, carbamyl, and/or phenyl in turn optionally substituted with halogen; or having an aryl fused thereto;
g) phenyl optionally substituted with one to four of halogen, cyano, trifluoromethyl; nitro, hydroxy, $C_{1-4}$alkoxy, haloalkoxy, $C_{1-6}$alkyl, $CO_2$alkyl, $SO_2$alkyl, $SO_2NH_2$, amino, $NH(C_{1-4}$alkyl$)$, $N(C_{1-4}$alkyl$)_2$, $NHC(=O)$alkyl, $C(=O)$alkyl, and/or $C_{1-4}$ alkyl in turn optionally substituted with one to three of trifluoromethyl; hydroxy, cyano, phenyl, pyridinyl; and/or a five or six membered heteroaryl or heterocyle in turn optionally substituted with keto or having a benzene ring fused thereto;
h) pyridinyl, thiazolyl, furanyl, thiophenyl, and pyrrolyl optionally substituted with one to two of halogen, alkyl, and phenyl in turn optionally substituted with halogen or trifluoromethyl;
$R_{10}$ is hydrogen, alkyl, or alkoxy;
$R_{11}$ is alkyl, substituted alkyl, alkoxy, heterocyclo, cycloalkyl, aryl, or heteroaryl;
or $R_{10}$ and $R_{11}$, taken together form a heterocyclo or heteroaryl;
$R_{23}$ is hydrogen, alkyl, hydroxyalkyl, or phenyl;
$R_{24}$ is alkyl, halogen, trifluoromethyl, cyano, halogen, hydroxy, $OCF_3$, methoxy, phenyloxy, benzyloxy, cyano, or acyl, or two $R_{24}$ groups join to form a fused cycloalkyl or benzene ring;
q is 0, 1, or 2;
x is 0 or 1; and
y is 0, 1, or 2.

Most preferred are compounds as immediately defined above wherein, $R_1$ is cyano or $—C(=O)R_9$; $R_9$ is optionally substituted phenyl or phenyl $C_{1-4}$alkyl; x is 0 or 1; and q and y are 1 or 2. For this most preferred structure, its S stereoisomer is preferred. And further preferred is for its L group to be deuterium.

Example Embodiments of Formula (I)

Compounds from [5-6], selected as specific anti-cancer therapeutics by the invention of this disclosure, selected because they inhibit the reverse, more than the forward, mode of ATP synthase. $EC_{50}$ and $IC_{50}$ used interchangeably. $EC_{50}$ values for $F_1F_0$ ATP hydrolysis, and $F_1F_0$ ATP synthesis, in NADH-linked and NADPH-linked sub-mitochondrial (SMP) assays respectively, sourced from [5-6], are presented. [5-6] refer to these $EC_{50}$ values as $IC_{50}$ values for inhibiting $F_1F_0$ ATP hydrolase (reverse mode) and $F_1F_0$ ATP synthase (forward mode). However, this in incorrect. Because, as identified by the invention of this disclosure, explained herein, although these molecules inhibit $F_1F_0$ ATP hydrolase, their reducing of $F_1F_0$ ATP synthesis is not (predominantly) because of inhibiting $F_1F_0$ ATP synthase, but by uncoupling. More preferred molecules of this invention have a low $EC_{50}$ for $F_1F_0$ ATP hydrolysis, and a higher $EC_{50}$ for $F_1F_0$ ATP synthesis, and their ratio difference is large.

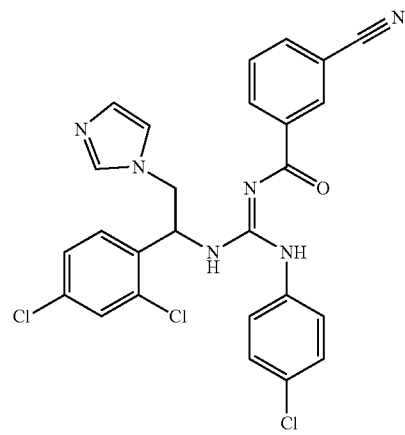

Racemate
$EC_{50}$ $F_1F_0$ ATP hydrolase = 0.033 ± 0.02 (μM)
$EC_{50}$ $F_1F_0$ ATP synthesis > 100 (μM)
$EC_{50}$ Ratio > 3,030

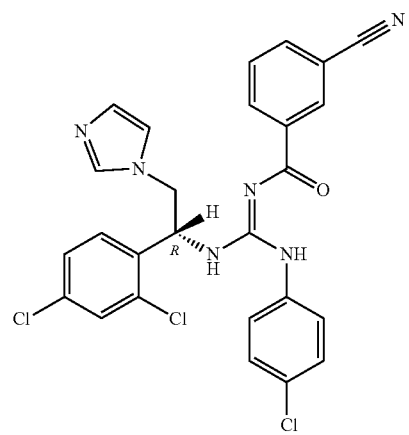

R stereoisomer
$EC_{50}$ $F_1F_0$ ATP hydrolase > 100 (μM)
$EC_{50}$ $F_1F_0$ ATP synthesis > 100 (μM)

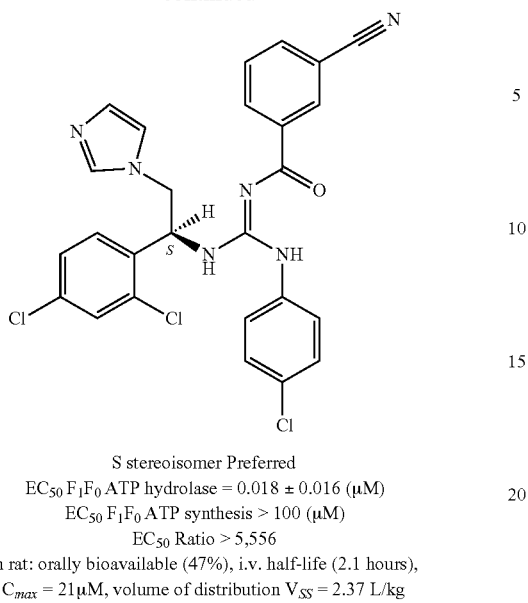

S stereoisomer Preferred
EC$_{50}$ F$_1$F$_0$ ATP hydrolase = 0.018 ± 0.016 (µM)
EC$_{50}$ F$_1$F$_0$ ATP synthesis > 100 (µM)
EC$_{50}$ Ratio > 5,556
In rat: orally bioavailable (47%), i.v. half-life (2.1 hours),
C$_{max}$ = 21µM, volume of distribution V$_{SS}$ = 2.37 L/kg Further example embodiments of Formula (I), with SMP data, reinterpreted (as aforementioned, these molecules don't significantly inhibit F$_1$F$_0$ ATP synthase but do reduce F$_1$F$_0$ ATP synthesis by uncoupling), from [5],

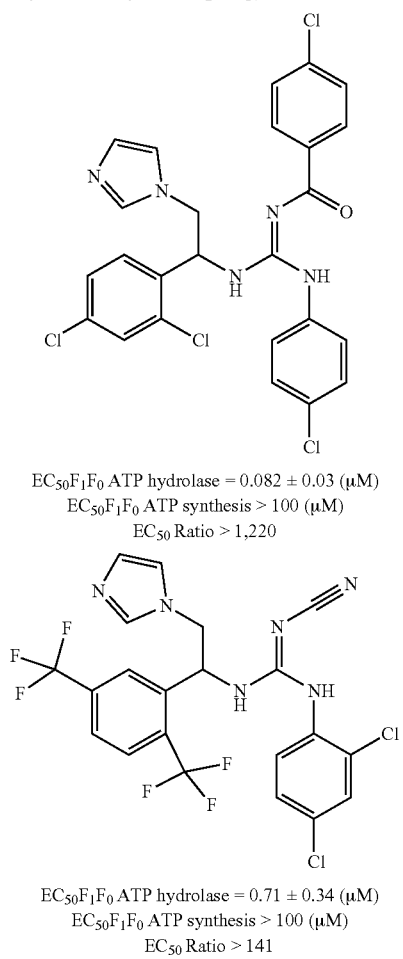

EC$_{50}$F$_1$F$_0$ ATP hydrolase = 0.082 ± 0.03 (µM)
EC$_{50}$F$_1$F$_0$ ATP synthesis > 100 (µM)
EC$_{50}$ Ratio > 1,220

EC$_{50}$F$_1$F$_0$ ATP hydrolase = 0.71 ± 0.34 (µM)
EC$_{50}$F$_1$F$_0$ ATP synthesis > 100 (µM)
EC$_{50}$ Ratio > 141

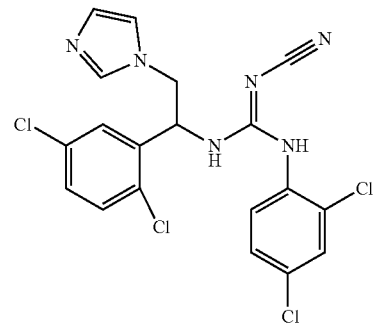

EC$_{50}$F$_1$F$_0$ ATP hydrolase = 0.60 ± 0.16 (µM)
EC$_{50}$F$_1$F$_0$ ATP synthesis > 100 (µM)
EC$_{50}$ Ratio > 167

Further examples [5]:

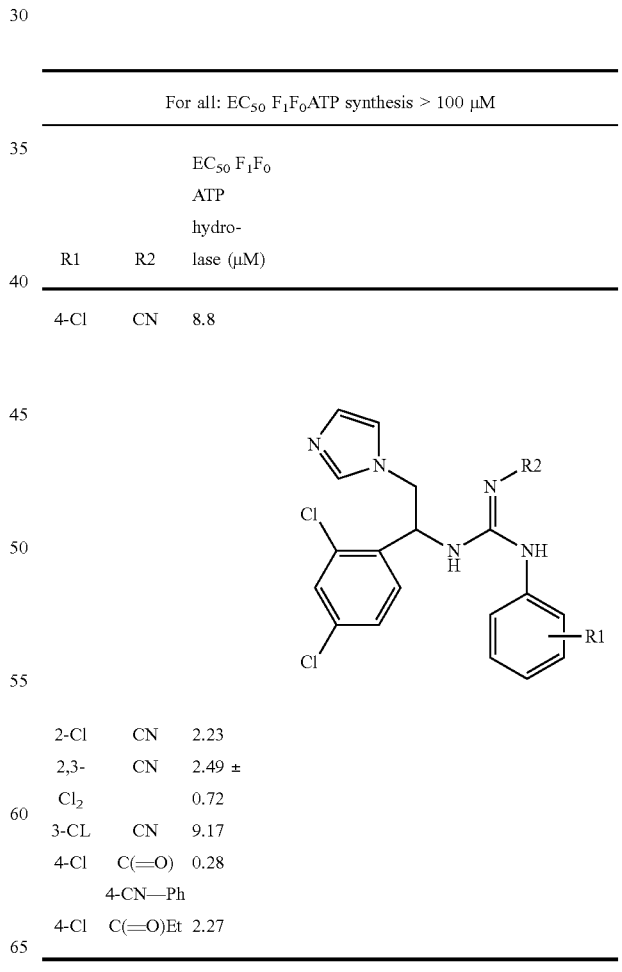

| | For all: EC$_{50}$ F$_1$F$_0$ATP synthesis > 100 µM | |
|---|---|---|
| R1 | R2 | EC$_{50}$ F$_1$F$_0$ ATP hydrolase (µM) |
| 4-Cl | CN | 8.8 |
| 2-Cl | CN | 2.23 |
| 2,3-Cl$_2$ | CN | 2.49 ± 0.72 |
| 3-CL | CN | 9.17 |
| 4-Cl | C(=O)4-CN—Ph | 0.28 |
| 4-Cl | C(=O)Et | 2.27 |

Example (II)

Summary of Formula (II)

This invention embodiment relates to compounds having the formula:

Formula (II)

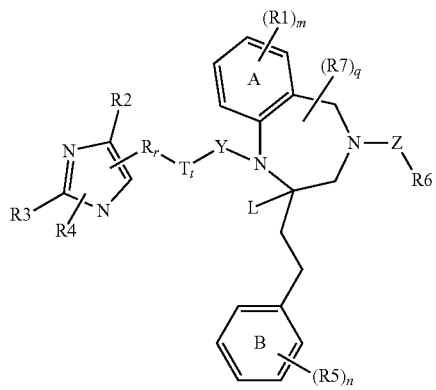

or pharmaceutically-acceptable salts, solvates, hydrates or prodrugs thereof, wherein:

L is alkyl, or substituted alkyl, or any atom or isotope permitted by valence, for example hydrogen or deuterium;

$R_1$ and $R_5$ are attached to any available carbon atom of phenyl rings A and B, respectively, and at each occurrence are independently selected from alkyl, substituted alkyl, halogen, cyano, nitro, $OR_8$, $NR_8R_9$, $C(=O)R_8$, $CO_2R_8$, $C(=O)NR_8R_9$, $NR_8C(=O)R_9$, $NR_8C(=O)OR_9$, $S(O)_oR_9$, $NR_8SO_2R_9$, $SO_2NR_8R_9$, cycloalkyl, heterocycle, aryl, and heteroaryl, and/or two of $R_1$ and/or two of $R_5$ join together to form a fused benzo ring;

$R_2$, $R_3$ and $R_4$ are independently selected from hydrogen, alkyl, and substituted alkyl, or one of $R_2$, $R_3$ and $R_4$ is a bond to R, T or Y and the other of $R_2$, $R_3$ and $R_4$ is selected from hydrogen, alkyl, and substituted alkyl;

Z and Y are independently selected from $C(=O)$, $-CO_2-$, $-SO_2-$, $-CH_2-$, $-CH_2C(=O)-$, and $-C(=O)C(=O)-$, or Z may be absent;

R and T are selected from $-CH_2-$, $-C(=O)-$, and $-CH[(CH_2)_p(Q)]-$, wherein Q is $NR_{10}R_{11}$, $OR_{1O}$ or CN;

$R_6$ is selected from alkyl, alkenyl, substituted alkyl, substituted alkenyl, aryl, cycloalkyl, heterocyclo, and heteroaryl; provided that where $R_2$ is hydrogen, $Z-R_6$ together are not $-SO_2$-Me or

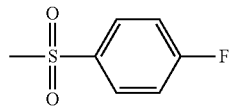

$R_7$ is selected from hydrogen, alkyl, substituted alkyl, alkenyl, substituted alkenyl, aminoalkyl, halogen, cyano, nitro, keto (=O), hydroxy, alkoxy, alkylthio, $C(=O)H$, acyl, $CO_2H$, alkoxycarbonyl, carbamyl, sulfonyl, sulfonamidyl, cycloalkyl, heterocycle, aryl, and heteroaryl;

$R_8$ and $R_9$ are independently selected from hydrogen, alkyl, substituted alkyl, cycloalkyl, heterocycle, aryl, and heteroaryl, or $R_8$ and $R_9$ taken together to form a heterocycle or heteroaryl, except $R_9$ is not hydrogen when attached to a sulfonyl group as in $SO_2R_9$;

$R_{10}$ and $R_{11}$ are independently selected from hydrogen, alkyl, and substituted alkyl;

m and n are independently selected from 0, 1, 2 and 3 o, p and q are independently 0, 1 or 2; and r and t are 0 or 1.

Preferred Compounds of Formula (II)

Preferred methods are to use, and preferred compounds are, compounds with the following formula, or pharmaceutically-acceptable salts, solvates, hydrates or prodrugs thereof,

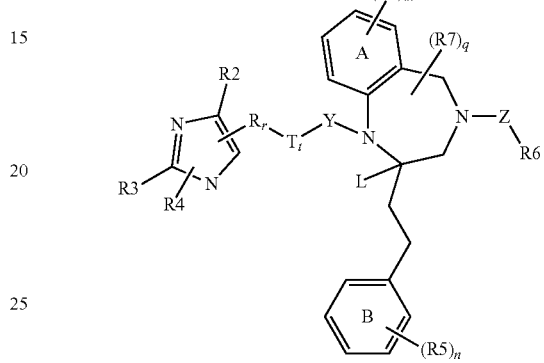

wherein:

L is hydrogen or deuterium;

$R_1$ and $R_5$ are attached to any available carbon atom of phenyl ring A and phenyl ring B, respectively, and at each occurrence are independently selected from alkyl, aralkyl, aminoalkyl, halogen, cyano, nitro, hydroxy, alkoxy, alkylthio, $NH_2$, NH(alkyl), N(alkyl)$_2$, $C(=O)H$, acyl, $CO_2H$, alkoxycarbonyl, carbamyl, sulfonyl, sulfonamide, cycloalkyl, heterocycle, aryl, and heteroaryl, and/or two of $R_1$ and/or two of $R_5$ join together to form a fused benzo ring;

$R_2$, $R_3$ and $R_4$ are independently selected from hydrogen and alkyl;

Z is $-CO_2-$, $-SO_2-$, or is absent;

Y, R and T are selected from $-CH_2-$ and $-C(=O)-$, $R_6$ is selected from:

$C_{1-4}$alkyl or $C_{1-4}$alkenyl optionally substituted with up to three of halogen, aryl and $CO_2C_{1-6}$alkyl;

phenyl optionally substituted with up to three $R_{12}$ and/or having fused thereto a benzo-ring or a five to six membered heteroaryl;

heteroaryl selected from thiophenyl, imidazolyl, pyrazolyl, and isoxazolyl wherein said heteroaryl is optionally substituted with up to two $R_{12}$, provided that where $R_2$ is hydrogen, $Z-R_6$ together are not $-SO_2$-Me or

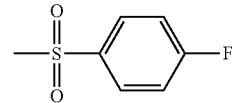

$R_7$ is selected from hydrogen, alkyl, substituted alkyl, alkenyl, substituted alkenyl, aminoalkyl, halogen, cyano, nitro, keto (=O), hydroxy, alkoxy, alkylthio, $C(=O)H$, acyl, $CO_2H$, alkoxycarbonyl, carbamyl, sulfonyl, sulfonamide, cycloalkyl, heterocycle, aryl, and heteroaryl;

$R_{12}$ at each occurrence is independently selected from each other $R_{12}$ from the group consisting of $C_{1-6}$alkyl, halogen, nitro, cyano, hydroxy, alkoxy, NHC(=O)alkyl, —CO$_2$alkyl, —SO$_2$phenyl, five to six membered monocyclic heteroaryl, and phenyloxy or benzyloxy in turn optionally substituted with halogen, $C_{1-4}$alkyl, and/or O($C_{1-4}$alkyl);

m and n are independently selected from 0, 1, 2 or 3; and q is 0, 1 or 2; and r and t are 0 or 1.

More preferred are compounds having the following formula, or pharmaceutically-acceptable salts, solvates, hydrates or prodrugs thereof,

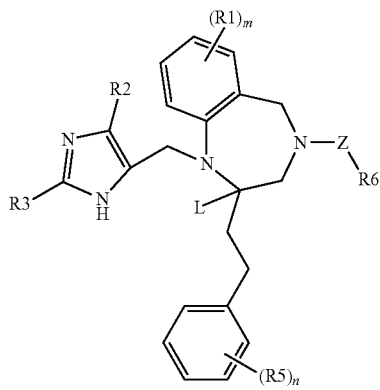

wherein $R_1$ and $R_5$ are attached to any available carbon atom of phenyl ring A and phenyl ring B, respectively, and at each occurrence are independently selected from alkyl, halogen, cyano, hydroxy, alkoxy, NH$_2$, NH(alkyl), N(alkyl)$_2$, C(=O)H, acyl, CO$_2$H, alkoxycarbonyl, and/or two of $R_1$ and/or two of $R_5$ join together to form a fused benzo ring;

$R_2$, $R_3$ and $R_4$ are independently selected from hydrogen and lower alkyl;

Z is —CO$_2$—, —SO$_2$—, or is absent;

$R_6$ is selected from:

$C_{1-4}$alkyl or $C_{1-4}$alkenyl optionally substituted with up to three of halogen, aryl and CO$_2$C$_{1-6}$alkyl;

phenyl optionally substituted with up to three $R_{12}$ and/or having fused thereto a benzo ring or a five to six membered heteroaryl;

heteroaryl selected from thiophenyl, imidazolyl, pyrazolyl, and isoxazolyl, wherein said heteroaryl is optionally substituted with up to two $R_{12}$, provided that where $R_2$ is hydrogen, Z—$R_6$ together are not —SO$_2$-Me or

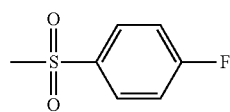

$R_{12}$ at each occurrence is independently selected from each other $R_{12}$ from the group consisting of $C_{1-6}$ alkyl, halogen, nitro, cyano, hydroxy, alkoxy, NHC(=O)alkyl, —CO$_2$alkyl, —SO$_2$phenyl, five to six membered monocyclic heteroaryl, and phenyloxy or benzyloxy in turn optionally substituted with halogen, $C_{1-4}$ alkyl, and/or O($C_{1-4}$ alkyl); and m and n are independently selected from 0, 1, or 2.

Even more preferred are compounds as immediately defined above wherein $R_6$ is selected from $C_{1-4}$alkyl, trifluoromethyl, benzyl, $C_{2-3}$alkenyl substituted with phenyl,

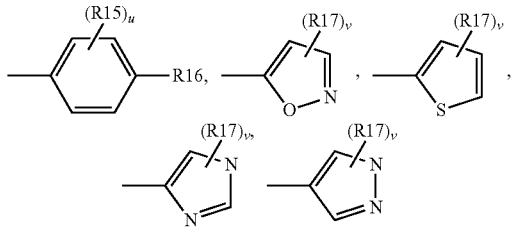

wherein:

$R_{15}$ is halogen, alkyl, nitro, cyano, hydroxy, alkoxy, NHC(=O)alkyl, and/or two $R_{15}$ groups are taken together to form a fused benzo ring or a five to six membered heteroaryl;

$R_{16}$ is selected from hydrogen, halogen, alkyl, nitro, cyano, hydroxy, alkoxy, NHC(=O)alkyl, and phenyloxy or benzyloxy in turn optionally substituted with 1 to 3 of halogen, cyano, and $C_{1-4}$alkoxy;

$R_{17}$ is selected from alkyl, alkoxy, CO$_2$C$_{1-6}$alkyl, and SO$_2$phenyl;

and u and v are independently 0, 1 or 2.

Most preferred compounds of Formula (II) are those having the formula:

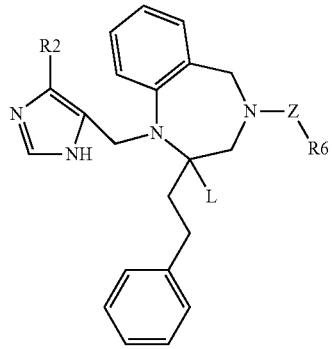

wherein

L is deuterium;

$R_2$ is hydrogen or CH$_3$;

Z is —CO$_2$—, —SO$_2$—, or is absent; and $R_6$ is selected from the groups recited immediately above, most preferably

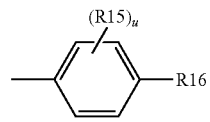

Example Embodiments of Formula (II)

Compounds from [8, 12], selected as specific anti-cancer therapeutics by the invention of this disclosure, selected because they inhibit the reverse, more than the forward, mode of ATP synthase. EC$_{50}$ and IC$_{50}$ used interchangeably.

EC$_{50}$ values for F$_1$F$_0$ ATP hydrolysis, and F$_1$F$_0$ ATP synthesis, in NADH-linked and NADPH-linked sub-mitochondrial (SMP) assays respectively, sourced from [8], are presented. [8] refer to these EC$_{50}$ values as IC$_{50}$ values for inhibiting F$_1$F$_0$ ATP hydrolase (reverse mode) and F$_1$F$_0$ ATP synthase (forward mode). However, this in incorrect. Because, as identified by the invention of this disclosure, explained herein, although these molecules inhibit F$_1$F$_0$ ATP hydrolase, their reducing of F$_1$F$_0$ ATP synthesis is not (predominantly) because of inhibiting F$_1$F$_0$ ATP synthase, but by uncoupling.

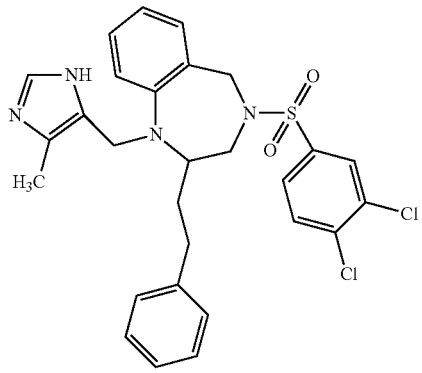

EC$_{50}$ F$_1$F$_0$ ATP hydrolase = 0.022 (μM)
EC$_{50}$ F$_1$F$_0$ ATP synthesis > 30 (μM)
EC$_{50}$ Ratio > 1,364

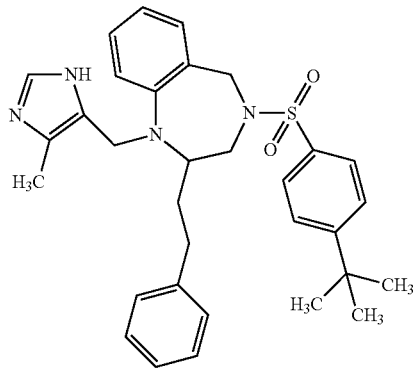

EC$_{50}$ F$_1$F$_0$ ATP hydrolase = 0.077 (μM)
EC$_{50}$ F$_1$F$_0$ ATP synthesis > 30 (μM)
EC$_{50}$ Ratio > 390

For all compounds;

| EC$_{50}$F$_1$F$_0$ATP synthesis > 30 μM | | | |
|---|---|---|---|
| R6 | R5 | Imidazole | EC$_{50}$F$_1$F$_0$ATP hydrolase (μM) |
| 4-F—Ph | SO$_2$ | 5-yl | 0.221 |
| Ph | SO$_2$ | 5-yl | 0.282 |
| 4-OH—Ph | SO$_2$ | 5-yl | 0.667 |
| 4-OMe—Ph | SO$_2$ | 5-yl | 0.077 |
| 2,5-di-Cl—Ph | SO$_2$ | 5-yl | 0.158 |
| 4-(AcNH)—Ph | SO$_2$ | 5-yl | 2.981 |
| 4-CN—Ph | SO$_2$ | 5-yl | 0.255 |
| 2-Cl-4-CN—Ph | SO$_2$ | 5-yl | 0.939 |
| 3-NO$_2$—Ph | SO$_2$ | 5-yl | 0.423 |
| Naphth-1-yl | SO$_2$ | 5-yl | 0.338 |
| Thiophen-2-yl | SO$_2$ | 5-yl | 0.636 |
| Benzofurazan-7-yl | SO$_2$ | 5-yl | 1.777 |
| Quinolin-8-yl | SO$_2$ | 5-yl | 2.935 |
| Bn | SO$_2$ | 5-yl | 2.405 |
| CF$_3$ | SO$_2$ | 5-yl | 0.077 |
| 4-t-Bu—Ph | SO$_2$ | 5-yl | 0.008 |
| 4-t-Bu—Ph | CH$_2$ | 5-yl | 2.138 |
| 4-t-Bu—Ph | CH$_2$ | 4-Me-5-yl | 2.352 |

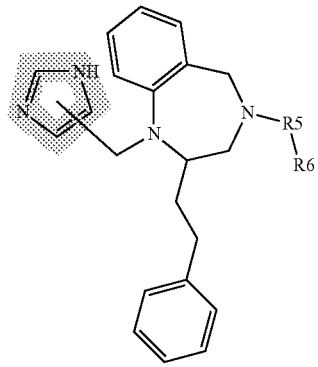

-continued

| | | | EC₅₀F₁F₀ATP synthesis > 30 μM |
|---|---|---|---|
| R6 | R5 | Imidazole | EC₅₀F₁F₀ATP hydrolase (μM) |
| 4-t-Bu—Ph | SO₂ | 2-yl | >10 |
| 4-F—Ph | SO₂ | 2-Me-5-yl | 9.623 |
| 4-F—Ph | SO₂ | 4-Me-5-yl | 0.151 |

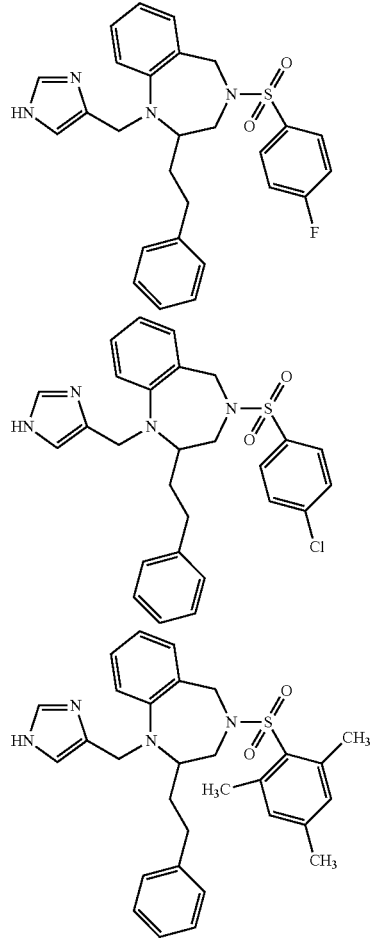

Example (III)

Summary of Formula (III)

This invention embodiment relates to compounds having the following formula:

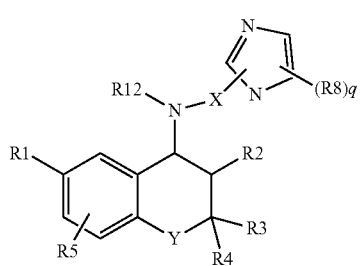

Formula (III)

or their enantiomers, diastereomers, pharmaceutically-acceptable salts, solvates, hydrates or prodrugs thereof, wherein:

Optionally, one or more places upon the structure have deuterium in place of hydrogen;

R2 is hydrogen, hydroxy, or —OC(O)R14;

R14 is hydrogen, alkyl, haloalkyl, aryl, arylalkyl, cycloalkyl or (cycloalkyl)alkyl;

R3 and R4 are each independently hydrogen, alkyl or arylalkyl;

or R3 and R4 taken together with the carbon atom to which they are attached form a 3- to 7-membered carbocyclic ring;

R5 is hydrogen, alkyl, halogen, heterocyclo, nitrile, haloalkyl or aryl;

R12 is aryl or heterocyclo;

X is alkyl;

Y is a single bond, —CH2—, —C(O)—, —O—, —S— or —N(R14)-;

A is nitrogen (N), or N⁺, or carbon;

E is absent, or alkyl, or substituted alkyl, or any atom or isotope permitted by valence, for example hydrogen or deuterium;

R8 is hydrogen, alkyl, halogen, carbamyl or carbamyl$C_{1-4}$alkyl, or two R8 groups join to form an optionally substituted fused phenyl ring;

q is 0, 1, 2 or 3.

R1 is any chemical group smaller than 300 Daltons, R9, cyano, hydrogen, halogen, alkyl, substituted alkyl, alkenyl, alkylene, alkoxy, thioalkyl, aminoalkyl, carbamyl, sulfonyl, sulfonamide, cycloalkyl, haloalkyl, haloalkoxy, aryl, heterocyclo, heteroaryl;

R9 is

R6 and R7 are independently hydrogen, alkyl, cycloalkyl, aryl, arylalkyl, haloalkyl, hydroxyalkyl, hydroxyalkyl substituted with a carboxylic ester or carboxylic acid, alkoxyalkyl, thioalkyl, (cycloalkyl)alkyl, morpholinylalkyl, heterocyclo or (heterocyclo)alkyl; or R6 and R7 taken together with the nitrogen atom to which they are attached form a 5- to 7-membered mono or bicyclic ring including fused rings such as 1-pyrrolidinyl, 1-piperidinyl, 1-azepinyl, 4-morpholinyl, 4-thiamorpholinyl, 4-thiamorpholine dioxide, 1-piperaZinyl, 4-alkyl-1-piperaZinyl, 4-arylalkyl-1-piperaZinyl, 4-diarylalkyl-1-piperazinyl; or 1-piperaZinyl, 1-pyrrolidinyl, 1-piperidinyl or 1-azepinyl substituted with one or more alkyl, alkoxy, alkylthio, halo, trifluoromethyl, hydroxy, aryl, arylalkyl, —COOR14 or —CO-substituted amino;

or R5 and R6 taken together with the atoms to which they are attached form a 5- to 7-membered ring optionally substituted with aryl;

Preferred Compounds of Formula (III)

Preferred methods are to use, and preferred compounds are, compounds of Formula (III), their enantiomers, diastereomers, pharmaceutically-acceptable salts, solvates, hydrates or prodrugs thereof, in which:

Y is oxygen;
R2 is hydroxyl;
R3 and R4 are methyl;
R6 and R7 are alkyl; or R6 and R7 taken together with the nitrogen atom to which they are attached form a 6-membered ring;
X is alkyl;
R12 is aryl or heterocyclo;
A is N;
E is absent or hydrogen;
R5 and R8 are hydrogen;

Example embodiments of Formula (III) Compounds from [7], selected as specific anti-cancer therapeutics by the invention of this disclosure. $EC_{50}$ values for $F_1F_0$ ATP hydrolysis, and $F_1F_0$ ATP synthesis, in NADH-linked and NADPH-linked sub-mitochondrial (SMP) assays respectively. [7] refers to these $EC_{50}$ values as $IC_{50}$ values for inhibiting $F_1F_0$ ATP hydrolase (reverse mode) and $F_1F_0$ ATP synthase (forward mode). However, this in incorrect. Because, as identified by the invention of this disclosure, explained herein, although these molecules inhibit $F_1F_0$ ATP hydrolase, their reducing of $F_1F_0$ ATP synthesis is not (predominantly) because of inhibiting $F_1F_0$ ATP synthase, but by uncoupling. The structure on the left is BMS-199264. It does not harm ex vivo rat heart at a concentration (10 μM [11]) that it exerts anti-cancer activity (discovery of this disclosure).

$EC_{50}$ $F_1F_0$ ATP hydrolase = 0.48 ± 0.23 (μM)
$EC_{50}$ $F_1F_0$ ATP synthesis = 18 ± 9.5 (μM)
$EC_{50}$ Ratio = 38
10 μM doesn't harm ex vivo rat heart 3S,4R
$EC_{50}$ $F_1F_0$ ATP hydrolase = 0.24 ± 0.13 (μM)
$EC_{50}$ $F_1F_0$ ATP synthesis = 3.8 ± 2.1 (μM)
3R,4S
$EC_{50}$ $F_1F_0$ ATP hydrolase = 0.48 ± 0.26 (μM)
$EC_{50}$ $F_1F_0$ ATP synthesis = 4 ± 0.45 (μM)

Example (IV)

Summary of Formula (IV)

This invention embodiment relates to compounds having the following formula:

Formula (IV)

or their enantiomers, diastereomers, pharmaceutically-acceptable salts, solvates, hydrates or prodrugs thereof, wherein:

X is selected from O or S;

A is selected from hydrogen, deuterium, alkyl, substituted alkyl, cycloalkyl, heterocycle, aryl, and heteroaryl;

n and m are 0, 1, or 2

$R_1$ through $R_5$ are independently selected from hydrogen, halogen, $NO_2$, CN, $C_{1-8}$alkyl, substituted $C_{1-8}$alkyl, $C_{3-8}$cycloalkyl, aryl, heterocyclo, heteroaryl, $OR_9$, $SR_9$, $COR_{11}$, $CO_2R_{11}$, $CONR_9R_{10}$ or $NR_9R_{10}$;

$R_6$ and $R_7$ are independently hydrogen, alkyl or substituted alkyl;

$R_8$ is hydrogen, deuterium, $C_{1-8}$alkyl, substituted $C_{1-8}$alkyl, aryl, heterocyclo or heteroaryl;

Z is hydrogen, alkyl, substituted alkyl, cycloalkyl, aryl, heterocyclo, heteroaryl, $COR_{11}$, $CO_2R_{11}$, $SO_2R_{11}$, $S(O)R_{11}$ or $CONR_9R_{10}$;

$R_9$ and $R_{10}$ are independently hydrogen, $C_{1-8}$alkyl, substituted $C_{1-8}$alkyl, $C_{3-10}$cycloalkyl, aryl, heterocyclo, heteroaryl, $COR_{13}$, $SO_2R_{13}$ or $S(O)R_{13}$; and $R_{11}$, $R_{12}$ and $R_{13}$ are independently hydrogen, $C_{1-8}$alkyl, substituted $C_{1-8}$alkyl, $C_{3-10}$cycloalkyl, aryl, heterocyclo or heteroaryl;

wherein each occurrence of $R_9$-$R_{13}$ is chosen independently.

Preferred Compounds of Formula (IV)

Preferred methods are to use, and preferred compounds are, compounds of Formula (IV), their enantiomers, diastereomers, pharmaceutically-acceptable salts, solvates, hydrates or prodrugs thereof, in which:

$R_2$, $R_3$ and $R_4$ are all hydrogen; and/or $R_6$ and $R_7$ are both hydrogen; and/or n and m are both 1; and/or $R_1$ and $R_5$ are both $C_{1-8}$ alkyl, preferably both $R_1$ and $R_5$ are isopropyl groups.

Other preferred methods use, and preferred compounds are, compounds of Formula (IV), their enantiomers, diastereomers, pharmaceutically-acceptable salts, solvates, hydrates or prodrugs thereof, in which:

Z is $C_{1-8}$alkyl, $C_{2-8}$alkenyl, $C_{1-8}$haloalkyl, cycloalkyl, aryl, arylalkyl, heteroaryl, heteroarylalkyl —$COR_{11}$, —$CO_2R_{11}$, —$SO_2R_{11}$, —$S(O)R_{11}$ or —$CONR_9R_{10}$; especially preferable is benzyl, —$C(O)_2H$ or —$C(O)_2C_{1-8}$alkyl;

$R_9$ is hydrogen;

$R_{10}$ is $C_{1-8}$alkyl or $C_{3-10}$cycloalkyl; aryl or arylalkyl; and $R_{11}$ is hydrogen, $C_{1-8}$alkyl, $C_{3-10}$cycloalkyl, $C_{3-10}$heterocycloalkyl, $C_{3-10}$aryl or $C_{3-10}$ arylalkyl.

Other preferred methods use, and preferred compounds are, compounds of Formula (IV), their enantiomers, diastereomers, pharmaceutically-acceptable salts, solvates, hydrates or prodrugs thereof, in which:

A is hydrogen, deuterium, $C_{1-8}$alkyl, heteroaryl, aryl, or alkyl substituted with heterocyclo, aryl, OH, SH, $ST^1$, —C(O), H, $T^3$-$NT^5T^6$, -$T^8$-$C(O)_tT^9$-$NT^5T^6$ or $T^3$-$N(T^2)T^4NT^5T^6$, $T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, -$T^8$-$S(O)_t$-$T^9$-, -$T^8$-$C(O)$-$T^9$-, -$T^8$-$C(S)$-$T^9$-, -$T^8$-$S$-$T^9$-, -$T^8$-$O$—$C(O)$-$T^9$-, -$T^8$-$C(O)_tT^9$-, -$T^8$-$C(=NT^{10})$-$T^9$- or -$T^8$-$C(O)$—$C(O)$-$T^9$-;

$T^5$, $T^6$, $T^7$, $T^8$ and $T^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$OT^{11}$, —$ST^{11}$, —$C(O)_tH$, —$C(O)_tT^{11}$, —O—$C(O)T^{11}$, $T^8C(O)N(T^{12})T^{11}$, —$SO_3H$, —$S(O)_tT^{11}$, $S(O)_tN(T^{12})T^{11}$, -$T^{13}$-$NT^{11}T^{12}$, -$T^{13}$-$N(T^{12})$-$T^4$-$NT^{11}T^{22}$, -$T^{13}$-$N(T^{11})$-$T^{12}$-$T^{11}$ and -$T^{13}$-$N(T^{18})$-$T^{14}$-H; or $T^8$ and $T^9$ are each independently a single bond, alkylene, alkenylene or alkynylene;

$T^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ is halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —$C(O)_tH$ or —$SO_3H$;

$T^{13}$ and $T^{14}$ are each independently a single bond, —$S(O)_t$—, —$C(O)$—, —$C(S)$—, —O—, —S—, —O—C(O)—, —$C(O)_t$—, —$C(=NT^{13})$- or —$C(O)$—$C(O)$—;

wherein each occurrence of $T^1$-$T^{14}$ is chosen independently; and t is 1 or 2.

Preferred compounds of the foregoing section are those in which A is hydrogen, deuterium, $C_{1-8}$alkyl, hydroxyalkyl, heterocycloalkyl, heteroaryl alkyl, aryl, arylalkyl, or alkyl substituted with a group selected from SH, $ST^4$, —$C(O)_tH$, $T^6$-$NT^8T^9$, -$T^{11}$-$C(O)_tT^{12}$-$NT^8T^9$ and $T^6$-$N(T^5)T^7NT^8T^9$.

More preferred are those compounds in which A is hydrogen, deuterium, methyl, —$CH_2(CH_3)_2$, —$(CH_2)_2(CH_3)_2$, —$CH(CH_3)CH_2(CH_3)$, —$(CH_2)OH$, hydroxyethyl, —$(CH_2)_2SCH_3$, —$CH_2SH$, phenyl, —$CH_2(phenyl)$, —$CH_2(p$-hydroxyphenyl), —$CH_2(indole)$, —$(CH_2)C(O)NH_2$, —$(CH_2)_2C(O)NH_2$, —$(CH_2)_2C(O)OH$, —$CH_2C(O)OH$, —$(CH_2)_4NH_2$, —$(CH_2)_3(=NH)CNH_2$, or —$CH_2(imidazole)$. Especially preferred A groups are —$CH(CH_3)CH_2(CH_3)$, phenyl, phenyl alkyl or —$CH_2(2$-indole).

Alternatively preferred methods use, and preferred compounds are, compounds of Formula (IVb), their enantiomers, diastereomers, pharmaceutically-acceptable salts, solvates, hydrates or prodrugs thereof, in which:

Formula (IVb)

wherein:

A is hydrogen, deuterium, $C_{1-8}$alkyl, heteroaryl, aryl, or alkyl substituted with heterocyclo, aryl, OH, SH, $ST^1$, —$C(O)_tH$, $T^3$-$NT^5T^6$, -$T^8$-$C(O)_tT^9$-$NT^5T6$ or $T^3$-$N(T^2)T^4NT^5T^6$;

$R^1$ and $R^5$ are independently $C_{1-8}$alkyl optionally substituted where valence allows;

$R^6$ and $R^7$ are independently hydrogen or $C_{1-8}$alkyl;

$R^8$ is hydrogen, deuterium, $C_{1-8}$alkyl or substituted $C_{1-8}$alkyl;

55

Z is hydrogen, $C_{1-8}$alkyl, $C_{2-8}$alkenyl, $C_{1-8}$haloalkyl, cycloalkyl, aryl, arylalkyl, heteroaryl, heteroarylalkyl —$COR^{11}$, —$CO_2R^{11}$, —$SO_2R^{11}$, —$S(O)R^{11}$ or —$CONR^9R^{10}$;

$R^9$ is hydrogen, $R^{10}$ is $C_{1-8}$alkyl or $C_{3-10}$cycloalkyl; aryl or arylalkyl;

$R^{11}$ is hydrogen, $C_{1-8}$alkyl, $C_{3-10}$cycloalkyl, $C_{3-10}$heterocycloalkyl, $C_{3-10}$aryl or $C_{3-10}$arylalkyl.

$T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, —V—S$(O)_t$-$T^9$-, -$T^8$-C(O)-$T^9$-, -$T^{18}$-C(S)-$T^9$-, -$T^8$-O-$T^9$-, -$T^8$-S-$T^9$-, -$T^8$-O—C(O)-$T^9$-, -$T^8$-C(O)$_t$$T^9$-, -$T^8$-C(=$NT^{10}$)-$T^9$- or -$T^8$-C(O)—C(O)-$T^9$-;

$T^5$, $T^6$, $T^7$, $T^8$ and $T^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$OT^{11}$, —$ST^{11}$, —$C(O)_tH$, —$C(O)_tT^{11}$, —O—C(O)$T^{11}$, $T^8C(O)_tN(T^{12})T^{11}$, —$SO_3H$, —$S(O)_tT^{11}$, $S(O)_tN(T^{12})T^{11}$, -$T^{13}$-$NT^{11}T^{12}$, -$T^{13}$-N($T^{12}$)-$T^4$-$NT^{11}T^{22}$, -$T^{13}$-N($T^{11}$)-$T^{12}$-$T^{11}$ and -$T^{13}$-N($T^{18}$)-$T^{14}$-H; or $T^8$ and $T^9$ are each independently a single bond, alkylene, alkenylene or alkynylene;

$T^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ is halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$C(O)_tH$ or —$SO_3H$;

$T^{13}$ and $T^{14}$ are each independently a single bond, —$S(O)_t$—, —C(O)—, —C(S)—, —O—, —S—, —O—C(O)—, —C(O)$_t$—, —C($NT^{13}$)- or —C(O)—C(O)—; and t is 1 or 2.

More preferred methods/compounds use/are:

A is hydrogen, deuterium, methyl, —$CH_2(CH_3)_2$, —$(CH_2)_2(CH_3)_2$, —$CH(CH_3)CH_2(CH_3)$, —$(CH_2)OH$, hydroxyethyl, —$(CH_2)_2SCH_3$, —$CH_2SH$, phenyl, —$CH_2$(phenyl), —$CH_2$(p-hydroxyphenyl), —$CH_2$(indole), —$(CH_2)C(O)NH_2$, —$(CH_2)_2C(O)NH_2$, —$(CH_2)_2C(O)OH$, —$CH_2C(O)OH$, —$(CH_2)_4NH_2$, —$(CH_2)_3(=NH)CNH_2$ or —$CH_2$(imidazole).

Especially preferred methods/compounds use/are:

A is —$CH(CH_3)CH_2(CH_3)$, phenyl, $CH_2$(phenyl) or —$CH_2$(2-indole).

Also, especially preferred methods/compounds use/are:

$R^8$ is hydrogen and the configuration about the carbon marked with the * is S, provided A is not H. Also preferred: $R^8$ is deuterium and the configuration about the carbon marked with the * is S, provided A is not H or deuterium.

Other preferred methods/compounds use/are:

$R^1$ and $R^5$ are both isopropyl; and/or $R^6R^7$ and $R^9$ are all hydrogen; and/or Z is $CH_2$(phenyl), —$C(O)_2H$ or —$C(O)_2C_{1-8}$alkyl.

56

Example (V)

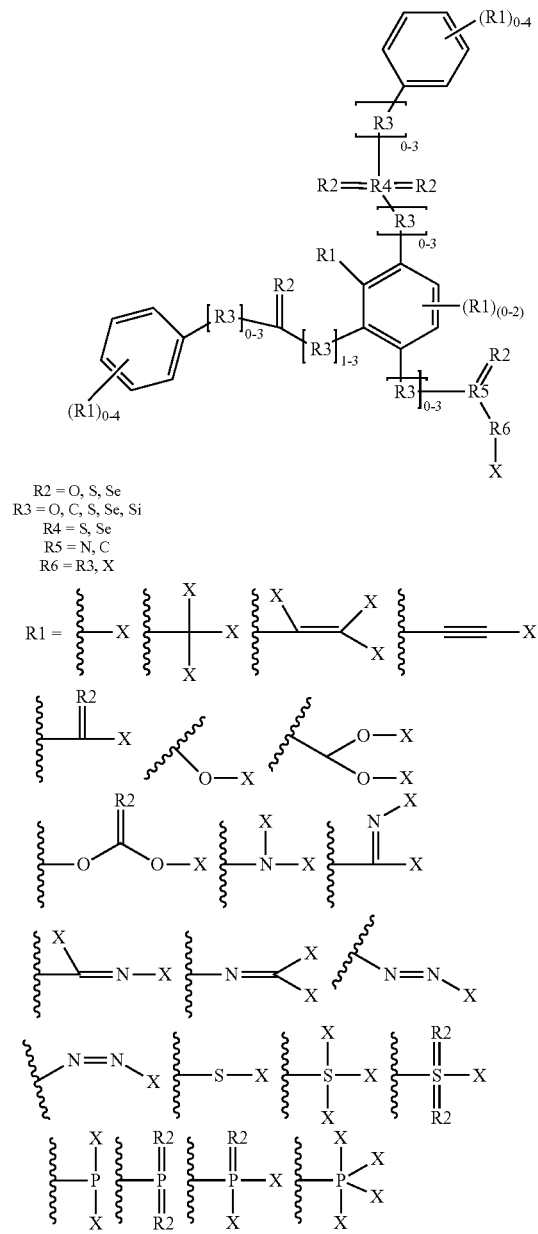

Molecular permutations of BTB06584. Enumerations of this Markush structure, and their pharmaceutically-acceptable salts, solvates, hydrates and prodrugs thereof, are disclosed as anti-cancer molecules: the process/method of their use as anti-cancer molecules is disclosed by this invention. As valence permits: R1 is selected from the options of R1 (independently in each case of R1), X is selected from the options of X (independently in each case of X), R2 is selected from the options of $R_2$ (independently in each case of R2), $R_3$ is selected from the options of $R_3$ (independently in each case of R3), $R_4$ is selected from the options of R4 (independently in each case of R4). In other embodiments one or more phenyl groups has one or more of its double bonds replaced with a single bond. In other embodiments, one or more phenyl groups is replaced with cyclohexane, each with the same possible substitutions as the phenyl it replaces. Hydrogen atoms aren't shown in this figure, but in further embodiments one or more hydrogen atoms is replaced with deuterium. In further embodiments: any possible isotopic substitution at one or more places.

Example Embodiment of Formula (V)

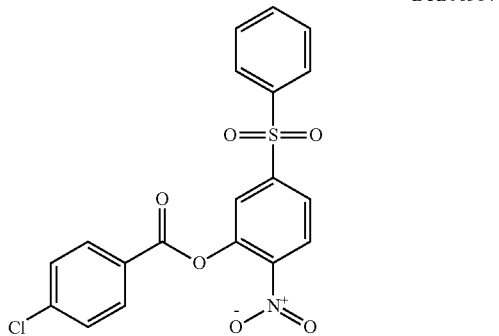

BTB06584

Definitions Used to Specify Formulas (I), (II), (III) and (IV)

The initial definition provided for a group or term herein applies to that group or term throughout the present specification, individually or as part of another group, unless otherwise indicated.

The term "alkyl" refers to straight or branched chain hydrocarbon groups having 1 to 21 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two, three, or four substituents selected from the group consisting of halogen, trifluoromethyl, alkenyl, alkynyl, nitro, cyano, keto (=O), $OR_a$, $SR_a$, $NR_aR_b$, $NR_aSO_2$, $NR_aSO_2R_c$, $SO_2R_c$, $SO_2NR_aR_b$, $CO_2R_a$, $C(=O)R_a$, $C(=O)NR_aR_b$, $OC(=O)R_a$, $-OC(=O)$ $NR_aR_b$, $NR_aC(=O)R_b$, $NR_aCO_2R_b$, =N—OH, =N—O-alkyl, aryl, heteroaryl, heterocyclo and cycloalkyl, wherein $R_a$ and $R_b$ are selected from hydrogen, alkyl, alkenyl, cycloalkyl, heterocyclo, aryl, and heteroaryl, and $R_c$ is selected from hydrogen, alkyl, cycloalkyl, heterocyclo aryl and heteroaryl. When a substituted alkyl includes an aryl, heterocyclo, heteroaryl, or cycloalkyl substituent, said ringed systems are as defined below and thus may in turn have zero to four substituents (preferably 0-2 substituents), also as defined below. When either $R_a$, $R_b$ or $R_c$ is an alkyl, said alkyl may optionally be substituted with 1-2 of halogen, trifluoromethyl, alkenyl, alkynyl, nitro, cyano, keto (=O), OH, O(alkyl), phenyloxy, benzyloxy, SH, S(alkyl), $NH_2$, NH(alkyl), $N(alkyl)_2$, $NHSO_2$, $NHSO_2(alkyl)$, $SO_2(alkyl)$, $SO_2NH_2$, $SO_2NH(alkyl)$, $CO_2H$, $CO_2(alkyl)$, C(=O)H, C(=O)alkyl, $C(=O)NH_2$, C(=O)NH(alkyl), C(=O)N(alkyl)$_2$, OC(=O)alkyl, $-OC(=O)NH_2$, -OC(=O)NH(alkyl), NHC(=O)alkyl, and/or $NHCO_2(alkyl)$.

"Alkyl" when used in conjunction with another group such as in arylalkyl refers to a substituted alkyl in which at least one of the substituents is the specifically named group. For example, the term arylalkyl includes benzyl, or any other straight or branched chain alkyl having at least one aryl group attached at any point of the alkyl chain. As a further example, the term carbamylalkyl includes the group —(CH2)$_n$-NH—C(=O)alkyl, Wherein n is 1 to 12.

The term "alkenyl" refers to straight or branched chain hydrocarbon groups having 2 to 21 carbon atoms and at least one double bond. Alkenyl groups of 2 to 6 carbon atoms and having one double bond are most preferred.

The term "alkynyl" refers to straight or branched chain hydrocarbon groups having 2 to 21 carbon atoms and at least one triple bond. Alkynyl groups of 2 to 6 carbon atoms and having one triple bond are most preferred.

The term "alkylene" refers to bivalent straight or branched chain hydrocarbon groups having 1 to 21 carbon atoms, preferably 1 to 8 carbon atoms, e.g., $\{-CH_2-\}_n$, Wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene group, these groups are substituted with one to four substituents as defined above for alkyl groups. A substituted alkylene, alkenylene, or alkynylene may have a ringed substituent attached in a spiro fashion as in

and so forth.

The term "alkoxy" refers to an alkyl or substituted alkyl group as defined above having one, two or three oxygen atoms (—O—) in the alkyl chain. For example, the term "alkoxy" includes the groups —O-$_{C1-12}$alkyl, —$C_{1-6}$alkylene-O—$C_{1-6}$alkyl, —$C_{1-4}$alkylene-O-phenyl, and so forth.

The term "thioalkyl" or "alkylthio" refers to an alkyl or substituted alkyl group as defined above having one or more sulphur (—S—) atoms in the alkyl chain. For example, the term "thioalkyl" or "alkylthio" includes the groups —(CH$_2$)$_n$—S—CH$_2$aryl, —(CH$_2$)$_n$—S-aryl, etc. etc.

The term "aminoalkyl" or "alkylamino" refers to an alkyl or substituted alkyl group as defined above having one or more nitrogen (—NR'—) atoms in the alkyl chain. For example, the term "aminoalkyl" includes the groups —NR'—C$_{1-12}$alkyl and —CH$_2$—NR'-aryl, etc. (where R' is hydrogen, alkyl or substituted alkyl as defined above.) "Amino" refers to the group —NH$_2$.

When a subscript is used as in $C_{1-8}$alkyl, the subscript refers to the number of carbon atoms the group may contain. Zero when used in a subscript denotes a bond, e.g., $C_{0-4}$ alkyl refers to a bond or an alkyl of 1 to 4 carbon atoms. When used with alkoxy, thioalkyl or aminoalkyl, a subscript refers to the number of carbon atoms that the group may contain in addition to heteroatoms. Thus, for example, monovalent. $C_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—$C_{1-12}$alkyl, —$C_{1-6}$alkylene-O—$C_{1-6}$alkyl, etc., whereas a bivalent alkoxy includes groups such as —O—$C_{1-2}$alkylene-, —$C_{1-6}$alkylene-O—$C_{1-6}$alkylene-, etc.

The term "acyl" refers to a carbonyl

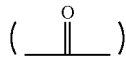

linked to an organic group i.e.

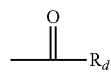

wherein $R_d$ may be selected from alkyl, alkenyl, substituted alkyl, substituted alkenyl, aryl, heterocyclo, cycloalkyl, or heteroaryl, as defined herein.

The term "alkoxycarbonyl" refers to a group having a carboxy or ester group

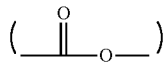

linked to an organic radical, i.e.,

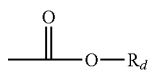

Wherein $R_d$ is as defined above for acyl.

The term "carbamyl" refers to a functional group in which a nitrogen atom is directly bonded to a carbonyl, i.e., as in —$NR_eC(=O)R_f$ or —$C(=O)NR_eR_f$, wherein $R_e$ and $R_f$ can be hydrogen, alkyl, substituted alkyl, alkenyl, substituted alkenyl, alkoxy, cycloalkyl, aryl, heterocyclo, or heteroaryl, or they may join to form a ring.

The term "sulfonyl" refers to a sulphoxide group (i.e., —$S(O)_{1-2}$) linked to an organic radical $R_c$, as defined above.

The term "sulfonamide" or "sulfonamido" refers to the group —$S(O)_2NR_eR_f$, wherein $R_e$ and $R_f$ are as defined above. Preferably when one of $R_e$ and $R_f$ is optionally substituted heteroaryl or heterocycle (as defined below), the other of $R_e$ and $R_f$ is hydrogen or alkyl.

The term "cycloalkyl" refers to fully saturated and partially unsaturated hydrocarbon rings of 3 to 9, preferably 3 to 7 carbon atoms. The term "cycloalkyl" includes such rings having zero to four substituents (preferably 0-2 substituents), selected from the group consisting of halogen, alkyl, substituted alkyl (e.g., trifluoromethyl), alkenyl, substituted alkenyl, alkynyl, nitro, cyano, keto, $OR_d$, $SR_d$ $NR_dR_e$ $NR_cSO_2$, $NR_cSO_2R_e$, $C(=O)H$, acyl, —$CO_2H$, alkoxycarbonyl, carbamyl, sulfonyl, sulfonamide, —OC($=O$)$R_d$, $=N$—OH, $=N$—O-alkyl, aryl, heteroaryl, heterocyclo, a 4 to 7 membered carbocyclic ring, and a five or six membered ketal, e.g., 1,3-dioxolane or 1,3-dioxane, wherein $R_c$, $R_d$ and $R_e$ are defined as above. The term "cycloalkyl" also includes such rings having a phenyl ring fused thereto or having a carbon-carbon bridge of 3 to 4 carbon atoms. Additionally, when a cycloalkyl is substituted with a further ring, i.e., aryl, arylalkyl, heteroaryl, heteroarylalkyl, heterocyclo, heterocycloalkyl, cycloalkylalkyl, or a further cycloalkyl ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and $NHCO_2$(alkyl).

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl, 2-naphthyl, and anthracenyl, with phenyl being preferred. The term "aryl" includes such rings having zero to four substituents (preferably 0-2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_c$, C(=O)H, acyl, —$CO_2H$, alkoxycarbonyl, carbamyl, sulfonyl, sulfonamide, —OC(=O)$R_d$, heteroaryl, heterocyclo, cycloalkyl, phenyl, benzyl, napthyl, including phenylethyl, phenyloxy, and phenylthio, wherein $R_c$, $R_d$ and $R_e$ are defined as above. Additionally, two substituents attached to an aryl, particularly a phenyl group, may join to form a further ring such as a fused or spiro-ring, e.g., cyclopentyl or cyclohexyl or fused heterocycle or heteroaryl. When an aryl is substituted with a further ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)2, $NHSO_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and $NHCO_2$(alkyl).

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom selected from O, S and N. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to four substituents (preferably 0-2 substituents), selected from the group consisting of halo, alkyl, substituted alkyl (e.g., trifluoromethyl), alkenyl, substituted alkenyl, alkynyl, nitro, cyano, keto, $OR_d$, $SR_d$, $NR_dR_e$, NR$_d$SO$_2$, NR$_d$SO$_2$R$_c$, SO$_2$R$_d$, C(=O)H, acyl, —CO$_2$H, alkoxycarbonyl, carbamyl, sulfonyl, sulfonamide, —OC(=O)R$_d$, =N—OH, =N—O-alkyl, aryl, heteroaryl, cycloalkyl, a five or six membered ketal, e.g., 1,3-dioxolane or 1,3-dioxane, or a monocyclic 4 to 7 membered non aromatic ring having one to four heteroatoms, wherein R$_c$, R$_d$ and R$_e$ are defined as above. The term "heterocyclo" also includes such rings having a phenyl ring fused thereto or having a carbon-carbon bridge of 3 to 4 carbon atoms. Additionally, when a heterocyclo is substituted with a further ring, i.e., aryl, arylalkyl, heteroaryl, heteroarylalkyl, cycloalkyl, cycloalkylalkyl, heterocycloalkyl, or a further heterocyclo ring, such ring in turn may be substituted with one to two of C$_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH (alkyl), NHC(=O)alkyl, and NHCO$_2$(alkyl).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom selected from O, S and N in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero to four substituents (preferably 0-2 substituents), selected from the group consisting of halo, alkyl, substituted alkyl (e.g., trifluoromethyl), alkenyl, substituted alkenyl, alkynyl, nitro, cyano, OR$_d$, SR$_d$, NR$_d$R$_e$, NR$_d$SO$_2$, NR$_d$SO$_2$R$_c$, SO$_2$R$_d$, C(=O)H, acyl, —CO$_2$H, alkoxycarbonyl, carbamyl, sulfonyl, sulfonamide, —OC(=O)R$_d$, heterocyclo, cycloalkyl, aryl, or a monocyclic 4 to 7 membered aromatic ring having one to four heteroatoms, including phenylethyl, phenyloxy, and phenylthio, wherein R$_c$, R$_d$ and R$_e$ are defined as above. Additionally, when a heteroaryl is substituted with a further ring, i.e., aryl, arylalkyl, heterocyclo, heterocycloalkyl, cycloalkyl, cycloalkylalkyl, heteroarylalkyl, or a further heteroaryl ring, such ring in turn may be substituted with one to two of C$_{0-4}$ alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl)$_n$, SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH(alkyl), NHC(=O)alkyl, and NHCO$_2$(alkyl).

Exemplary monocyclic heteroaryl groups include pyrrolyl, pyrazolyl, pyrazolinyl, imidazolyl, oxazolyl, isoxazolyl, thiazolyl (i.e. 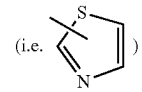)

thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

When the term "unsaturated" is used herein to refer to a ring or group, the ring or group may be fully unsaturated or partially unsaturated.

The phrase "optionally substituted" is intended to include substituted or unsubstituted possibilities. Accordingly, the phrase "each group of which may be optionally substituted means that each group includes both substituted and unsubstituted groups.

The use of the phrase "Where valence allows" means that the groups may be substituted only to the degree and nature allowed by valency of the group. This is commonly understood by those of skill in the art. For example, a hydrogen substituent cannot be further substituted nor can a phenyl group be directly substituted by an oxo group due to limits on valency.

Stereoisomers

All stereoisomers of Formula [X], such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

For the molecules presented in this invention's Description and Drawings: the present invention contemplates all geometric/conformational isomers, rotamers, atropisomers, stereoisomers, optically active forms, tautomers, keto-enol tautomers, cis- and trans-isomers, E and Z isomers, R- and S-enantiomers, diastereomers, (D)-isomers, (L)-isomers, the racemic mixtures thereof, other mixtures thereof and isotopic variants (e.g. deuterium in place of hydrogen in some or all places upon the molecule{s}) as falling within the scope of the invention. All such isomers, as well as mixtures thereof, are intended to be included in this invention. As well as analogues and pharmaceutically/physiologically acceptable salts/solvates/hydrates/chelates/metal complexes/mixtures/prodrugs/radionuclides/polymorphs/esters/derivatives/ carriers/crystalline forms/liposomes thereof. Unless indicated otherwise, chemical structures and graphical representations of compounds herein encompass all stereoisomers. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

The invention also embraces isotopically labelled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Salts, Solvates, Prodrugs

Throughout the specification, groups and substituents thereof may be chosen by one skilled in the field to provide stable moieties and compounds.

The compounds of Formula [X] form salts which are also within the scope of this invention. Reference to a compound of the Formula [X] herein is understood to include reference to salts thereof, unless otherwise indicated.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of ordinary skill in the art, "salts" of the compounds of the present invention may be derived from inorganic or organic acids and bases. For therapeutic use, salts of the compounds of the present invention are contemplated as being pharmaceutically acceptable (i.e., non-toxic, physiologically acceptable). However, salts of acids and bases that are non-pharmaceutically acceptable may also find use, for example, in the preparation, isolation or purification of a pharmaceutically acceptable compound.

The term "salt(s)", as employed herein, denotes acidic and/or basic salts formed with inorganic and/or organic acids and bases. In addition, when a compound of Formula [X] contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein.

Salts of the compounds of the Formula [X] may be formed, for example, by reacting a compound of the Formula [X] with an amount of acid or base, such as an equivalent amount, in a medium such as one in which the salt precipitates or in an aqueous medium followed by lyophilization.

The compounds of Formula [X] which contain a basic moiety, such as, but not limited to an amine or a pyridine or imidazole ring, may form salts with a variety of organic and inorganic acids. Exemplary acid addition salts include acetates (such as those formed with acetic acid or trihalo acetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methane-sulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula [X] which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the Formula [X], and salts thereof, may exist in their tautomeric form (for example, as an amide or imino ether). All such tautomeric forms are contemplated herein as part of the present invention.

In addition, compounds of the Formulas [X] may have prodrug forms. Any compound that will be converted in vivo to provide the bioactive agent (i.e., a compound of Formula [X]) is a prodrug within the scope and spirit of the invention.

For example, pro-drug compounds of the Formulas [X] may be carboxylate ester moieties. A carboxylate ester may be conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, p. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of Formula [X] are also within the scope of the present invention. Methods of solvation are generally known in the art.

Chelates, metal complexes, mixtures, radio-nuclides and liposomes of Formula [X] are within the scope of this invention.

Dosage

As used herein, the term "effective amount" refers to the amount of a compound sufficient to effect beneficial or desired results. An effective amount can be administered in one or more administrations, applications or dosages and is not intended to be limited to a particular formulation or administration route.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

An exemplary effective amount of compounds of Formula [X] may be within the dosage range of about 0.001 to about 300 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses. But more exactly it depends upon the compound used, the condition and its advancement/severity, the route of administration, type of dosing (e.g. pulse or consistent etc.), what other treatments are undertaken alongside or previously (e.g. chemotherapeutics, surgery, radiotherapy etc.), the age, sex, condition, previous/other diseases of the patient, pharmacokinetics of compound in that patient, response to treatment and exceptions to this dosage range may be contemplated by the present invention, and they might be changed during treatment to find the optimum. Optimal dosages to be administered to a subject may be determined by those skilled in the art. When the compounds described herein are co-administered with another agent, the effective amount may be less than when the agent is used alone.

Pharmaceutical Composition

As used herein, the term "pharmaceutical composition" refers to the combination of an active agent with a carrier, inert or active, making the composition especially suitable for diagnostic or therapeutic use in vivo. Disclosed is a pharmaceutical composition of a therapeutically effective amount of a compound(s) of Formula [X] or a pharmaceutically acceptable salt thereof, and one or more pharmaceutically acceptable carriers, additives and/or diluents.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

Administration

The compounds of Formula [X] may be administered by any means suitable for the condition to be treated. For example: oral, parenteral, enteral, infusion, injection, sublingual, topical, rectal, transdermal, intramuscular and inhalation. The compound may be delivered orally, such as in the form of tablets, capsules, granules, microgranules, pellets, soft-gels, powders, or liquid formulations including syrups, liquids, solutions, elixirs, suspensions, emulsions or magmas; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavouring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavours, colouring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

Co-Administration

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/ therapies lowers the requisite dosage of a known potentially harmful (e.g., toxic) agent(s).

PATENTS, OR PATENT APPLICATIONS, CITED

[P1] Hamann L G, Pudzianowski A T, inventors; Bristol-Myers Squibb Company, assignee. N-substituted phenylurea inhibitors of mitochondrial F 1F0 ATP hydrolase. U.S. Pat. No. 6,846,836. 2005 Jan. 25.

[P2] Ding C, Hamann L, Stein P, Pudzianowski A, inventors; Ding Charles Z., Hamann Lawrence G., Stein Philip D., Pudzianowski Andrew T., assignee. Benzodiazepine inhibitors of mitochondial F1F0 ATP hydrolase and methods of inhibiting F1F0 ATP hydrolase. U.S. patent application Ser. No. 10/461,736. 2003 Jun. 13.

[P3] Atwal K S, Grover G J, Ding C Z, Stein P D, Lloyd J, Ahmad S, Hamann L G, Green D, Ferrara F N, inventors; Bristol-Myers Squibb Co., assignee. (1-phenyl-2-heteoaryl) ethyl-guanidine compounds as inhibitors of mitochondrial F1F0 ATP hydrolase. U.S. Pat. No. 6,916,813. 2005 Jul. 12.

[P4] Ding C Z, Atwal K S, inventors; Bristol-Myers Squibb Company, assignee. Sulfonamido substituted benzopyran derivatives. U.S. Pat. No. 5,869,478. 1999 Feb. 9.

NON-PATENT REFERENCES

[1] Stryer L, Berg J M, Tymoczko J L (2002) Biochemistry, 4$^{th}$ Ed. New York, NY WH Freeman.

[2] Alberts B, Johnson A, Lewis J, Raff M, Roberts K, Walter P (1994) Molecular Biology Of The Cell, 3$^{rd}$ Ed. New York, NY Garland Publishing.

[3] Nicholls D G, Ferguson S (2013) Bioenergetics. Academic Press.

[4] Hong S, Pedersen P L (2008) ATP synthase and the actions of inhibitors utilized to study its roles in human health, disease, and other scientific areas. Microbiology and Molecular Biology Reviews 72(4):590-641.

[5] Atwal K S, Ahmad S, Ding C Z, Stein P D, Lloyd J, Hamann L G, Green D W, Ferrara F N, Wang P, Rogers W L, Doweyko L M, Miller A V, Bisaha S N, Schmidt J B, Li L, Yost K J, Lan H J, Madsen C S (2004) N-[1-Aryl-2-(1-imidazolo)ethyl]-guanidine derivatives as potent inhibitors of the bovine mitochondrial $F_1F_0$ ATP hydrolase. Bioorg. Med. Chem. Lett. 141027-1030.

[6] Bisaha S N, Malley M F, Pudzianowski A, Monshizadegan H, Wang P, Madsen C S, Gougoutas J Z, Stein P D (2005) A switch in enantiomer preference between mitochondrial F 1 F 0-ATPase chemotypes. Bioorganic & medicinal chemistry letters 15(11):2749-51.

[7] Atwal K S, Wang P, Rogers W L, Sleph P, Monshizadegan H, Ferrara F N, Traeger S, Green D W, Grover G J (2004) Small molecule mitochondrial $F_1F_0$ ATPase hydrolase inhibitors as cardioprotective agents. Identification of 4-(N-arylimidazole)-substituted benzopyran derivatives as selective hydrolase inhibitors. J. Med. Chem. 471081-1084. INCLUDING this paper's supplementary material.

[8] Hamann L G, Ding C Z, Miller A V, Madsen C S, Wang P, Stein P D, Pudzianowski A T, Green D W, Monshizadegan H, Atwal K S (2004) Benzodiazepine-based selective inhibitors of mitochondrial $F_1F_0$ ATP hydrolase. Bioorg. Med. Chem. Lett. 141031-1034.

[9] Grover G J, Marone P A, Koetzner L, Seto-Young D (2008) Energetic signalling in the control of mitochondrial F 1 F 0 ATP synthase activity in health and disease. The international journal of biochemistry & cell biology 40(12):2698-2701.

[10] Grover G J, Malm J (2008) Pharmacological Profile of the Selective Mitochondrial F1F0 ATP Hydrolase Inhibitor BMS-199264 in Myocardial Ischemia. Cardiovascular therapeutics 26(4):287-296.

[11] Grover G J, Atwal K S, Sleph P G, Wang F L, Monshizadegan H, Monticello T, Green D W (2004) Excessive ATP hydrolysis in ischemic myocardium by mitochondrial F1F0-ATPase: effect of selective pharmacological inhibition of mitochondrial ATPase hydrolase activity. American Journal of Physiology-Heart and Circulatory Physiology 287(4):H1747-H1755.

[12] Ivanes F (2013) New mechanisms of protection of cardiomyocytes from ischemia/reperfusion injury (Doctoral dissertation, Université Claude Bernard-Lyon I).

[13] Ivanes F, Faccenda D, Gatliff J, Ahmed A A, Cocco S, Cheng C H K, . . . & Campanella M (2014) The compound BTB06584 is an IF1-dependent selective inhibitor of the mitochondrial F1Fo-ATPase. British journal of pharmacology 171(18):4193-4206.

[14] Salomon A R, Voehringer D W, Herzenberg L A, Khosla C (2000) Understanding and exploiting the mechanistic basis for selectivity of polyketide inhibitors of F0F1-ATPase. Proceedings of the National Academy of Sciences. 97(26):14766-71.

[15] Kramar R, Hohenegger M, Srour A N, Khanakah G. Oligomycin toxicity in intact rats. Inflammation Research. 1984 Dec. 1; 15(5):660-3.

[16] National Cancer Institute (NCI) Developmental Therapeutics Program (DTP) Screening Data Database https://dtp.cancer.gov/dtpstandard/dwindex/index.jsp. Accessed on Jun. 29, 2017

[17] Gao C, Shen Y, Jin F, Miao Y, Qiu X (2016) Cancer stem cells in small cell lung cancer cell line H446: higher dependency on oxidative phosphorylation and mitochondrial substrate-level phosphorylation than non-stem cancer cells. PloS one. 11(5):e0154576.

[18] Cuezva J M, Krajewska M, de Heredia M L, Krajewski S, Santamaría G, Kim H, Zapata J M, Marusawa H, Chamorro M, Reed J C (2002) The bioenergetic signature of cancer. Cancer research. 62(22):6674-81.

[19] Aldea M, Clofent J, De Arenas C N, Chamorro M, Velasco M, Berrendero J R, Navarro C, Cuezva J M (2011) Reverse phase protein microarrays quantify and validate the bioenergetic signature as biomarker in colorectal cancer. Cancer letters. 311(2):210-8.

[20] Hjerpe E, Brage S E, Carlson J, Stolt M F, Schedvins K, Johansson H, Shoshan M, Åvall-Lundqvist E (2013) Metabolic markers GAPDH, PKM2, ATP5B and BEC-index in advanced serous ovarian cancer. BMC clinical pathology. 13(1):30.

[21] Sgarbi G, Barbato S, Costanzini A, Solaini G, Baracca A. The role of the ATPase inhibitor factor 1 (IF1) in cancer cells adaptation to hypoxia and anoxia. Biochimica et Biophysica Acta (BBA)-Bioenergetics. 2018 Feb. 1; 1859(2):99-109.

[22] Walenta S, Wetterling M, Lehrke M, Schwickert G, Sundfor K, Rofstad E K, Mueller-Klieser W (2000) High lactate levels predict likelihood of metastases, tumor recurrence, and restricted patient survival in human cervical cancers. Cancer research. 60(4):916-21.

[23] Paull K D, Shoemaker R H, Hodes L, Monks A, Scudiero D A, Rubinstein L, Plowman J, Boyd M R (1989) Display and analysis of patterns of differential activity of drugs against human tumor cell lines: development of mean graph and COMPARE algorithm. JNCI: Journal of the National Cancer Institute. 81(14):1088-92.

[24] https://dtp.cancer.gov/databases_tools/compare.htm. Accessed on Jun. 29, 2017

[25] Holbeck S L, Collins J M, Doroshow J H (2010) Analysis of Food and Drug Administration—approved anticancer agents in the NCI60 panel of human tumor cell lines. Molecular cancer therapeutics. 9(5):1451-60.

[26] Reinhold W C, Sunshine M, Liu H, Varma S, Kohn K W, Morris J, Doroshow J, Pommier Y (2012) CellMiner: a web-based suite of genomic and pharmacologic tools to explore transcript and drug patterns in the NCI-60 cell line set. Cancer research. 72(14):3499-511.

[27] https://discover.nci.nih.gov/cellminer/home.do. Accessed on Jun. 29, 2017

[28] Gholami A M, Hahne H, Wu Z, Auer F J, Meng C, Wilhelm M, Kuster B (2013) Global proteome analysis of the NCI-60 cell line panel. Cell reports. 4(3):609-20.

[29] Shoemaker R H (2006) The NCI60 human tumour cell line anticancer drug screen. Nature Rev Cancer 6:813-23.

[30] NCI-60 Screening Methodology. Details of both the one-dose and five-dose assays. https://dtp.cancer.gov/discover_development/nci-60/methodology.htm (accessed on 25 Jun. 2017).

[31] Marvin cheminformatics suite (version 16.3.21; academic license; ChemAxon Kft., Budapest, Hungary; www.chemaxon.com)

[32] Martineau L C (2012) Simple thermodynamic model of unassisted proton shuttle uncoupling and prediction of activity from calculated speciation, lipophilicity, and molecular geometry. Journal of theoretical biology. 303: 33-61.

[33] Jacques V, Czarnik A W, Judge T M, Van der Ploeg L H, DeWitt S H (2015) Differentiation of antiinflammatory and antitumorigenic properties of stabilized enantiomers of thalidomide analogs. Proceedings of the National Academy of Sciences. 112(12):E1471-9.

[34] Gordon C J (2012) Thermal physiology of laboratory mice: Defining thermoneutrality. Journal of Thermal Biology. 37(8):654-85.

[35] Yin T, Lu L, Xiong Z, Wei S, Cui D (2015) ATPase inhibitory factor 1 is a prognostic marker and contributes to proliferation and invasion of human gastric cancer cells. Biomedicine & Pharmacotherapy. 70:90-6.

[36] Zheng J, Ramirez V D (2000) Inhibition of mitochondrial proton F0F1-ATPase/ATP synthase by polyphenolic phytochemicals. British journal of pharmacology. 130(5): 1115-23.

[37] Crystallographic data (excluding structure factors) for 6b have been deposited with the Cambridge Crystallographic Data Centre as supplementary publication numbers CCDC 251489 and 251490. Copies of the data can be obtained, free of charge, on application to CCDC, 12 Union Road, Cambridge, CB2 1EZ, UK [fax: +44 (0) 1223 336033 or e-mail: deposit@ccdc.cam.ac.uk].

[38] CCDC Number: 251490; S. N. Bisaha, M. F. Malley, A. Pudzianowski, H. Monshizadegan, P. Wang, C. S. Madsen, J. Z. Gougoutas, P. D. Stein CCDC 251490: Experimental Crystal Structure Determination, 2014, DOI: 10.5517/cc8fply

[39] CCDC Number: 251489; S. N. Bisaha, M. F. Malley, A. Pudzianowski, H. Monshizadegan, P. Wang, C. S. Madsen, J. Z. Gougoutas, P. D. Stein CCDC 251489: Experimental Crystal Structure Determination, 2014, DOI: 10.5517/cc8fpkx

[40] Zhu A, Lee D, Shim H. Metabolic positron emission tomography imaging in cancer detection and therapy response (2011) In Seminars in oncology (Vol. 38, No. 1, pp. 55-69). W B Saunders.

[41] Zhang L, Martins A F, Mai Y, Zhao P, Funk A M, Clavijo Jordan M V, Zhang S, Chen W, Wu Y, Sherry A D. Imaging Extracellular Lactate In Vitro and In Vivo Using CEST MRI and a Paramagnetic Shift Reagent (2017) Chemistry—A European Journal. 23(8):1752-6.

[42] Chen L Q, Pagel M D (2015) Evaluating pH in the Extracellular Tumor Microenvironment Using CEST MRI and Other Imaging Methods. Advances in radiology.

[43] Anderson M, Moshnikova A, Engelman D M, Reshetnyak Y K, Andreev O A (2016) Probe for the measurement of cell surface pH in vivo and ex vivo. Proceedings of the National Academy of Sciences. 201608247.

[44] Manzoor A A, Schroeder T, Dewhirst M W (2008) One-stop-shop tumor imaging: buy hypoxia, get lactate free. The Journal of clinical investigation. 118(5):1616.

[45] Garedew A, Henderson S O, Moncada S (2010) Activated macrophages utilize glycolytic ATP to maintain mitochondrial membrane potential and prevent apoptotic cell death. Cell Death & Differentiation. 17(10):1540-50.

[46] Mantovani A, Marchesi F, Malesci A, Laghi L, Allavena P (2017) Tumour-associated macrophages as treatment targets in oncology. Nature reviews Clinical oncology.

[47] Colotta F, Allavena P, Sica A, Garlanda C, Mantovani A (2009) Cancer-related inflammation, the seventh hallmark of cancer: links to genetic instability. Carcinogenesis. 30(7):1073-81.

[48] Honeycutt J B, Wahl A, Baker C, Spagnuolo R A, Foster J, Zakharova O, Wietgrefe S, Caro-Vegas C, Madden V, Sharpe G, Haase A T (2016) Macrophages sustain HIV replication in vivo independently of T cells. The Journal of clinical investigation. 126(4):1353.

[49] Arainga M, Edagwa B, Mosley R L, Poluektova L Y, Gorantla S, Gendelman H E. A mature macrophage is a principal HIV-1 cellular reservoir in humanized mice after treatment with long acting antiretroviral therapy (2017) Retrovirology. 14(1):17.

[50] Appelberg K S, Wallet M A, Taylor J P, Cash M N, Sleasman J W, Goodenow M M. HIV-1 Infection Primes Macrophages through STAT Signaling to Promote Enhanced Inflammation and Viral Replication (2017) AIDS Research and Human Retroviruses.

[51] Burdo T H, Lentz M R, Autissier P, Krishnan A, Halpern E, Letendre S, Rosenberg E S, Ellis R J, Williams K C (2011) Soluble CD163 made by monocyte/macrophages is a novel marker of HIV activity in early and chronic infection prior to and after anti-retroviral therapy. Journal of Infectious Diseases. 204(1):154-63.

The invention claimed is:

1. A compound, or a pharmaceutical composition comprising at least one compound (and one or more of a pharmaceutically-acceptable carrier [s], additive [s], diluent [s]), having the formula,

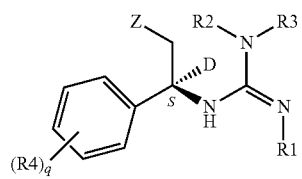

or a pharmaceutically-acceptable salt, solvate, hydrate or prodrug thereof, wherein:

there is deuterium (D) enrichment at the chiral centre, and optionally at other locations;

wherein there is an enantiomeric excess (ee) of the S stereoisomer;

$R_1$ is cyano, $-SO_2R_8$, $-C(=O)R_9$, or heteroaryl;

$R_2$ is (i) independently hydrogen, alkyl, benzyl, or substituted alkyl, or (ii) taken together with $R_3$ forms a heterocyclo;

$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) phenyl optionally substituted with one or more groups selected from $C_{1-4}$alkyl, halogen, trifluoromethyl, $OCF_3$, cyano, nitro, amino, hydroxy, or methoxy, or (iii) independently selected from $C_{1-4}$alkyl, alkylthio, aminoalkyl, $-B_B$-aryl, $-B_B$-heterocyclo, $B_B$-cycloalkyl, and $-B_B$-heteroaryl, optionally having one to three substituents selected from $R_{3a}$; and/or having fused thereto a five or six membered carbocyclic ring, or (iv) taken together with $R_2$ forms a heterocyclo optionally substituted with alkyl or substituted alkyl;

$B_B$ is a bond, $C_{1-4}$alkylene, $C_{2-4}$alkenylene, substituted $C_{1-4}$alkylene, substituted $C_{2-4}$alkenylene, substituted $C_{1-4}$alkylene-C(=O)NH—, —C(=O)NH—, —$C_{1-4}$alkylene-C(=O)NH—, —C(=O)NR$_{19}$—, —$C_{1-4}$alkylene-C(=O)NR$_{19}$—, or substituted $C_{1-4}$alkylene-C(=O)NR$_{19}$—, —(CHR$_{14}$)$_m$—(CR$_{15}$R$_{16}$)$_n$— or —(CHR$_{14}$)$_p$—C(=O)NH—;

$R_{3a}$ at each occurrence is selected independently from alkyl, substituted alkyl, halogen, haloalkoxy, cyano, nitro, keto, trifluoromethyl, —NR$_{17}$R$_{18}$, —SR$_{17}$, —OR$_{17}$, —SO$_2$R$_{17a}$, —SO$_2$NR$_{17}$R$_{18}$, —NR$_{17}$C(=O)R$_{18}$, —CO$_2$R$_{17}$, —C(=O)R$_{17}$, cycloalkyl, aryl, heterocyclo, and heteroaryl, wherein when $R_{3a}$ is cycloalkyl, aryl, heterocyclo or heteroaryl, said cycloalkyl, aryl, heterocyclo and heteroaryl in turn is optionally substituted with alkyl or substituted alkyl;

Z is a heteroaryl, provided that when $R_1$ is cyano, Z is not 2-pyridinyl; and/or Z is selected from 5-membered heteroaryl groups containing 1, 2 or 3 heteroatoms each independently selected from N, O and S; and/or Z is triazolyl optionally substituted with one to two $R_7$ substituents or imidazolyl optionally substituted with one to two $R_7$ substituents and/or having fused thereto a benzene ring in turn optionally substituted with one to two $R_7$ substituents; and $R_7$ is alkyl, carbamyl, or substituted alkyl;

$R_4$ at each occurrence is selected independently of each other $R_4$ from the group consisting of halogen, trifluoromethyl, $OCF_3$, alkyl, substituted alkyl, haloalkyl, nitro, cyano, haloalkoxy, OR$_{25}$, SR$_{25}$, NR$_{25}$R$_{26}$, NR$_{25}$SO$_2$R$_{27}$, SO$_2$R$_{27}$, SO$_2$NR$_{25}$R$_{26}$, CO$_2$R$_{26}$, C(=O)R$_{26}$, C(=O)NR$_{25}$R$_{26}$, OC(=O)R$_{25}$, —OC(=O)NR$_{25}$R$_{26}$, NR$_{25}$C(=O)R$_{26}$, NR$_{25}$CO$_2$R$_{26}$, aryl, heteroaryl, heterocyclo and cycloalkyl;

$R_8$ is $C_{1-4}$alkyl or phenyl optionally substituted with alkyl, halogen, haloalkoxy, cyano, nitro, or trifluoromethyl;

$R_9$ is —NR$_{10}$R$_{11}$, alkyl, substituted alkyl, alkoxy, alkylthio, cycloalkyl, aryl, heteroaryl, heterocyclo, or —CO$_2$R$_{12}$, alkyl or phenyl optionally substituted with one to four of halogen, cyano, trifluoromethyl, nitro, hydroxy, phenyl, pyridinyl, $C_{1-4}$alkoxy, haloalkoxy, $C_{1-6}$alkyl, CO$_2$alkyl, SO$_2$alkyl, SO$_2$NH$_2$, amino, NH (C$_{1-4}$alkyl), N (C$_{1-4}$alkyl)$_2$, NHC(=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto or a) $C_{1-4}$alkyl optionally substituted with one to two of:
  i) SR$_{13}$, OR$_{13}$, NR$_{13a}$R$_{13b}$, halogen, trifluoromethyl, CO$_2$R$_{13a}$, and C(=O)NR$_{13a}$R$_{13b}$;
  ii) cycloalkyl optionally substituted with one to two of C(=O)H, $C_{1-4}$acyl, alkenyl, carbamyl, and/or phenyl in turn optionally substituted with halogen;
  iii) phenyl or napthyl optionally substituted with one to two of halogen, nitro, amino, alkyl, hydroxy, $C_{1-4}$alkoxy, or having fused thereto a five or six membered heterocyclo;
  iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;

b) 3 to 6 membered cycloalkyl optionally having up to four substituents selected from alkyl, halogen, cyano, alkenyl, acyl, alkylthio, carbamyl, phenyl in turn optionally substituted with halogen; or having an aryl fused thereto;

c) phenyl optionally substituted with one to four of halogen, cyano, trifluoromethyl, nitro, hydroxy, $C_{1-4}$alkoxy, haloalkoxy, $C_{1-4}$alkyl, CO$_2$alkyl, SO$_2$alkyl, SO$_2$NH$_2$, amino NH (C$_{1-4}$alkyl), N (C$_{1-4}$alkyl)$_2$, NHC(=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto;

d) pyridinyl, thiazolyl, furanyl, thiophenyl, and pyrrolyl optionally substituted with one to two of halogen, alkyl, and phenyl in turn optionally substituted with halogen or trifluoromethyl;

$R_{10}$ and $R_{11}$ are (i) independently selected from hydrogen, alkyl, substituted alkyl, alkoxy, heterocyclo, cycloalkyl, aryl, heteroaryl or $C_{1-4}$alkyl optionally substituted with one to two of —CO$_2$alkyl, —C(=O)NH (aryl), NH (aryl), cycloalkyl, phenyloxy, phenyl in turn optionally substituted with $C_{1-4}$alkyl, hydroxy, $C_{1-4}$alkoxy, halogen, amino, nitro, tetrahydrofuranyl, and/or five or six membered heterocyclo, or having a five or six membered heterocyclo fused thereto; pyrrolidinyl optionally substituted with keto; napthyl, anthracenyl, pyridinyl, thiophenyl, furanyl, imidazolyl, benzimidazolyl, or indolyl in turn optionally substituted with $C_{1-4}$alkyl or $C_{1-4}$alkoxy; or (ii) taken together form a heteroaryl or heterocyclo selected from pyrrolidinyl, piperazinyl, piperidinyl, morpholinyl, tetrahydropyridinyl, and imidazolidinyl, wherein said heterocyclo formed by $R_{10}$ and $R_{11}$ is optionally substituted with one to two of keto, CO$_2$H, $C_{1-4}$alkoxy, CO$_2$alkyl, $C_{1-4}$carbamyl, benzyl; phenyl in turn optionally substituted with alkyl, halogen, or $C_{1-4}$alkoxy; tetrahydropyridinyl in turn optionally substituted with keto and/or phenyl; alkyl optionally substituted with amino or NHR$_{21}$ wherein $R_{21}$ is alkyl or phenyl optionally substituted with alkyl; and/or has a benzene ring fused thereto in turn optionally substituted with one to two of alkyl, $C_{1-4}$alkoxy, CO$_2$alkyl, and/or $C_{1-4}$carbamyl;

$R_{12}$ and $R_{19}$ are hydrogen or alkyl;

$R_{13}$ is hydrogen or alkyl;

$R_{13a}$ and $R_{13b}$ are selected from hydrogen, alkyl, and aryl;

$R_{14}$, $R_{15}$ and $R_{16}$ at each occurrence are independently selected from hydrogen, alkyl, hydroxy, hydroxy $C_{1-4}$alkyl, $C_{1-4}$alkoxy, and phenyl, and/or one of $R_{15}$ and one of $R_{16}$ join together to form a 3 to 6 membered cycloalkyl;

$R_{17}$ and $R_{18}$ are independently selected from hydrogen, alkyl, substituted alkyl, aryl, phenyl, or benzyl wherein the phenyl or benzyl is optionally substituted with alkyl, hydroxy, or hydroxyalkyl;

$R_{17a}$ is alkyl or substituted alkyl;

$R_{25}$ and $R_{26}$ are independently selected from hydrogen, alkyl, or substituted alkyl, or taken together form a heterocyclo or heteroaryl ring;

$R_{27}$ is alkyl or substituted alkyl;

q is 0, 1, 2, or 3;

m and n are 0, 1 or 2; and p is 0, 1, 2, or 3.

2. A compound according to claim 1, wherein z is

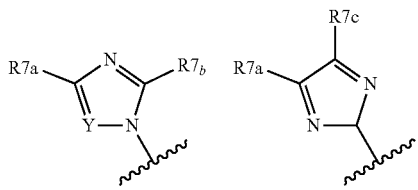

Y is CH, N or $CR_{7c}$;

$R_1$ is cyano, —$SO_2R_8$, —C(=O)$R_9$, or heteroaryl;

$R_2$ is (i) independently hydrogen, alkyl, or substituted alkyl, or (ii) taken together with $R_3$ forms a heterocyclo;

$R_3$ is (i) independently selected from
(a) alkyl optionally substituted with one to two of hydroxy and alkoxy;
(b) alkylthio or aminoalkyl optionally substituted with hydroxy or alkoxy;
(c)-$A_1$-aryl, wherein the aryl is optionally substituted with up to four substituents selected from alkyl, substituted alkyl, halogen, haloalkyl, cyano, nitro, —$NR_{17}R_{18}$, —$SR_{17}$, —$OR_{17}$, —$SO_2R_{17a}$, —$SO_2NR_{17}R_{18}$, —$NR_{17}C(=O)R_{18}$, —$CO_2R_{17}$, —$C(=O)R_{17}$, cycloalkyl, aryl, heterocyclo, and heteroaryl, and/or has fused thereto a five or six membered cycloalkyl ring;
(d)-$A_2$-heteroaryl wherein the heteroaryl is a five or six membered monocyclic ring having 1 to 3 heteroatoms selected from N, O, and S, or an eight or nine membered bicyclic ringed system having at least one aromatic ring and 1 to 4 heteroatoms selected from N, O, and S in at least one of the rings, said heteroaryl being optionally substituted with halogen, alkyl, alkoxycarbonyl, sulfonamide, nitro, cyano, trifluoromethyl, alkylthio, alkoxy, keto, —C(=O)H, acyl, benzyloxy, hydroxy, hydroxyalkyl, or phenyl optionally substituted with alkyl or substituted alkyl;
(e)-$A_2$-heterocyclo wherein the heterocyclo is optionally substituted with one to two groups selected from alkyl, keto, hydroxy, hydroxyalkyl, —C(=O)H, acyl, $CO_2H$, alkoxycarbonyl, phenyl, and/or benzyl, and/or has a bridged carbon-carbon chain or fused benzene ring joined thereto;
(f)-$A_2$-cycloalkyl wherein the cycloalkyl is optionally substituted with one to two groups selected from alkyl, keto, —C(=O)H, acyl, $CO_2H$, alkoxycarbonyl, and/or benzyl, and/or has a bridged carbon-carbon chain or fused benzene ring joined thereto; or
(ii) taken together with $R_2$ forms a heterocyclo;

$R_4$ at each occurrence is selected independently of each other $R_4$ from the group consisting of halogen, alkyl, haloalkyl, cyano, and haloalkoxy;

$R_{7a}$, $R_{7b}$ and $R_{7c}$ are independently selected from hydrogen, alkyl, carbamyl, or carbamylalkyl, or $R_{7a}$ and $R_{7c}$ join to form an aryl or heteroaryl;

$R_8$ is alkyl, arylalkyl, or aryl;

$R_9$ is —$NR_{10}R_{11}$, alkyl, substituted alkyl, alkoxy, alkylthio, cycloalkyl, aryl, heteroaryl, heterocyclo, $CO_2R_{12}$, or phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, NH ($C_{1-4}$alkyl), N ($C_{1-4}$alkyl)$_2$, NHC (=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto;

$R_{10}$ is independently hydrogen, alkyl, or alkoxy; and $R_{11}$ is independently hydrogen, alkyl, substituted alkyl, alkoxy heterocyclo cycloalkyl, aryl, or heteroaryl; or $R_{10}$ and $R_{11}$ taken together form a heterocyclo or heteroaryl optionally substituted with alkyl, keto, $CO_2H$, alkoxycarbonyl, hydroxy, alkoxy, alkyl, carbamyl, aryl, or substituted alkyl, wherein when the $R_{10}$ and $R_{11}$ group comprises a phenyl ring, said phenyl ring is optionally substituted with one to two of alkyl, halogen, and alkoxy;

$R_{12}$ is hydrogen or alkyl;

$A_1$ is —$(CHR_{14})_m$—V—$(CR_{15}R_{16})_n$—or —$(CHR_{14})_p$—(C=O)NH—;

$A_2$ is —$(CHR_{14})_m$—V—$(CR_{15}R_{16})_n$;

V is a bond, S, or —$NR_{22}$—;

$R_{14}$, $R_{15}$ and $R_{16}$ at each occurrence are independently selected from hydrogen, alkyl, hydroxy, hydroxy $C_{1-4}$alkyl, $C_{1-4}$alkoxy, and phenyl, and/or one of $R_{15}$ and one of $R_{16}$ join together to form a three to six membered cycloalkyl;

$R_{17}$ and $R_{18}$ are independently selected from hydrogen, alkyl, phenyl, and benzyl, wherein the phenyl and benzyl is optionally substituted with alkyl, hydroxy, or hydroxyalkyl;

$R_{17a}$ is alkyl or substituted alkyl;

$R_{22}$ is hydrogen or alkyl;

m and n are 0, 1, 2, or 3;

p is 0, 1, 2, or 3; and q is 0, 1, 2, or 3.

3. A compound according to claim 2 having the formula,

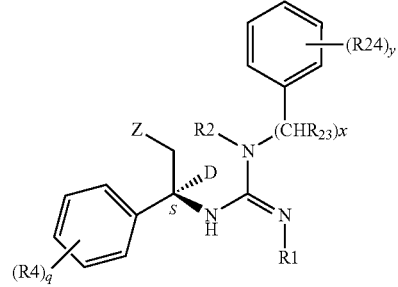

or a pharmaceutically-acceptable salt, solvate, hydrate or prodrug thereof, wherein:

$R_{7a}$, $R_{7b}$ and $R_{7c}$ are independently selected from hydrogen, alkyl, carbamyl or carbamyl$C_{1-4}$alkyl, or $R_{7a}$ and $R_{7c}$ join to form a fused phenyl ring;

$R_{23}$ is selected from hydrogen, alkyl, hydroxyalkyl, or phenyl;

$R_{24}$ is selected from alkyl, halogen, trifluoromethyl, cyano, halogen, hydroxy, $OCF_3$, methoxy, phenyloxy, benzyloxy, cyano, acyl, or two $R_{24}$ groups join to form a fused cycloalkyl or benzene ring; and x is 0, 1, or 2; and y is 0, 1, 2, or 3.

4. A compound according to claim 1 having the structure

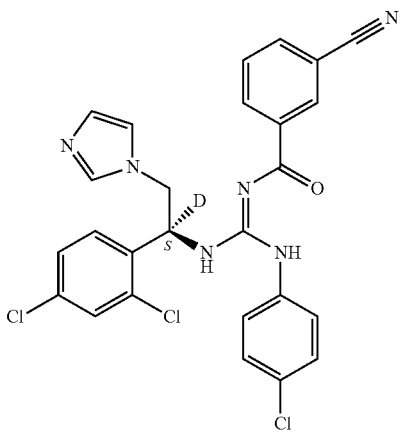

or a pharmaceutically-acceptable salt, solvate, hydrate or prodrug thereof, wherein:

there is deuterium (D) enrichment at the chiral centre, and optionally at other locations; and wherein there is an enantiomeric excess (ee) of the S stereoisomer.

5. A compound/composition according to claim 1, wherein $R_1$ is thiazolyl; and/or wherein Z is an optionally-substituted bicyclic heteroaryl.

6. A compound/composition according to claim 4, wherein deuterium (D) enrichment at the chiral centre exceeds 40% deuterium incorporation, and optionally exceeds 90%; and wherein the enantiomeric excess (ee) of the S stereoisomer exceeds 70%, and optionally exceeds 90%.

7. A method of treating or ameliorating cancer in a subject wherein the cancer is selected from breast cancer, prostate cancer, renal cancer, ovarian cancer, skin cancer, Central Nervous System (CNS) cancer, colon cancer, lung cancer, blood cancer;

wherein the method comprises administering an effective amount to the subject of at least one compound and/or composition selected from claim 1.

8. A method of treating or ameliorating cancer in a subject wherein the cancer is selected from breast cancer, prostate cancer, renal cancer, ovarian cancer, skin cancer, Central Nervous System (CNS) cancer, colon cancer, lung cancer, blood cancer;

wherein the method comprises administering to the subject an effective amount of at least one compound, or a pharmaceutical composition(s) comprising at least one compound (and one or more of a pharmaceutically-acceptable carrier [s], additive [s], diluent [s]), of the following formula:

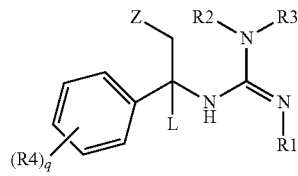

or a pharmaceutically-acceptable salt, solvate, hydrate or prodrug thereof, or a stereoisomer or a pharmaceutically-acceptable salt, solvate, hydrate or prodrug thereof, wherein:

L is alkyl, substituted alkyl or any atom or isotope permitted by valence except hydrogen at natural abundance;

$R_1$ is cyano, $-SO_2R_8$, $-C(=O)R_9$, or heteroaryl;

$R_2$ is (i) independently hydrogen, alkyl, benzyl, or substituted alkyl, or (ii) taken together with $R_3$ forms a heterocyclo;

$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) phenyl optionally substituted with one or more groups selected from $C_{1-4}$alkyl, halogen, trifluoromethyl, $OCF_3$, cyano, nitro, amino, hydroxy, or methoxy, or (iii) independently selected from $C_{1-4}$alkyl, alkylthio, aminoalkyl, -$B_B$-aryl, -$B_B$-heterocyclo, $B_B$-cycloalkyl, and -$B_B$-heteroaryl, optionally having one to three substituents selected from $R_{3a}$; and/or having fused thereto a five or six membered carbocyclic ring, or (iv) taken together with $R_2$ forms a heterocyclo optionally substituted with alkyl or substituted alkyl; $B_B$ is a bond, $C_{1-4}$alkylene, $C_{2-4}$alkenylene, substituted $C_{1-4}$alkylene, substituted $C_{2-4}$alkenylene, substituted $C_{1-4}$alkylene-C(=O)NH—, —C(=O)NH—, —$C_{1-4}$alkylene-C(=O)NH—, —C(=O)$NR_{19}$—, —$C_{1-4}$alkylene-C(=O)$NR_{19}$—, or substituted $C_{1-4}$alkylene-C(=O)$NR_{19}$—, —$(CHR_{14})_m$—$(CR_{15}R_{16})$ nor —$(CHR_{14})_p$—C(=O)NH—;

$R_{3a}$ at each occurrence is selected independently from alkyl, substituted alkyl, halogen, haloalkoxy, cyano, nitro, keto, trifluoromethyl, —$NR_{17}R_{18}$, —$SR_{17}$, —$OR_{17}$, —$SO_2R_{17a}$, —$SO_2NR_{17}R_{18}$, —$NR_{17}C(=O)R_{18}$, —$CO_2R_{17}$, —C(=O)$R_{17}$, cycloalkyl, aryl, heterocyclo, and heteroaryl, wherein when $R_{3a}$ is cycloalkyl, aryl, heterocyclo or heteroaryl, said cycloalkyl, aryl, heterocyclo and heteroaryl in turn is optionally substituted with alkyl or substituted alkyl;

Z is a heteroaryl, provided that when $R_1$ is cyano, Z is not 2-pyridinyl; and/or Z is selected from 5-membered heteroaryl groups containing 1, 2 or 3 heteroatoms each independently selected from N, O and S; and/or Z is triazolyl optionally substituted with one to two $R_7$ substituents or imidazolyl optionally substituted with one to two $R_7$ substituents and/or having fused thereto a benzene ring in turn optionally substituted with one to two $R_7$ substituents; and $R_7$ is alkyl, carbamyl, or substituted alkyl;

$R_4$ at each occurrence is selected independently of each other $R_4$ from the group consisting of halogen, trifluoromethyl, $OCF_3$, alkyl, substituted alkyl, haloalkyl, nitro, cyano, haloalkoxy, $OR_{25}$, $SR_{25}$, $NR_{25}R_{26}$, $NR_{25}SO_2R_{27}$, $SO_2R_{27}$, $SO_2NR_{25}R_{26}$, $CO_2R_{26}$, $C(\!=\!O)R_{26}$, $C(\!=\!O)NR_{25}R_{26}$, $OC(\!=\!O)R_{25}$, $-OC(O)NR_{25}R_{26}$, $NR_{25}C(\!=\!O)R_{26}$, $NR_{25}CO_2R_{26}$, aryl, heteroaryl, heterocyclo and cycloalkyl;

$R_8$ is $C_{1-4}$alkyl or phenyl optionally substituted with alkyl, halogen, haloalkoxy, cyano, nitro, or trifluoromethyl;

$R_9$ is $-NR_{10}R_{11}$, alkyl, substituted alkyl, alkoxy, alkylthio, cycloalkyl, aryl, heteroaryl, heterocyclo, or $-CO_2R_{12}$, alkyl or phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, $NH$ ($C_{1-4}$alkyl), $N$ ($C_{1-4}$alkyl)$_2$, $NHC(\!=\!O)$ alkyl, $C(\!=\!O)$ alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto or a) $C_{1-4}$alkyl optionally substituted with one to two of:
i) $SR_{13}$, $OR_{13}$, $NR_{13a}R_{13b}$, halogen, trifluoromethyl, $CO_2R_{13a}$, and $C(\!=\!O)NR_{13a}R_{13b}$;
ii) cycloalkyl optionally substituted with one to two of $C(\!=\!O)H$, $C_{1-4}$acyl, alkenyl, carbamyl, and/or phenyl in turn optionally substituted with halogen;
iii) phenyl or napthyl optionally substituted with one to two of halogen, nitro, amino, alkyl, hydroxy, $C_{1-4}$alkoxy, or having fused thereto a five or six membered heterocyclo;
iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;

b) 3 to 6 membered cycloalkyl optionally having up to four substituents selected from alkyl, halogen, cyano, alkenyl, acyl, alkylthio, carbamyl, phenyl in turn optionally substituted with halogen; or having an aryl fused thereto;

c) phenyl optionally substituted with one to four of halogen, cyano, trifluoromethyl, nitro, hydroxy, $C_{1-4}$alkoxy, haloalkoxy, $C_{1-4}$alkyl, $CO_2$alkyl, $SO_2$alkyl, $SO_2NH_2$, amino $NH$ ($C_{1-4}$alkyl), $N$ ($C_{1-4}$alkyl)$_2$, $NHC(\!=\!O)$ alkyl, $C(\!=\!O)$ alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto;

d) pyridinyl, thiazolyl, furanyl, thiophenyl, and pyrrolyl optionally substituted with one to two of halogen, alkyl, and phenyl in turn optionally substituted with halogen or trifluoromethyl;

$R_{10}$ and $R_{11}$ are (i) independently selected from hydrogen, alkyl, substituted alkyl, alkoxy, heterocyclo, cycloalkyl, aryl, heteroaryl or $C_{1-4}$alkyl optionally substituted with one to two of $-CO_2$alkyl, $-C(\!=\!O)NH$ (aryl), $NH$ (aryl), cycloalkyl, phenyloxy, phenyl in turn optionally substituted with $C_{1-4}$alkyl, hydroxy, $C_{1-4}$alkoxy, halogen, amino, nitro, tetrahydrofuranyl, and/or five or six membered heterocyclo, or having a five or six membered heterocyclo fused thereto; pyrrolidinyl optionally substituted with keto; napthyl, anthracenyl, pyridinyl, thiophenyl, furanyl, imidazolyl, benzimidazolyl, or indolyl in turn optionally substituted with $C_{1-4}$alkyl or $C_{1-4}$alkoxy; or (ii) taken together form a heteroaryl or heterocyclo selected from pyrrolidinyl, piperazinyl, piperidinyl, morpholinyl, tetrahydropyridinyl, and imidazolidinyl, wherein said heterocyclo formed by $R_{10}$ and $R_{11}$ is optionally substituted with one to two of keto, $CO_2H$, $C_{1-4}$alkoxy, $CO_2$alkyl, $C_{1-4}$carbamyl, benzyl; phenyl in turn optionally substituted with alkyl, halogen, or $C_{1-4}$alkoxy; tetrahydropyridinyl in turn optionally substituted with keto and/or phenyl; alkyl optionally substituted with amino or $NHR_{21}$ wherein $R_{21}$ is alkyl or phenyl optionally substituted with alkyl; and/or has a benzene ring fused thereto in turn optionally substituted with one to two of alkyl, $C_{1-4}$alkoxy, $CO_2$alkyl, and/or $C_{1-4}$carbamyl;

$R_{12}$ and $R_{19}$ are hydrogen or alkyl;
$R_{13}$ is hydrogen or alkyl;
$R_{13a}$ and $R_{13b}$ are selected from hydrogen, alkyl, and aryl;
$R_{14}$, $R_{15}$ and $R_{16}$ at each occurrence are independently selected from hydrogen, alkyl, hydroxy, hydroxy $C_{1-4}$alkyl, $C_{1-4}$alkoxy, and phenyl, and/or one of $R_{15}$ and one of $R_{16}$ join together to form a 3 to 6 membered cycloalkyl;

$R_{17}$ and $R_{18}$ are independently selected from hydrogen, alkyl, substituted alkyl, aryl, phenyl, or benzyl wherein the phenyl or benzyl is optionally substituted with alkyl, hydroxy, or hydroxyalkyl;

$R_{17a}$ is alkyl or substituted alkyl;
$R_{25}$ and $R_{26}$ are independently selected from hydrogen, alkyl, or substituted alkyl, or taken together form a heterocyclo or heteroaryl ring;
$R_{27}$ is alkyl or substituted alkyl;
q is 0, 1, 2, or 3;
m and n are 0, 1 or 2; and
p is 0, 1, 2, or 3.

9. A method of treating or ameliorating cancer in a subject wherein the cancer is selected from breast cancer, prostate cancer, renal cancer, ovarian cancer, skin cancer, Central Nervous System (CNS) cancer, colon cancer, lung cancer, blood cancer;

wherein the method comprises administering to the subject an effective amount of at least one compound, or a pharmaceutical composition(s) comprising at least one compound (and one or more of a pharmaceutically-acceptable carrier [s], additive [s], diluent [s]), of the following formula:

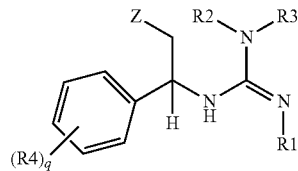

or a pharmaceutically-acceptable salt, solvate, hydrate or prodrug thereof, or a stereoisomer or a pharmaceutically-acceptable salt, solvate, hydrate or prodrug thereof, wherein:

$R_1$ is cyano, $-SO_2R_8$, $-C(\!=\!O)R_9$, or heteroaryl;
$R_2$ is (i) independently hydrogen, alkyl, benzyl, or substituted alkyl, or (ii) taken together with $R_3$ forms a heterocyclo;
$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) phenyl optionally substituted with one or more groups selected from $C_{1-4}$alkyl, halogen, trifluoromethyl, $OCF_3$, cyano, nitro, amino, hydroxy, or methoxy, or (iii) independently selected from $C_{1-4}$alkyl, alkylthio, aminoalkyl, -$B_B$-aryl, -$B_B$-heterocyclo, $B_B$-cycloalkyl, and -$B_B$-heteroaryl, optionally having one to three substituents selected from $R_{3a}$; and/or having fused thereto a five or six membered carbocyclic ring, or (iv) taken together with $R_2$ forms a heterocyclo optionally substituted with alkyl or substituted alkyl;

$B_B$ is a bond, $C_{1-4}$alkylene, $C_{2-4}$alkenylene, substituted $C_{1-4}$alkylene, substituted $C_{2-4}$alkenylene, substituted $C_{1-4}$alkylene-C(=O)NH—, —C(=O)NH—, —$C_{1-4}$alkylene-C(=O)NH—, —C(=O)$NR_{19}$—, —$C_{1-4}$alkylene-C(=O)$NR_{19}$—, or substituted $C_{1-4}$alkylene-C(=O)$NR_{19}$—, —$(CHR_{14})_m$—$(CR_{15}R_{16})$ nor —$(CHR_{14})_p$—C(=O)NH—;

$R_{3a}$ at each occurrence is selected independently from alkyl, substituted alkyl, halogen, haloalkoxy, cyano, nitro, keto, trifluoromethyl, —$NR_{17}R_{18}$, —$SR_{17}$, —$OR_{17}$, —$SO_2R_{17a}$, —$SO_2NR_{17}R_{18}$, —$NR_{17}$C(=O)$R_{18}$, —$CO_2R_{17}$, —C(=O)$R_{17}$, cycloalkyl, aryl, heterocyclo, and heteroaryl, wherein when $R_{3a}$ is cycloalkyl, aryl, heterocyclo or heteroaryl, said cycloalkyl, aryl, heterocyclo and heteroaryl in turn is optionally substituted with alkyl or substituted alkyl;

Z is a heteroaryl, provided that when $R_1$ is cyano, Z is not 2-pyridinyl; and/or Z is selected from 5-membered heteroaryl groups containing 1, 2 or 3 heteroatoms each independently selected from N, O and S; and/or Z is triazolyl optionally substituted with one to two $R_7$ substituents or imidazolyl optionally substituted with one to two $R_7$ substituents and/or having fused thereto a benzene ring in turn optionally substituted with one to two $R_7$ substituents; and $R_7$ is alkyl, carbamyl, or substituted alkyl;

$R_4$ at each occurrence is selected independently of each other $R_4$ from the group consisting of halogen, trifluoromethyl, $OCF_3$, alkyl, substituted alkyl, haloalkyl, nitro, cyano, haloalkoxy, $OR_{25}$, $SR_{25}$, $NR_{25}R_{26}$, $NR_{25}SO_2R_{27}$, $SO_2R_{27}$, $SO_2NR_{25}R_{26}$, $CO_2R_{26}$, C(=O)$R_{26}$, C(=O)$NR_{25}R_{26}$, OC(=O)$R_{25}$, —OC(=O)$NR_{25}R_{26}$, $NR_{25}$C(=O)$R_{26}$, $NR_{25}CO_2R_{26}$, aryl, heteroaryl, heterocyclo and cycloalkyl;

$R_8$ is $C_{1-4}$alkyl or phenyl optionally substituted with alkyl, halogen, haloalkoxy, cyano, nitro, or trifluoromethyl;

$R_9$ is —$NR_{10}R_{11}$, alkyl, substituted alkyl, alkoxy, alkylthio, cycloalkyl, aryl, heteroaryl, heterocyclo, or —$CO_2R_{12}$, alkyl or phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, NH ($C_{1-4}$alkyl), N ($C_{1-4}$alkyl)$_2$, NHC(=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto or a) $C_{1-4}$alkyl optionally substituted with one to two of:
i) $SR_{13}$, $OR_{13}$, $NR_{13a}R_{13b}$, halogen, trifluoromethyl, $CO_2R_{13a}$, and C(=O)$NR_{13a}R_{13b}$;
ii) cycloalkyl optionally substituted with one to two of C(=O)H, $C_{1-4}$acyl, alkenyl, carbamyl, and/or phenyl in turn optionally substituted with halogen;
iii) phenyl or napthyl optionally substituted with one to two of halogen, nitro, amino, alkyl, hydroxy, $C_{1-4}$alkoxy, or having fused thereto a five or six membered heterocyclo;
iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;

b) 3 to 6 membered cycloalkyl optionally having up to four substituents selected from alkyl, halogen, cyano, alkenyl, acyl, alkylthio, carbamyl, phenyl in turn optionally substituted with halogen; or having an aryl fused thereto;

c) phenyl optionally substituted with one to four of halogen, cyano, trifluoromethyl, nitro, hydroxy, $C_{1-4}$alkoxy, haloalkoxy, $C_{1-4}$alkyl, $CO_2$alkyl, $SO_2$alkyl, $SO_2NH_2$, amino NH ($C_{1-4}$alkyl), N ($C_{1-4}$alkyl)$_2$, NHC(=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto;

d) pyridinyl, thiazolyl, furanyl, thiophenyl, and pyrrolyl optionally substituted with one to two of halogen, alkyl, and phenyl in turn optionally substituted with halogen or trifluoromethyl;

$R_{10}$ and $R_{11}$ are (i) independently selected from hydrogen, alkyl, substituted alkyl, alkoxy, heterocyclo, cycloalkyl, aryl, heteroaryl or $C_{1-4}$alkyl optionally substituted with one to two of —$CO_2$alkyl, —C(=O)NH (aryl), NH (aryl), cycloalkyl, phenyloxy, phenyl in turn optionally substituted with $C_{1-4}$alkyl, hydroxy, $C_{1-4}$alkoxy, halogen, amino, nitro, tetrahydrofuranyl, and/or five or six membered heterocyclo, or having a five or six membered heterocyclo fused thereto; pyrrolidinyl optionally substituted with keto; napthyl, anthracenyl, pyridinyl, thiophenyl, furanyl, imidazolyl, benzimidazolyl, or indolyl in turn optionally substituted with $C_{1-4}$alkyl or $C_{1-4}$alkoxy; or (ii) taken together form a heteroaryl or heterocyclo selected from pyrrolidinyl, piperazinyl, piperidinyl, morpholinyl, tetrahydropyridinyl, and imidazolidinyl, wherein said heterocyclo formed by $R_{10}$ and Ru is optionally substituted with one to two of keto, $CO_2H$, $C_{1-4}$alkoxy, $CO_2$alkyl, $C_{1-4}$carbamyl, benzyl; phenyl in turn optionally substituted with alkyl, halogen, or $C_{1-4}$alkoxy; tetrahydropyridinyl in turn optionally substituted with keto and/or phenyl; alkyl optionally substituted with amino or $NHR_{21}$ wherein $R_{21}$ is alkyl or phenyl optionally substituted with alkyl; and/or has a benzene ring fused thereto in turn optionally substituted with one to two of alkyl, $C_{1-4}$alkoxy, $CO_2$alkyl, and/or $C_{1-4}$carbamyl;

$R_{12}$ and $R_{19}$ are hydrogen or alkyl;

$R_{13}$ is hydrogen or alkyl;

$R_{13a}$ and $R_{13b}$ are selected from hydrogen, alkyl, and aryl;

$R_{14}$, $R_{15}$ and $R_{16}$ at each occurrence are independently selected from hydrogen, alkyl, hydroxy, hydroxy $C_{1-4}$alkyl, $C_{1-4}$alkoxy, and phenyl, and/or one of $R_{15}$ and one of $R_{16}$ join together to form a 3 to 6 membered cycloalkyl;

$R_{17}$ and $R_{18}$ are independently selected from hydrogen, alkyl, substituted alkyl, aryl, phenyl, or benzyl wherein the phenyl or benzyl is optionally substituted with alkyl, hydroxy, or hydroxyalkyl;

$R_{17a}$ is alkyl or substituted alkyl;

$R_{25}$ and $R_{26}$ are independently selected from hydrogen, alkyl, or substituted alkyl, or taken together form a heterocyclo or heteroaryl ring;

$R_{27}$ is alkyl or substituted alkyl;

q is 0, 1, 2, or 3;
m and n are 0, 1 or 2; and
p is 0, 1, 2, or 3.

10. A method according to claim 9, wherein there is an enantiomeric excess (ee) of the S stereoisomer.

11. A method according to claim 10, using the compound:

or a pharmaceutically-acceptable salt, solvate, hydrate or prodrug thereof, wherein:
there is an enantiomeric excess (ee) of the S stereoisomer.

12. A method according to claim 8 wherein a compound administered to the subject has the ability/property to preferentially inhibit/and reduce the activity of the ATP-hydrolysing, as compared to the ATP-synthesizing, mode of ATP synthase,
wherein the differential between the compound's $EC_{50}$ $F_1F_0$ ATP synthesis and a smaller valued $EC_{50}$ $F_1F_0$ ATP hydrolysis in a Sub-Mitochondrial Particle [SMP] assay of the art is one or more of >10, >100, >1000, >5000 times difference.

13. A method according to claim 9 wherein a compound administered to the subject has the ability to preferentially inhibit and reduce the activity of the ATP-hydrolysing, as compared to the ATP-synthesizing, mode of ATP synthase,
wherein the differential between the compound's $EC_{50}$ $F_1F_0$ ATP synthesis and a smaller valued $EC_{50}$ $F_1F_0$ ATP hydrolysis in a Sub-Mitochondrial Particle [SMP] assay of the art is one or more of >10, >100, >1000, >5000 times difference.

14. A method according to claim 10,
wherein the enantiomeric excess (ee) of the S stereisomer exceeds 70%, and optionally exceeds 90%.

15. A method according to claim 11,
wherein the enantiomeric excess (ee) of the S stereisomer exceeds 70%, and optionally exceeds 90%.

16. A method of claim 8 wherein the Central Nervous system (CNS) cancer is astrocytoma or Glioblastoma Multiforme (GBM).

17. A method of claim 8 wherein the lung cancer is Non-Small Cell Lung Cancer (NSCLC).

18. A method of claim 8 wherein the skin cancer is melanoma.

19. A method of claim 8 wherein the blood cancer is selected from leukemia, lymphoma, Multiple myeloma.

20. A method of claim 19 wherein the leukemia is selected from Chronic Myeloid Leukemia (CML), Acute Myeloid Leukemia (AML), Acute Lymphoblastic Leukemia (ALL).

21. A method of claim 8 wherein the cancer is carcinoma.

22. A method of claim 21 wherein the carcinoma is selected from adenocarcinoma, squamous cell carcinoma, large cell carcinoma.

23. A method of claim 8 wherein the cancer is selected from Triple Negative Breast Cancer (TNBC), Androgen Receptor (AR) negative prostate cancer, amelanotic melanoma, clear cell renal carcinoma, mesothelioma.

24. A method of claim 9 wherein the Central Nervous system (CNS) cancer is astrocytoma or Glioblastoma Multiforme (GBM).

25. A method of claim 9 wherein the lung cancer is Non-Small Cell Lung Cancer (NSCLC).

26. A method of claim 9 wherein the skin cancer is melanoma.

27. A method of claim 9 wherein the blood cancer is selected from leukemia, lymphoma, Multiple myeloma.

28. A method of claim 27 wherein the leukemia is selected from Chronic Myeloid Leukemia (CML), Acute Myeloid Leukemia (AML), Acute Lymphoblastic Leukemia (ALL).

29. A method of claim 9 wherein the cancer is carcinoma.

30. A method of claim 29 wherein the carcinoma is selected from adenocarcinoma, squamous cell carcinoma, large cell carcinoma.

31. A method of claim 9 wherein the cancer is selected from Triple Negative Breast Cancer (TNBC), Androgen Receptor (AR) negative prostate cancer, amelanotic melanoma, clear cell renal carcinoma, mesothelioma.

32. A method of claim 8 wherein the cancer exhibits the Warburg effect.

33. A method of claim 9 wherein the cancer exhibits the Warburg effect.

34. A method of treating or ameliorating cancer in a subject wherein the cancer performs $F_1F_0$ ATP hydrolysis;
wherein the method comprises administering to the subject an effective amount of at least one compound, or a pharmaceutical composition(s) comprising at least one compound (and one or more of a pharmaceutically-acceptable carrier [s], additive [s], diluent [s]), of the following formula:

or a pharmaceutically-acceptable salt, solvate, hydrate or prodrug thereof, or a stereoisomer or a pharmaceutically-acceptable salt, solvate, hydrate or prodrug thereof, wherein:
L is alkyl, substituted alkyl or any atom or isotope permitted by valence;
$R_1$ is cyano, —$SO_2R_8$, —$C(=O)R_9$, or heteroaryl;
$R_2$ is (i) independently hydrogen, alkyl, benzyl, or substituted alkyl, or (ii) taken together with $R_3$ forms a heterocyclo;
$R_3$ is (i) independently alkyl, substituted alkyl, alkylthio, aminoalkyl, carbamyl, $B_B$-aryl, $B_B$-heterocyclo, $B_B$-heteroaryl, or $B_B$-cycloalkyl, or (ii) phenyl optionally substituted with one or more groups selected from $C_{1-4}$alkyl, halogen, trifluoromethyl, $OCF_3$, cyano, nitro, amino, hydroxy, or methoxy, or (iii) independently selected from $C_{1-4}$alkyl, alkylthio, aminoalkyl, -$B_B$-aryl, -$B_B$-heterocyclo, $B_B$-cycloalkyl, and -$B_B$-heteroaryl, optionally having one to three substituents selected from $R_{3a}$, and/or having fused thereto a five or six membered carbocyclic ring, or (iv) taken together with $R_2$ forms a heterocyclo optionally substituted with alkyl or substituted alkyl;

$B_B$ is a bond, $C_{1-4}$alkylene, $C_{2-4}$alkenylene, substituted $C_{1-4}$alkylene, substituted $C_{2-4}$alkenylene, substituted $C_{1-4}$alkylene-C(=O)NH—, —C(=O)NH—, —$C_{1-4}$alkylene-C(=O)NH—, —C(=O)NR$_{19}$—, —$C_{1-4}$alkylene-C(=O)NR$_{19}$—, or substituted $C_{1-4}$alkylene-C(=O)NR$_{19}$—, —(CHR$_{14}$)$_m$—(CR$_{15}$R$_{16}$) nor —(CHR$_{14}$)$_p$—C(=O)NH—;

$R_{3a}$ at each occurrence is selected independently from alkyl, substituted alkyl, halogen, haloalkoxy, cyano, nitro, keto, trifluoromethyl, —NR$_{17}$R$_{18}$, —SR$_{17}$, —OR$_{17}$, —SO$_2$R$_{17a}$, —SO$_2$NR$_{17}$R$_{18}$, —NR$_{17}$C(=O)R$_{18}$, —CO$_2$R$_{17}$, —C(=O)R$_{17}$, cycloalkyl, aryl, heterocyclo, and heteroaryl, wherein when $R_{3a}$ is cycloalkyl, aryl, heterocyclo or heteroaryl, said cycloalkyl, aryl, heterocyclo and heteroaryl in turn is optionally substituted with alkyl or substituted alkyl;

Z is a heteroaryl, provided that when $R_1$ is cyano, Z is not 2-pyridinyl; and/or Z is selected from 5-membered heteroaryl groups containing 1, 2 or 3 heteroatoms each independently selected from N, O and S; and/or Z is triazolyl optionally substituted with one to two $R_7$ substituents or imidazolyl optionally substituted with one to two $R_7$ substituents and/or having fused thereto a benzene ring in turn optionally substituted with one to two $R_7$ substituents; and $R_7$ is alkyl, carbamyl, or substituted alkyl;

$R_4$ at each occurrence is selected independently of each other $R_4$ from the group consisting of halogen, trifluoromethyl, OCF$_3$, alkyl, substituted alkyl, haloalkyl, nitro, cyano, haloalkoxy, OR$_{25}$, SR$_{25}$, NR$_{25}$R$_{26}$, NR$_{25}$SO$_2$R$_{27}$, SO$_2$R$_{27}$, SO$_2$NR$_{25}$R$_{26}$, CO$_2$R$_{26}$, C(=O)R$_{26}$, C(=O)NR$_{25}$R$_{26}$, OC(=O)R$_{25}$, —OC(=O)NR$_{25}$R$_{26}$, NR$_{25}$C(=O)R$_{26}$, NR$_{25}$CO$_2$R$_{26}$, aryl, heteroaryl, heterocyclo and cycloalkyl;

$R_8$ is $C_{1-4}$alkyl or phenyl optionally substituted with alkyl, halogen, haloalkoxy, cyano, nitro, or trifluoromethyl;

$R_9$ is —NR$_{10}$R$_{11}$, alkyl, substituted alkyl, alkoxy, alkylthio, cycloalkyl, aryl, heteroaryl, heterocyclo, or —CO$_2$R$_{12}$, alkyl or phenyl optionally substituted with one to four of halogen, cyano, trifluoromethyl, nitro, hydroxy, $C_{1-4}$alkoxy, haloalkoxy, $C_{1-6}$alkyl, CO$_2$alkyl, SO$_2$alkyl, SO$_2$NH$_2$, amino, NH (C$_{1-4}$alkyl), N (C$_{1-4}$alkyl)$_2$, NHC(=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto or a) $C_{1-4}$alkyl optionally substituted with one to two of:

i) SR$_{13}$, OR$_{13}$, NR$_{13a}$R$_{13b}$, halogen, trifluoromethyl, CO$_2$R$_{13a}$, and C(=O)NR$_{13a}$R$_{13b}$;

ii) cycloalkyl optionally substituted with one to two of C(=O)H, $C_{1-4}$acyl, alkenyl, carbamyl, and/or phenyl in turn optionally substituted with halogen;

iii) phenyl or napthyl optionally substituted with one to two of halogen, nitro, amino, alkyl, hydroxy, $C_{1-4}$alkoxy, or having fused thereto a five or six membered heterocyclo;

iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;

b) 3 to 6 membered cycloalkyl optionally having up to four substituents selected from alkyl, halogen, cyano, alkenyl, acyl, alkylthio, carbamyl, phenyl in turn optionally substituted with halogen; or having an aryl fused thereto;

c) phenyl optionally substituted with one to four of halogen, cyano, trifluoromethyl, nitro, hydroxy, $C_{1-4}$alkoxy, haloalkoxy, $C_{1-4}$alkyl, CO$_2$alkyl, SO$_2$alkyl, SO$_2$NH$_2$, amino NH (C$_{1-4}$alkyl), N (C$_{1-4}$alkyl)$_2$, NHC(=O) alkyl, C(=O) alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituted with keto or having a benzene ring fused thereto;

d) pyridinyl, thiazolyl, furanyl, thiophenyl, and pyrrolyl optionally substituted with one to two of halogen, alkyl, and phenyl in turn optionally substituted with halogen or trifluoromethyl;

$R_{10}$ and $R_{11}$ are (i) independently selected from hydrogen, alkyl, substituted alkyl, alkoxy, heterocyclo, cycloalkyl, aryl, heteroaryl or $C_{1-4}$alkyl optionally substituted with one to two of —CO$_2$alkyl, —C(=O)NH (aryl), NH (aryl), cycloalkyl, phenyloxy, phenyl in turn optionally substituted with $C_{1-4}$alkyl, hydroxy, $C_{1-4}$alkoxy, halogen, amino, nitro, tetrahydrofuranyl, and/or five or six membered heterocyclo, or having a five or six membered heterocyclo fused thereto; pyrrolidinyl optionally substituted with keto; napthyl, anthracenyl, pyridinyl, thiophenyl, furanyl, imidazolyl, benzimidazolyl, or indolyl in turn optionally substituted with $C_{1-4}$alkyl or $C_{1-4}$alkoxy; or (ii) taken together form a heteroaryl or heterocyclo selected from pyrrolidinyl, piperazinyl, piperidinyl, morpholinyl, tetrahydropyridinyl, and imidazolidinyl, wherein said heterocyclo formed by $R_{10}$ and $R_{11}$ is optionally substituted with one to two of keto, CO$_2$H, $C_{1-4}$alkoxy, CO$_2$alkyl, $C_{1-4}$carbamyl, benzyl; phenyl in turn optionally substituted with alkyl, halogen, or $C_{1-4}$alkoxy; tetrahydropyridinyl in turn optionally substituted with keto and/or phenyl; alkyl optionally substituted with amino or NHR$_{21}$ wherein R$_{21}$ is alkyl or phenyl optionally substituted with alkyl; and/or has a benzene ring fused thereto in turn optionally substituted with one to two of alkyl, $C_{1-4}$alkoxy, CO$_2$alkyl, and/or $C_{1-4}$carbamyl;

$R_{12}$ and $R_{19}$ are hydrogen or alkyl;

$R_{13}$ is hydrogen or alkyl;

$R_{13a}$ and $R_{13b}$ are selected from hydrogen, alkyl, and aryl;

$R_{14}$, $R_{15}$ and $R_{16}$ at each occurrence are independently selected from hydrogen, alkyl, hydroxy, hydroxy $C_{1-4}$alkyl, $C_{1-4}$alkoxy, and phenyl, and/or one of $R_{15}$ and one of $R_{16}$ join together to form a 3 to 6 membered cycloalkyl;

$R_{17}$ and $R_{18}$ are independently selected from hydrogen, alkyl, substituted alkyl, aryl, phenyl, or benzyl wherein the phenyl or benzyl is optionally substituted with alkyl, hydroxy, or hydroxyalkyl;

$R_{17a}$ is alkyl or substituted alkyl;

$R_{25}$ and $R_{26}$ are independently selected from hydrogen, alkyl, or substituted alkyl, or taken together form a heterocyclo or heteroaryl ring;

$R_{27}$ is alkyl or substituted alkyl;

q is 0, 1, 2, or 3;

m and n are 0, 1 or 2; and p is 0, 1, 2, or 3.

* * * * *